US011787845B1

(12) United States Patent
Adams et al.

(10) Patent No.: US 11,787,845 B1
(45) Date of Patent: Oct. 17, 2023

(54) SYNTHETIC PLASMODIUM ANTIGENS, COMPOSITIONS, AND USES THEREOF

(71) Applicants: University of South Florida, Tampa, FL (US); Washington University, St. Louis, MO (US); Case Western Reserve University, Cleveland, OH (US)

(72) Inventors: John H. Adams, Tampa, FL (US); Christopher L. King, Moreland Hills, OH (US); Niraj H. Tolia, St. Louis, MO (US); Edwin Chen, St. Louis, MO (US); Nichole Diane Salinas, St. Louis, MO (US); Miriam Thankam George, Nilgris (IN); Francis B. Ntumngia, Tampa, FL (US); Samantha Jones Barnes, Tampa, FL (US)

(73) Assignees: UNIVERSITY OF SOUTH FLORIDA, Tampa, FL (US); WASHINGTON UNIVERSITY, St. Louis, MO (US); CASE WESTERN RESERVE UNIVERSITY, Cleveland, OH (US)

( * ) Notice: Subject to any disclaimer, the term of this patent is extended or adjusted under 35 U.S.C. 154(b) by 193 days.

(21) Appl. No.: 17/103,275

(22) Filed: Nov. 24, 2020

Related U.S. Application Data

(62) Division of application No. 15/160,784, filed on May 20, 2016, now Pat. No. 10,927,153.

(60) Provisional application No. 62/245,721, filed on Oct. 23, 2015, provisional application No. 62/164,343, filed on May 20, 2015.

(51) Int. Cl.

*C07K 14/445* (2006.01)
*A61K 39/015* (2006.01)
*C07K 14/00* (2006.01)
*A61K 39/00* (2006.01)

(52) U.S. Cl.

CPC .......... *C07K 14/445* (2013.01); *A61K 39/015* (2013.01); *C07K 14/001* (2013.01); *A61K 2039/55566* (2013.01); *A61K 2039/575* (2013.01)

(58) Field of Classification Search

CPC .. C07K 14/445; C07K 14/001; A61K 39/015; A61K 2039/55566; A61K 39/575

See application file for complete search history.

(56) References Cited

U.S. PATENT DOCUMENTS 8,784,832 B2 7/2014 Adams et al.
9,120,869 B1 9/2015 Adams et al.

FOREIGN PATENT DOCUMENTS

WO 2010143194 A1 12/2010

OTHER PUBLICATIONS

Price et al., 2007. Vivax malaria: neglected and not benign. The American journal of tropical medicine and hygiene 77:79-87.

Mendis, et al., 2001. The neglected burden of Plasmodium vivax malaria. The American journal of tropical medicine and hygiene 64:97-106.

Alexandre, et al., 2010. Severe Plasmodium vivax malaria, Brazilian Amazon. Emerging infectious diseases 16:1611-1614.

Kochar, et al., 2009. Severe Plasmodium vivax malaria: a report on serial cases from Bikaner in northwestern India. The American journal of tropical medicine and hygiene 80:194-198.

Mohan & Maithani, 2010. Congenital malaria due to chloroquine-resistant Plasmodium vivax: a case report. J Trop Pediatr 56(6): 454-455.

Genton, et al., 2008. Plasmodium vivax and mixed infections are associated with severe malaria in children: a prospective cohort study from Papua New Guinea. PLoS medicine 5:e127.

Collins & Jeffery, 1996. Primaquine resistance in Plasmodium vivax. The American journal of tropical medicine and hygiene 55:243-249.

Adams, et al., 1992. A family of erythrocyte binding proteins of malaria parasites. Proceedings of the National Academy of Sciences of the United States of America 89:7085-7089.

Chitnis, et al., 1996. The domain on the Duffy blood group antigen for binding Plasmodium vivax and P. knowlesi malarial parasites to erythrocytes. J Exp Med 184:1531-1536.

Barnwell & Galinski, 1995. Plasmodium vivax: a glimpse into the unique and shared biology of the merozoite. Annals of tropical medicine and parasitology 89:113-120.

Miller, et al., 1976. The resistance factor to Plasmodium vivax in blacks. The Duffy-blood-group genotype, FyFy. The New England journal of medicine 295:302-304.

Barnwell, et al., 1989. In vitro evaluation of the role of the Duffy blood group in erythrocyte invasion by Plasmodium vivax. J Exp Med 169:1795-1802.

Ryan, et al., 2006. Evidence for transmission of Plasmodium vivax among a duffy antigen negative population in Western Kenya. The American journal of tropical medicine and hygiene 75(4): 575-581.

Menard, et al., 2010. Plasmodium vivax clinical malaria is commonly observed in Duffy-negative Malagasy people. Proceedings of the National Academy of Sciences of the United States of America (Mar. 2010) Early Edition: 1-5.

(Continued)

*Primary Examiner* — Robert A Zeman

(74) *Attorney, Agent, or Firm* — QUARLES & BRADY LLP

(57) ABSTRACT

Provided herein are synthetic *P. vivax* antigens, antibodies and pharmaceutical formulations and vaccines thereof. Also provided herein are methods of treating and/or preventing *Plasmodium* infection and/or disease by administering the synthetic *P. vivax* antigens, antibodies and pharmaceutical formulations and vaccines thereof.

3 Claims, 54 Drawing Sheets

Specification includes a Sequence Listing.

(56) References Cited

OTHER PUBLICATIONS

Cavasini, et al., 2007. Plasmodium vivax infection among Duffy antigen-negative individuals from the Brazilian Amazon region: an exception? Transactions of the Royal Society of Tropical Medicine and Hygiene 101:1042-1044.
Wurtz, et al., 2011. Vivax malaria in Mauritania includes infection of a Duffynegative individual. Malaria journal 10:336.
VanBuskirk, et al., 2004. Conserved residues in the Plasmodium vivax Duffybinding protein ligand domain are critical for erythrocyte receptor recognition. Proceedings of the National Academy of Sciences of the United States of America 101:15754-15759.
Hans, et al., 2005. Mapping binding residues in the Plasmodium vivax domain that binds Duffy antigen during red cell invasion. Mol Microbiol 55:1423-1434.
Ampudia, et al., 1996. Genetic polymorphism of the Duffy receptor binding domain of Plasmodium vivax in Colombian wild isolates. Mol Biochem Parasitol 78:269-272.
Xainli, et al., 2000. The erythrocyte binding motif of plasmodium vivax duffy binding protein is highly polymorphic and functionally conserved in isolates from Papua New Guinea. Mol Biochem Parasitol 111:253-260.
Cole-Tobian & King, 2003. Diversity and natural selection in Plasmodium vivax Duffy binding protein gene. Mol Biochem Parasitol 127:121-132.
Tsuboi, et al., 1994. Natural variation within the principal adhesion domain of the Plasmodium vivax duffy binding protein. Infect Immun 62:5581-5586.
Batchelor, et al., 2011. Dimerization of Plasmodium vivax DBP is induced upon receptor binding and drives recognition of DARC. Nat Struct Mol Biol. 18(8): 908-914.
VanBuskirk, et al., 2004. Antigenic drift in the ligand domain of Plasmodium vivax duffy binding protein confers resistance to inhibitory antibodies. The Journal of infectious diseases 190:1556-1562.
Ntumngia, et al., 2012. Conserved and Variant Epitopes of Plasmodium vivax Duffy Binding Protein as Targets of Inhibitory Monoclonal Antibodies. Infection and immunity 80:1203-1208.
McHenry, et al., 2011. Determination of the molecular basis for a limited dimorphism, N417K, in the Plasmodium vivax Duffy-binding protein. PloS one 6:e20192.
Chootong, et al., 2010. Mapping epitopes of the Plasmodium vivax Duffy binding protein with naturally acquired inhibitory antibodies. Infect Immun 78:1089-1095.
Cole-Tobian, et al., 2009. Strain-specific duffy binding protein antibodies correlate with protection against infection with homologous compared to heterologous plasmodium vivax strains in Papua New Guinean children. Infect Immun 77:4009-4017.
King, et al., 2008. Naturally acquired Duffy-binding protein-specific binding inhibitory antibodies confer protection from blood-stage Plasmodium vivax infection. Proceedings of the National Academy of Sciences of the United States of America 105:8363-8368.
Michon, et al., 2000. Naturally acquired and vaccine-elicited antibodies block erythrocyte cytoadherence of the Plasmodium vivax Duffy binding protein. Infect Immun 68:3164-3171.
Xainli, et al., 2002. Age-dependent cellular immune responses to Plasmodium vivax Duffy binding protein in humans. J Immunol 169:3200-3207.
Xainli, et al., 2003. Epitope-specific humoral immunity to Plasmodium vivax Duffy binding protein. Infect Immun 71:2508-2515.
Grimberg, et al., 2007. Plasmodium vivax invasion of human erythrocytes inhibited by antibodies directed against the Duffy binding protein. PLoS medicine 4:e337.
Ceravolo, et al., 2009. Naturally acquired inhibitory antibodies to Plasmodium vivax Duffy binding protein are short-lived and allele-specific following a single malaria infection. Clin Exp Immunol 156:502-510.
Ceravolo, et al., 2008. Inhibitory properties of the antibody response to Plasmodium vivax Duffy binding protein in an area with unstable malaria transmission. Scandinavian journal of immunology 67:270-278.
Ntumngia & Adams, 2012. Design and immunogenicity of a novel synthetic antigen based on the ligand domain of the Plasmodium vivax duffy binding protein. Clinical and vaccine immunology : CVI 19:30-36.
Ntumngia, et al., 2013. Immunogenicity of single versus mixed allele vaccines of Plasmodium vivax Duffy binding protein region II. Vaccine 31:4382-4388.
Singh, et al., 2001. Biochemical, biophysical, and functional characterization of bacterially expressed and refolded receptor binding domain of Plasmodium vivax duffybinding protein. J Biol Chem 276:17111-17116.
Chitnis & Miller, 1994. Identification of the erythrocyte binding domains of Plasmodium vivax and Plasmodium knowlesi proteins involved in erythrocyte invasion. J Exp Med 180:497-506.
Hodder, et al., 2001. Specificity of the protective antibody response to apical membrane antigen 1. Infect Immun 69:3286-3294.
Genton, et al., 2002. A recombinant blood-stage malaria vaccine reduces Plasmodium falciparum density and exerts selective pressure on parasite populations in a phase 1-2b trial in Papua New Guinea. The Journal of infectious diseases 185:820-827.
Chen, et al., 2015. Structural Analysis of the Synthetic Duffy Binding Protein (DBP) Antigen DEKnull Relevant for Plasmodium vivax Malaria Vaccine Design. PLoS neglected tropical diseases 9:e0003644.
Genton, et al., 2000. Safety and immunogenicity of a three-component blood-stage malaria vaccine in adults living in an endemic area of Papua New Guinea. Vaccine 18:2504-2511.
Thera, et al., 2011. A field trial to assess a blood-stage malaria vaccine. The New England journal of medicine 365:1004-1013.
Gething, et al., 2012. A long neglected world malaria map: Plasmodium vivax endemicity in 2010. PLoS Negl Trop Dis 6:e 1814.
Garnham, 1951. Some effects on the community of malaria eradication with special reference to the relapse phenomenon. East Afr Med J 28:6-10.
Krotoski, et al., 1982. Demonstration of hypnozoites in sporozoite-transmitted Plasmodium vivax infection, Am J Trop Med Hyg 31: 1291-1293.
Rieckmann, et al., 1989. Plasmodium vivax resistance to chloroquine? Lancet 2: 1I83-I 184.
Baird, et al., 1991. Resistance to chloroquine by Plasmodium vivax in Irian Jaya, Indonesia. Am J Trop Med Hyg 44:547-552.
Price, et al., 2014. Global extent of chloroquine-resistant Plasmodium vivax: a systematic review and meta-analysis. Lancet Infect Dis 14:982-991.
Ellis (Vaccines, W.B. Saunders Company, Chapter 29, 1988, pp. 568-574).
Boslego et al. (Vaccines and Immunotherapy, 1991, Chapter 17).
Skolnick et al. (Trends in Biotechnology 18: 34-39, 2000).
Greenspan et al, (Nature Biotechnology 17:936-937, 1999).
Harlow et al (Antibodies A Laboratory Manual, Cold Spring Harbor Laboratory Press Inc., 1988).
Colman et al. (Research in Immunology 145: 33-36, 1994).
Houghten et al. (New Approaches to Immunization, Vaccines 86, Cold Spring Harbor Laboratory, p. 21-25, 1986).
Burgess et al (J. of Cell Bio. 111 :2129-2138, 1990).
Lazar et al. (Molecular and Cellular Biology, 1988, 8:1247-1252).
Bork (Genome Research, 2000, 10:398-400).
Bowie et al (Science, 1990, 257:1306-1310).
Baird & Hoffman, 2004. Primaquine therapy for malaria. Clin Infect Dis 39:1336-1345.
Pybus, et al., 2013. The metabolism of primaquine to its active metabolite is dependent on CYP 2D6. Malar J 12:212.
Bennett, et al., 2013. Primaquine failure and cytochrome P-450 2D6 in Plasmodium vjvax malaria. N Engl J Med 369:1381-1382.
Yazdani, et al., 2006. Immune responses to asexual blood-stages of malaria parasites. Curr Mol Med 6:187-203.
Marsh & Kinyanjui, 2006. Immune effector mechanisms in malaria. Parasite Immunol 28:51-60.

(56) References Cited

OTHER PUBLICATIONS

Mueller, et al., 2013. Natural acquisition of immunity to Plasmodium vivax: epidemiological observations and potential targets. Adv Parasitol 81:77-131.
Wertheimer & Barnwell, 1989. Plasmodium vivax interaction with the human Duffy blood group glycoprotein: identification of a parasite receptor-like protein. Exp Parasitol 69:340-350.
Miller, et al., 1975. Erythrocyte receptors for (Plasmodium knowlesi) malaria: Duffy blood group determinants. Science 189:561-563.
Adams, et al., 1990. The Duffy receptor family of Plasmodium knowlesi is located within the micronemes of invasive malaria merozoites. Cell 63:141-153.
Menard, et al., 2013. Whole genome sequencing of field isolates reveals a common duplication of the Duffy binding protein gene in Malagasy Plasmodium vivax strains. PLoS Negl Trop Dis 7:e2489.
Adams, et al., 2001. An expanding ebl family of Plasmodium falciparum. Trends Parasitol 17:297-299.
Mayer, et al., 2001. Characterization of a Plasmodium falciparum erythrocyte-binding protein paralogous to EBA-175. Proc Natl Acad Sci USA 98:5222-5227.
Narum, et al., 2002. A novel Plasmodium falciparum erythrocyte binding protein~2 (EBP2/BAEBL) involved in erythrocyte receptor binding. Mol Biochem Parasitol 119:159-168.
Peterson, et al., 1995. Isolation of multiple sequences from the Plasmodium falciparum genome that encode conserved domains homologous to those in erythrocyte-binding proteins. Proc Natl Acad Sci USA 92:7100-7104.
Ranjan & Chitnis, 1999. Mapping regions containing binding residues within functional domains of Plasmodium vivax and Plasmodium knowlesi erythrocyte~binding proteins. Proc Natl Acad Sci USA 96:14067-14072.
Batchelor, et al., 2014. Red blood cell invasion by Plasmodium vivax: structural basis for DBP engagement of DARC. . PLoS Pathog 10:el003869.
Tolia, et al., 2005. Structural basis for the EBA~175 erythrocyte invasion pathway of the malaria parasite Plasmodium falciparum. Cell 122:183-193.
Baum, et al., 2002. Natural selection on the erythrocyte surface. Mol Biol Evol 19:223-229.
Smith, 1985. Filamentous fusion phage: novel expression vectors that display cloned antigens on the virion surface. Science 228: 1315-1317.
Wilson & Finlay, 1998. Phage display: applications, innovations, and issues in phage and host biology. Can J Microbiol 44:313-329.
Coley, et al., 2001. Rapid and precise epitope mapping of monoclonal antibodies against Plasmodium falciparum AMA 1 by combined phage display of fragments and random peptides. Protein Eng 14:691-698.
Sabo, et al., 2007. Mimotopes of Apical Membrane Antigen 1: Structures of Phage-Derived Peptides Recognized by the Inhibitory Monoclonal Antibody 4G2dc1 and Design of a More Active Analogue. Infection and Immunity 75:61-73.
Casey, et al., 2004. Antibodies to malaria peptide mimics inhibit Plasmodium falciparum invasion of erythrocytes. Infect Immun 72:1126-1134.
Narum, et al., 2006. Passive Immunization with a Multicomponent Vaccine against Conserved Domains of Apical Membrane Antigen 1 and 235-Kilodalton Rhoptry Proteins Protects Mice against Plasmodium yoelii Blood-Stage Challenge Infection. Infection and Immunity 74:5529-5536.
Demangel, et al., 1996. Reproducing the immune response against, the Plasmodium vivax merozoite surface protein 1 with mimotopes selected from a phage-displayed peptide library. Mol Immunol 33:909-916.
Greenwood, et al., 1991. Multiple display of foreign peptides on a filamentous bacteriophage. Peptides from Plasmodium falciparum circumsporozoite protein as antigens. J Mol Biol. 220:821-827.
Willis, et al., 1993. Immunological properties of foreign peptides in multiple display on a filamentous bacteriophage. Gene 128:79-83.
Monette, et al., 2001. Structure of a malaria parasite antigenic determinant displayed on filamentous bacteriophage determined by NMR spectroscopy: implications for the structure of continuous peptide epitopes of proteins. Protein Sci 10:1150-1159.
Adda, et al., 1999. Isolation of peptides that mimic epitopes on a malarial antigen from random peptide libraries displayed on phage. Infect Immun 67:4679-4688.
Coley, et al., 2006. The most polymorphic residue on Plasmodium falciparum apical membrane antigen 1 determines binding of an invasion-inhibitory antibody. Infect Immun 74:2628-2636.
Ju, et al., 2012. Genetic polymorphism and natural selection of Duffy binding protein of Plasmodium vivax Myanmar isolates. Malar J 11:60.
Hwang, et al., 2009. Genetic characteristics of polymorphic antigenic markers among Korean isolates of Plasmodium vivax. Korean J Parasitol 47 Suppl: S51-58.
Premaratne, et al., 2011. Genetic diversity of Plasmodium vivax Duffy Binding Protein II (PvDBII) under unstable transmission and low intensity malaria in Sri Lanka, Infect Genet Evol 11:1327-1339.
Babaeekho, et al., 2009. Genetic mapping of the duffy binding protein (DBP) ligand domain of Plasmodium vivax from unstable malaria region in the Middle East. Am J Trop Med Hyg 80:112-118.
Ju, et al., 2013. Genetic diversity and natural selection of Duffy binding protein of Plasmodium vivax Korean isolates. Acta Trop 125:67-74.
Cole-Tobian, et al., 2002. Age-acquired immunity to a Plasmodium vivax invasion ligand, the duffy binding protein. J Infect Dis 186:531-539.
Michon, et al., 1998. Serologic responses to recombinant Plasmodium vivax Duffy binding protein in a Colombian village. Am J Trop Med Hyg 59:597-599.
Fraser, et al., 1997. Expression and serologic activity of a soluble recombinant Plasmodium vivax Duffy binding protein. Infect Immun 65:2772-2777.
Devi, et al., 2007. Immunogenicity of Plasmodium vivax combination subunit vaccine formulated with human compatible adjuvants in mice. Vaccine 25:5166-5174.
Arevalo-Herrera, et al., 2005. Immunogenicity and protective efficacy of recombinant vaccine based on the receptor-binding domain of the Plasmodium vivax Duffy binding protein in Aotus monkeys. Am J Trop Med Hyg 73:25-31.
Adams, et al., 2002. PHENIX: building new software for automated crystallographic structure determination. Acta Crystallogr D Biol Crystllogr 58, 1948-1954.
Aricescu, et al., 2006. A time- and cost-efficient system for high-level protein production in mammalian cells. Acta Crystallogr D Biol Crystallogr 62, 1243-1250.
Baum, et al., 2003. Evidence for diversifying selection on erythrocyte-binding antigens of Plasmodium falciparum and P. vivax. Genetics 163, 1327-1336.
Carlton, et al., 2011. Why is Plasmodium vivax a neglected tropical disease? PLoS Negl Trop Dis 5, e1160.
Chen, et al., 2013. Structural and functional basis for inhibition of erythrocyte invasion by antibodies that target Plasmodium falciparum EBA-175. PLoS Pathog 9, e1003390.
Cohen, et al., 1988. Expression of herpes simplex virus type 1 glycoprotein D deletion mutants In mammalian cells. J Virol 62, 1932-1940.
Davis, et al., 2007. MolProbity: all-atom contacts and structure validation for proteins and nucleic acids. Nucleic Acids Res 35, W375-383.
Dormitzer, et al., 2012. Structural vaccinology starts to deliver. Nat Rev Microbiol 10, 807-813.
Dutta, et al., 2013. Overcoming antigenic diversity by enhancing the immunogenicity of conserved epitopes on the malaria vaccine candidate apical membrane antigen-1. PLoS Pathog 9, e 1003840.
Ekiert & Wilson, 2012. Broadly neutralizing antibodies against influenza virus and prospects for universal therapies. Curr Opin Viro 2, 134-141.
Emsley & Cowtan, 2004. Coot: model-building tools for molecular graphics. Acta Crystallogr D Biol Crystallogr 60, 2126-2132.

(56) References Cited

OTHER PUBLICATIONS

Fischer, et al., 2010. Determination of the molecular weight of proteins in solution from a single small-angle X-ray scattering measurement on a relative scale. Journal of Applied Crystallography 43, 101-109.
Guerra, et al., 2010. The international limits and population at risk of Plasmodium vivax transmission in 2009. PLoS Negl Trop Dis 4, e774.
Haste, et al., 2006. Prediction of residues in discontinuous B-cell epitopes using protein 3D structures. Protein Sci 15, 2558-2567.
Hura, et al., 2013. Comprehensive macromolecular conformations mapped by quantitative SAXS analyses. Nat Methods 10, 453-454.
Hura, et al., 2009. Robust, high-throughput solution structural analyses by small angle X-ray scattering (SAXS). Nat Methods 6, 606-612.
Kabsch, 2010. Xds. Acta Crystallogr D Biol Crystallogr 66, 125-132.
Khunrae, et al., 2009. Structural comparison of two CSPG-binding DBL domains from the VAR2CSA protein important in malaria during pregnancy. J Mol Biol 393, 202-213.
Lawrence & Colman, 1993. Shape complementarity at protein/protein interfaces. J Mol Biol 234, 946-950.
Lin, et al., 2012. Crystal and solution structures of Plasmodium falciparum erythrocyte-binding antigen 140 reveal determinants of receptor specificity during erythrocyte invasion. J Biol Chem 287, 36830-36836.
Malpede, et al., 2013. Molecular basis for sialic acid-dependent receptor recognition by the Plasmodium falciparum invasion protein erythrocyte-binding antigen-140/BAEBL. J Biol Chem 288, 12406-12415.
Marcatili, et al., 2008. PIGS: automatic prediction of antibody structures. Bioinformatics 24, 1953-1954.
McCoy, et al., 2007. Phaser crystallographic software. J Appl Crystallogr 40, 658-674.
Ntumngia, et al., 2014. Immunogenicity of a synthetic vaccine based on Plasmodium vivax Duffy binding protein region II. Clin Vaccine Immunol 21, 1215-1223.
Petoukhov, et al., 2012. New developments in the ATSAS program package for small-angle scattering data analysis. J Appl Crystallogr 45, 342-350.
Petoukhov & Svergun, 2005. Global rigid body modeling of macromolecular complexes against small-angle scattering data. Biophys J 89, 1237-1250.
Salinas, et al., 2014. Critical Glycosylated Residues in Exon Three of Erythrocyte Glycophorin A Engage Plasmodium falciparum EBA-175 and Define Receptor Specificity. MBio 5(5): e01606-14.
Salinas & Tolia, 2014. A quantitative assay for binding and inhibition of Plasmodium falciparum Erythrocyte Binding Antigen 175 reveals high affinity binding depends on both DBL domains. Protein Expr Purif 95, 188-194.
Schroder, et al., 2010. Super-resolution biomolecular crystallography with low-resolution data. Nature 464, 1218-1222.
Siddiqui, et al., 2012. Fine specificity of Plasmodium vivax Duffy binding protein binding engagement of the Duffy antigen on human erythrocytes. Infect Immun 80, 2920-2928.
Sim, et al., 1994. Receptor and ligand domains for invasion of erythrocytes by Plasmodium falciparum. Science 264, 1941-1944.
Tournamille, et al., 1997. Close association of the first and fourth extracellular domains of the Duffy antigen/receptor for chemokines by a disulfide bond is required for ligand binding. J Biol Chem 272, 16274-16280.
Welsh & Fujinami, 2007. Pathogenic epitopes, heterologous Immunity and vaccine design. Nat Rev Microbiol 5, 555-563.
Zhou, et al., 2015. Structural Repertoire of HIV-I-Neutralizing Antibodies Targeting the CD4 Supersite in 14 Donors. Cell 161, 1280-1292.
World Malaria Report 2013 (WHO).
Shetty (2012). The Numbers Game, Nature 484: 514-515.
Breman, et al., 2001. AM J Trop Med Hyg 64: iv-vii.
Horuk, et al., 1993. Science 261:1182-1184.
Putnam, C.D., Hammel, M, Hura, G.L, and Trainer, J.A. Q. Rev. Biophys. 2007. 191-285.

SEQ ID NO: 1

T I S S A I I N H A F L Q N T
V M K N C N Y K R K R R E R D W D C N T
K K D V C I P D R R Y Q L C M K E L T N
L V N N T D T N F H R D I T F R K L Y L
K R K L I Y D A A V E G D L L L K L N N
Y K Y N K D F C K D I K W S L G D F G D
I I M G T D M E G I G Y S K V V E N N L
R S I F G T D E K A Q Q R R K Q W W N E
S K A Q I W T A M M Y S V K K R L K G N
F I W I C K L N V A V N I E P Q I Y R W
I R E W G R D Y V S E L P T E V Q K L K
E K C D G K I N Y T D K K V C K V P P C
Q N A C K S Y D Q W I T R K K N Q W D V
L S N K F I S V K N A E K V Q T A G I V
T P Y D I L K Q E L D E F N E V A F E N
E I N K R D G A Y I E L C V C S V E E A
K K N T Q E V V T

FIG. 3 mAb-3D10 mAb-3C9

DBPII

I I N H A F L Q N T V M K N C N Y K R K R R

SEQ ID NO.: 12

M1

V G N L D F S R F H K S S L D Y K R G Q

SEQ ID NO.: 14

M2

V K F T D R Y K Y S S M K G Y A R Q G R

SEQ ID NO.: 15

M3

K I N M Y K E V R T R Q L S V R P S P E

SEQ ID NO.: 16

FIG. 7B

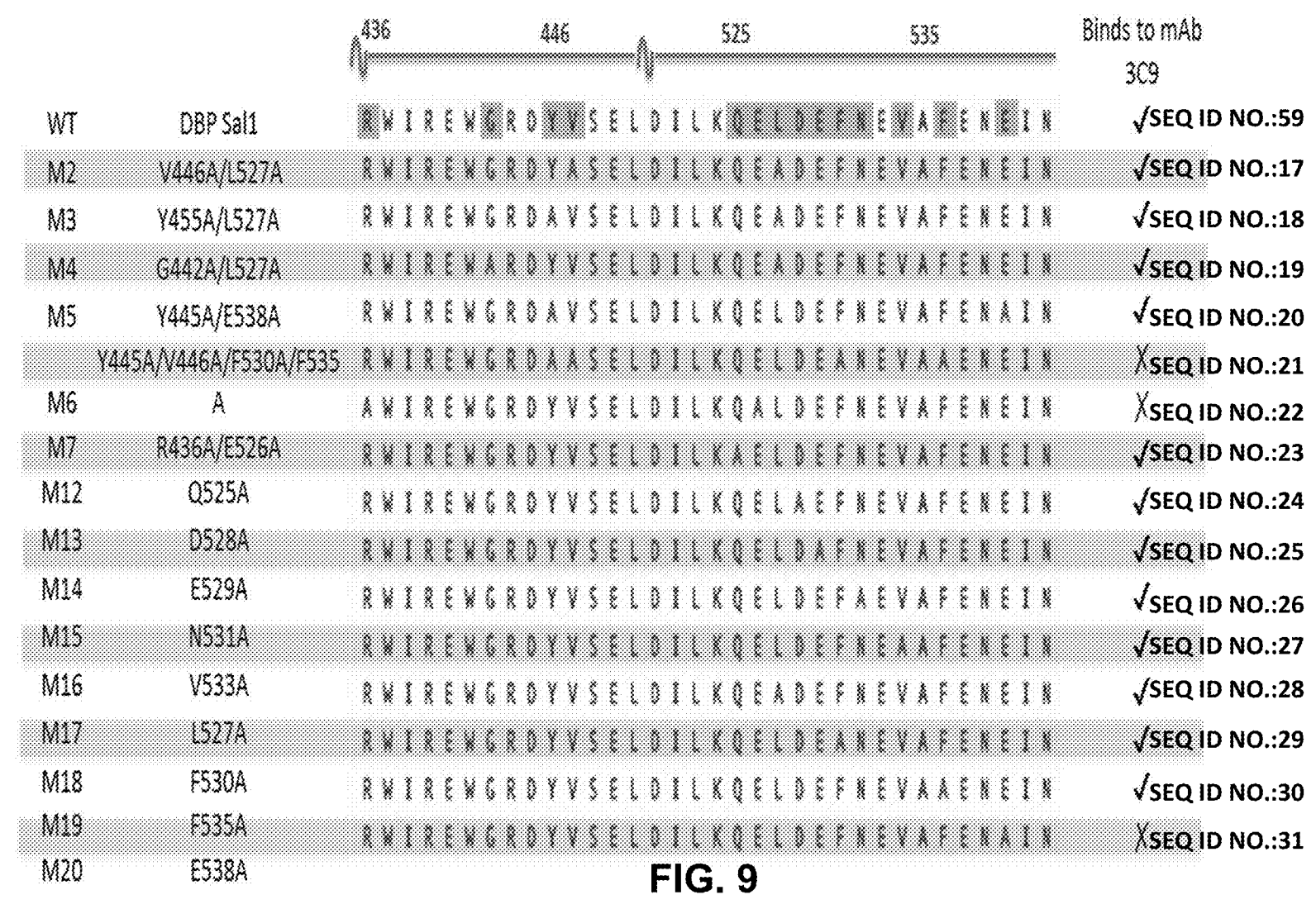

| | | 436 446 525 535 | Binds to mAb 3C9 |
|---|---|---|---|
| WT | DBP Sal1 | R W I R E W G R D Y V S E L D I L K Q E L D E F N E V A F E N E I N | √SEQ ID NO.:59 |
| M2 | V446A/L527A | R W I R E W G R D Y A S E L D I L K Q E A D E F N E V A F E N E I N | √SEQ ID NO.:17 |
| M3 | Y455A/L527A | R W I R E W G R D A V S E L D I L K Q E A D E F N E V A F E N E I N | √SEQ ID NO.:18 |
| M4 | G442A/L527A | R W I R E W A R D Y V S E L D I L K Q E A D E F N E V A F E N E I N | √SEQ ID NO.:19 |
| M5 | Y445A/E538A | R W I R E W G R D A V S E L D I L K Q E L D E F N E V A F E N A I N | √SEQ ID NO.:20 |
| | Y445A/V446A/F530A/F535 | R W I R E W G R D A A S E L D I L K Q E L D E A N E V A A E N E I N | XSEQ ID NO.:21 |
| M6 | A | A W I R E W G R D Y V S E L D I L K Q A L D E F N E V A F E N E I N | XSEQ ID NO.:22 |
| M7 | R436A/E526A | R W I R E W G R D Y V S E L D I L K A E L D E F N E V A F E N E I N | √SEQ ID NO.:23 |
| M12 | Q525A | R W I R E W G R D Y V S E L D I L K Q E L A E F N E V A F E N E I N | √SEQ ID NO.:24 |
| M13 | D528A | R W I R E W G R D Y V S E L D I L K Q E L D A F N E V A F E N E I N | √SEQ ID NO.:25 |
| M14 | E529A | R W I R E W G R D Y V S E L D I L K Q E L D E F A E V A F E N E I N | √SEQ ID NO.:26 |
| M15 | N531A | R W I R E W G R D Y V S E L D I L K Q E L D E F N E A A F E N E I N | √SEQ ID NO.:27 |
| M16 | V533A | R W I R E W G R D Y V S E L D I L K Q E A D E F N E V A F E N E I N | √SEQ ID NO.:28 |
| M17 | L527A | R W I R E W G R D Y V S E L D I L K Q E L D E A N E V A F E N E I N | √SEQ ID NO.:29 |
| M18 | F530A | R W I R E W G R D Y V S E L D I L K Q E L D E F N E V A A E N E I N | √SEQ ID NO.:30 |
| M19 | F535A | R W I R E W G R D Y V S E L D I L K Q E L D E F N E V A F E N A I N | XSEQ ID NO.:31 |
| M20 | E538A | | |

FIG. 9

CDR1 CDR2

2D10 Heavy QLQQSGPELVKPGASVKISCKASGYAFISSWMNWVKQRPGKGLEWIGRIYPGDGDTHYNG
SEQ ID NO.:32
2H2 Heavy PLQQSGPELVKPGASVKISCKASGYAFSSSWMNWVKQRPGKGLEWIGRIYPGDGDTNYNG
SEQ ID NO.:33

CDR3

2D10 Heavy KFKGKATLTADKSSSTAYMQLSSLTSEDSAVYFCAREETAQTGGFDYWGQGTTLTVSS

2H2 Heavy KFKGKATLTADKSSSTAYMQLSSLTSEDSAVYFCAGEVYDRYYAMDYWGQGTSVTVSS

CDR1 CDR2

2D10 Light DIVITQDELSNPVTSGESVSISCRSSKSLLYQDGKTYLNWFLQRPGQSPQLLIYLMSTRA
SEQ ID NO.:34
2H2 Light DIVITQDELSNPVTSGESVSISCRSSKSLLYQDGKTYLNWFLQRPGQSPQLLIYLMSTRA
SEQ ID NO.:35

CDR3

2D10 Light SGVSDRFSGSGSGTDFTLEISRVEAEDVGVYYCQQLVEYPLTFGAGTKLELKRAD

2H2 Light SGVSDRFSGSGSGTDFTLEISRVKAEDVGVYYCQQFVEYPYTFGGGTKLEIKRAD

FIG. 14C

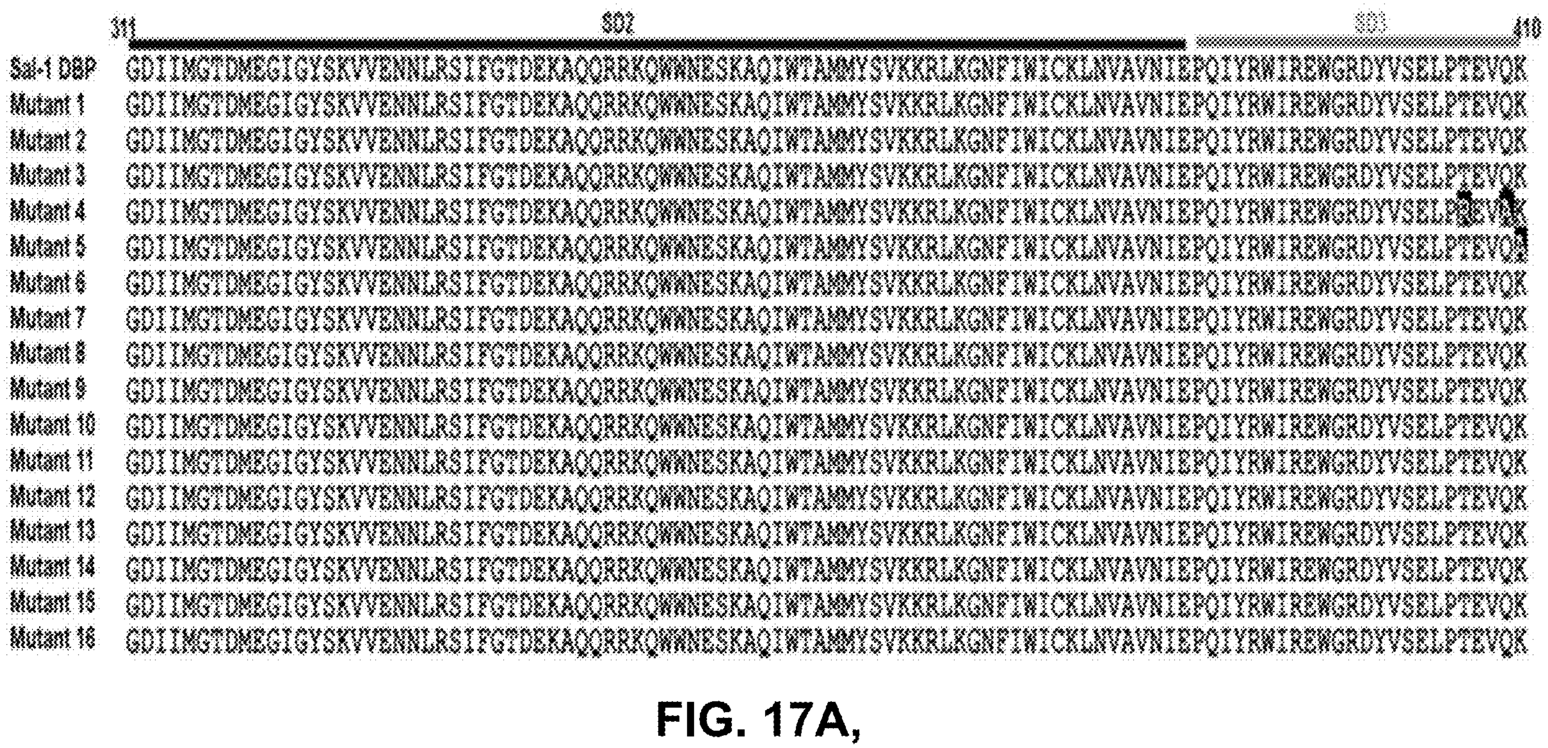
FIG. 17A, cont'd

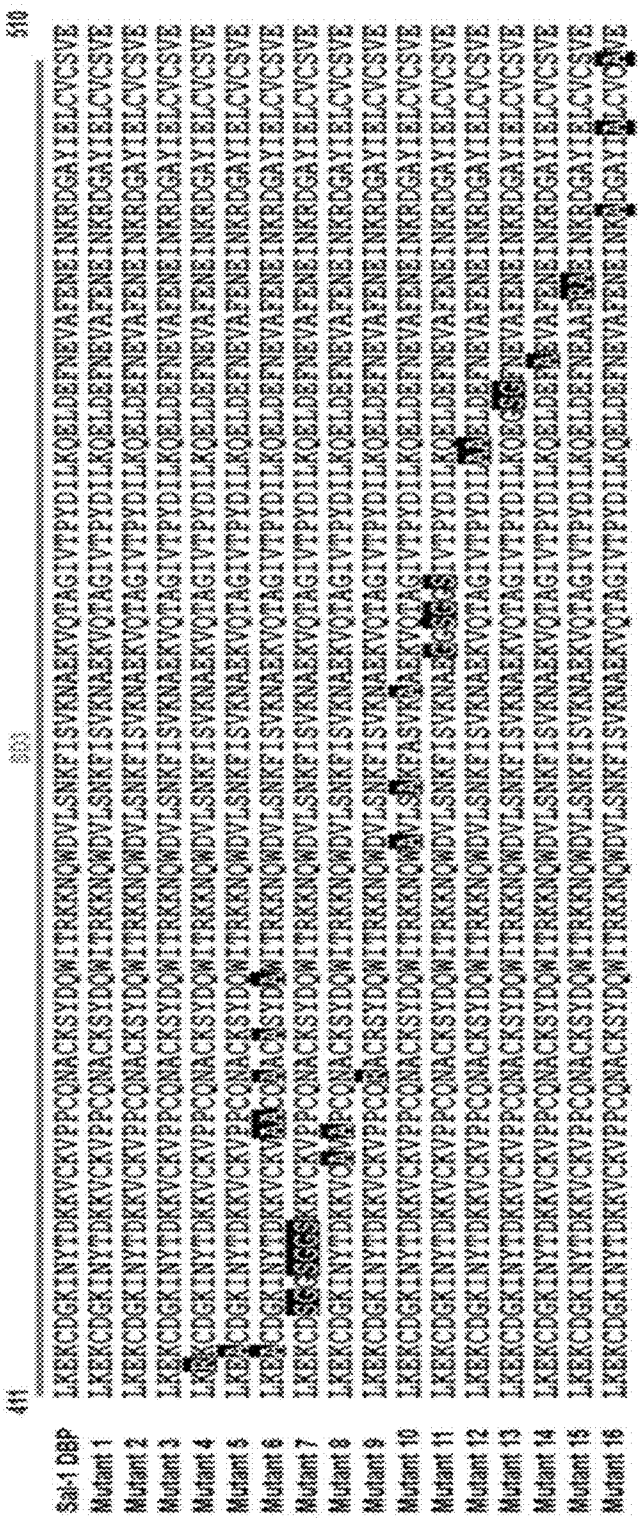
FIG. 17A, cont'd

| | 511 525 |
|---|---|
| Sal-1 DBP | EAKKNTQEVVTNVDN |
| Mutant 1 | EAKKNTQEVVTNVDN |
| Mutant 2 | EAKKNTQEVVTNVDN |
| Mutant 3 | EAKKNTQEVVTNVDN |
| Mutant 4 | EAKKNTQEVVTNVDN |
| Mutant 5 | EAKKNTQEVVTNVDN |
| Mutant 6 | EAKKNTQEVVTNVDN |
| Mutant 7 | EAKKNTQEVVTNVDN |
| Mutant 8 | EAKKNTQEVVTNVDN |
| Mutant 9 | EAKKNTQEVVTNVDN |
| Mutant 10 | EAKKNTQEVVTNVDN |
| Mutant 11 | EAKKNTQEVVTNVDN |
| Mutant 12 | EAKKNTQEVVTNVDN |
| Mutant 13 | EAKKNTQEVVTNVDN |
| Mutant 14 | EAKKNTQEVVTNVDN |
| Mutant 15 | EAKKNTQEVVTNVDN |
| Mutant 16 | EAKKNTQEVVTNVDN |

FIG. 17A, cont'd

| Mutant in Fig. 17A | SEQ ID NO: |
|---|---|
| Sal-1 DBP | 36 |
| 1 | 37 |
| 2 | 38 |
| 3 | 39 |
| 4 | 40 |
| 5 | 41 |
| 6 | 42 |
| 7 | 43 |
| 8 | 44 |
| 9 | 45 |
| 10 | 46 |
| 11 | 47 |
| 12 | 48 |
| 13 | 49 |
| 14 | 50 |
| 15 | 51 |
| 16 | 52 |

FIG. 17B

NTVMKNCNYKRKRRERDWDCNTKKDVCIPDRRYQLCMKELTNLVNNTDTNFHRDITFRKLYLK
RKLIYDAAVEGDLLLKLNNYRYNKDFCKDIRWSLGDFGDIIMGTDMEGIGYSKVVENNLRSIF
GTDEKAQQRRKQWWNESKAQIWTAMMYSVKKRLKGNFIWICKLNVAVNIEPQIYRWIREWGRD
YVSELPTEVQKLKEKCDGKINYTDKKVCKVPPCQNACKSYDQWITRKKNQWDVLSNKFISVKN
AEKVQTAGIVTPYDILKQELDEFNEVAFENEINKRDGAYIELCVCSVEEAKKNTQEVVTNVDN

SEQ ID NO.:36

FIG. 19B

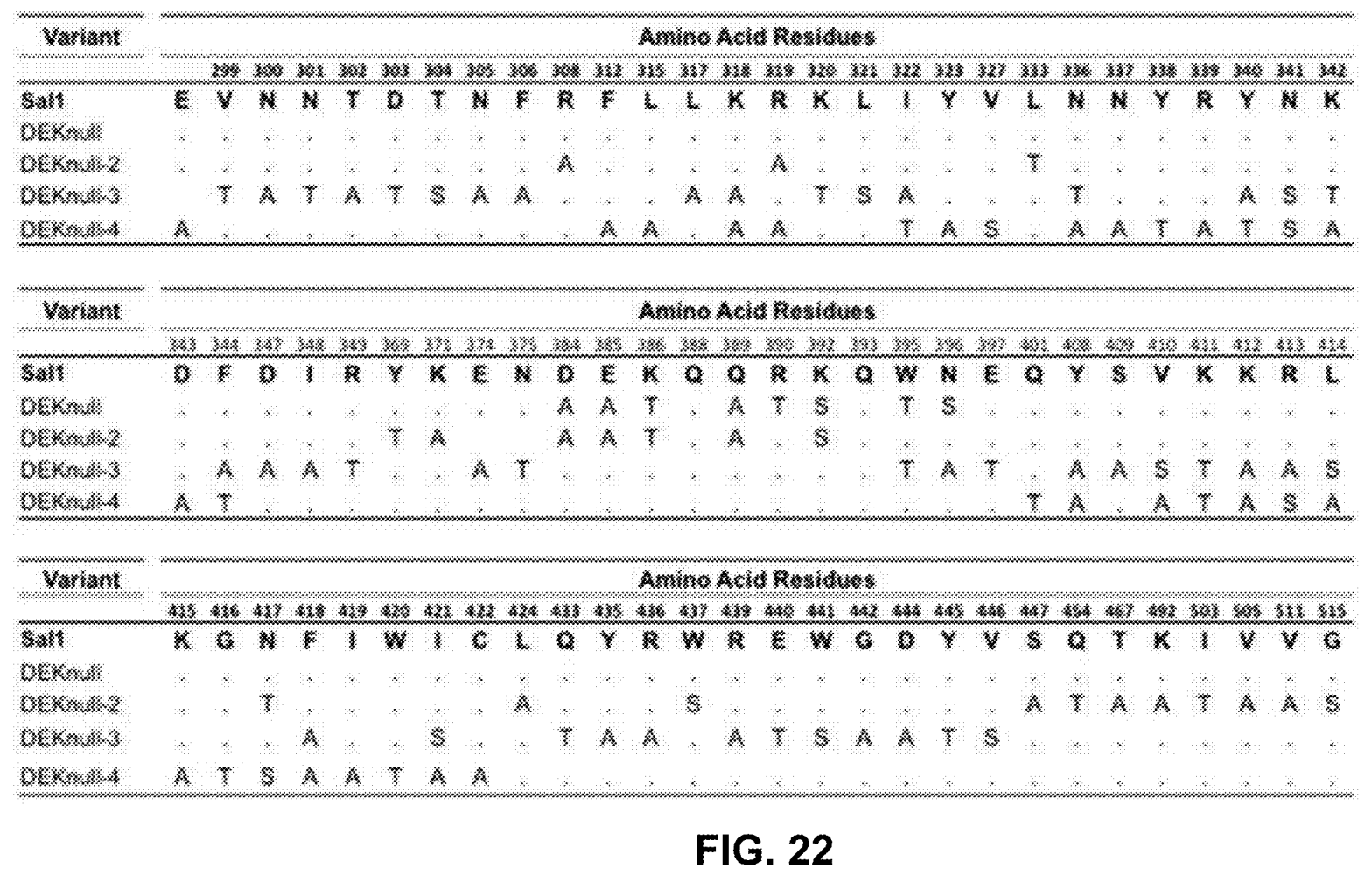

| Variant | Amino Acid Residues | | | | | | | | | | | | | | | | | | | | | | | | | | |
|---|---|---|---|---|---|---|---|---|---|---|---|---|---|---|---|---|---|---|---|---|---|---|---|---|---|---|---|
| | | 299 | 300 | 301 | 302 | 303 | 304 | 305 | 306 | 308 | 312 | 315 | 317 | 318 | 319 | 320 | 321 | 322 | 323 | 327 | 333 | 336 | 337 | 338 | 339 | 340 | 341 | 342 |
| Sal1 | E | V | N | N | T | D | T | N | F | R | F | L | L | K | R | K | L | I | Y | V | L | N | N | Y | R | Y | N | K |
| DEKnull | . | . | . | . | . | . | . | . | . | . | . | . | . | . | . | . | . | . | . | . | . | . | . | . | . | . | . | . |
| DEKnull-2 | . | . | . | . | . | . | . | . | . | A | . | . | . | . | A | . | . | . | . | . | T | . | . | . | . | . | . | . |
| DEKnull-3 | | T | A | T | A | T | S | A | A | . | . | . | A | A | . | T | S | A | . | . | . | T | . | . | . | A | S | T |
| DEKnull-4 | A | . | . | . | . | . | . | . | . | . | A | A | . | A | A | . | . | T | A | S | . | A | A | T | A | T | S | A |

| Variant | Amino Acid Residues | | | | | | | | | | | | | | | | | | | | | | | | | | |
|---|---|---|---|---|---|---|---|---|---|---|---|---|---|---|---|---|---|---|---|---|---|---|---|---|---|---|---|
| | 343 | 344 | 347 | 348 | 349 | 369 | 371 | 374 | 375 | 384 | 385 | 386 | 388 | 389 | 390 | 392 | 393 | 395 | 396 | 397 | 401 | 408 | 409 | 410 | 411 | 412 | 413 | 414 |
| Sal1 | D | F | D | I | R | Y | K | E | N | D | E | K | Q | Q | R | K | Q | W | N | E | Q | Y | S | V | K | K | R | L |
| DEKnull | . | . | . | . | . | . | . | . | . | A | A | T | . | A | T | S | . | T | S | . | . | . | . | . | . | . | . | . |
| DEKnull-2 | . | . | . | . | . | T | A | | | A | A | T | . | A | . | S | . | . | . | . | . | . | . | . | . | . | . | . |
| DEKnull-3 | . | A | A | A | T | . | . | A | T | . | . | . | . | . | . | . | . | T | A | T | . | A | A | S | T | A | A | S |
| DEKnull-4 | A | T | . | . | . | . | . | . | . | . | . | . | . | . | . | . | . | . | . | . | T | A | . | A | T | A | S | A |

| Variant | Amino Acid Residues | | | | | | | | | | | | | | | | | | | | | | | | | | |
|---|---|---|---|---|---|---|---|---|---|---|---|---|---|---|---|---|---|---|---|---|---|---|---|---|---|---|---|
| | 415 | 416 | 417 | 418 | 419 | 420 | 421 | 422 | 424 | 433 | 435 | 436 | 437 | 439 | 440 | 441 | 442 | 444 | 445 | 446 | 447 | 454 | 467 | 492 | 503 | 505 | 511 | 515 |
| Sal1 | K | G | N | F | I | W | I | C | L | Q | Y | R | W | R | E | W | G | D | Y | V | S | Q | T | K | I | V | V | G |
| DEKnull | . | . | . | . | . | . | . | . | . | . | . | . | . | . | . | . | . | . | . | . | . | . | . | . | . | . | . | . |
| DEKnull-2 | . | . | T | . | . | . | . | . | A | . | . | . | S | . | . | . | . | . | . | . | A | T | A | A | T | A | A | S |
| DEKnull-3 | . | . | . | A | . | . | S | . | . | T | A | A | . | A | T | S | A | A | T | S | . | . | . | . | . | . | . | . |
| DEKnull-4 | A | T | S | A | A | T | A | A | . | . | . | . | . | . | . | . | . | . | . | . | . | . | . | . | . | . | . | . |

FIG. 22

>2C6 Light Chain (SEQ ID NO: 63 )

NIMMTQSPSSLAVSAGEKVTMSCKSSQSVLYSSNQKNYLAWYQQ
KPGQSPKLLIYWASSRESGVPDRFTGSGSGTDFTLTISSVQPEDLAV
YYCHQYLSSWTFGGGTKLEITRAD

>2C6 Heavy Chain (SEQ ID NO: 64 )

QVQLQQSDAELVKPGASVKISCKVSGYTFTDHSIHWMKQRPEQGL
EWIGYIYPRDGSTEYNEKFKGKATLTTDKSSSTAYMQLNSLTSADSA
VYFCARWFGYYFDYWGQGTTLTVSS

SEQUENCE LISTING

<160> NUMBER OF SEQ ID NOS: 64

<210> SEQ ID NO 1
<211> LENGTH: 328
<212> TYPE: PRT
<213> ORGANISM: Artificial Sequence
<220> FEATURE:
<223> OTHER INFORMATION: Sal1 DBP-II

<400> SEQUENCE: 1

```
Thr Ile Ser Ser Ala Ile Ile Asn His Ala Phe Leu Gln Asn Thr Val
1               5                   10                  15

Met Lys Asn Cys Asn Tyr Lys Arg Lys Arg Arg Glu Arg Asp Trp Asp
            20                  25                  30

Cys Asn Thr Lys Lys Asp Val Cys Ile Pro Asp Arg Arg Tyr Gln Leu
        35                  40                  45

Cys Met Lys Glu Leu Thr Asn Leu Val Asn Asn Thr Asp Thr Asn Phe
    50                  55                  60

His Arg Asp Ile Thr Phe Arg Lys Leu Tyr Leu Lys Arg Lys Leu Ile
65                  70                  75                  80

Tyr Asp Ala Ala Val Glu Gly Asp Leu Leu Leu Lys Leu Asn Asn Tyr
                85                  90                  95

Arg Tyr Asn Lys Asp Phe Cys Lys Asp Ile Arg Trp Ser Leu Gly Asp
            100                 105                 110

Phe Gly Asp Ile Ile Met Gly Thr Asp Met Glu Gly Ile Gly Tyr Ser
        115                 120                 125

Lys Val Val Glu Asn Asn Leu Arg Ser Ile Phe Gly Thr Asp Glu Lys
    130                 135                 140

Ala Gln Gln Arg Arg Lys Gln Trp Trp Asn Glu Ser Lys Ala Gln Ile
145                 150                 155                 160

Trp Thr Ala Met Met Tyr Ser Val Lys Lys Arg Leu Lys Gly Asn Phe
                165                 170                 175

Ile Trp Ile Cys Lys Leu Asn Val Ala Val Asn Ile Glu Pro Gln Ile
            180                 185                 190

Tyr Arg Trp Ile Arg Glu Trp Gly Arg Asp Tyr Val Ser Glu Leu Pro
        195                 200                 205

Thr Glu Val Gln Lys Leu Lys Glu Lys Cys Asp Gly Lys Ile Asn Tyr
    210                 215                 220

Thr Asp Lys Lys Val Cys Lys Val Pro Pro Cys Gln Asn Ala Cys Lys
225                 230                 235                 240

Ser Tyr Asp Gln Trp Ile Thr Arg Lys Lys Asn Gln Trp Asp Val Leu
                245                 250                 255

Ser Asn Lys Phe Ile Ser Val Lys Asn Ala Glu Lys Val Gln Thr Ala
            260                 265                 270

Gly Ile Val Thr Pro Tyr Asp Ile Leu Lys Gln Glu Leu Asp Glu Phe
        275                 280                 285

Asn Glu Val Ala Phe Glu Asn Glu Ile Asn Lys Arg Asp Gly Ala Tyr
    290                 295                 300

Ile Glu Leu Cys Val Cys Ser Val Glu Glu Ala Lys Lys Asn Thr Gln
305                 310                 315                 320

Glu Val Val Thr Asn Val Asp Asn
                325
```

<210> SEQ ID NO 2
<211> LENGTH: 328
<212> TYPE: PRT

-continued

<213> ORGANISM: Artificial Sequence
<220> FEATURE:
<223> OTHER INFORMATION: DEKnull

<400> SEQUENCE: 2

Thr Ile Ser Ser Ala Ile Ile Asn His Ala Phe Leu Gln Asn Thr Val
1 5 10 15

Met Lys Asn Cys Asn Tyr Lys Arg Lys Arg Arg Glu Arg Asp Trp Asp
20 25 30

Cys Asn Thr Lys Lys Asp Val Cys Ile Pro Asp Arg Arg Tyr Gln Leu
35 40 45

Cys Met Lys Glu Leu Thr Asn Leu Val Asn Asn Thr Asp Thr Asn Phe
50 55 60

His Arg Asp Ile Thr Phe Arg Lys Leu Tyr Leu Lys Arg Lys Leu Ile
65 70 75 80

Tyr Asp Ala Ala Val Glu Gly Asp Leu Leu Leu Lys Leu Asn Asn Tyr
85 90 95

Arg Tyr Asn Lys Asp Phe Cys Lys Asp Ile Arg Trp Ser Leu Gly Asp
100 105 110

Phe Gly Asp Ile Ile Met Gly Thr Asp Met Glu Gly Ile Gly Tyr Ser
115 120 125

Lys Val Val Glu Asn Asn Leu Arg Ser Ile Phe Gly Thr Ala Ala Thr
130 135 140

Ala Gln Ala Thr Arg Ser Gln Trp Thr Ser Glu Ser Lys Ala Gln Ile
145 150 155 160

Trp Thr Ala Met Met Tyr Ser Val Lys Lys Arg Leu Lys Gly Asn Phe
165 170 175

Ile Trp Ile Cys Lys Leu Asn Val Ala Val Asn Ile Glu Pro Gln Ile
180 185 190

Tyr Arg Trp Ile Arg Glu Trp Gly Arg Asp Tyr Val Ser Glu Leu Pro
195 200 205

Thr Glu Val Gln Lys Leu Lys Glu Lys Cys Asp Gly Lys Ile Asn Tyr
210 215 220

Thr Asp Lys Lys Val Cys Lys Val Pro Pro Cys Gln Asn Ala Cys Lys
225 230 235 240

Ser Tyr Asp Gln Trp Ile Thr Arg Lys Lys Asn Gln Trp Asp Val Leu
245 250 255

Ser Asn Lys Phe Ile Ser Val Lys Asn Ala Glu Lys Val Gln Thr Ala
260 265 270

Gly Ile Val Thr Pro Tyr Asp Ile Leu Lys Gln Glu Leu Asp Glu Phe
275 280 285

Asn Glu Val Ala Phe Glu Asn Glu Ile Asn Lys Arg Asp Gly Ala Tyr
290 295 300

Ile Glu Leu Cys Val Cys Ser Val Glu Glu Ala Lys Lys Asn Thr Gln
305 310 315 320

Glu Val Val Thr Asn Val Asp Asn
325

<210> SEQ ID NO 3
<211> LENGTH: 328
<212> TYPE: PRT
<213> ORGANISM: Artificial Sequence
<220> FEATURE:
<223> OTHER INFORMATION: DEKnull-2

<400> SEQUENCE: 3

-continued

Thr Ile Ser Ser Ala Ile Ile Asn His Ala Phe Leu Gln Asn Thr Val
1               5                   10                  15

Met Lys Asn Cys Asn Tyr Lys Arg Lys Arg Arg Glu Arg Asp Trp Asp
            20                  25                  30

Cys Asn Thr Lys Lys Asp Val Cys Ile Pro Asp Arg Arg Tyr Gln Leu
        35                  40                  45

Cys Met Lys Glu Leu Thr Asn Leu Val Asn Asn Thr Asp Thr Asn Phe
    50                  55                  60

His Ala Asp Ile Thr Phe Arg Lys Leu Tyr Leu Lys Ala Lys Leu Ile
65                  70                  75                  80

Tyr Asp Ala Ala Val Glu Gly Asp Leu Leu Thr Lys Leu Asn Asn Tyr
                85                  90                  95

Arg Tyr Asn Lys Asp Phe Cys Lys Asp Ile Arg Trp Ser Leu Gly Asp
            100                 105                 110

Phe Gly Asp Ile Ile Met Gly Thr Asp Met Glu Gly Ile Gly Thr Ser
        115                 120                 125

Ala Val Val Glu Asn Asn Leu Arg Ser Ile Phe Gly Thr Ala Ala Thr
    130                 135                 140

Ala Gln Ala Arg Arg Ser Gln Trp Thr Ser Glu Ser Lys Ala Gln Ile
145                 150                 155                 160

Trp Thr Ala Met Met Tyr Ser Val Lys Lys Arg Leu Lys Gly Thr Phe
                165                 170                 175

Ile Trp Ile Cys Lys Ala Asn Val Ala Val Asn Ile Glu Pro Gln Ile
            180                 185                 190

Tyr Arg Ser Ile Arg Glu Trp Gly Arg Asp Tyr Val Ala Glu Leu Pro
        195                 200                 205

Thr Glu Val Thr Lys Leu Lys Glu Lys Cys Asp Gly Lys Ile Asn Tyr
    210                 215                 220

Ala Asp Lys Lys Val Cys Lys Val Pro Pro Cys Gln Asn Ala Cys Lys
225                 230                 235                 240

Ser Tyr Asp Gln Trp Ile Thr Arg Lys Ala Asn Gln Trp Asp Val Leu
                245                 250                 255

Ser Asn Lys Phe Thr Ser Ala Lys Asn Ala Glu Lys Ala Gln Thr Ala
            260                 265                 270

Ser Ile Val Thr Pro Tyr Asp Ile Leu Lys Gln Glu Leu Asp Glu Phe
        275                 280                 285

Asn Glu Val Ala Phe Glu Asn Glu Ile Asn Lys Arg Asp Gly Ala Tyr
    290                 295                 300

Ile Glu Leu Cys Val Cys Ser Val Glu Glu Ala Lys Lys Asn Thr Gln
305                 310                 315                 320

Glu Val Val Thr Asn Val Asp Asn
                325

<210> SEQ ID NO 4
<211> LENGTH: 328
<212> TYPE: PRT
<213> ORGANISM: Artificial Sequence
<220> FEATURE:
<223> OTHER INFORMATION: DEKnull-3

<400> SEQUENCE: 4

Thr Ile Ser Ser Ala Ile Ile Asn His Ala Phe Leu Gln Asn Thr Val
1               5                   10                  15

Met Lys Asn Cys Asn Tyr Lys Arg Lys Arg Arg Glu Arg Asp Trp Asp
            20                  25                  30

-continued

```
Cys Asn Thr Lys Lys Asp Val Cys Ile Pro Asp Arg Arg Tyr Gln Leu
        35                  40                  45

Cys Met Lys Glu Leu Thr Asn Leu Thr Ala Thr Ala Thr Ser Ala Ala
    50                  55                  60

His Arg Asp Ile Thr Phe Arg Lys Leu Tyr Ala Ala Arg Thr Ser Ala
65                  70                  75                  80

Tyr Asp Ala Ala Val Glu Gly Asp Leu Leu Leu Lys Leu Thr Asn Tyr
                85                  90                  95

Arg Ala Ser Thr Asp Ala Cys Lys Ala Ala Thr Trp Ser Leu Gly Asp
            100                 105                 110

Phe Gly Asp Ile Ile Met Gly Thr Asp Met Glu Gly Ile Gly Tyr Ser
        115                 120                 125

Lys Val Val Ala Thr Asn Leu Arg Ser Ile Phe Gly Thr Asp Glu Lys
    130                 135                 140

Ala Gln Gln Arg Arg Lys Gln Trp Thr Ala Thr Ser Lys Ala Gln Ile
145                 150                 155                 160

Trp Thr Ala Met Met Ala Ala Ser Thr Ala Ala Ser Lys Gly Asn Ala
                165                 170                 175

Ile Trp Ser Cys Lys Leu Asn Val Ala Val Asn Ile Glu Pro Thr Ile
            180                 185                 190

Ala Ala Trp Ile Ala Thr Ser Ala Arg Ala Thr Ser Ser Glu Leu Pro
        195                 200                 205

Thr Glu Val Gln Lys Leu Lys Glu Lys Cys Asp Gly Lys Ile Asn Tyr
    210                 215                 220

Thr Asp Lys Lys Val Cys Lys Val Pro Pro Cys Gln Asn Ala Cys Lys
225                 230                 235                 240

Ser Tyr Asp Gln Trp Ile Thr Arg Lys Lys Asn Gln Trp Asp Val Leu
                245                 250                 255

Ser Asn Lys Phe Ile Ser Val Lys Asn Ala Glu Lys Val Gln Thr Ala
            260                 265                 270

Gly Ile Val Thr Pro Tyr Asp Ile Leu Lys Gln Glu Leu Asp Glu Phe
        275                 280                 285

Asn Glu Val Ala Phe Glu Asn Glu Ile Asn Lys Arg Asp Gly Ala Tyr
    290                 295                 300

Ile Glu Leu Cys Val Cys Ser Val Glu Glu Ala Lys Lys Asn Thr Gln
305                 310                 315                 320

Glu Val Val Thr Asn Val Asp Asn
                325


<210> SEQ ID NO 5
<211> LENGTH: 328
<212> TYPE: PRT
<213> ORGANISM: Artificial Sequence
<220> FEATURE:
<223> OTHER INFORMATION: DEKnull-4

<400> SEQUENCE: 5

Thr Ile Ser Ser Ala Ile Ile Asn His Ala Phe Leu Gln Asn Thr Val
1               5                   10                  15

Met Lys Asn Cys Asn Tyr Lys Arg Lys Arg Arg Glu Arg Asp Trp Asp
            20                  25                  30

Cys Asn Thr Lys Lys Asp Val Cys Ile Pro Asp Arg Arg Tyr Gln Leu
        35                  40                  45

Cys Met Lys Ala Leu Thr Asn Leu Val Asn Asn Thr Asp Thr Asn Phe
    50                  55                  60
```

-continued

```
His Arg Asp Ile Thr Ala Arg Lys Ala Tyr Leu Ala Ala Lys Leu Thr
65                  70                  75                  80

Ala Asp Ala Ala Ser Glu Gly Asp Leu Leu Leu Lys Leu Ala Ala Thr
                85                  90                  95

Ala Thr Ser Ala Ala Thr Cys Lys Asp Ile Arg Trp Ser Leu Gly Asp
            100                 105                 110

Phe Gly Asp Ile Ile Met Gly Thr Asp Met Glu Gly Ile Gly Tyr Ser
        115                 120                 125

Lys Val Val Glu Asn Asn Leu Arg Ser Ile Phe Gly Thr Asp Glu Lys
    130                 135                 140

Ala Gln Gln Arg Arg Lys Gln Trp Trp Asn Glu Ser Lys Ala Thr Ile
145                 150                 155                 160

Trp Thr Ala Met Met Ala Ser Ala Thr Ala Ser Ala Ala Thr Ser Ala
                165                 170                 175

Ala Thr Ala Ala Lys Leu Asn Val Ala Val Asn Ile Glu Pro Gln Ile
            180                 185                 190

Tyr Arg Trp Ile Arg Glu Trp Gly Arg Asp Tyr Val Ser Glu Leu Pro
        195                 200                 205

Thr Glu Val Gln Lys Leu Lys Glu Lys Cys Asp Gly Lys Ile Asn Tyr
    210                 215                 220

Thr Asp Lys Lys Val Cys Lys Val Pro Pro Cys Gln Asn Ala Cys Lys
225                 230                 235                 240

Ser Tyr Asp Gln Trp Ile Thr Arg Lys Lys Asn Gln Trp Asp Val Leu
                245                 250                 255

Ser Asn Lys Phe Ile Ser Val Lys Asn Ala Glu Lys Val Gln Thr Ala
            260                 265                 270

Gly Ile Val Thr Pro Tyr Asp Ile Leu Lys Gln Glu Leu Asp Glu Phe
        275                 280                 285

Asn Glu Val Ala Phe Glu Asn Glu Ile Asn Lys Arg Asp Gly Ala Tyr
    290                 295                 300

Ile Glu Leu Cys Val Cys Ser Val Glu Glu Ala Lys Lys Asn Thr Gln
305                 310                 315                 320

Glu Val Val Thr Asn Val Asp Asn
                325
```

<210> SEQ ID NO 6
<211> LENGTH: 984
<212> TYPE: DNA
<213> ORGANISM: Artificial Sequence
<220> FEATURE:
<223> OTHER INFORMATION: DEKnull-2

<400> SEQUENCE: 6

```
accattagca gcgcgattat taaccatgcg tttctgcaga acaccgtgat gaaaaactgc     60

aactataaac gcaaacgccg cgaacgcgat tgggattgca acaccaaaaa agatgtgtgc    120

attccggatc gccgctatca gctgtgcatg aaagaactga ccaacctggt gaacaacacc    180

gataccaact ttcatgcgga tattaccttt cgcaaactgt atctgaaagc gaaactgatt    240

tatgatgcgg cggtggaagg cgatctgctg accaaactga acaactatcg ctataacaaa    300

gatttttgca aagatattcg ctggagcctg ggcgattttg gcgatattat tatgggcacc    360

gatatggaag gcattggcac cagcgcggtg gtggaaaaca acctgcgcag catttttggc    420

accgcggcga ccgcgcaggc gcgccgcagc cagtggacca gcgaaagcaa agcgcagatt    480

tggaccgcga tgatgtatag cgtgaaaaaa cgcctgaaag gcacctttat ttggatttgc    540
```

```
aaagcgaacg tggcggtgaa cattgaaccg cagatttatc gcagcattcg cgaatggggc    600

cgcgattatg tggcggaact gccgaccgaa gtgaccaaac tgaaagaaaa atgcgatggc    660

aaaattaact atgcggataa aaaagtgtgc aaagtgccgc cgtgccagaa cgcgtgcaaa    720

agctatgatc agtggattac ccgcaaaagcg aaccagtggg atgtgctgag caacaaattt    780

accagcgcga aaaacgcgga aaaagcgcag accgcgagca ttgtgacccc gtatgatatt    840

ctgaaacagg aactggatga atttaacgaa gtggcgtttg aaaacgaaat taacaaacgc    900

gatggcgcgt atattgaact gtgcgtgtgc agcgtggaag aagcgaaaaa aaacacccag    960

gaagtggtga ccaacgtgga taac                                            984


<210> SEQ ID NO 7
<211> LENGTH: 984
<212> TYPE: DNA
<213> ORGANISM: Artificial Sequence
<220> FEATURE:
<223> OTHER INFORMATION: DEKnull-2 consensus codons
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
```

<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)

<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (381)..(381)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (426)..(426)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (432)..(432)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:

<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (585)..(585)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (750)..(750)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (786)..(786)

<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (921)..(921)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (933)..(933)
<223> OTHER INFORMATION: n is a, c, g, or t
<220> FEATURE:
<221> NAME/KEY: misc_feature
<222> LOCATION: (936)..(936)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t

<400> SEQUENCE: 7
acnathwsnw sngcnathat haaycaygcn ttyytncara ayacngtnat gaaraaytgy 60
aaytayaarm gnaarmgnmg ngarmgngay tgggaytgya ayacnaaraa rgaygtntgy 120
athccngaym gnmgntayca rytntgyatg aargarytna cnaayytngt naayaayacn 180
gayacnaayt tycaygcnga yathacntty mgnaarytnt ayytnaargc naarytnath 240
taygaygcng cngtngargg ngayytnytn acnaarytna ayaaytaymg ntayaayaar 300
gayttytgya argayathmg ntggwsnytn ggngayttyg gngayathat hatgggnacn 360
gayatggarg gnathggnac nwsngcngtn gtngaraaya ayytnmgnws nathttyggn 420
acngcngcna cngcncargc nmgnmgnwsn cartggacnw sngarwsnaa rgcncarath 480
tggacngcna tgatgtayws ngtnaaraar mgnytnaarg gnacnttyat htggathtgy 540
aargcnaayg tngcngtnaa yathgarccn carathtaym gnwsnathmg ngartggggn 600
mgngaytayg tngcngaryt nccnacngar gtnacnaary tnaargaraa rtgygayggn 660
aarathaayt aygcngayaa raargtntgy aargtnccnc cntgycaraa ygcntgyaar 720
wsntaygayc artggathac nmgnaargcn aaycartggg aygtnytnws naayaartty 780
acnwsngcna araaygcnga raargcncar acngcnwsna thgtnacncc ntaygayath 840
ytnaarcarg arytngayga rttyaaygar gtngcnttyg araaygarat haayaarmgn 900
gayggngcnt ayathgaryt ntgygtntgy wsngtngarg argcnaaraa raayacncar 960
gargtngtna cnaaygtnga yaay 984

<210> SEQ ID NO 8
<211> LENGTH: 984
<212> TYPE: DNA
<213> ORGANISM: Artificial Sequence
<220> FEATURE:
<223> OTHER INFORMATION: DEKnull-3

<400> SEQUENCE: 8
accattagca gcgcgattat taaccatgcg tttctgcaga acaccgtgat gaaaaactgc 60
aactataaac gcaaacgccg cgaacgcgat tgggattgca acaccaaaaa agatgtgtgc 120
attccggatc gccgctatca gctgtgcatg aaagaactga ccaacctgac cgcgaccgcg 180

-continued

```
accagcgcgg cgcatcgcga tattaccttt cgcaaactgt atgcggcgcg caccagcgcg    240

tatgatgcgg cggtggaagg cgatctgctg ctgaaactga ccaactatcg cgcgagcacc    300

gatgcgtgca aagcggcgac ctggagcctg ggcgattttg gcgatattat tatgggcacc    360

gatatggaag gcattggcta tagcaaagtg gtggcgacca acctgcgcag catttttggc    420

accgatgaaa aagcgcagca gcgccgcaaa cagtggaccg cgaccagcaa agcgcagatt    480

tggaccgcga tgatggcggc gagcaccgcg gcgagcaaag gcaacgcgat ttggagctgc    540

aaactgaacg tggcggtgaa cattgaaccg accattgcgg cgtggattgc gaccagcgcg    600

cgcgcgacca gcagcgaact gccgaccgaa gtgcagaaac tgaaagaaaa atgcgatggc    660

aaaattaact ataccgataa aaaagtgtgc aaagtgccgc cgtgccagaa cgcgtgcaaa    720

agctatgatc agtggattac ccgcaaaaaa aaccagtggg atgtgctgag caacaaattt    780

attagcgtga aaaacgcgga aaaagtgcag accgcgggca ttgtgacccc gtatgatatt    840

ctgaaacagg aactggatga atttaacgaa gtggcgtttg aaaacgaaat taacaaacgc    900

gatggcgcgt atattgaact gtgcgtgtgc agcgtggaag aagcgaaaaa aaacacccag    960

gaagtggtga ccaacgtgga taac                                           984
```

```
<210> SEQ ID NO 9
<211> LENGTH: 984
<212> TYPE: DNA
<213> ORGANISM: Artificial Sequence
<220> FEATURE:
<223> OTHER INFORMATION: DEKnull-3 consensus codons
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)
<223> OTHER INFORMATION: n is a, c, g, or t
```

<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (183)..(183)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (207)..(207)

<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (396)..(396)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:

<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (459)..(459)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (465)..(465)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (573)..(573)
<223> OTHER INFORMATION: n is a, c, g, or t
<220> FEATURE:
<221> NAME/KEY: misc_feature
<222> LOCATION: (579)..(579)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (597)..(597)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (606)..(606)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (612)..(612)

<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:
<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (921)..(921)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (933)..(933)
<223> OTHER INFORMATION: n is a, c, g, or t
<220> FEATURE:

<221> NAME/KEY: misc_feature
<222> LOCATION: (936)..(936)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t

<400> SEQUENCE: 9
acnathwsnw sngcnathat haaycaygcn ttyytncara ayacngtnat gaaraaytgy 60
aaytayaarm gnaarmgnmg ngarmgngay tgggaytgya ayacnaaraa rgaygtntgy 120
athccngaym gnmgntayca rytntgyatg aargarytna cnaayytnac ngcnacngcn 180
acnwsngcng cncaymgnga yathacntty mgnaarytnt aygcngcnmg nacnwsngcn 240
taygaygcng cngtngargg ngayytnytn ytnaarytna cnaaytaymg ngcnwsnacn 300
gaygcntgya argcngcnac ntggwsnytn ggngayttyg gngayathat hatgggnacn 360
gayatggarg gnathggnta ywsnaargtn gtngcnacna ayytnmgnws nathttyggn 420
acngaygara argcncarca rmgnmgnaar cartggacng cnacnwsnaa rgcncarath 480
tggacngcna tgatggcngc nwsnacngcn gcnwsnaarg gnaaygcnat htggwsntgy 540
aarytnaayg tngcngtnaa yathgarccn acnathgcng cntggathgc nacnwsngcn 600
mgngcnacnw snwsngaryt nccnacngar gtncaraary tnaargaraa rtgygayggn 660
aarathaayt ayacngayaa raargtntgy aargtnccnc cntgycaraa ygcntgyaar 720
wsntaygayc artggathac nmgnaaraar aaycartggg aygtnytnws naayaartty 780
athwsngtna araaygcnga raargtncar acngcnggna thgtnacncc ntaygayath 840
ytnaarcarg arytngayga rttyaaygar gtngcnttyg araaygarat haayaarmgn 900
gayggngcnt ayathgaryt ntgygtntgy wsngtngarg argcnaaraa raayacncar 960
gargtngtna cnaaygtnga yaay 984

<210> SEQ ID NO 10
<211> LENGTH: 984
<212> TYPE: DNA
<213> ORGANISM: Artificial Sequence
<220> FEATURE:
<223> OTHER INFORMATION: DEKnull-4

<400> SEQUENCE: 10
accattagca gcgcgattat taaccatgcg tttctgcaga acaccgtgat gaaaaactgc 60
aactataaac gcaaacgccg cgaacgcgat tgggattgca acaccaaaaa agatgtgtgc 120
attccggatc gccgctatca gctgtgcatg aaagcgctga ccaacctggt gaacaacacc 180

```
gataccaact ttcatcgcga tattaccgcg cgcaaagcgt atctggcggc gaaactgacc    240

gcggatgcgg cgagcgaagg cgatctgctg ctgaaactgg cggcgaccgc gaccagcgcg    300

gcgacctgca aagatattcg ctggagcctg ggcgattttg gcgatattat tatgggcacc    360

gatatggaag gcattggcta tagcaaagtg gtggaaaaca acctgcgcag catttttggc    420

accgatgaaa aagcgcagca gcgccgcaaa cagtggtgga acgaaagcaa agcgaccatt    480

tggaccgcga tgatggcgag cgcgaccgcg agcgcggcga ccagcgcggc gaccgcggcg    540

aaactgaacg tggcggtgaa cattgaaccg cagatttatc gctggattcg cgaatggggc    600

cgcgattatg tgagcgaact gccgaccgaa gtgcagaaac tgaaagaaaa atgcgatggc    660

aaaattaact ataccgataa aaaagtgtgc aaagtgccgc cgtgccagaa cgcgtgcaaa    720

agctatgatc agtggattac ccgcaaaaaa aaccagtggg atgtgctgag caacaaattt    780

attagcgtga aaaacgcgga aaaagtgcag accgcgggca ttgtgacccc gtatgatatt    840

ctgaaacagg aactggatga atttaacgaa gtggcgtttg aaaacgaaat taacaaacgc    900

gatggcgcgt atattgaact gtgcgtgtgc agcgtggaag aagcgaaaaa aaacacccag    960

gaagtggtga ccaacgtgga taac                                           984
```

<210> SEQ ID NO 11
<211> LENGTH: 984
<212> TYPE: DNA
<213> ORGANISM: Artificial Sequence
<220> FEATURE:
<223> OTHER INFORMATION: DEKnull-4 consensus codons
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (45)..(45)
<223> OTHER INFORMATION: n is a, c, g, or t
<220> FEATURE:
<221> NAME/KEY: misc_feature
<222> LOCATION: (48)..(48)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (78)..(78)
<223> OTHER INFORMATION: n is a, c, g, or t
<220> FEATURE:
<221> NAME/KEY: misc_feature
<222> LOCATION: (81)..(81)

<223> OTHER INFORMATION: n is a, c, g, or t
<220> FEATURE:
<221> NAME/KEY: misc_feature
<222> LOCATION: (87)..(87)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (117)..(117)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (132)..(132)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (156)..(156)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (162)..(162)
<223> OTHER INFORMATION: n is a, c, g, or t
<220> FEATURE:
<221> NAME/KEY: misc_feature
<222> LOCATION: (168)..(168)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (180)..(180)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (207)..(207)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (243)..(243)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (255)..(255)
<223> OTHER INFORMATION: n is a, c, g, or t
<220> FEATURE:
<221> NAME/KEY: misc_feature
<222> LOCATION: (261)..(261)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (282)..(282)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (294)..(294)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:

<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (330)..(330)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (357)..(357)
<223> OTHER INFORMATION: n is a, c, g, or t
<220> FEATURE:
<221> NAME/KEY: misc_feature
<222> LOCATION: (360)..(360)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (384)..(384)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (393)..(393)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (423)..(423)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (447)..(447)
<223> OTHER INFORMATION: n is a, c, g, or t
<220> FEATURE:
<221> NAME/KEY: misc_feature
<222> LOCATION: (468)..(468)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (477)..(477)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (498)..(498)
<223> OTHER INFORMATION: n is a, c, g, or t
<220> FEATURE:
<221> NAME/KEY: misc_feature
<222> LOCATION: (501)..(501)
<223> OTHER INFORMATION: n is a, c, g, or t
<220> FEATURE:
<221> NAME/KEY: misc_feature
<222> LOCATION: (504)..(504)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (510)..(510)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (516)..(516)
<223> OTHER INFORMATION: n is a, c, g, or t
<220> FEATURE:
<221> NAME/KEY: misc_feature
<222> LOCATION: (519)..(519)
<223> OTHER INFORMATION: n is a, c, g, or t
<220> FEATURE:
<221> NAME/KEY: misc_feature
<222> LOCATION: (522)..(522)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (528)..(528)
<223> OTHER INFORMATION: n is a, c, g, or t
<220> FEATURE:
<221> NAME/KEY: misc_feature
<222> LOCATION: (531)..(531)

<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (540)..(540)
<223> OTHER INFORMATION: n is a, c, g, or t
<220> FEATURE:
<221> NAME/KEY: misc_feature
<222> LOCATION: (546)..(546)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (555)..(555)
<223> OTHER INFORMATION: n is a, c, g, or t
<220> FEATURE:
<221> NAME/KEY: misc_feature
<222> LOCATION: (558)..(558)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (591)..(591)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (621)..(621)
<223> OTHER INFORMATION: n is a, c, g, or t
<220> FEATURE:
<221> NAME/KEY: misc_feature
<222> LOCATION: (624)..(624)
<223> OTHER INFORMATION: n is a, c, g, or t
<220> FEATURE:
<221> NAME/KEY: misc_feature
<222> LOCATION: (627)..(627)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (660)..(660)
<223> OTHER INFORMATION: n is a, c, g, or t
<220> FEATURE:
<221> NAME/KEY: misc_feature
<222> LOCATION: (675)..(675)
<223> OTHER INFORMATION: n is a, c, g, or t
<220> FEATURE:
<221> NAME/KEY: misc_feature
<222> LOCATION: (687)..(687)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (744)..(744)
<223> OTHER INFORMATION: n is a, c, g, or t
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (768)..(768)
<223> OTHER INFORMATION: n is a, c, g, or t
<220> FEATURE:
<221> NAME/KEY: misc_feature
<222> LOCATION: (771)..(771)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (798)..(798)
<223> OTHER INFORMATION: n is a, c, g, or t
<220> FEATURE:
<221> NAME/KEY: misc_feature
<222> LOCATION: (807)..(807)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
<221> NAME/KEY: misc_feature
<222> LOCATION: (816)..(816)
<223> OTHER INFORMATION: n is a, c, g, or t
<220> FEATURE:
<221> NAME/KEY: misc_feature
<222> LOCATION: (819)..(819)
<223> OTHER INFORMATION: n is a, c, g, or t
<220> FEATURE:

<221> NAME/KEY: misc_feature
<222> LOCATION: (825)..(825)
<223> OTHER INFORMATION: n is a, c, g, or t
<220> FEATURE:
<221> NAME/KEY: misc_feature
<222> LOCATION: (828)..(828)
<223> OTHER INFORMATION: n is a, c, g, or t
<220> FEATURE:
<221> NAME/KEY: misc_feature
<222> LOCATION: (831)..(831)
<223> OTHER INFORMATION: n is a, c, g, or t
<220> FEATURE:
<221> NAME/KEY: misc_feature
<222> LOCATION: (843)..(843)
<223> OTHER INFORMATION: n is a, c, g, or t
<220> FEATURE:
<221> NAME/KEY: misc_feature
<222> LOCATION: (855)..(855)
<223> OTHER INFORMATION: n is a, c, g, or t
<220> FEATURE:
<221> NAME/KEY: misc_feature
<222> LOCATION: (873)..(873)
<223> OTHER INFORMATION: n is a, c, g, or t
<220> FEATURE:
<221> NAME/KEY: misc_feature
<222> LOCATION: (876)..(876)
<223> OTHER INFORMATION: n is a, c, g, or t
<220> FEATURE:
<221> NAME/KEY: misc_feature
<222> LOCATION: (900)..(900)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (909)..(909)
<223> OTHER INFORMATION: n is a, c, g, or t
<220> FEATURE:
<221> NAME/KEY: misc_feature
<222> LOCATION: (921)..(921)
<223> OTHER INFORMATION: n is a, c, g, or t
<220> FEATURE:
<221> NAME/KEY: misc_feature
<222> LOCATION: (927)..(927)
<223> OTHER INFORMATION: n is a, c, g, or t
<220> FEATURE:
<221> NAME/KEY: misc_feature
<222> LOCATION: (933)..(933)
<223> OTHER INFORMATION: n is a, c, g, or t
<220> FEATURE:
<221> NAME/KEY: misc_feature
<222> LOCATION: (936)..(936)
<223> OTHER INFORMATION: n is a, c, g, or t
<220> FEATURE:
<221> NAME/KEY: misc_feature
<222> LOCATION: (945)..(945)
<223> OTHER INFORMATION: n is a, c, g, or t
<220> FEATURE:
<221> NAME/KEY: misc_feature
<222> LOCATION: (957)..(957)
<223> OTHER INFORMATION: n is a, c, g, or t
<220> FEATURE:
<221> NAME/KEY: misc_feature
<222> LOCATION: (966)..(966)
<223> OTHER INFORMATION: n is a, c, g, or t
<220> FEATURE:
<221> NAME/KEY: misc_feature
<222> LOCATION: (969)..(969)
<223> OTHER INFORMATION: n is a, c, g, or t
<220> FEATURE:
<221> NAME/KEY: misc_feature
<222> LOCATION: (972)..(972)
<223> OTHER INFORMATION: n is a, c, g, or t
<220> FEATURE:
<221> NAME/KEY: misc_feature
<222> LOCATION: (978)..(978)
<223> OTHER INFORMATION: n is a, c, g, or t -continued

<400> SEQUENCE: 11

```
acnathwsnw sngcnathat haaycaygcn ttyytncara ayacngtnat gaaraaytgy     60
aaytayaarm gnaarmgnmg ngarmgngay tgggaytgya ayacnaaraa rgaygtntgy    120
athccngaym gnmgntayca rytntgyatg aargcnytna cnaayytngt naayaayacn    180
gayacnaayt tycaymgnga yathacngcn mgnaargcnt ayytngcngc naarytnacn    240
gcngaygcng cnwsngargg ngayytnytn ytnaarytng cngcnacngc nacnwsngcn    300
gcnacntgya argayathmg ntggwsnytn ggngayttyg gngayathat hatgggnacn    360
gayatggarg gnathggnta ywsnaargtn gtngaraaya ayytnmgnws nathttyggn    420
acngaygara argcncarca rmgnmgnaar cartggtgga aygarwsnaa rgcnacnath    480
tggacngcna tgatggcnws ngcnacngcn wsngcngcna cnwsngcngc nacngcngcn    540
aarytnaayg tngcngtnaa yathgarccn carathtaym gntggathmg ngartggggn    600
mgngaytayg tnwsngaryt nccnacngar gtncaraary tnaargaraa rtgygayggn    660
aarathaayt ayacngayaa raargtntgy aargtnccnc cntgycaraa ygcntgyaar    720
wsntaygayc artggathac nmgnaaraar aaycartggg aygtnytnws naayaartty    780
athwsngtna araaygcnga raargtncar acngcnggna thgtnacncc ntaygayath    840
ytnaarcarg arytngayga rttyaaygar gtngcnttyg araaygarat haayaarmgn    900
gayggngcnt ayathgaryt ntgygtntgy wsngtngarg argcnaaraa raayacncar    960
gargtngtna cnaaygtnga yaay                                           984
```

<210> SEQ ID NO 12
<211> LENGTH: 22
<212> TYPE: PRT
<213> ORGANISM: Artificial Sequence
<220> FEATURE:
<223> OTHER INFORMATION: degenerate peptide from DBPII Sal1 determined from phage panning with mAbs 3D10

<400> SEQUENCE: 12

```
Ile Ile Asn His Ala Phe Leu Gln Asn Thr Val Met Lys Asn Cys Asn
1               5                   10                  15

Tyr Lys Arg Lys Arg Arg
            20
```

<210> SEQ ID NO 13
<211> LENGTH: 18
<212> TYPE: PRT
<213> ORGANISM: Artificial Sequence
<220> FEATURE:
<223> OTHER INFORMATION: degenerate peptide from DBP-II Sal1 determined by phage panning with mAb3C9

<400> SEQUENCE: 13

```
Asp Ile Leu Lys Gln Glu Leu Asp Glu Phe Asn Glu Val Ala Phe Glu
1               5                   10                  15

Asn Glu
```

<210> SEQ ID NO 14
<211> LENGTH: 20
<212> TYPE: PRT
<213> ORGANISM: Artificial Sequence
<220> FEATURE:
<223> OTHER INFORMATION: Mab-3D10 mimotope

<400> SEQUENCE: 14

```
Val Gly Asn Leu Asp Phe Ser Arg Phe His Lys Ser Ser Leu Asp Tyr
1               5                   10                  15

Lys Arg Gly Gln
            20


<210> SEQ ID NO 15
<211> LENGTH: 20
<212> TYPE: PRT
<213> ORGANISM: Artificial Sequence
<220> FEATURE:
<223> OTHER INFORMATION: mAb 3D10 mimotope

<400> SEQUENCE: 15

Val Lys Phe Thr Asp Arg Tyr Lys Tyr Ser Ser Met Lys Gly Tyr Ala
1               5                   10                  15

Arg Gln Gly Arg
            20


<210> SEQ ID NO 16
<211> LENGTH: 20
<212> TYPE: PRT
<213> ORGANISM: Artificial Sequence
<220> FEATURE:
<223> OTHER INFORMATION: mAb 3D10 mimotope

<400> SEQUENCE: 16

Lys Ile Asn Met Tyr Lys Glu Val Arg Thr Arg Gln Leu Ser Val Arg
1               5                   10                  15

Pro Ser Pro Glu
            20


<210> SEQ ID NO 17
<211> LENGTH: 34
<212> TYPE: PRT
<213> ORGANISM: Artificial Sequence
<220> FEATURE:
<223> OTHER INFORMATION: DBP II Sal1 Mutant 2
<220> FEATURE:
<221> NAME/KEY: NON_CONS
<222> LOCATION: (14)..(15)
<223> OTHER INFORMATION: Nonconsecutive portion is identical to wild-
      type DBP II SalI

<400> SEQUENCE: 17

Arg Trp Ile Arg Glu Trp Gly Arg Asp Tyr Ala Ser Glu Leu Asp Ile
1               5                   10                  15

Leu Lys Gln Glu Ala Asp Glu Phe Asn Glu Val Ala Phe Glu Asn Glu
            20                  25                  30

Ile Asn


<210> SEQ ID NO 18
<211> LENGTH: 34
<212> TYPE: PRT
<213> ORGANISM: Artificial Sequence
<220> FEATURE:
<223> OTHER INFORMATION: DBP II Sal1 mutant 3
<220> FEATURE:
<221> NAME/KEY: NON_CONS
<222> LOCATION: (14)..(15)
<223> OTHER INFORMATION: Nonconsecutive portion is identical to wild-
      type DBP II SalI

<400> SEQUENCE: 18

Arg Trp Ile Arg Glu Trp Gly Arg Asp Ala Val Ser Glu Leu Asp Ile
1               5                   10                  15
```

```
Leu Lys Gln Glu Ala Asp Glu Phe Asn Glu Val Ala Phe Glu Asn Glu
            20                  25                  30

Ile Asn


<210> SEQ ID NO 19
<211> LENGTH: 34
<212> TYPE: PRT
<213> ORGANISM: Artificial Sequence
<220> FEATURE:
<223> OTHER INFORMATION: DBP II Sal1 mutant 4
<220> FEATURE:
<221> NAME/KEY: NON_CONS
<222> LOCATION: (14)..(15)
<223> OTHER INFORMATION: Nonconsecutive portion is identical to wild-
      type DBP II SalI

<400> SEQUENCE: 19

Arg Trp Ile Arg Glu Trp Ala Arg Asp Tyr Val Ser Glu Leu Asp Ile
1               5                   10                  15

Leu Lys Gln Glu Ala Asp Glu Phe Asn Glu Val Ala Phe Glu Asn Glu
            20                  25                  30

Ile Asn


<210> SEQ ID NO 20
<211> LENGTH: 34
<212> TYPE: PRT
<213> ORGANISM: Artificial Sequence
<220> FEATURE:
<223> OTHER INFORMATION: DBP II Sal1 mutant 5
<220> FEATURE:
<221> NAME/KEY: NON_CONS
<222> LOCATION: (14)..(15)
<223> OTHER INFORMATION: Nonconsecutive portion is identical to wild-
      type DBP II SalI

<400> SEQUENCE: 20

Arg Trp Ile Arg Glu Trp Gly Arg Asp Ala Val Ser Glu Leu Asp Ile
1               5                   10                  15

Leu Lys Gln Glu Leu Asp Glu Phe Asn Glu Val Ala Phe Glu Asn Ala
            20                  25                  30

Ile Asn


<210> SEQ ID NO 21
<211> LENGTH: 34
<212> TYPE: PRT
<213> ORGANISM: Artificial Sequence
<220> FEATURE:
<223> OTHER INFORMATION: DBP II Sal1 mutant
<220> FEATURE:
<221> NAME/KEY: NON_CONS
<222> LOCATION: (14)..(15)
<223> OTHER INFORMATION: Nonconsecutive portion is identical to wild-
      type DBP II SalI

<400> SEQUENCE: 21

Arg Trp Ile Arg Glu Trp Gly Arg Asp Ala Ala Ser Glu Leu Asp Ile
1               5                   10                  15

Leu Lys Gln Glu Leu Asp Glu Ala Asn Glu Val Ala Ala Glu Asn Glu
            20                  25                  30

Ile Asn


<210> SEQ ID NO 22
<211> LENGTH: 34
<212> TYPE: PRT
```

```
<213> ORGANISM: Artificial Sequence
<220> FEATURE:
<223> OTHER INFORMATION: DBP II Sal1 mutant 6
<220> FEATURE:
<221> NAME/KEY: NON_CONS
<222> LOCATION: (14)..(15)
<223> OTHER INFORMATION: Nonconsecutive portion is identical to wild-
      type DBP II SalI

<400> SEQUENCE: 22

Ala Trp Ile Arg Glu Trp Gly Arg Asp Tyr Val Ser Glu Leu Asp Ile
1               5                   10                  15

Leu Lys Gln Ala Leu Asp Glu Phe Asn Glu Val Ala Phe Glu Asn Glu
            20                  25                  30

Ile Asn


<210> SEQ ID NO 23
<211> LENGTH: 34
<212> TYPE: PRT
<213> ORGANISM: Artificial Sequence
<220> FEATURE:
<223> OTHER INFORMATION: DBP II Sal1 mutant 7
<220> FEATURE:
<221> NAME/KEY: NON_CONS
<222> LOCATION: (14)..(15)
<223> OTHER INFORMATION: Nonconsecutive portion is identical to wild-
      type DBP II SalI

<400> SEQUENCE: 23

Arg Trp Ile Arg Glu Trp Gly Arg Asp Tyr Val Ser Glu Leu Asp Ile
1               5                   10                  15

Leu Lys Ala Glu Leu Asp Glu Phe Asn Glu Val Ala Phe Glu Asn Glu
            20                  25                  30

Ile Asn


<210> SEQ ID NO 24
<211> LENGTH: 33
<212> TYPE: PRT
<213> ORGANISM: Artificial Sequence
<220> FEATURE:
<223> OTHER INFORMATION: DBP II Sal1 mutant 12
<220> FEATURE:
<221> NAME/KEY: NON_CONS
<222> LOCATION: (14)..(15)
<223> OTHER INFORMATION: Nonconsecutive portion is identical to wild-
      type DBP II SalI

<400> SEQUENCE: 24

Arg Trp Ile Arg Glu Gly Arg Asp Tyr Val Ser Glu Leu Asp Ile Leu
1               5                   10                  15

Lys Gln Glu Leu Ala Glu Phe Asn Glu Val Ala Phe Glu Asn Glu Ile
            20                  25                  30

Asn


<210> SEQ ID NO 25
<211> LENGTH: 34
<212> TYPE: PRT
<213> ORGANISM: Artificial Sequence
<220> FEATURE:
<223> OTHER INFORMATION: DBP II Sal1 mutant 13
<220> FEATURE:
<221> NAME/KEY: NON_CONS
<222> LOCATION: (14)..(15)
<223> OTHER INFORMATION: NNonconsecutive portion is identical to wild-
      type DBP II SalI

<400> SEQUENCE: 25
```

Arg Trp Ile Arg Glu Trp Gly Arg Asp Tyr Val Ser Glu Leu Asp Ile
1 5 10 15

Leu Lys Gln Glu Leu Asp Ala Phe Asn Glu Val Ala Phe Glu Asn Glu
20 25 30

Ile Asn

<210> SEQ ID NO 26
<211> LENGTH: 34
<212> TYPE: PRT
<213> ORGANISM: Artificial Sequence
<220> FEATURE:
<223> OTHER INFORMATION: DBP II Sal1 mutant 14
<220> FEATURE:
<221> NAME/KEY: NON_CONS
<222> LOCATION: (14)..(15)
<223> OTHER INFORMATION: Nonconsecutive portion is identical to wild-type DBP II SalI

<400> SEQUENCE: 26

Arg Trp Ile Arg Glu Trp Gly Arg Asp Tyr Val Ser Glu Leu Asp Ile
1 5 10 15

Leu Lys Gln Glu Leu Asp Glu Phe Ala Glu Val Ala Phe Glu Asn Glu
20 25 30

Ile Asn

<210> SEQ ID NO 27
<211> LENGTH: 34
<212> TYPE: PRT
<213> ORGANISM: Artificial Sequence
<220> FEATURE:
<223> OTHER INFORMATION: DBP II Sal1 mutant 15
<220> FEATURE:
<221> NAME/KEY: NON_CONS
<222> LOCATION: (14)..(15)
<223> OTHER INFORMATION: Nonconsecutive portion is identical to wild-type DBP II SalI

<400> SEQUENCE: 27

Arg Trp Ile Arg Glu Trp Gly Arg Asp Tyr Val Ser Glu Leu Asp Ile
1 5 10 15

Leu Lys Gln Glu Leu Asp Glu Phe Asn Glu Ala Ala Phe Glu Asn Glu
20 25 30

Ile Asn

<210> SEQ ID NO 28
<211> LENGTH: 34
<212> TYPE: PRT
<213> ORGANISM: Artificial Sequence
<220> FEATURE:
<223> OTHER INFORMATION: DBP II Sal1 mutant 16
<220> FEATURE:
<221> NAME/KEY: NON_CONS
<222> LOCATION: (14)..(15)
<223> OTHER INFORMATION: Nonconsecutive portion is identical to wild-type DBP II SalI

<400> SEQUENCE: 28

Arg Trp Ile Arg Glu Trp Gly Arg Asp Tyr Val Ser Glu Leu Asp Ile
1 5 10 15

Leu Lys Gln Glu Ala Asp Glu Phe Asn Glu Val Ala Phe Glu Asn Glu
20 25 30

Ile Asn

<210> SEQ ID NO 29
<211> LENGTH: 34
<212> TYPE: PRT
<213> ORGANISM: Artificial Sequence
<220> FEATURE:
<223> OTHER INFORMATION: DBP II Sal1 mutant 17
<220> FEATURE:
<221> NAME/KEY: NON_CONS
<222> LOCATION: (14)..(15)
<223> OTHER INFORMATION: Nonconsecutive portion is identical to wild-
type DBP II SalI

<400> SEQUENCE: 29

```
Arg Trp Ile Arg Glu Trp Gly Arg Asp Tyr Val Ser Glu Leu Asp Ile
1               5                   10                  15

Leu Lys Gln Glu Leu Asp Glu Ala Asn Glu Val Ala Phe Glu Asn Glu
            20                  25                  30

Ile Asn
```

<210> SEQ ID NO 30
<211> LENGTH: 34
<212> TYPE: PRT
<213> ORGANISM: Artificial Sequence
<220> FEATURE:
<223> OTHER INFORMATION: DBP II Sal1 mutant 18
<220> FEATURE:
<221> NAME/KEY: NON_CONS
<222> LOCATION: (14)..(15)
<223> OTHER INFORMATION: Nonconsecutive portion is identical to wild-
type DBP II SalI

<400> SEQUENCE: 30

```
Arg Trp Ile Arg Glu Trp Gly Arg Asp Tyr Val Ser Glu Leu Asp Ile
1               5                   10                  15

Leu Lys Gln Glu Leu Asp Glu Phe Asn Glu Val Ala Ala Glu Asn Glu
            20                  25                  30

Ile Asn
```

<210> SEQ ID NO 31
<211> LENGTH: 34
<212> TYPE: PRT
<213> ORGANISM: Artificial Sequence
<220> FEATURE:
<223> OTHER INFORMATION: DBP II Sal1 mutant 19
<220> FEATURE:
<221> NAME/KEY: NON_CONS
<222> LOCATION: (14)..(15)
<223> OTHER INFORMATION: Nonconsecutive portion is identical to wild-
type DBP II SalI

<400> SEQUENCE: 31

```
Arg Trp Ile Arg Glu Trp Gly Arg Asp Tyr Val Ser Glu Leu Asp Ile
1               5                   10                  15

Leu Lys Gln Glu Leu Asp Glu Phe Asn Glu Val Ala Phe Glu Asn Ala
            20                  25                  30

Ile Asn
```

<210> SEQ ID NO 32
<211> LENGTH: 118
<212> TYPE: PRT
<213> ORGANISM: Artificial Sequence
<220> FEATURE:
<223> OTHER INFORMATION: 2D10 heavy chain sequence

<400> SEQUENCE: 32

```
Gln Leu Gln Gln Ser Gly Pro Glu Leu Val Lys Pro Gly Ala Ser Val
```

```
1               5                   10                  15

Lys Ile Ser Cys Lys Ala Ser Gly Tyr Ala Phe Ile Ser Ser Trp Met
            20                  25                  30

Asn Trp Val Lys Gln Arg Pro Gly Lys Gly Leu Glu Trp Ile Gly Arg
        35                  40                  45

Ile Tyr Pro Gly Asp Gly Asp Thr His Tyr Asn Gly Lys Phe Lys Gly
    50                  55                  60

Lys Ala Thr Leu Thr Ala Asp Lys Ser Ser Ser Thr Ala Tyr Met Gln
65                  70                  75                  80

Leu Ser Ser Leu Thr Ser Glu Asp Ser Ala Val Tyr Phe Cys Ala Arg
                85                  90                  95

Glu Glu Thr Ala Gln Thr Gly Gly Phe Asp Tyr Trp Gly Gln Gly Thr
            100                 105                 110

Thr Leu Thr Val Ser Ser
        115


<210> SEQ ID NO 33
<211> LENGTH: 118
<212> TYPE: PRT
<213> ORGANISM: Artificial Sequence
<220> FEATURE:
<223> OTHER INFORMATION: 2H2 Heavy chain

<400> SEQUENCE: 33

Pro Leu Gln Gln Ser Gly Pro Glu Leu Val Lys Pro Gly Ala Ser Val
1               5                   10                  15

Lys Ile Ser Cys Lys Ala Ser Gly Tyr Ala Phe Ser Ser Ser Trp Met
            20                  25                  30

Asn Trp Val Lys Gln Arg Pro Gly Lys Gly Leu Glu Trp Ile Gly Arg
        35                  40                  45

Ile Tyr Pro Gly Asp Gly Asp Thr Asn Tyr Asn Gly Lys Phe Lys Gly
    50                  55                  60

Lys Ala Thr Leu Thr Ala Asp Lys Ser Ser Ser Thr Ala Tyr Met Gln
65                  70                  75                  80

Leu Ser Ser Leu Thr Ser Glu Asp Ser Ala Val Tyr Phe Cys Ala Gly
                85                  90                  95

Glu Val Tyr Asp Arg Tyr Tyr Ala Met Asp Tyr Trp Gly Gln Gly Thr
            100                 105                 110

Ser Val Thr Val Ser Ser
        115


<210> SEQ ID NO 34
<211> LENGTH: 114
<212> TYPE: PRT
<213> ORGANISM: Artificial Sequence
<220> FEATURE:
<223> OTHER INFORMATION: 2D10 light chain

<400> SEQUENCE: 34

Asp Ile Val Ile Thr Gln Asp Glu Leu Ser Asn Pro Val Thr Ser Gly
1               5                   10                  15

Glu Ser Val Ser Ile Ser Cys Arg Ser Ser Lys Ser Leu Leu Tyr Gln
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60
```

Asp Arg Phe Ser Gly Ser Gly Ser Gly Thr Asp Phe Leu Glu Ile Ser
65 70 75 80

Arg Val Glu Ala Glu Asp Val Gly Val Tyr Tyr Cys Gln Gln Leu Val
85 90 95

Glu Tyr Pro Leu Thr Phe Gly Ala Gly Thr Lys Leu Glu Leu Lys Arg
100 105 110

Ala Asp

<210> SEQ ID NO 35
<211> LENGTH: 114
<212> TYPE: PRT
<213> ORGANISM: Artificial Sequence
<220> FEATURE:
<223> OTHER INFORMATION: 2H2 light chain

<400> SEQUENCE: 35

Asp Ile Val Ile Thr Gln Asp Glu Leu Ser Asn Pro Val Thr Ser Gly
1 5 10 15

Glu Ser Val Ser Ile Ser Cys Arg Ser Ser Lys Ser Leu Leu Tyr Gln
20 25 30

Asp Gly Lys Thr Tyr Leu Asn Trp Phe Leu Gln Arg Pro Gly Gln Ser
35 40 45

Pro Gln Leu Leu Ile Tyr Leu Met Ser Thr Arg Ala Ser Gly Val Ser
50 55 60

Asp Arg Phe Ser Gly Ser Gly Ser Gly Thr Asp Phe Leu Glu Ile Ser
65 70 75 80

Arg Val Lys Ala Glu Asp Val Gly Val Tyr Tyr Cys Gln Gln Phe Val
85 90 95

Glu Tyr Pro Tyr Thr Phe Gly Gly Gly Thr Lys Leu Glu Ile Lys Arg
100 105 110

Ala Asp

<210> SEQ ID NO 36
<211> LENGTH: 315
<212> TYPE: PRT
<213> ORGANISM: Artificial Sequence
<220> FEATURE:
<223> OTHER INFORMATION: PvDBP

<400> SEQUENCE: 36

Asn Thr Val Met Lys Asn Cys Asn Tyr Lys Arg Lys Arg Arg Glu Arg
1 5 10 15

Asp Trp Asp Cys Asn Thr Lys Lys Asp Val Cys Ile Pro Asp Arg Arg
20 25 30

Tyr Gln Leu Cys Met Lys Glu Leu Thr Asn Leu Val Asn Asn Thr Asp
35 40 45

Thr Asn Phe His Arg Asp Ile Thr Phe Arg Lys Leu Tyr Leu Lys Arg
50 55 60

Lys Leu Ile Tyr Asp Ala Ala Val Glu Gly Asp Leu Leu Leu Lys Leu
65 70 75 80

Asn Asn Tyr Arg Tyr Asn Lys Asp Phe Cys Lys Asp Ile Arg Trp Ser
85 90 95

Leu Gly Asp Phe Gly Asp Ile Ile Met Gly Thr Asp Met Glu Gly Ile
100 105 110

Gly Tyr Ser Lys Val Val Glu Asn Asn Leu Arg Ser Ile Phe Gly Thr
115 120 125

Asp Glu Lys Ala Gln Gln Arg Arg Lys Gln Trp Trp Asn Glu Ser Lys

```
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190

Glu Leu Pro Thr Glu Val Gln Lys Leu Lys Glu Lys Cys Asp Gly Lys
        195                 200                 205

Ile Asn Tyr Thr Asp Lys Lys Val Cys Lys Val Pro Pro Cys Gln Asn
    210                 215                 220

Ala Cys Lys Ser Tyr Asp Gln Trp Ile Thr Arg Lys Lys Asn Gln Trp
225                 230                 235                 240

Asp Val Leu Ser Asn Lys Phe Ile Ser Val Lys Asn Ala Glu Lys Val
                245                 250                 255

Gln Thr Ala Gly Ile Val Thr Pro Tyr Asp Ile Leu Lys Gln Glu Leu
            260                 265                 270

Asp Glu Phe Asn Glu Val Ala Phe Glu Asn Glu Ile Asn Lys Arg Asp
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315


<210> SEQ ID NO 37
<211> LENGTH: 315
<212> TYPE: PRT
<213> ORGANISM: Artificial Sequence
<220> FEATURE:
<223> OTHER INFORMATION: Sal-1 DBP mutant 1

<400> SEQUENCE: 37

Asn Thr Val Met Lys Asn Cys Ser Tyr Lys Gly Ser Gly Arg Glu Arg
1               5                   10                  15

Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Tyr Arg Tyr Asn Lys Asp Phe Cys Lys Asp Ile Arg Trp Ser
                85                  90                  95

Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
```

```
            180                 185                 190

Glu Leu Pro Thr Glu Val Gln Lys Leu Lys Glu Lys Cys Asp Gly Lys
        195                 200                 205

Ile Asn Tyr Thr Asp Lys Lys Val Cys Lys Val Pro Pro Cys Gln Asn
    210                 215                 220

Ala Cys Lys Ser Tyr Asp Gln Trp Ile Thr Arg Lys Lys Asn Gln Trp
225                 230                 235                 240

Asp Val Leu Ser Asn Lys Phe Ile Ser Val Lys Asn Ala Glu Lys Val
                245                 250                 255

Gln Thr Ala Gly Ile Val Thr Pro Tyr Asp Ile Leu Lys Gln Glu Leu
            260                 265                 270

Asp Glu Phe Asn Glu Val Ala Phe Glu Asn Glu Ile Asn Lys Arg Asp
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315


<210> SEQ ID NO 38
<211> LENGTH: 315
<212> TYPE: PRT
<213> ORGANISM: Artificial Sequence
<220> FEATURE:
<223> OTHER INFORMATION: Sal1-DBP mutant 2

<400> SEQUENCE: 38

Asn Thr Val Met Lys Asn Cys Asn Tyr Lys Arg Lys Arg Arg Glu Arg
1               5                   10                  15

Asp Trp Gly Cys Ser Gly Gly Ser Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Tyr Arg Tyr Asn Lys Asp Phe Cys Lys Asp Ile Arg Trp Ser
                85                  90                  95

Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190

Glu Leu Pro Thr Glu Val Gln Lys Leu Lys Glu Lys Cys Asp Gly Lys
        195                 200                 205

Ile Asn Tyr Thr Asp Lys Lys Val Cys Lys Val Pro Pro Cys Gln Asn
    210                 215                 220

Ala Cys Lys Ser Tyr Asp Gln Trp Ile Thr Arg Lys Lys Asn Gln Trp
```

```
225                 230                 235                 240

Asp Val Leu Ser Asn Lys Phe Ile Ser Val Lys Asn Ala Glu Lys Val
                245                 250                 255

Gln Thr Ala Gly Ile Val Thr Pro Tyr Asp Ile Leu Lys Gln Glu Leu
            260                 265                 270

Asp Glu Phe Asn Glu Val Ala Phe Glu Asn Glu Ile Asn Lys Arg Asp
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315


<210> SEQ ID NO 39
<211> LENGTH: 315
<212> TYPE: PRT
<213> ORGANISM: Artificial Sequence
<220> FEATURE:
<223> OTHER INFORMATION: Sal-1 DBP mutant 3

<400> SEQUENCE: 39

Asn Thr Val Met Lys Asn Cys Asn Tyr Lys Arg Lys Arg Arg Glu Arg
1               5                   10                  15

Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Gly Gly Ser Gly Lys Asp Phe Cys Lys Asp Ile Arg Trp Ser
                85                  90                  95

Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190

Glu Leu Pro Thr Glu Val Gln Lys Leu Lys Glu Lys Cys Asp Gly Lys
        195                 200                 205

Ile Asn Tyr Thr Asp Lys Lys Val Cys Lys Val Pro Pro Cys Gln Asn
    210                 215                 220

Ala Cys Lys Ser Tyr Asp Gln Trp Ile Thr Arg Lys Lys Asn Gln Trp
225                 230                 235                 240

Asp Val Leu Ser Asn Lys Phe Ile Ser Val Lys Asn Ala Glu Lys Val
                245                 250                 255

Gln Thr Ala Gly Ile Val Thr Pro Tyr Asp Ile Leu Lys Gln Glu Leu
            260                 265                 270

Asp Glu Phe Asn Glu Val Ala Phe Glu Asn Glu Ile Asn Lys Arg Asp
```

```
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315


<210> SEQ ID NO 40
<211> LENGTH: 315
<212> TYPE: PRT
<213> ORGANISM: Artificial Sequence
<220> FEATURE:
<223> OTHER INFORMATION: Sal-1 DBP mutant 4

<400> SEQUENCE: 40

Asn Thr Val Met Lys Asn Cys Asn Tyr Lys Arg Lys Arg Arg Glu Arg
1               5                   10                  15

Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Tyr Arg Tyr Asn Lys Asp Phe Cys Lys Asp Ile Arg Trp Ser
                85                  90                  95

Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190

Glu Leu Pro Arg Glu Val Ala Lys Leu Lys Arg Lys Cys Asp Gly Lys
        195                 200                 205

Ile Asn Tyr Thr Asp Lys Lys Val Cys Lys Val Pro Pro Cys Gln Asn
    210                 215                 220

Ala Cys Lys Ser Tyr Asp Gln Trp Ile Thr Arg Lys Lys Asn Gln Trp
225                 230                 235                 240

Asp Val Leu Ser Asn Lys Phe Ile Ser Val Lys Asn Ala Glu Lys Val
                245                 250                 255

Gln Thr Ala Gly Ile Val Thr Pro Tyr Asp Ile Leu Lys Gln Glu Leu
            260                 265                 270

Asp Glu Phe Asn Glu Val Ala Phe Glu Asn Glu Ile Asn Lys Arg Asp
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315
```

-continued

```
<210> SEQ ID NO 41
<211> LENGTH: 315
<212> TYPE: PRT
<213> ORGANISM: Artificial Sequence
<220> FEATURE:
<223> OTHER INFORMATION: Sal-1 DBP mutant 5

<400> SEQUENCE: 41

Asn Thr Val Met Lys Asn Cys Asn Tyr Lys Arg Lys Arg Arg Glu Arg
1               5                   10                  15

Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Tyr Arg Tyr Asn Lys Asp Phe Cys Lys Asp Ile Arg Trp Ser
                85                  90                  95

Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190

Glu Leu Pro Thr Glu Val Gln Ala Leu Lys Glu Ala Cys Asp Gly Lys
        195                 200                 205

Ile Asn Tyr Thr Asp Lys Lys Val Cys Lys Val Pro Pro Cys Gln Asn
    210                 215                 220

Ala Cys Lys Ser Tyr Asp Gln Trp Ile Thr Arg Lys Lys Asn Gln Trp
225                 230                 235                 240

Asp Val Leu Ser Asn Lys Phe Ile Ser Val Lys Asn Ala Glu Lys Val
                245                 250                 255

Gln Thr Ala Gly Ile Val Thr Pro Tyr Asp Ile Leu Lys Gln Glu Leu
            260                 265                 270

Asp Glu Phe Asn Glu Val Ala Phe Glu Asn Glu Ile Asn Lys Arg Asp
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315


<210> SEQ ID NO 42
<211> LENGTH: 315
<212> TYPE: PRT
<213> ORGANISM: Artificial Sequence
<220> FEATURE:
<223> OTHER INFORMATION: Sal-1 DBP mutant 6

<400> SEQUENCE: 42
```

-continued

```
Asn Thr Val Met Lys Asn Cys Asn Tyr Lys Arg Lys Arg Arg Glu Arg
1               5                   10                  15

Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Tyr Arg Tyr Asn Lys Asp Phe Cys Lys Asp Ile Arg Trp Ser
                85                  90                  95

Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190

Glu Leu Pro Thr Glu Val Gln Lys Leu Lys Glu Ala Cys Asp Gly Lys
        195                 200                 205

Ile Asn Tyr Thr Asp Lys Lys Val Cys Lys Val Ala Ala Cys Gln Ala
    210                 215                 220

Ala Cys Ala Ser Tyr Asp Ala Trp Ile Thr Arg Lys Lys Asn Gln Trp
225                 230                 235                 240

Asp Val Leu Ser Asn Lys Phe Ile Ser Val Lys Asn Ala Glu Lys Val
                245                 250                 255

Gln Thr Ala Gly Ile Val Thr Pro Tyr Asp Ile Leu Lys Gln Glu Leu
            260                 265                 270

Asp Glu Phe Asn Glu Val Ala Phe Glu Asn Glu Ile Asn Lys Arg Asp
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315
```

<210> SEQ ID NO 43
<211> LENGTH: 315
<212> TYPE: PRT
<213> ORGANISM: Artificial Sequence
<220> FEATURE:
<223> OTHER INFORMATION: Sal-1 DBP mutant 7

<400> SEQUENCE: 43

```
Asn Thr Val Met Lys Asn Cys Asn Tyr Lys Arg Lys Arg Arg Glu Arg
1               5                   10                  15

Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45
```

```
Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Tyr Arg Tyr Asn Lys Asp Phe Cys Lys Asp Ile Arg Trp Ser
                85                  90                  95

Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190

Glu Leu Pro Thr Glu Val Gln Lys Leu Lys Glu Lys Cys Asp Ser Gly
        195                 200                 205

Gly Ser Gly Gly Ser Lys Lys Val Cys Ala Val Ala Pro Cys Gln Asn
    210                 215                 220

Ala Cys Lys Ser Tyr Asp Gln Trp Ile Thr Arg Lys Lys Asn Gln Trp
225                 230                 235                 240

Asp Val Leu Ser Asn Lys Phe Ile Ser Val Lys Asn Ala Glu Lys Val
                245                 250                 255

Gln Thr Ala Gly Ile Val Thr Pro Tyr Asp Ile Leu Lys Gln Glu Leu
            260                 265                 270

Asp Glu Phe Asn Glu Val Ala Phe Glu Asn Glu Ile Asn Lys Arg Asp
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315


<210> SEQ ID NO 44
<211> LENGTH: 315
<212> TYPE: PRT
<213> ORGANISM: Artificial Sequence
<220> FEATURE:
<223> OTHER INFORMATION: Sal-1 DBP mutant 8

<400> SEQUENCE: 44

Asn Thr Val Met Lys Asn Cys Asn Tyr Lys Arg Lys Arg Arg Glu Arg
1               5                   10                  15

Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Tyr Arg Tyr Asn Lys Asp Phe Cys Lys Asp Ile Arg Trp Ser
                85                  90                  95
```

```
Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190

Glu Leu Pro Thr Glu Val Gln Lys Leu Lys Glu Lys Cys Asp Gly Lys
        195                 200                 205

Ile Asn Tyr Thr Asp Lys Lys Val Cys Lys Val Pro Pro Cys Gln Asn
    210                 215                 220

Ala Cys Lys Ser Tyr Asp Gln Trp Ile Thr Arg Lys Lys Asn Gln Trp
225                 230                 235                 240

Asp Val Leu Ser Asn Lys Phe Ile Ser Val Lys Asn Ala Glu Lys Val
                245                 250                 255

Gln Thr Ala Gly Ile Val Thr Pro Tyr Asp Ile Leu Lys Gln Glu Leu
            260                 265                 270

Asp Glu Phe Asn Glu Val Ala Phe Glu Asn Glu Ile Asn Lys Arg Asp
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315
```

<210> SEQ ID NO 45
<211> LENGTH: 315
<212> TYPE: PRT
<213> ORGANISM: Artificial Sequence
<220> FEATURE:
<223> OTHER INFORMATION: Sal-1 DBP mutant 9

<400> SEQUENCE: 45

```
Asn Thr Val Met Lys Asn Cys Asn Tyr Lys Arg Lys Arg Arg Glu Arg
1               5                   10                  15

Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Tyr Arg Tyr Asn Lys Asp Phe Cys Lys Asp Ile Arg Trp Ser
                85                  90                  95

Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140
```

-continued

```
Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190

Glu Leu Pro Thr Glu Val Gln Lys Leu Lys Glu Lys Cys Asp Gly Lys
        195                 200                 205

Ile Asn Tyr Thr Asp Lys Lys Val Cys Lys Val Pro Pro Cys Gln Arg
    210                 215                 220

Ala Cys Lys Ser Tyr Asp Gln Trp Ile Thr Arg Lys Lys Asn Gln Trp
225                 230                 235                 240

Asp Val Leu Ser Asn Lys Phe Ile Ser Val Lys Asn Ala Glu Lys Val
                245                 250                 255

Gln Thr Ala Gly Ile Val Thr Pro Tyr Asp Ile Leu Lys Gln Glu Leu
            260                 265                 270

Asp Glu Phe Asn Glu Val Ala Phe Glu Asn Glu Ile Asn Lys Arg Asp
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315


<210> SEQ ID NO 46
<211> LENGTH: 315
<212> TYPE: PRT
<213> ORGANISM: Artificial Sequence
<220> FEATURE:
<223> OTHER INFORMATION: Sal-1 DBP mutant 10

<400> SEQUENCE: 46

Asn Thr Val Met Lys Asn Cys Asn Tyr Lys Arg Lys Arg Arg Glu Arg
1               5                   10                  15

Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Tyr Arg Tyr Asn Lys Asp Phe Cys Lys Asp Ile Arg Trp Ser
                85                  90                  95

Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190
```

```
Glu Leu Pro Thr Glu Val Gln Lys Leu Lys Glu Lys Cys Asp Gly Lys
        195                 200                 205

Ile Asn Tyr Thr Asp Lys Lys Val Cys Lys Val Pro Pro Cys Gln Asn
    210                 215                 220

Ala Cys Lys Ser Tyr Asp Gln Trp Ile Thr Arg Lys Lys Asn Gln Trp
225                 230                 235                 240

Ala Val Leu Ser Ala Lys Phe Ala Ser Val Lys Ala Ala Glu Lys Val
                245                 250                 255

Gln Thr Ala Gly Ile Val Thr Pro Tyr Asp Ile Leu Lys Gln Glu Leu
            260                 265                 270

Asp Glu Phe Asn Glu Val Ala Phe Glu Asn Glu Ile Asn Lys Arg Asp
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315


<210> SEQ ID NO 47
<211> LENGTH: 315
<212> TYPE: PRT
<213> ORGANISM: Artificial Sequence
<220> FEATURE:
<223> OTHER INFORMATION: Sal-1 DBP mutant 11

<400> SEQUENCE: 47

Asn Thr Val Met Lys Asn Cys Asn Tyr Lys Arg Lys Arg Arg Glu Arg
1               5                   10                  15

Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Tyr Arg Tyr Asn Lys Asp Phe Cys Lys Asp Ile Arg Trp Ser
                85                  90                  95

Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190

Glu Leu Pro Thr Glu Val Gln Lys Leu Lys Glu Lys Cys Asp Gly Lys
        195                 200                 205

Ile Asn Tyr Thr Asp Lys Lys Val Cys Lys Val Pro Pro Cys Gln Asn
    210                 215                 220

Ala Cys Lys Ser Tyr Asp Gln Trp Ile Thr Arg Lys Lys Asn Gln Trp
225                 230                 235                 240
```

```
Asp Val Leu Ser Asn Lys Phe Ile Ser Val Lys Asn Ala Glu Gly Gly
            245                 250                 255

Ser Gly Gly Ser Ile Val Thr Pro Tyr Asp Ile Leu Lys Gln Glu Leu
            260                 265                 270

Asp Glu Phe Asn Glu Val Ala Phe Glu Asn Glu Ile Asn Lys Arg Asp
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315


<210> SEQ ID NO 48
<211> LENGTH: 315
<212> TYPE: PRT
<213> ORGANISM: Artificial Sequence
<220> FEATURE:
<223> OTHER INFORMATION: Sal-1 DBP mutant 12

<400> SEQUENCE: 48

Asn Thr Val Met Lys Asn Cys Asn Tyr Lys Arg Lys Arg Arg Glu Arg
1               5                   10                  15

Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Tyr Arg Tyr Asn Lys Asp Phe Cys Lys Asp Ile Arg Trp Ser
                85                  90                  95

Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190

Glu Leu Pro Thr Glu Val Gln Lys Leu Lys Glu Lys Cys Asp Gly Lys
        195                 200                 205

Ile Asn Tyr Thr Asp Lys Lys Val Cys Lys Val Pro Pro Cys Gln Asn
    210                 215                 220

Ala Cys Lys Ser Tyr Asp Gln Trp Ile Thr Arg Lys Lys Asn Gln Trp
225                 230                 235                 240

Asp Val Leu Ser Asn Lys Phe Ile Ser Val Lys Asn Ala Glu Lys Val
                245                 250                 255

Gln Thr Ala Gly Ile Val Thr Pro Tyr Asp Ile Leu Ala Ala Glu Leu
            260                 265                 270

Asp Glu Phe Asn Glu Val Ala Phe Glu Asn Glu Ile Asn Lys Arg Asp
        275                 280                 285
```

```
Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315


<210> SEQ ID NO 49
<211> LENGTH: 315
<212> TYPE: PRT
<213> ORGANISM: Artificial Sequence
<220> FEATURE:
<223> OTHER INFORMATION: Sal-1 DBP mutant 13

<400> SEQUENCE: 49

Asn Thr Val Met Lys Asn Cys Asn Tyr Lys Arg Lys Arg Arg Glu Arg
1               5                   10                  15

Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Tyr Arg Tyr Asn Lys Asp Phe Cys Lys Asp Ile Arg Trp Ser
                85                  90                  95

Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190

Glu Leu Pro Thr Glu Val Gln Lys Leu Lys Glu Lys Cys Asp Gly Lys
        195                 200                 205

Ile Asn Tyr Thr Asp Lys Lys Val Cys Lys Val Pro Pro Cys Gln Asn
    210                 215                 220

Ala Cys Lys Ser Tyr Asp Gln Trp Ile Thr Arg Lys Lys Asn Gln Trp
225                 230                 235                 240

Asp Val Leu Ser Asn Lys Phe Ile Ser Val Lys Asn Ala Glu Lys Val
                245                 250                 255

Gln Thr Ala Gly Ile Val Thr Pro Tyr Asp Ile Leu Lys Gln Glu Gly
            260                 265                 270

Ser Gly Phe Asn Glu Val Ala Phe Glu Asn Glu Ile Asn Lys Arg Asp
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315


<210> SEQ ID NO 50
<211> LENGTH: 315
```

<212> TYPE: PRT
<213> ORGANISM: Artificial Sequence
<220> FEATURE:
<223> OTHER INFORMATION: Sal-1 DBP mutant 14

<400> SEQUENCE: 50

Asn Thr Val Met Lys Asn Cys Asn Tyr Lys Arg Lys Arg Arg Glu Arg
1 5 10 15

Asp Trp Asp Cys Asn Thr Lys Lys Asp Val Cys Ile Pro Asp Arg Arg
20 25 30

Tyr Gln Leu Cys Met Lys Glu Leu Thr Asn Leu Val Asn Asn Thr Asp
35 40 45

Thr Asn Phe His Arg Asp Ile Thr Phe Arg Lys Leu Tyr Leu Lys Arg
50 55 60

Lys Leu Ile Tyr Asp Ala Ala Val Glu Gly Asp Leu Leu Leu Lys Leu
65 70 75 80

Asn Asn Tyr Arg Tyr Asn Lys Asp Phe Cys Lys Asp Ile Arg Trp Ser
85 90 95

Leu Gly Asp Phe Gly Asp Ile Ile Met Gly Thr Asp Met Glu Gly Ile
100 105 110

Gly Tyr Ser Lys Val Val Glu Asn Asn Leu Arg Ser Ile Phe Gly Thr
115 120 125

Asp Glu Lys Ala Gln Gln Arg Arg Lys Gln Trp Trp Asn Glu Ser Lys
130 135 140

Ala Gln Ile Trp Thr Ala Met Met Tyr Ser Val Lys Lys Arg Leu Lys
145 150 155 160

Gly Asn Phe Ile Trp Ile Cys Lys Leu Asn Val Ala Val Asn Ile Glu
165 170 175

Pro Gln Ile Tyr Arg Trp Ile Arg Glu Trp Gly Arg Asp Tyr Val Ser
180 185 190

Glu Leu Pro Thr Glu Val Gln Lys Leu Lys Glu Lys Cys Asp Gly Lys
195 200 205

Ile Asn Tyr Thr Asp Lys Lys Val Cys Lys Val Pro Pro Cys Gln Asn
210 215 220

Ala Cys Lys Ser Tyr Asp Gln Trp Ile Thr Arg Lys Lys Asn Gln Trp
225 230 235 240

Asp Val Leu Ser Asn Lys Phe Ile Ser Val Lys Asn Ala Glu Lys Val
245 250 255

Gln Thr Ala Gly Ile Val Thr Pro Tyr Asp Ile Leu Lys Gln Glu Leu
260 265 270

Asp Glu Phe Ala Glu Val Ala Phe Glu Asn Glu Ile Asn Lys Arg Asp
275 280 285

Gly Ala Tyr Ile Glu Leu Cys Val Cys Ser Val Glu Glu Ala Lys Lys
290 295 300

Asn Thr Gln Glu Val Val Thr Asn Val Asp Asn
305 310 315

<210> SEQ ID NO 51
<211> LENGTH: 315
<212> TYPE: PRT
<213> ORGANISM: Artificial Sequence
<220> FEATURE:
<223> OTHER INFORMATION: Sal-1 DBP mutant 15

<400> SEQUENCE: 51

Asn Thr Val Met Lys Asn Cys Asn Tyr Lys Arg Lys Arg Arg Glu Arg
1 5 10 15

```
Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60

Lys Leu Ile Tyr Asp Ala Ala Val Glu Gly Asp Leu Leu Leu Lys Leu
65                  70                  75                  80

Asn Asn Tyr Arg Tyr Asn Lys Asp Phe Cys Lys Asp Ile Arg Trp Ser
                85                  90                  95

Leu Gly Asp Phe Gly Asp Ile Ile Met Gly Thr Asp Met Glu Gly Ile
            100                 105                 110

Gly Tyr Ser Lys Val Val Glu Asn Asn Leu Arg Ser Ile Phe Gly Thr
        115                 120                 125

Asp Glu Lys Ala Gln Gln Arg Arg Lys Gln Trp Trp Asn Glu Ser Lys
    130                 135                 140

Ala Gln Ile Trp Thr Ala Met Met Tyr Ser Val Lys Lys Arg Leu Lys
145                 150                 155                 160

Gly Asn Phe Ile Trp Ile Cys Lys Leu Asn Val Ala Val Asn Ile Glu
                165                 170                 175

Pro Gln Ile Tyr Arg Trp Ile Arg Glu Trp Gly Arg Asp Tyr Val Ser
            180                 185                 190

Glu Leu Pro Thr Glu Val Gln Lys Leu Lys Glu Lys Cys Asp Gly Lys
        195                 200                 205

Ile Asn Tyr Thr Asp Lys Lys Val Cys Lys Val Pro Pro Cys Gln Asn
    210                 215                 220

Ala Cys Lys Ser Tyr Asp Gln Trp Ile Thr Arg Lys Lys Asn Gln Trp
225                 230                 235                 240

Asp Val Leu Ser Asn Lys Phe Ile Ser Val Lys Asn Ala Glu Lys Val
                245                 250                 255

Gln Thr Ala Gly Ile Val Thr Pro Tyr Asp Ile Leu Lys Gln Glu Leu
            260                 265                 270

Asp Glu Phe Asn Glu Ala Ala Phe Arg Ala Glu Ile Asn Lys Arg Asp
        275                 280                 285

Gly Ala Tyr Ile Glu Leu Cys Val Cys Ser Val Glu Glu Ala Lys Lys
    290                 295                 300

Asn Thr Gln Glu Val Val Thr Asn Val Asp Asn
305                 310                 315


<210> SEQ ID NO 52
<211> LENGTH: 315
<212> TYPE: PRT
<213> ORGANISM: Artificial Sequence
<220> FEATURE:
<223> OTHER INFORMATION: Sal-1 DBP mutant 16

<400> SEQUENCE: 52

Asn Thr Val Met Lys Asn Cys Asn Tyr Lys Arg Lys Arg Arg Glu Arg
1               5                   10                  15

Asp Trp Asp Cys Asn Thr Lys Lys Asp Val Cys Ile Pro Asp Arg Arg
            20                  25                  30

Tyr Gln Leu Cys Met Lys Glu Leu Thr Asn Leu Val Asn Asn Thr Asp
        35                  40                  45

Thr Asn Phe His Arg Asp Ile Thr Phe Arg Lys Leu Tyr Leu Lys Arg
    50                  55                  60
```

Lys Leu Ile Tyr Asp Ala Ala Val Glu Gly Asp Leu Leu Leu Lys Leu
65 70 75 80

Asn Asn Tyr Arg Tyr Asn Lys Asp Phe Cys Lys Asp Ile Arg Trp Ser
85 90 95

Leu Gly Asp Phe Gly Asp Ile Ile Met Gly Thr Asp Met Glu Gly Ile
100 105 110

Gly Tyr Ser Lys Val Val Glu Asn Asn Leu Arg Ser Ile Phe Gly Thr
115 120 125

Asp Glu Lys Ala Gln Gln Arg Arg Lys Gln Trp Trp Asn Glu Ser Lys
130 135 140

Ala Gln Ile Trp Thr Ala Met Met Tyr Ser Val Lys Lys Arg Leu Lys
145 150 155 160

Gly Asn Phe Ile Trp Ile Cys Lys Leu Asn Val Ala Val Asn Ile Glu
165 170 175

Pro Gln Ile Tyr Arg Trp Ile Arg Glu Trp Gly Arg Asp Tyr Val Ser
180 185 190

Glu Leu Pro Thr Glu Val Gln Lys Leu Lys Glu Lys Cys Asp Gly Lys
195 200 205

Ile Asn Tyr Thr Asp Lys Lys Val Cys Lys Val Pro Pro Cys Gln Asn
210 215 220

Ala Cys Lys Ser Tyr Asp Gln Trp Ile Thr Arg Lys Lys Asn Gln Trp
225 230 235 240

Asp Val Leu Ser Asn Lys Phe Ile Ser Val Lys Asn Ala Glu Lys Val
245 250 255

Gln Thr Ala Gly Ile Val Thr Pro Tyr Asp Ile Leu Lys Gln Glu Leu
260 265 270

Asp Glu Phe Asn Glu Val Ala Phe Glu Asn Glu Ile Asn Lys Ala Asp
275 280 285

Gly Ala Tyr Ile Ala Leu Cys Val Cys Ala Val Glu Glu Ala Lys Lys
290 295 300

Asn Thr Gln Glu Val Val Thr Asn Val Asp Asn
305 310 315

<210> SEQ ID NO 53
<211> LENGTH: 18
<212> TYPE: PRT
<213> ORGANISM: Artificial Sequence
<220> FEATURE:
<223> OTHER INFORMATION: Control peptide

<400> SEQUENCE: 53

Thr Pro Asp Glu Arg Tyr Arg Glu Leu Asp Ser His Ala Gln Asn Glu
1 5 10 15

Ser Cys

<210> SEQ ID NO 54
<211> LENGTH: 19
<212> TYPE: DNA
<213> ORGANISM: Artificial Sequence
<220> FEATURE:
<223> OTHER INFORMATION: GSP1 IgG1 heavy chain RACE primer

<400> SEQUENCE: 54
tgcatttgaa ctccttgcc 19

<210> SEQ ID NO 55
<211> LENGTH: 19

<212> TYPE: DNA
<213> ORGANISM: Artificial Sequence
<220> FEATURE:
<223> OTHER INFORMATION: GSP2 for IgG1 heavy chain RACE primer

<400> SEQUENCE: 55
ctttgggggg aagatgaag 19

<210> SEQ ID NO 56
<211> LENGTH: 19
<212> TYPE: DNA
<213> ORGANISM: Artificial Sequence
<220> FEATURE:
<223> OTHER INFORMATION: GSP1 for Ck light chain RACE primer

<400> SEQUENCE: 56
cactcattcc tgttgaagc 19

<210> SEQ ID NO 57
<211> LENGTH: 20
<212> TYPE: DNA
<213> ORGANISM: Artificial Sequence
<220> FEATURE:
<223> OTHER INFORMATION: GSP2 for Ck light chain RACE primer

<400> SEQUENCE: 57
cttgtgagtg gcctcacagg 20

<210> SEQ ID NO 58
<211> LENGTH: 15
<212> TYPE: PRT
<213> ORGANISM: Artificial Sequence
<220> FEATURE:
<223> OTHER INFORMATION: (GGGGS)3 linker

<400> SEQUENCE: 58

Gly Gly Gly Gly Ser Gly Gly Gly Gly Ser Gly Gly Gly Gly Ser
1 5 10 15

<210> SEQ ID NO 59
<211> LENGTH: 34
<212> TYPE: PRT
<213> ORGANISM: Artificial Sequence
<220> FEATURE:
<223> OTHER INFORMATION: segment of wild-type DBP Sal1 from amino acid
436 to 541 with an omission of amino acids 450-521, which would be
between E(13) and L(14) of this sequence entry

<400> SEQUENCE: 59

Arg Trp Ile Arg Glu Trp Gly Arg Asp Tyr Val Ser Glu Leu Asp Ile
1 5 10 15

Leu Lys Gln Glu Leu Asp Glu Phe Asn Glu Val Ala Phe Glu Asn Glu
20 25 30

Ile Asn

<210> SEQ ID NO 60
<211> LENGTH: 29
<212> TYPE: PRT
<213> ORGANISM: Artificial Sequence
<220> FEATURE:
<223> OTHER INFORMATION: antibody epitope

<400> SEQUENCE: 60

Glu Lys Cys Asp Gly Lys Ile Asn Tyr Thr Asp Lys Lys Val Cys Lys
1 5 10 15

Val Pro Pro Cys Gln Asn Ala Cys Lys Ser Tyr Asp Gln
20 25

<210> SEQ ID NO 61
<211> LENGTH: 29
<212> TYPE: PRT
<213> ORGANISM: Artificial Sequence
<220> FEATURE:
<223> OTHER INFORMATION: antibody epitope

<400> SEQUENCE: 61

Glu Lys Cys Asp Gly Lys Ile Asn Tyr Thr Asp Lys Lys Val Cys Lys
1 5 10 15

Val Pro Pro Cys Gln Asn Ala Cys Lys Ser Tyr Asp Gln
20 25

<210> SEQ ID NO 62
<211> LENGTH: 14
<212> TYPE: PRT
<213> ORGANISM: Artificial Sequence
<220> FEATURE:
<223> OTHER INFORMATION: antibody epitope

<400> SEQUENCE: 62

Lys Val Gln Thr Ala Gly Ile Val Thr Pro Tyr Asp Ile Leu
1 5 10

<210> SEQ ID NO 63
<211> LENGTH: 115
<212> TYPE: PRT
<213> ORGANISM: Artificial Sequence
<220> FEATURE:
<223> OTHER INFORMATION: 2C6 Light Chain

<400> SEQUENCE: 63

Asn Ile Met Met Thr Gln Ser Pro Ser Ser Leu Ala Val Ser Ala Gly
1 5 10 15

Glu Lys Val Thr Met Ser Cys Lys Ser Ser Gln Ser Val Leu Tyr Ser
20 25 30

Ser Asn Gln Lys Asn Tyr Leu Ala Trp Tyr Gln Gln Lys Pro Gly Gln
35 40 45

Ser Pro Lys Leu Leu Ile Tyr Trp Ala Ser Ser Arg Glu Ser Gly Val
50 55 60

Pro Asp Arg Phe Thr Gly Ser Gly Ser Gly Thr Asp Phe Thr Leu Thr
65 70 75 80

Ile Ser Ser Val Gln Pro Glu Asp Leu Ala Val Tyr Tyr Cys His Gln
85 90 95

Tyr Leu Ser Ser Trp Thr Phe Gly Gly Gly Thr Lys Leu Glu Ile Thr
100 105 110

Arg Ala Asp
115

<210> SEQ ID NO 64
<211> LENGTH: 117
<212> TYPE: PRT
<213> ORGANISM: Artificial Sequence
<220> FEATURE:
<223> OTHER INFORMATION: 2C6 Heavy Chain

<400> SEQUENCE: 64

Gln Val Gln Leu Gln Gln Ser Asp Ala Glu Leu Val Lys Pro Gly Ala
1 5 10 15

-continued

```
Ser Val Lys Ile Ser Cys Lys Val Ser Gly Tyr Thr Phe Thr Asp His
            20                  25                  30

Ser Ile His Trp Met Lys Gln Arg Pro Glu Gln Gly Leu Glu Trp Ile
        35                  40                  45

Gly Tyr Ile Tyr Pro Arg Asp Gly Ser Thr Glu Tyr Asn Glu Lys Phe
    50                  55                  60

Lys Gly Lys Ala Thr Leu Thr Thr Asp Lys Ser Ser Ser Thr Ala Tyr
65                  70                  75                  80

Met Gln Leu Asn Ser Leu Thr Ser Ala Asp Ser Ala Val Tyr Phe Cys
                85                  90                  95

Ala Arg Trp Phe Gly Tyr Tyr Phe Asp Tyr Trp Gly Gln Gly Thr Thr
            100                 105                 110

Leu Thr Val Ser Ser
        115
```

SYNTHETIC PLASMODIUM ANTIGENS, COMPOSITIONS, AND USES THEREOF

CROSS-REFERENCE TO RELATED APPLICATIONS

This application claims the benefit of and priority to U.S. Provisional Patent Application No. 62/164,343, filed on May 20, 2015, entitled "NEXT GENERATION OF A SYNTHETIC ANTIGEN BASED ON THE LIGAND DOMAIN OF THE *PLASMODIUM VIVAX* DUFFY BINDING PROTEIN," and U.S. Provisional Patent Application No. 62/245,721, filed on Oct. 23, 2015, entitled "SYNTHETIC ANTIGEN BASED ON THE LIGAND DOMAIN OF THE *PLASMODIUM VIVAX* DUFFY BINDING PROTEIN," the contents of which are incorporated by reference herein in their entirety.

STATEMENT REGARDING FEDERALLY SPONSORED RESEARCH OR DEVELOPMENT

This invention was made with government support under Grant Numbers: R01 AI064478 and R01 AI080792 awarded by the National Institutes of Health. The government has certain rights in the invention.

BACKGROUND

Malaria is a significant global public health problem, particularly in underdeveloped tropical and sub-tropical countries. Malaria is caused by protozoa of the genus *Plasmodium* including *P. falciparum* and *P. vivax*. Most research, treatments, and preventatives have been directed to *P. falciparum* as it is responsible for most of the malaria-attributed deaths. However, more people are at risk worldwide from *P. vivax* then *P. falciparum* and there is increasing evidence of drug-resistant *P. vivax* strains. The emergence of more virulent *P. vivax* strains and associated morbidity and mortality as well as the formation of hypnozoites with the potential for relapse supports the urgent and unmet need for improved *P. vivax* prevention and/or treatments.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 2A demonstrates a small scale digest of DBPII Sal1 with DNAseI was carried out to determine DNAseI concentration to obtain the broadest spread of fragments. FIG. 2B Lane 3 shows DBPII Sal1 and lane 3 shows DBPII Sal1 DNAseI digested which was later blunt-ended with Vent polymerase. FIG. 2C Lane 2 shows undigested pHENH-6 and lane 3 shows pHENH-6 restriction digested with pstl and blunt-end polished with Vent polymerase. The digested and Vent polymerase blunt-ended fragments were electroporated into TG1 *E. coli*, the number of transfromants were 7.2×105 cfu/μg DNA.

FIG. 3 shows a schematic showing sequences generated from DBPII Sal1 gene fragment library. DNase I digested PCR product of DBPII was cloned into the pHENH6 phagemid vector and transformed into TG1 *E. coli*. Sequencing of PCR products generated by screening 40 individual clones revealed that the gene fragments in the library spanned the entire coding sequence, with no bias towards any particular region. The different shaded underlines represent the lengths of the various gene fragments generated.

FIGS. 7A-7B demonstrate panning a random peptide on mAb-3D10. FIG. 7A depicts ELISA showing reactivity of phage clones from rounds of panning on mAb-3D10. mAb-5G8 served as a negative control antibody, while a mAb-5G8 positive binding phage clone (Pos C) served as a positive control. The bars represent mean of triplicate wells while the error bars represent ±SD. FIG. 7B depicts alignment of a sequence of the mAb-3D10 binding epitope on sd1 of DBPII (top) and sequences of three mimotopes (M1, M2 and M3) from random peptide library with affinity for mAb-3D10. The underlined residues show a three amino acid motif common to the DBPII epitope and the sequences from the mimotopes isolated form the random peptide library.

In FIG. 8A, mice immunized with 3C9-e1 produced an antibody response that recognized rDBPII by ELISA. The numbers for each curve correspond to sera from a mouse. Each point on the curve represent mean OD of triplicate wells and error bars indicate ±SD. In FIG. 8B, pooled group sera was used to test for erythrocyte-DBPII binding inhibition by in vitro COS7 assay. The curves correspond to the different alleles of DBPII that were tested. Each point on the curve represent percent inhibition of two experiments each with triplicate wells and error bars indicate ±SD.

FIG. 9 demonstrates an amino acid sequence alignment of DBPII Sal1 to mutants. Site directed mutagenesis of DBPII Sal1 with alanine substitutions at specific sites depicted in red.

FIG. 11A depicts residues important for binding to mAb 3C9, in red single substitution of mutant 20 and in blue multiple substitutions of mutant 6. FIG. 11B is a cartoon representation of DBPII monomer in yellow and 3C9 epitope in blue. FIG. 11C depicts polar interactions in green that appear to be important for mAb 3C9 binding.

FIG. 12A demonstrates the overall structure of the DBP-II/2D10$_{scFv}$ complex shown in ribbon representation. The DBP-II domain is colored in green. The scFv heavy chain (VH) is in blue and the light chain (VL) in orange. FIG. 12B demonstrates a ribbon representation of DBP-II mapping the 2D10 epitopes. Residues contacted by the scFv are shown in stick. Residues contacted by the heavy chain are colored blue, residues contacted by the light chain are colored orange, and residues contacted by both are in beige. Residues not contacted by antibody are in green. Regions of disorder are shown as a dotted line. FIG. 12C demonstrates a surface representation of the DBP-II. Color scheme as in (FIG. 12B).

FIGS. 14A-14E demonstrate that mAbs 2D10 and 2H2 share an epitope that is distinct from that of 2C6. FIG. 14A demonstrates a plot of scattering intensity (I) against scattering momentum (Q) and statistical fit of theoretical scatter from the DBP-II/2D10$_{scFv}$ crystal structure (blue line) with experimental SAXS profile of the DBP-II/2D10$_{Fab}$ complex (red line) with an $X^2$ of 2.3, FIG. 14B demonstrate a SAXS Pair-wise comparison of 2D10, 2H2, and 2C6, FIG. 14C demonstrates a sequence alignment of heavy and light variable chains of Mab 2D10 and 2H2, FIG. 14D demonstrates a plot of scattering intensity (l) against scattering momentum (Q) and statistical fit of theoretical scatter from the DBP-II/2D10$_{scFv}$ crystal structure (blue line) with experimental SAXS profile of the DBP-II/2H2$_{Fab}$ complex (red line) with an $X^2$ of 1.9. FIG. 14E demonstrates a plot of scattering intensity (l) against scattering momentum (Q) and statistical fit of theoretical scatter from the DBP-II/2D10$_{scFv}$ crystal structure (blue line) with experimental SAXS profile of the DBP-II/2C6$_{Fab}$ complex (red line) with an $X^2$ of 5.1.

FIG. 15A demonstrates Sal-1 DBP wild type. FIG. 15B demonstrates Mutant 6. FIG. 15C demonstrates Mutant 9. FIG. 15D demonstrates Mutant 1. FIG. 15E demonstrates Mutant 12. FIG. 15F demonstrates Mutant 8. FIG. 15G demonstrates results from mAb's 2D10, 2H2, 3D10, and 2C6 that were tested at different molar ratios to 2D10 (0.1×, 1×, and 10×) for the ability to out bind 2D10 binding to DBP.

FIGS. 17A-17B demonstrate an alignment of mutant sequences. An alignment of the sequences of all mutants tested in this study and wild-type Sal-1 DBP with mutated residues highlighted in black and the Sub Domains of DBP (SD1-red, SD2-blue, SD3-green) outlined above the alignment.

(FIG. 18A) BSA, (FIG. 18B) Mutant 2, (FIG. 18C) Mutant 3, (FIG. 18D) Mutant 4, (FIG. 18E) Mutant 5, (FIG. 18F) Mutant 7, (FIG. 18G) Mutant 10, (FIG. 18H) Mutant 11, (FIG. 18I) Mutant 13, (FIG. 18J) Mutant 14, (FIG. 18K) Mutant 15, (FIG. 18L) Mutant 16.

FIGS. 19A-19B demonstrate epitopes of 2D10, 2H2, 2C6 and 3D10 mapped on PvDBP, revealing that the epitopes are broadly conserved. FIG. 19A demonstrates epitopes mapped on the surface of PvDBP with 2D10 in Orange, 2H2 specific residues in Purple, 3D10 in Blue, and 2C6 in Green. FIG. 19B demonstrates sequence of Sal-I DBP-II region with identified polymorphic sites highlighted in red, structurally identified 2D10 in Orange, 2H2 in Purple, 3D10 in Blue, and 2C6 in Green.

(FIG. 21A) DEKnull: mutated immunodominant 'DEK' epitope (36); (FIG. 21B) DEKnull-2: mutated polymorphic residues; (FIG. 21C) DEKnull-3: mutated binding residues; and (FIG. 21D) DEKnull-4: mutated dimerization residues.

FIG. 22 demonstrates the mutated residues in Sal1 to create DEKnull variants. Positions of mutated residues in DEKnull variants with reference to the BPBII-Sal1 (bold) are demonstrated. Conserved residues are represented by a dot (.).

FIG. 23A demonstrates Coomassie-stained SDS-PAGE gel of recombinant DEKnull variants purified by affinity chromatography on Ni+ Sepharose resins. (FIGS. 23B-23D) Differential mobility of refolded recombinant DEKnull-2, DEKnull-3 and DEKnull-4 respectively on SDS-PAGE gel before (−)

and after (+) reduction with DTT, is a simple indicator of presence of disulfide bonds in the refolded antigens. Production of recombinant Sal1 and DEKnull were previously reported (Ntumngia and Adams. 2012. Clin. Vacc. Immunol. 19:30-36).

Figure 24A:
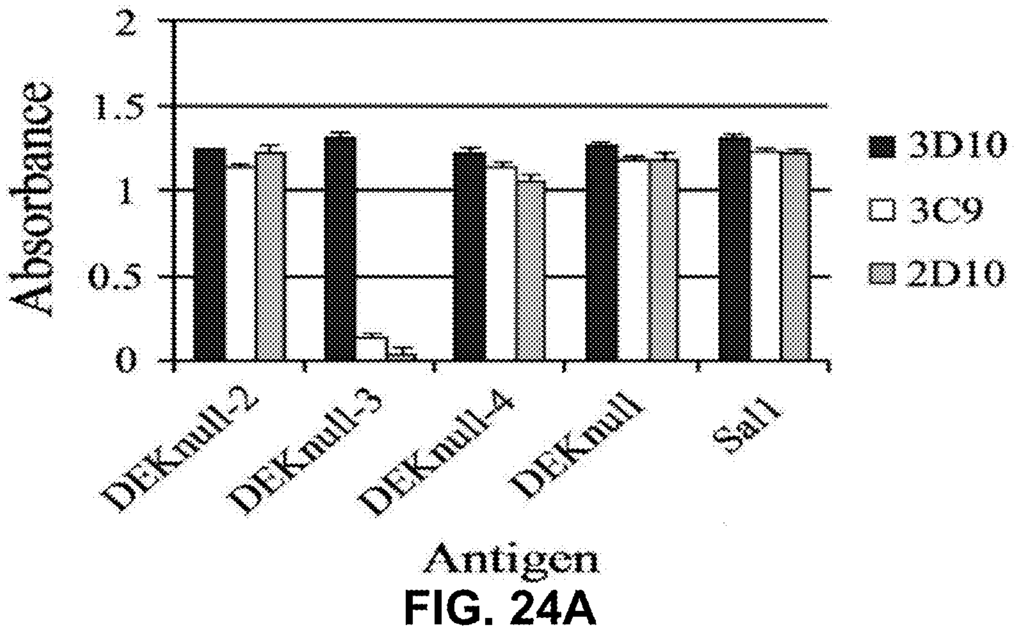
Figure 24B:
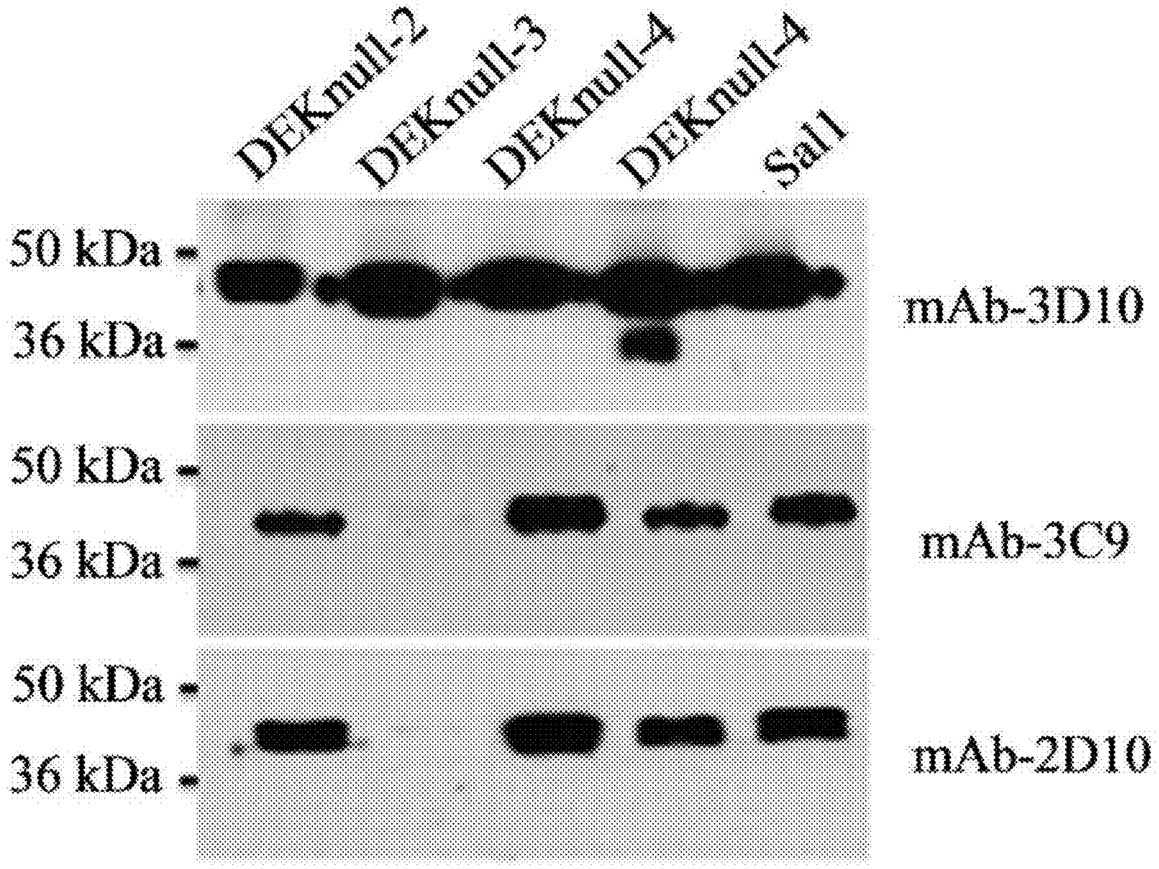

FIGS. 24A-24B show a graph (FIG. 24A) and blot (FIG. 24B) demonstrating the reactivity of recombinant DEKnull antigens with conformational dependent anti-DBPII mAbs-3C9 and 2D10 and nonconformational dependent antibody, mAb-3D10 by (FIG. 24A) ELISA and (FIG. 24B) Western blot analysis. Recombinant Sal1 was used as control antigen. Bars indicate then mean OD values. Error bars indicate ±standard deviation for triplicate wells.

Figure 25:
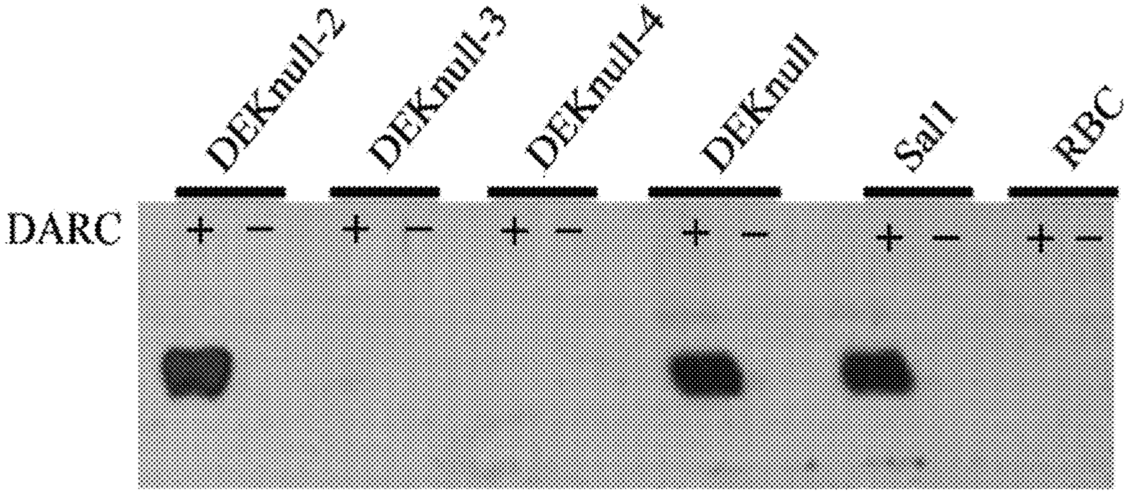
Figures 26A, 26B, 26C, 26D, 26E, 26F, 26G, 26H, 26I, 26J:
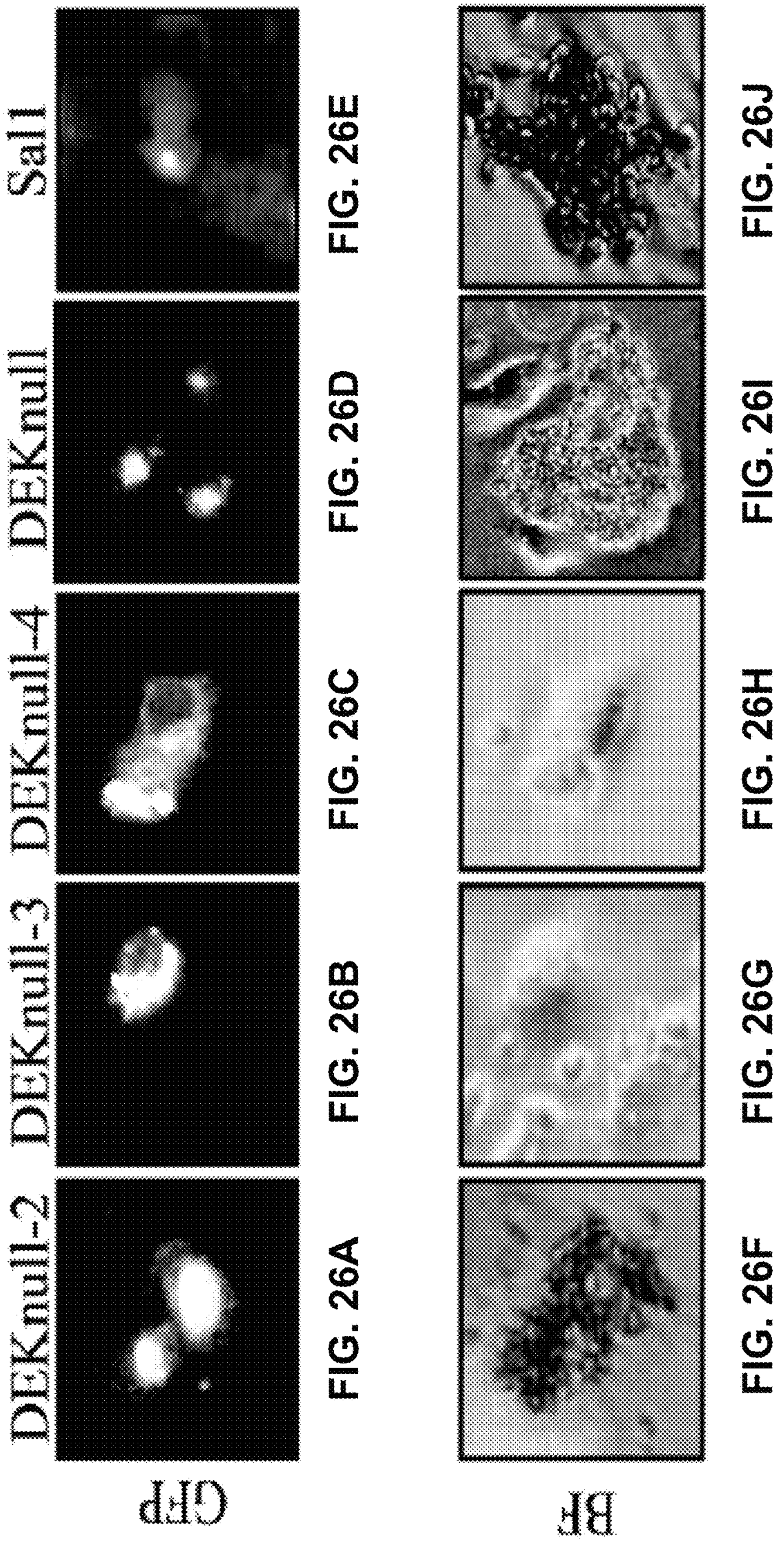

FIG. 25 shows a blot demonstrating a functional analysis of the DEKnull variant antigens. Refolded recombinant DEKnull-2, DEKnull and Sal1 were observed to bind to DARC positive erythrocytes (+) but not to DARC negative erythrocytes (−) while recombinant DEKnull-3 and DEKnull-4 did not bind either. Recombinant Sal1 and DARC positive erythrocytes incubated with PBS alone without any antigen served as control.

FIGS. 26A-26J show images demonstrating COS7 cell surface-expressed Sal1 and DEKnull-2 was observed to bind to DARC positive erythrocytes in the standard in vitro COS7 cell binding assay while DEKnull-3 and -4 did not.

Figures 27A, 27B, 27C, 27D, 27E, 27F, 27G, 27H, 27I, 27J, 27K, 27L, 27M, 27N, 27O:
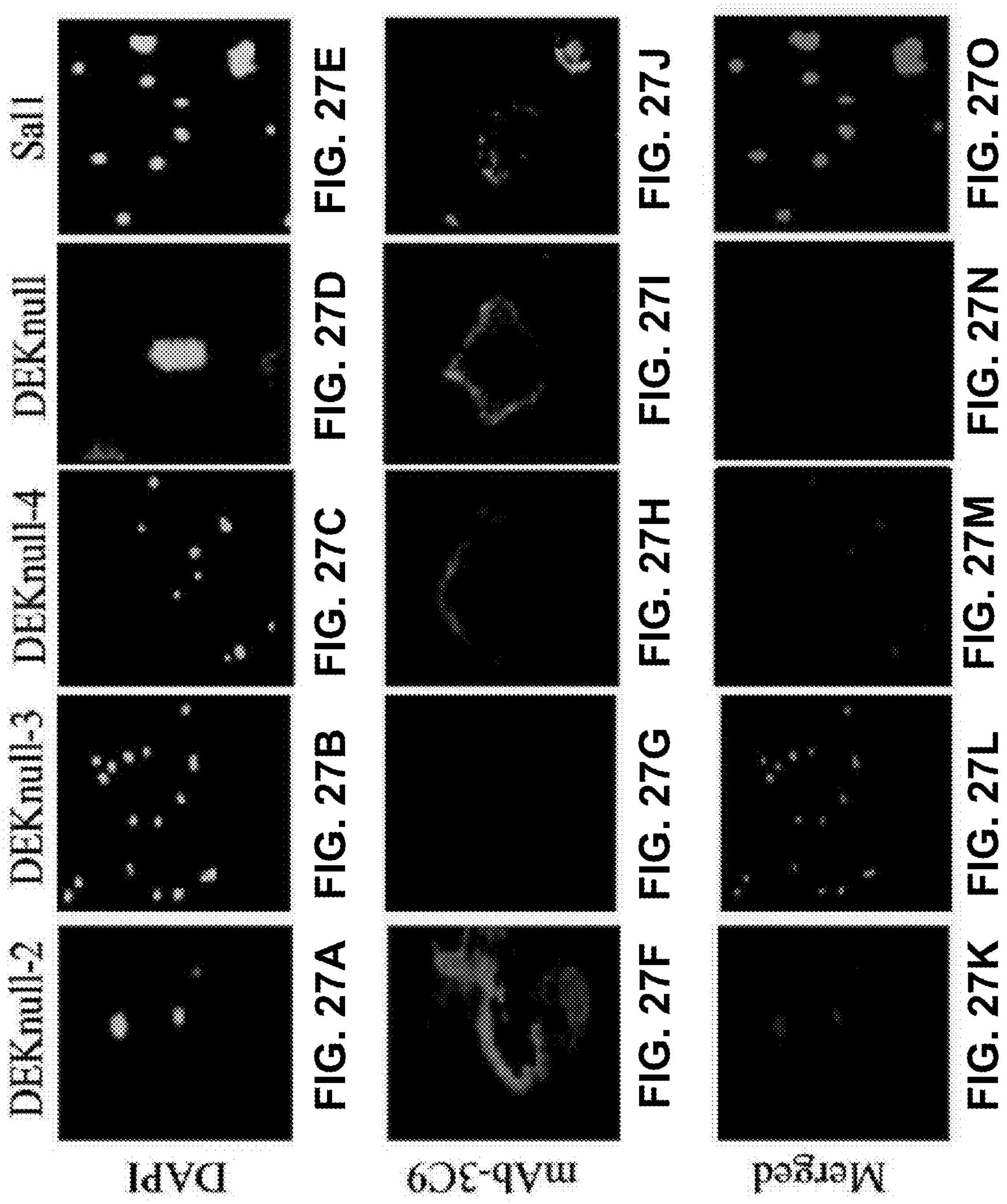

FIGS. 27A-O show IFA images demonstrating cell surface expression of the recombinant DEKnull antigens and native Sal1 on the surface of COS7 cells.

Figure 28A:
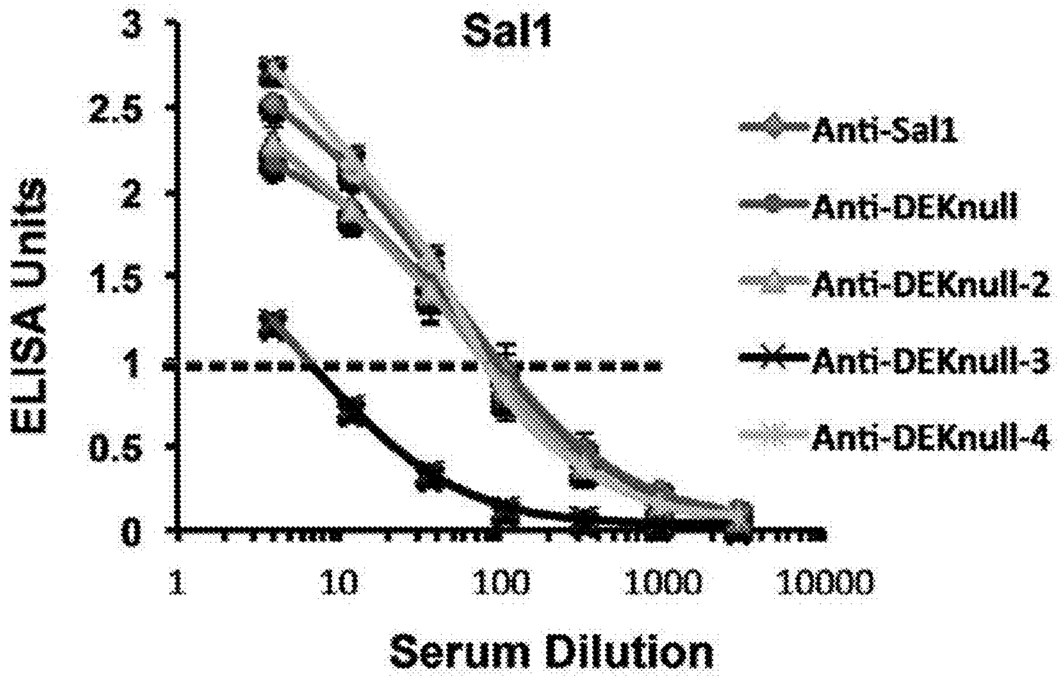
Figure 28B:
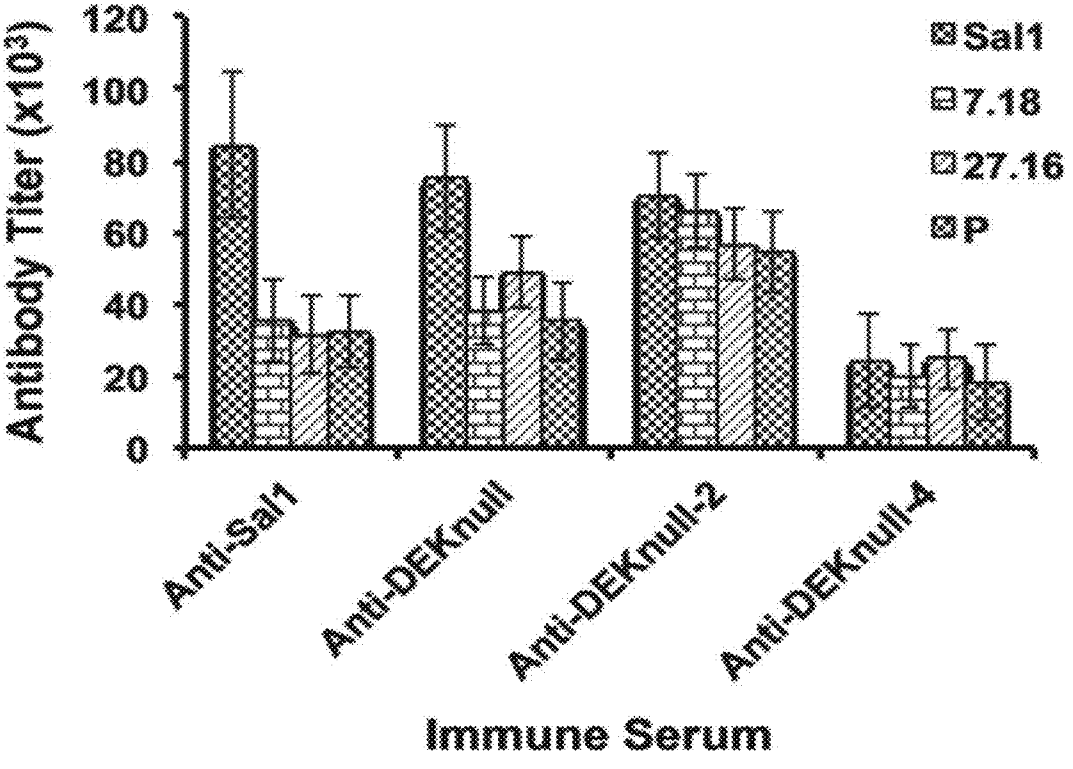
Figure 29A:
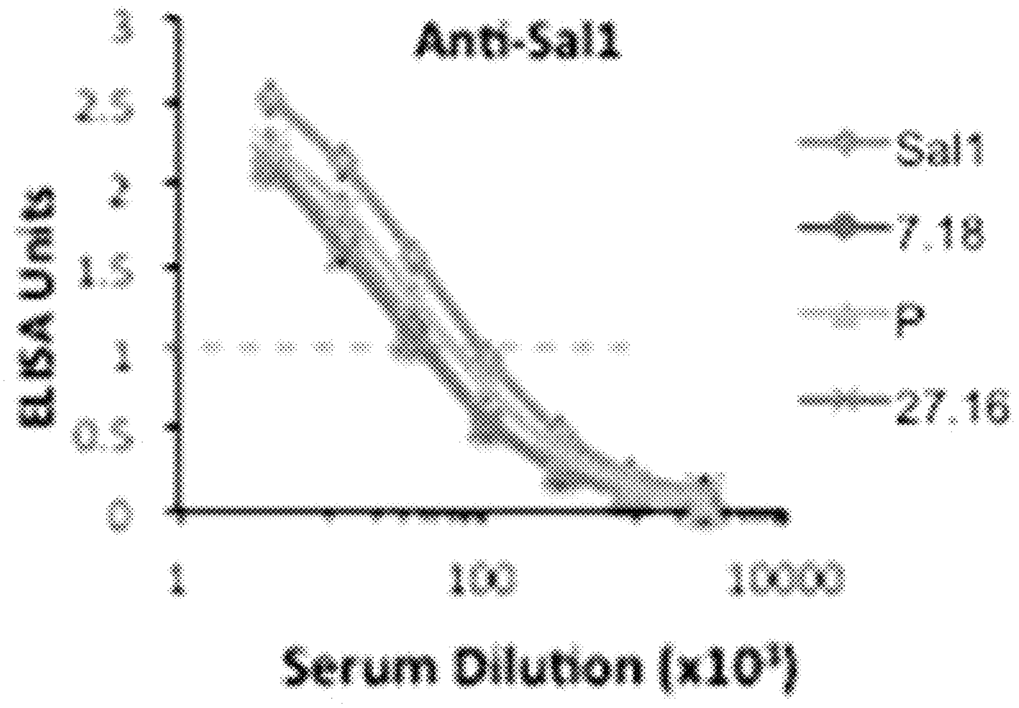
Figure 29B:
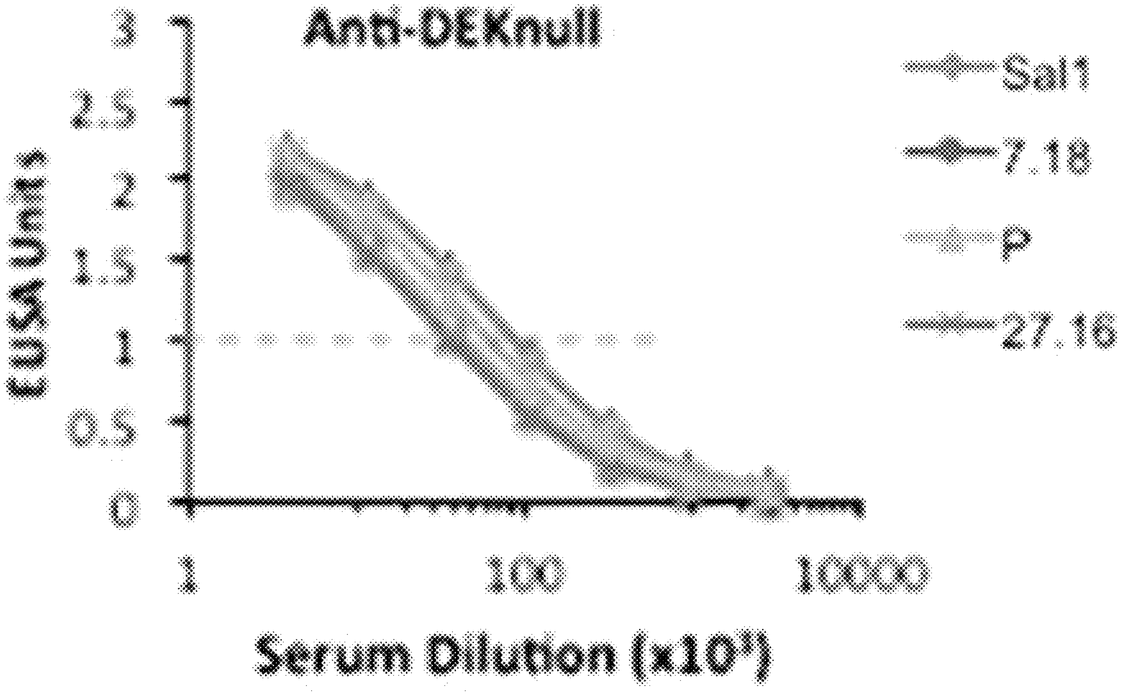
Figure 29C:
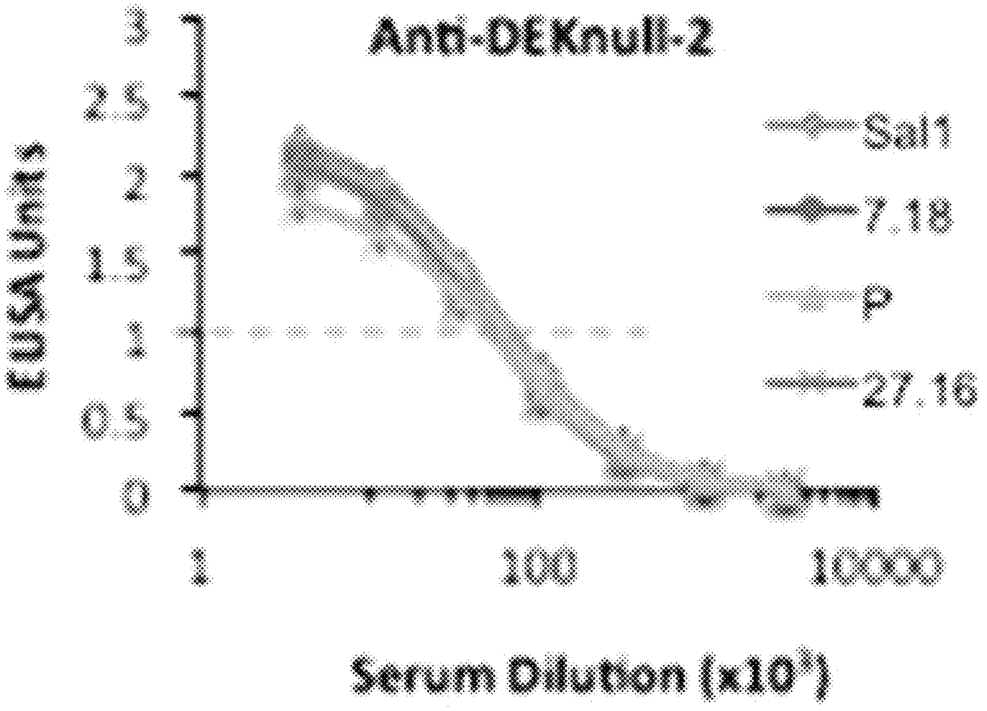
Figure 29D:
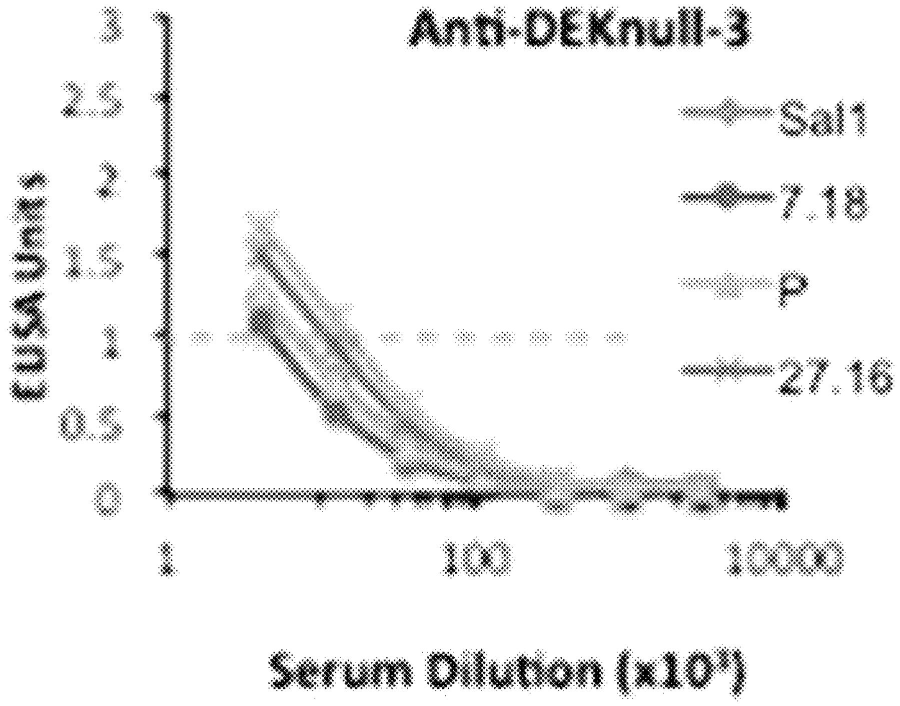
Figure 29E:
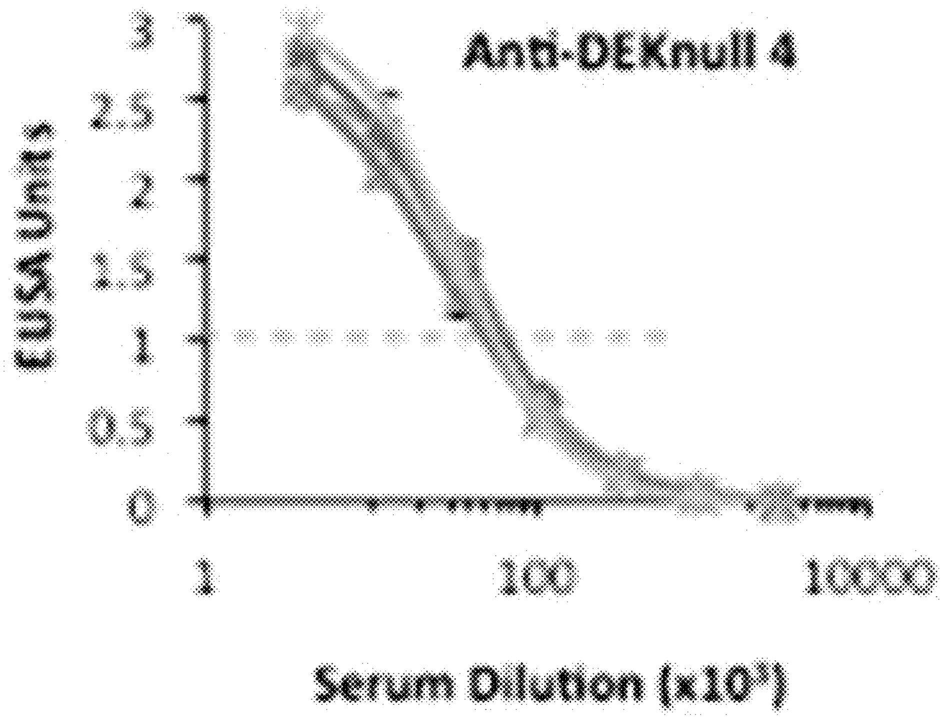

FIGS. 28A-28B show graphs demonstrating anti-DBPII reactivity profiles. Mouse antisera raised against refolded recombinant DEKnull antigens were evaluated in an ELISA by end-point dilution for reactivity with the parent antigen Sal1 (FIG. 28A) and four naturally occurring variant DBPII alleles (FIG. 22). 2 μg/ml of antigen preparations were absorbed onto wells of micro titer plates and allowed to react with different dilutions of antiserum from individual mice. All OD values were converted to ELISA Units (EU) by normalizing against the OD of a standard anti-DBPII monoclonal antibody, mAb-3D10. Each curve represents a 4-parameter logistic regression curve for antisera from each antigen (n=15) against the different alleles (FIG. 28B) An EU=1.0 was used to quantitatively compare the reactivity of the different antibodies to the variant DBPII alleles. Each bar represents the serum dilution at EU=1.0. Error bars represent ±SD.

FIGS. 29A-29E show graphs demonstrating anti-DBPII reactivity profiles. Mouse antisera raised against refolded recombinant DEKnull antigens were evaluated in an ELISA by end-point dilution for reactivity with the homologous antigens and for cross reactivity with variant recombinant DBPII alleles. Recombinant antigens at 2 μg/ml were absorbed on to wells of micro titer plates and allowed to react with different dilutions of antiserum from individual mouse. All OD values were converted to ELISA units (EU) by normalizing against the OD of a standard anti-DBPII antibody, mAb-3D10 (25). Each curve represents a 4-parameter logistic regression for antisera from each antigen (n=15), against the different alleles and error bars represent ±SD. The broken horizontal line represents EU=1.0 used as bases for comparing the reactivity of the different sera.

Figure 30A:
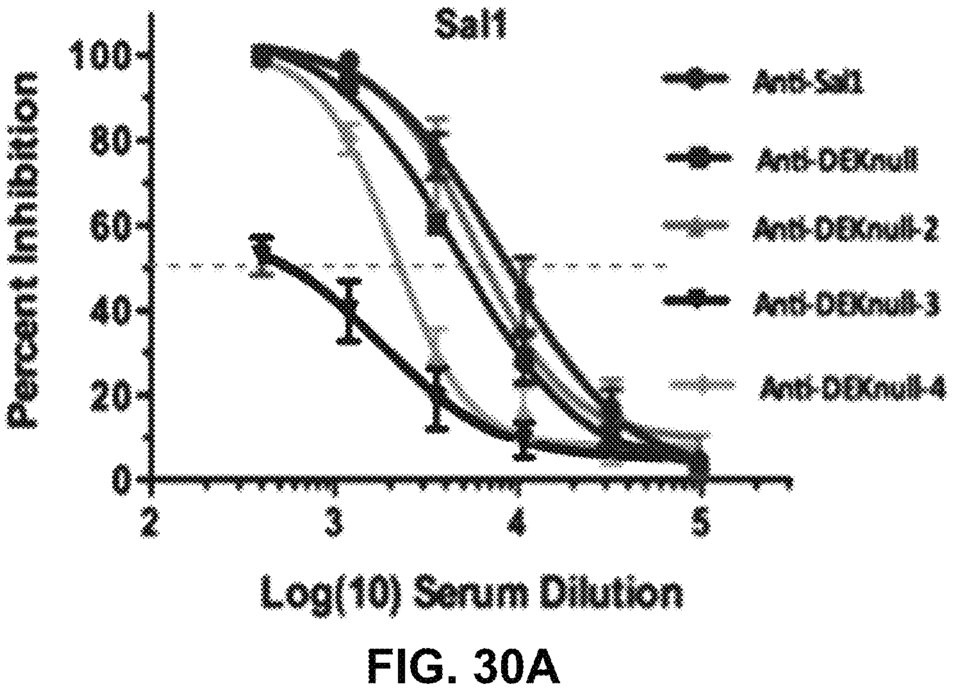
Figure 30B:
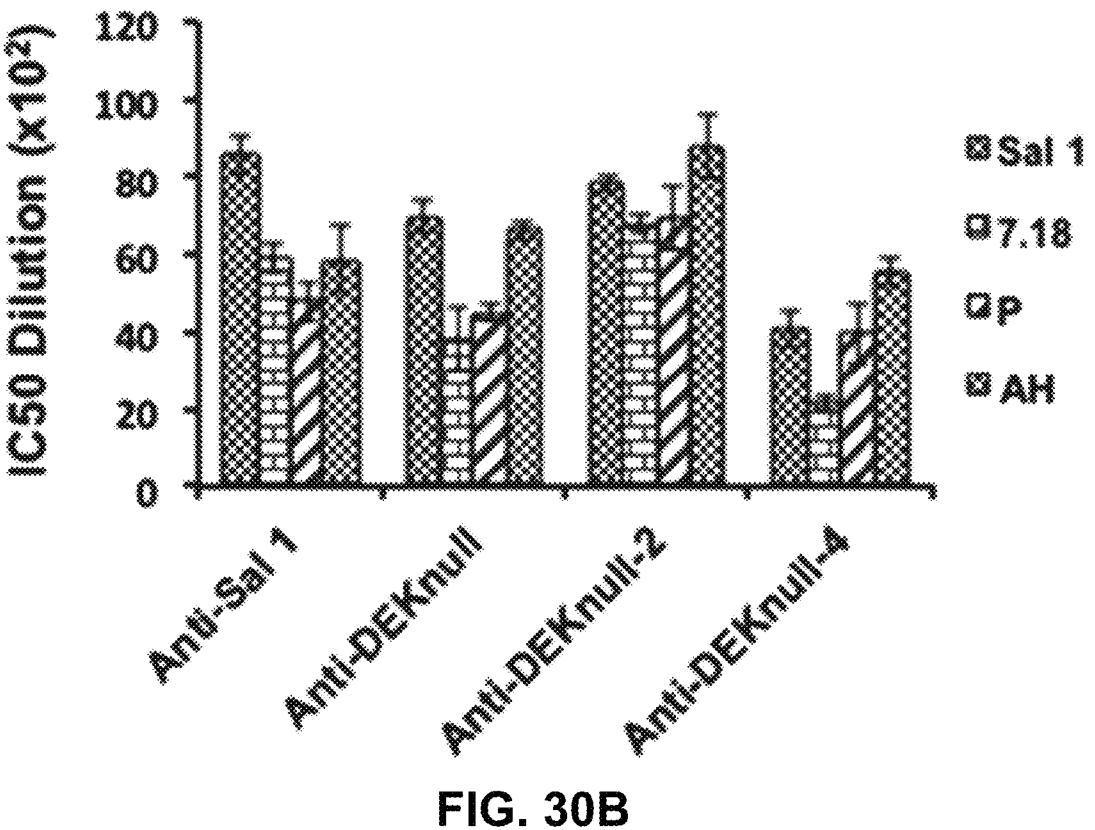
Figure 31A:
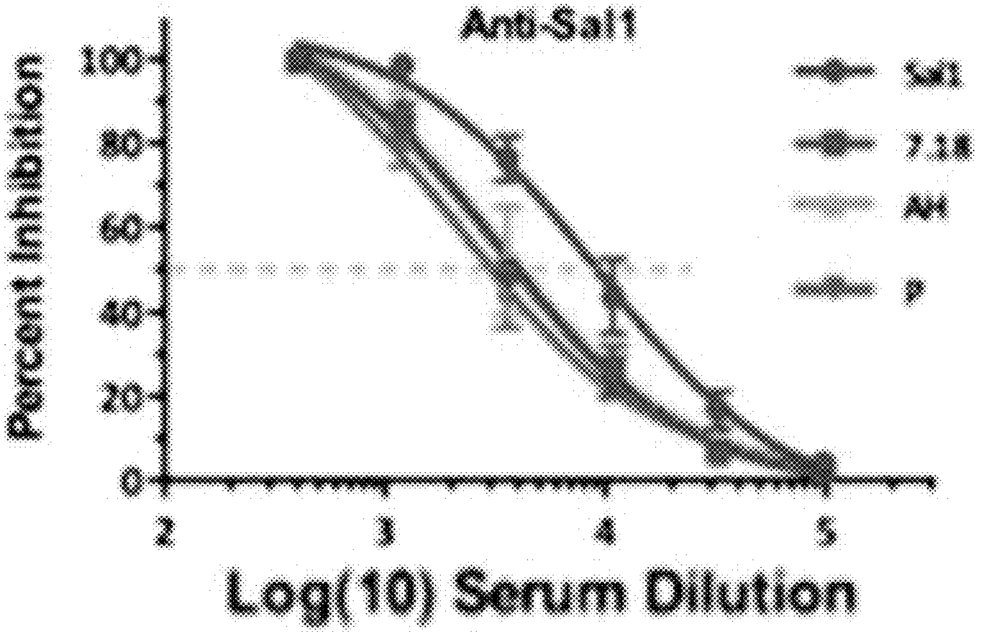
Figure 31B:
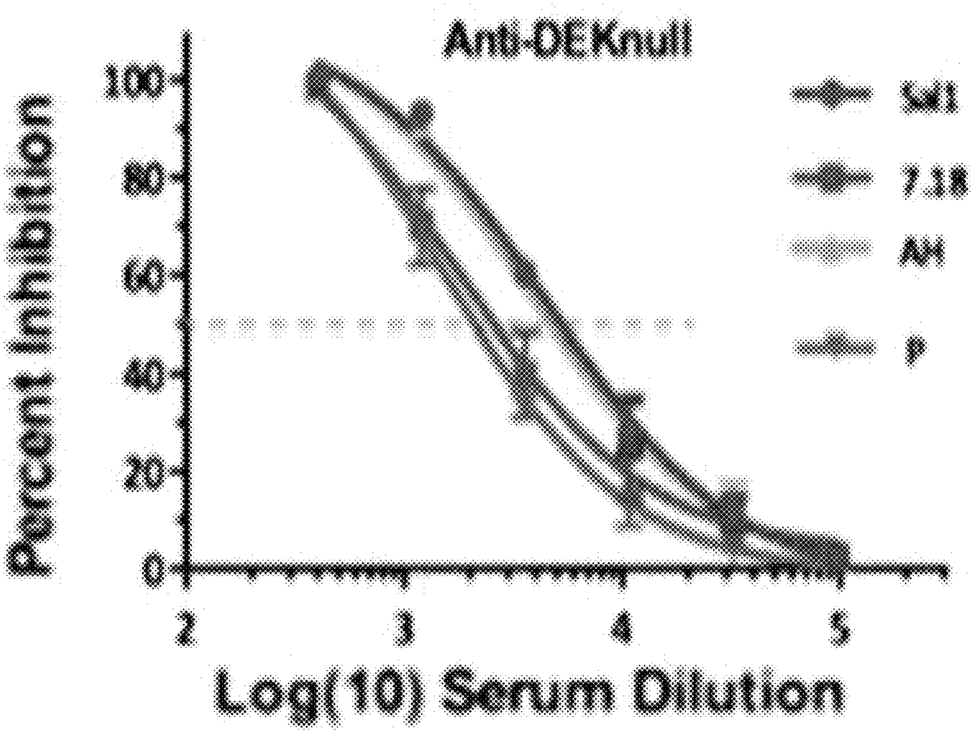
Figure 31C:
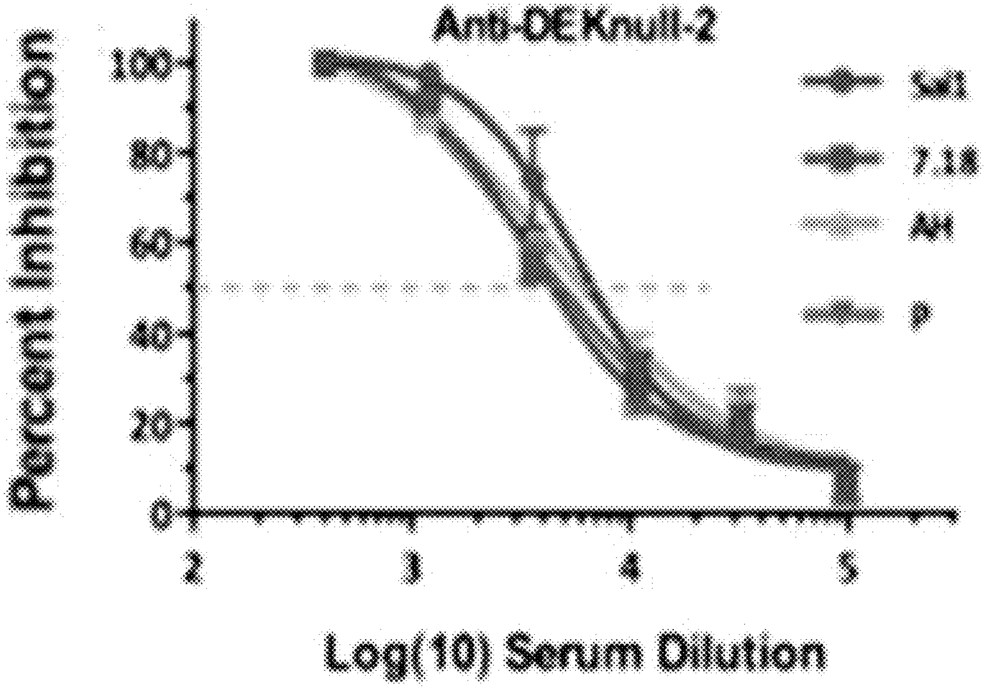
Figure 31D:
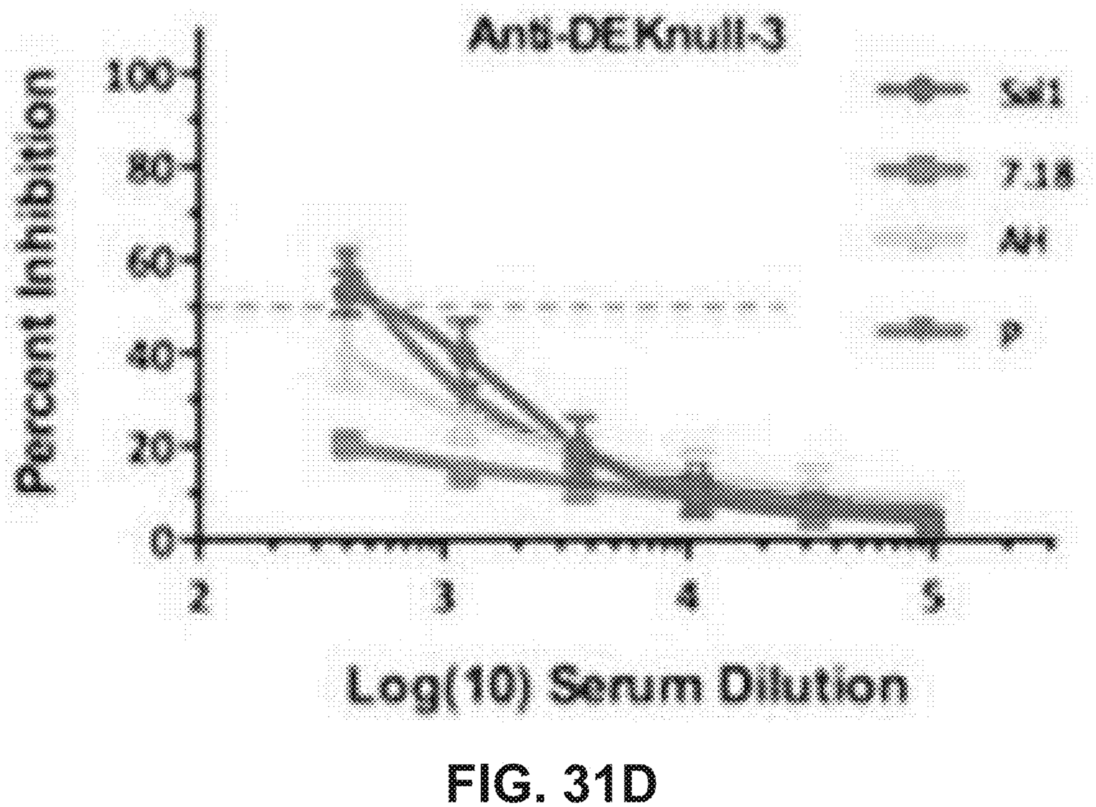
Figure 31E:
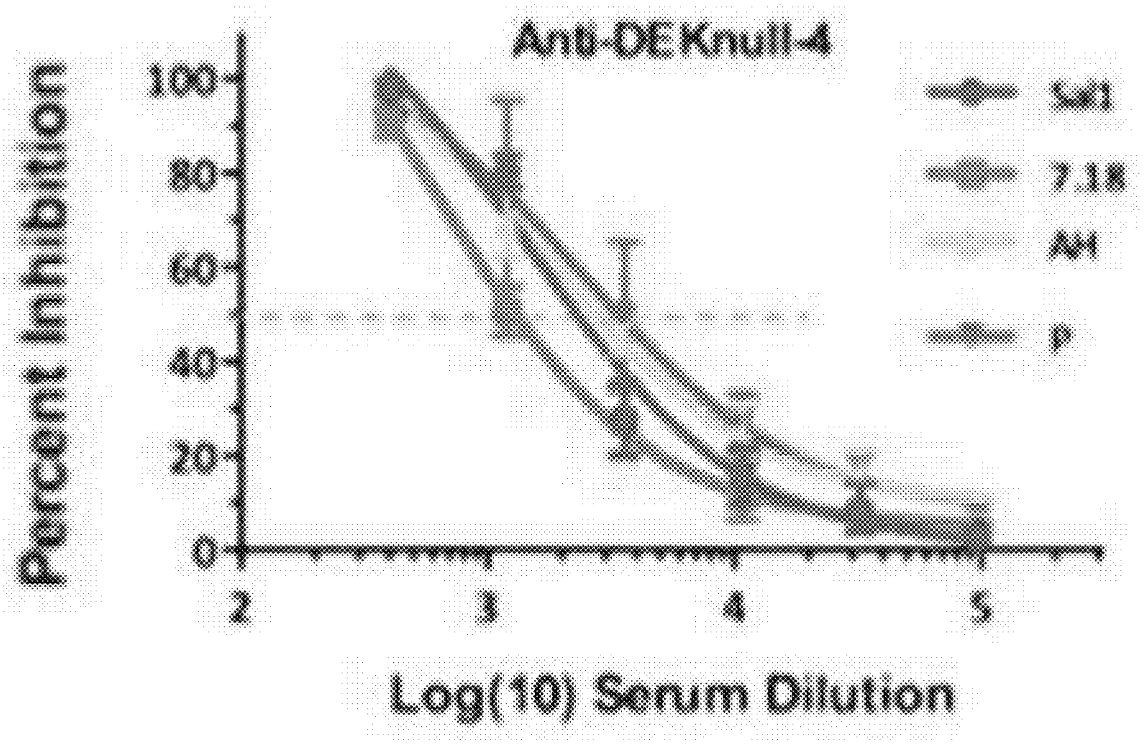

FIGS. 30A-30B show graphs demonstrating inhibition of DBPII binding to DARC on human erythrocytes. (FIG. 30A) Antisera were tested for inhibition of DBPII-Sal1-DARC binding and three other native variant DBPII alleles (FIGS. 31A-31E) by end point dilution. Transfected COS7 cells were incubated with various dilutions of mouse sera prior to addition of human erythrocytes. DBPII-DARC binding was scored by counting rosettes in 30 microscope fields at a magnification of 20×. Percent binding-inhibition was determined relative to a 1:1000 dilution of pooled pre-immune sera used as control. Each curve on the charts represents non-linear regression of two independent experiments, with each dilution tested in triplicate and horizontal broken line shows the 50% inhibition. (FIG. 30B) The IC50 serum dilution was used as bases to quantitatively compare the anti-DBPII inhibitory activity of the different sera against the variant DBPII alleles. Error bars represent ±standard deviation.

FIGS. 31A-31E show graphs demonstrating anti-DBPII inhibitory profile. Transfected COS7 cells expressing variant DBPII alleles were incubated with various dilutions of mouse sera raised against the different recombinant DEKnull antigens prior to addition of human erythrocytes. DBPII-DARC binding was scored by counting rosettes in 30 microscope fields at a magnification of 20×. Percent binding-inhibition was determined relative to a 1:1000 dilution of pooled pre-immune sera used as control. Each curve on the charts represents the non-linear regression of two independent experiments, with each dilution tested in triplicate. Error bars represent ±standard deviation. The horizontal broken line indicates the 50% inhibition.

Figures 32, 33:
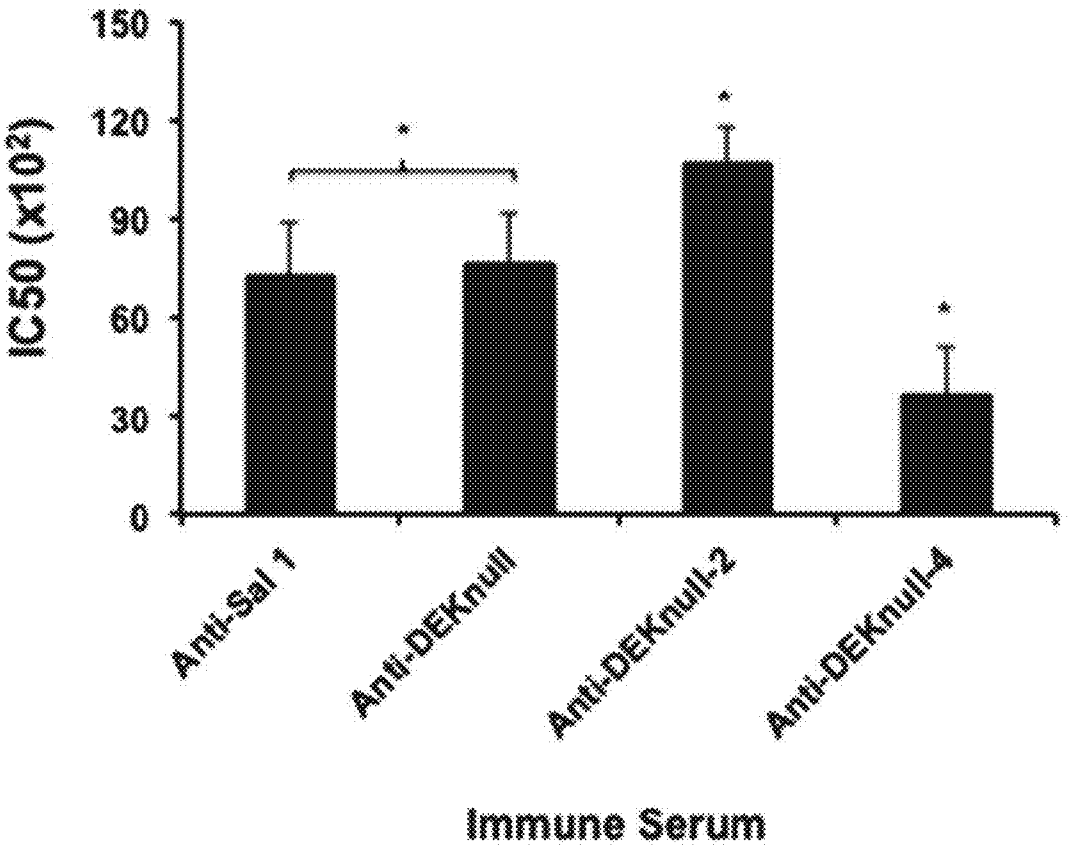

FIG. 32 shows a graph demonstrating multiple comparisons of anti-DBPII binding-inhibitory responses. The overall inhibitory response of each antiserum against all four COS7 cellexpressed DBPII alleles was compared with Dennett's adjustment multiple comparisons, with Sal1 as control. Bars represent the mean IC50 value of each antiserum dilution against all the variant DBPII alleles tested in the COS7 assay. Sera were placed into three groups (DEKnull-2, Sal1 and DEKnull, and DEKnull-4). Asterisk (*) indicates that there is a significant difference in the inhibitory responses between the immune sera from the DEKnull-2 group and the DEKnull/Sal1 group and the DEKnull-4 group (p=0.05).

FIG. 33 shows mAb 2C6 heavy and light chain sequences.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "about," "approximately," and the like, in the context of a numerical value or range means±15% of the numerical value.

As used herein, "animal" can mean a multicellular, eukaryotic organism classified in the kingdom Animalia or Metazoa. "Animal" can include, but is not limited to, mammals. Mammals can include, but are not limited to, rodents, aquatic mammals, domestic animals such as dogs and cats, farm animals such as sheep, pigs, cows, and horses, and humans.

As used herein, "patient" can refer to an animal, such as a mammal, that is receiving, can receive, and/or is intended to receive a treatment and/or prevention as provided herein.

As used herein, "therapeutically effective amount" can refer to the amount of a composition and/or therapy provided herein sufficient to result in the prevention, reduction, mitigation, and/or elimination of one or more symptoms of malaria. The term "therapeutically effective amount" can also refer to the amount of a composition and/or therapy provided herein sufficient to prevent and/or treat an infection, a disease, and/or a symptom thereof caused by an organism of the genus *Plasmodium*, including but not limited to *P. vivax*.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein "biodegradable" generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

The term "hydrophilic", as used herein, can refer to substances that have strongly polar groups that readily interact with water.

The term "hydrophobic", as used herein, can refer to substances that lack an affinity for water; tending to repel and not absorb water as well as not dissolve in or mix with water.

The term "lipophilic", as used herein, can refer to compounds having an affinity for lipids.

The term "amphiphilic", as used herein, can refer to a molecule combining hydrophilic and lipophilic (hydrophobic) properties.

The term "biocompatible", as used herein, can refer to a material that along with any metabolites or degradation products thereof that are generally non-toxic to the recipient and do not cause any significant adverse effects to the recipient. Generally speaking, biocompatible materials are materials which do not elicit a significant inflammatory or immune response when administered to a patient.

As used herein, "cell," "cell line," and "cell culture" can include progeny. It is also understood that all progeny may not be precisely identical in DNA content, due to deliberate or inadvertent mutations. Variant progeny that have the same function or biological property, as screened for in the originally transformed cell, are included.

As used herein, "control" can refer to an alternative subject or sample used in an experiment for comparison purpose and included to minimize or distinguish the effect of variables other than an independent variable.

As used herein, "positive control" can refer to a "control" that is designed to produce the desired result, provided that all reagents are functioning properly and that the experiment is properly conducted.

As used herein, "negative control" can refer to a "control" that is designed to produce no effect or result, provided that all reagents are functioning properly and that the experiment is properly conducted. Other terms that are interchangeable with "negative control" include "sham," "placebo," and "mock."

As used herein, "effective amount" can refer to an amount sufficient to effect beneficial or desired biological, emotional, medical, or clinical response of a cell, tissue, system, animal, or human. An effective amount can be administered in one or more administrations, applications, or dosages. The term also includes within its scope amounts effective to enhance normal physiological function.

The terms "sufficient" and "effective", as used interchangeably herein, can refer to an amount (e.g. mass, volume, dosage, concentration, and/or time period) needed to achieve one or more desired result(s). For example, a therapeutically effective amount refers to an amount needed to achieve one or more therapeutic effects.

As used herein, "expression" can refer to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein, "encode," "encoding," and the like refers to biological relationship between nucleic acids that form codons and the proteins that they translate into.

As used herein, "codon" can refer to a sequence of three DNA or RNA nucleotides that corresponds with a specific amino acid or stop signal during protein synthesis. It will be appreciated that one codon translates into only one amino acid. However, one amino acid can be translated from more than one codon. This phenomena is also known in the art as Codon degeneracy. It will also be appreciated that due to codon degeneracy, where a polypeptide sequence is given, unless specified otherwise, all possible nucleic acid sequences that can encode the polypeptide are contemplated and within the scope of this disclosure.

As used herein, "isolated" means separated from constituents, cellular and otherwise, in which the polynucleotide, peptide, polypeptide, protein, antibody, or fragments thereof, are normally associated with in nature. A non-naturally occurring polynucleotide, peptide, polypeptide, protein, antibody, or fragments thereof, do not require "isolation" to distinguish it from its naturally occurring counterpart.

As used herein, "concentrated" refers to a molecule, including but not limited to a polynucleotide, peptide, polypeptide, protein, antibody, or fragments thereof, that is distinguishable from its naturally occurring counterpart in that the concentration or number of molecules per volume is greater than that of its naturally occurring counterpart.

As used herein, "diluted" refers to a molecule, including but not limited to a polynucleotide, peptide, polypeptide, protein, antibody, or fragments thereof, that is distinguishable from its naturally occurring counterpart in that the concentration or number of molecules per volume is less than that of its naturally occurring counterpart.

As used herein, "separated" refers to the state of being physically divided from the original source or population such that the separated compound, agent, particle, or molecule can no longer be considered part of the original source or population.

As used interchangeably herein, "subject," "individual," or "patient" can refer to a vertebrate organism.

As used herein, "therapeutic" can refer to treating, healing, and/or ameliorating a disease, disorder, condition, side effect, and/or symptom thereof, and/or to decreasing in the rate of advancement of a disease, disorder, condition, side effect, and/or symptom thereof. The term also can include enhancing normal physiological function, palliative treatment, and partial remediation of a disease, disorder, condition, side effect, and/or symptom thereof. The disease, disorder, condition, can be infection with a species of the genus *Plasmodium*, including but not limited to *P. vivax* or a symptom thereof. The disease, disorder, or condition can be malaria or a symptom thereof.

The terms "treating" and "treatment" as used herein refer generally to obtaining a desired pharmacological and/or physiological effect. The effect may be prophylactic in terms of preventing or partially preventing a disease, symptom or condition thereof, such as disease or disorders resulting from infection with a species of the genus *Plasmodium*, including but not limited to *P. vivax* and/or may be therapeutic in terms of a partial or complete cure of a disease, condition, symptom or adverse effect attributed to the disease, disorder, or condition. For example the disease or disorder can be malaria. The term "treatment" as used herein can cover any treatment of Malaria and/or infection with a species of the genus *Plasmodium*, including but not limited to *P. vivax* in a mammal, particularly a human, and can include: (a) preventing the disease from occurring in a subject which may be predisposed to the disease but has not yet been diagnosed as having it; (b) inhibiting the disease, i.e., arresting its development; or (c) relieving the disease, i.e., mitigating or ameliorating the disease and/or its symptoms or conditions. The term "treatment" as used herein can refer to both therapeutic treatment and prophylactic or preventative measures. Those in need of treatment include those already with the disorder as well as those in which the disorder is to be prevented.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "pharmaceutically acceptable salt" refers to any acid or base addition salt whose counter-ions are non-toxic to the subject to which they are administered in pharmaceutical doses of the salts.

As used herein, "preventative" and "prevent" refers to hindering or stopping a disease or condition before it occurs, even if undiagnosed, or while the disease or condition is still in the sub-clinical phase.

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "tangible medium of expression" refers to a medium that is physically tangible and is not a mere abstract thought or an unrecorded spoken word. Tangible medium of expression includes, but is not limited to, words on a cellulosic or plastic material or data stored on a suitable device such as a flash memory or CD-ROM.

As used herein, "chemotherapeutic agent" or "chemotherapeutic" refer to a therapeutic agent utilized to prevent or treat cancer.

As used herein, "matrix" refers to a material, in which one or more specialized structures, molecules, or compositions, are embedded.

As used herein, "aptamer" refers to single-stranded DNA or RNA molecules that can bind to pre-selected targets including proteins with high affinity and specificity. Their specificity and characteristics are not directly determined by their primary sequence, but instead by their tertiary structure.

As used herein, "immunomodulator," refers to an agent, such as a therapeutic agent, which is capable of modulating or regulating one or more immune function or response.

As used herein, "antibody" refers to a glycoprotein comprising at least two heavy (H) chains and two light (L) chains inter-connected by disulfide bonds, or an antigen binding portion thereof. Each heavy chain is comprised of a heavy chain variable region (abbreviated herein as VH) and a heavy chain constant region. Each light chain is comprised of a light chain variable region and a light chain constant region. The VH and VL regions retain the binding specificity to the antigen and can be further subdivided into regions of hypervariability, termed complementarity determining regions (CDR). The CDRs are interspersed with regions that are more conserved, termed framework regions (FR). Each VH and VL is composed of three CDRs and four framework regions, arranged from amino-terminus to carboxy-terminus in the following order: FR1, CDR1, FR2, CDR2, FR3, CDR3, and FR4. The variable regions of the heavy and light chains contain a binding domain that interacts with an antigen. The antibody can be monoclonal, polyclonal, or a recombinant antibody, and can be prepared by techniques that are well known in the art such as immunization of a host and collection of sera (polyclonal) or by preparing continuous hybrid cell lines and collecting the secreted protein (monoclonal), or by cloning and expressing nucleotide sequences, or mutagenized versions thereof, coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b and IgG3, IgM, IgY, etc. Fragments thereof may include Fab, Fv and $F(ab')_2$, Fab', scFv, and the like. In addition, aggregates, polymers, and conjugates of immunoglobulins or their fragments can be used where appropriate so long as binding affinity for a particular molecule is maintained.

As used herein, "protein" as used herein can refer to a molecule composed of one or more chains of amino acids in a specific order. The term protein is used interchangeable with "polypeptide." The order is determined by the base sequence of nucleotides in the gene coding for the protein. Proteins are required for the structure, function, and regulation of the body's cells, tissues, and organs. Each protein has a unique function.

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used herein, "nucleic acid" and "polynucleotide" generally refer to a string of at least two base-sugar-phosphate combinations and refers to, among others, single-and double-stranded DNA, DNA that is a mixture of single-and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids may contain other types of backbones, but contain the same bases. Thus, DNAs or RNAs with backbones modified for stability or for other reasons are "nucleic acids" or "polynucleotide" as that term is intended herein.

As used herein, "deoxyribonucleic acid (DNA)" and "ribonucleic acid (RNA)" generally refer to any polyribonucleotide or polydeoxribonucleotide, which may be unmodified RNA or DNA or modified RNA or DNA. RNA may be in the form of a tRNA (transfer RNA), snRNA (small nuclear RNA), rRNA (ribosomal RNA), mRNA (messenger RNA), anti-sense RNA, RNAi (RNA interference construct), siRNA (short interfering RNA), or ribozymes.

As used herein, "nucleic acid sequence" and "oligonucleotide" also encompasses a nucleic acid and polynucleotide as defined above.

As used herein, "DNA molecule" includes nucleic acids/polynucleotides that are made of DNA.

As used herein, "gene" can refer to a hereditary unit corresponding to a sequence of DNA that occupies a specific location on a chromosome and that contains the genetic instruction for a characteristic(s) or trait(s) in an organism. "Genes" do not necessarily have to be translated into proteins can also produce only RNA products.

As used herein, the term "recombinant" generally refers to a non-naturally occurring nucleic acid, nucleic acid construct, or polypeptide. Such non-naturally occurring nucleic acids may include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a fusion protein (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g., a nucleic acid and a constitutive promoter), etc.). Recombinant also refers to the polypeptide encoded by the recombinant nucleic acid. Non-naturally occurring nucleic acids or polypeptides include nucleic acids and polypeptides modified by man.

As used herein, "variant" refers to a polypeptide that differs from a reference polypeptide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally. "Variant" can include functional and structural variants.

As used herein, “identity,” is a relationship between two or more polypeptide sequences, as determined by comparing the sequences. In the art, “identity” also refers to the degree of sequence relatedness between polypeptide as determined by the match between strings of such sequences. “Identity” can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, N.J., 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure.

As used herein, “plasmid” as used herein refers to a non-chromosomal double-stranded DNA sequence including an intact “replicon” such that the plasmid is replicated in a host cell.

As used herein, the term “vector” or is used in reference to a vehicle used to introduce an exogenous nucleic acid sequence into a cell. A vector may include a DNA molecule, linear or circular (e.g. plasmids), which includes a segment encoding a polypeptide of interest operatively linked to additional segments that provide for its transcription and translation upon introduction into a host cell or host cell organelles. Such additional segments may include promoter and terminator sequences, and may also include one or more origins of replication, one or more selectable markers, an enhancer, a polyadenylation signal, etc. Expression vectors are generally derived from yeast or bacterial genomic or plasmid DNA, or viral DNA, or may contain elements of both.

As used herein, “wild-type” can refer to the typical form of an organism, variety, strain, gene, protein, or characteristic as it occurs in nature, as distinguished from mutant forms that may result from selective breeding or transformation with a transgene.

As used herein, “purified” or “purify” can be used in reference to a nucleic acid sequence, peptide, or polypeptide that has increased purity relative to the natural environment.

As used herein, “dose,” “unit dose,” or “dosage” refers to physically discrete units suitable for use in a subject, each unit containing a predetermined quantity of the synthetic *P. vivax* antigen and/or antibody, a composition containing the synthetic *P. vivax* antigen and/or antibody, and/or a pharmaceutical formulation thereof calculated to produce the desired response or responses in association with its administration.

As used herein, “specific binding partner” or “binding partner” is a compound or molecule to which a second compound or molecule binds with a higher affinity than all other molecules or compounds.

As used herein, “specifically binds” or “specific binding” refers to binding that occurs between such paired species such as enzyme/substrate, receptor/agonist or antagonist, antibody/antigen, lectin/carbohydrate, oligo DNA primers/DNA, enzyme or protein/DNA, and/or RNA molecule to other nucleic acid (DNA or RNA) or amino acid, which may be mediated by covalent or non-covalent interactions or a combination of covalent and non-covalent interactions. When the interaction of the two species produces a non-covalently bound complex, the binding that occurs is typically electrostatic, hydrogen-bonding, or the result of lipophilic interactions. Accordingly, “specific binding” occurs between a paired species where there is interaction between the two which produces a bound complex having the characteristics of an antibody/antigen, enzyme/substrate, DNA/DNA, DNA/RNA, DNA/protein, RNA/protein, RNA/amino acid, receptor/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins.

As used herein, “anti-infective” refers to compounds or molecules that can either kill an infectious agent or inhibit it from spreading. Anti-infectives include, but are not limited to, antibiotics, antibacterials, antifungals, antivirals, and antiprotozoans.

As used herein “induces,” “inducing,” or “induced” refers to activating or stimulating a process or pathway within a cell, such as endocytosis, secretion, and exocytosis.

As used herein, “derivative” refers to any compound having the same or a similar core structure to the compound but having at least one structural difference, including substituting, deleting, and/or adding one or more atoms or functional groups. The term “derivative” does not mean that the derivative is synthesized from the parent compound either as a starting material or intermediate, although this may be the case. The term “derivative” can include prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form methyl and ethyl esters, or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides. “Derivatives” also includes extensions of the replacement of the cyclopentane ring with saturated or unsaturated cyclohexane or other more complex, e.g., nitrogen-containing rings, and extensions of these rings with side various groups.

As used herein, “synergistic effect,” “synergism,” or “synergy” refers to an effect arising between two or more molecules, compounds, substances, factors, or compositions that is greater than or different from the sum of their individual effects.

As used herein, “additive effect” refers to an effect arising between two or more molecules, compounds, substances, factors, or compositions that is equal to or the same as the sum of their individual effects.

The term "immune response" can refer to the reaction of the molecules, components, pathways, organs, fluids and/or cells of the body to the presence of a substance that is foreign or recognized by the body as foreign to the body.

The phrase "modulate or modulation of the immune response" can refer to change in the immune response that results from the introduction of a composition, vaccine, or other compound or formulation described herein in a recipient subject as compared to a suitable control.

As used herein, the term "vaccine" can refer to a compound, molecule, compositions, and formulations that are capable of inducing an immune response in a subject. The term "vaccine" can also be used to refer to a compound, molecule, compositions, and formulations that are capable of providing protective immunity against an organism. The vaccine may provide protection against a same (i.e. homologous) or different (i.e. heterologous) strain of an organism. The vaccine can be capable of providing protection against homologous and heterologous species, variants or strains.

As used herein, the term "antigen" refers to a molecule with one or more epitopes that stimulate a host's immune system to make a secretory, humoral and/or cellular antigen-specific response, or to a DNA molecule that is capable of producing such an antigen in a vertebrate.

The term is also used interchangeably with "immunogen." For example, a specific antigen can be complete protein, portions of a protein, peptides, fusion proteins, glycosylated proteins and combinations thereof.

As used herein, the term "immunization" can refer to the process of inducing a continuing protective level of antibody and/or cellular immune response which is directed against a strain of a species of the genus *Plasmodium*, including a *P. vivax*, or antigen thereof, either before or after exposure of the subject to *P. vivax*.

As used herein, "administering" can refer to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, by catheters, stents or via an implanted reservoir or other device that administers, either actively or passively (e.g. by diffusion) a composition the perivascular space and adventitia. The term "parenteral" can include subcutaneous, intravenous, intramuscular, intra-articular, intra-synovial, intrasternal, intrathecal, intrahepatic, intralesional, and intracranial injections or infusion techniques.

As used herein, "adjuvant" can refer to an additional compound, composition, or ingredient that can facilitate stimulation an immune response in addition to the main antigen of a composition, formulation, or vaccine. Generally, an adjuvant can increase the immune response of an antigen as compared to the antigen alone. This can improve and/or facilitate any protective immunity developed in the recipient subject in response to the antigen. "Adjuvant" as used herein can refer to a component that potentiates the immune responses to an antigen and/or modulates it towards the desired immune response(s).

As used herein, "promoter" includes all sequences capable of driving transcription of a gene. In particular, the term "promoter" as used herein can refer to a DNA sequence generally described as the 5' regulator region of a gene, located proximal to the start codon. The transcription of an adjacent gene sequence is initiated at the promoter region. The term "promoter" also includes fragments of a promoter that are functional in initiating transcription of the gene. The term "promoter" can encompass constitutive promoters and inducible promoters.

The term "operatively linked" as used herein can refer to the association of nucleic acid sequences on a single nucleic acid fragment so that the function of one is regulated by the other. For example, a promoter is operatively linked with a coding sequence when it is capable of regulating the expression of that coding sequence (i.e., the coding sequence is under the transcriptional control of the promoter). Coding sequences can be operatively linked to regulatory sequences in a sense or antisense orientation. In one example, the complementary RNA regions can be operatively linked, either directly or indirectly, 5' to the target mRNA, or 3' to the target mRNA, or within the target mRNA, or a first complementary region is 5' and its complement is 3' to the target mRNA. The term "operatively linked" as used herein can also refer to the direct or indirect linkage of any two nucleic acid sequences on a singly nucleic acid fragment such that they are indirectly or directly physically connected on the same nucleic acid fragment. The term "operatively linked" as used herein can also refer to the insertion of a nucleic acid within the 5' and 3' end of another nucleic or the direct coupling of a nucleic acid to the 5' or 3' end of another nucleic acid.

Unless otherwise defined herein, all technical and scientific terms used herein have the same meaning as commonly understood by one of ordinary skill in the art.

Discussion

Malaria is widespread vector-borne disease that causes massive mortality and morbidity worldwide. *Plasmodium vivax* is an often neglected causative agent of human malaria, one whose social and economic burden is severely underestimated (Carlton et al., 2011). More people are at risk from *P. vivax* than *P. falciparum*, with large disease epicenters in poor regions of Southeast Asia and Central and South America (Guerra et al., 2010; Price et al., 2007). Recent studies show comparable mortality rates between that of *P. vivax* and *P. falciparum*, and frequent clinical manifestations of debilitating symptoms result in high morbidity—both of which place tremendous burdens on the healthcare infrastructure in the billions of United States dollars annually (Guerra et al., 2010; Price et al., 2007). Similarly, the clinical sequela from *P. vivax* malaria imparts a tremendous hidden cost in the form of decreased economic productivity and standard of living (Price et al., 2007). It is easy to envision that *P. vivax* malaria continuously traps affected countries in an inescapable cycle of poverty (Carlton et al., 2011). Effective control methods for *P. vivax* malaria are desperately needed so that these immeasurable costs can be recovered. Vaccines are amongst the leading avenues of intervention because they are cost-effective and efficient, and individuals living in regions with *P. vivax* develop naturally acquired humoral immunity that correlate with results from in vitro functional assays (Grimberg et al., 2007; King et al., 2008; Ntumngia et al., 2014).

Of the five malaria species to plague humans, *P. vivax* has the most widespread distribution. In particular, *P. vivax* is the second most prevalent cause of human malaria and is the most widely distributed leaving about 40% of the world's population at risk. Although *vivax* malaria is historically called 'benign tertian malaria' there have been increasing reports of clinical severity with emerging virulent forms of the parasite, recurrent clinical episodes due to reactivation of the dormant forms in the liver, and widespread drug resistance, which potentially includes strains with low sensitivity to primaquine, the only drug against relapse, or in people with a poor ability to metabolize the drug to its active form. Therefore, there is an urgent need to develop new therapies and preventatives, including vaccines, to control and prevent *vivax* malaria.

With that said, described herein are antibodies and antigens that can be used as therapies and/or preventatives for *P. vivax* infection, including malaria. Also provided herein are methods of making and using the antibodies and antigens provided herein. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Synthetic P. *Vivax* Antigens and Antibodies

Malaria can be caused by species of *Plasmodium* including *P. falciparum*, which is associated with a high mortality and *P. vivax*, which is currently associated with a high morbidity although more virulent strains are emerging. The *Plasmodium* parasites are transmitted by Anopheline mosquito vectors. *P. vivax* has cell surface proteins that facilitate the invasion and infection of a host. Duffy Binding Protein (DBP) is one such cell surface protein and is included in the Erythrocyte Binding Ligand (EBL) invasion protein family. DBP binds to the Duffy Antigen Receptor for Chemokines (DARC) on host reticulocytes through a conserved cysteine-rich Duffy Binding-Like (DBL) domain, which is also referred to as region II (DBP-II). The interaction between DBP-II and DARC plays a major role in establishing clinical symptomatic *P. vivax* invasion and infection. In most circumstances, *P. vivax* merozoites almost exclusively use DARC as a receptor to invade reticulocytes.

DBP-II engages DARC in a stepwise fashion that involves dimerization with the host receptor reminiscent of PfEBA-175, which is another EBL-family member present in *P. falciparum*. During *P. vivax* invasion, DBP-II first binds to a single DARC molecule and dimerizes to form a heterotrimer. The heterotrimer then matures into a final heterotetramer of a 2:2 complex of DBP-II and DARC. DBP-II is a three sub-domain protein. Subdomain 2 (SD2) contribute residues that facilitate dimerization and receptor binding. Antibodies that engage the dimer interface and/or receptor binding residues of DBL domains can be potently neutralizing as they interfere with and/or block the ability for the DBP and DARC to bind, dimerize, and mature into a final heterotetramer. Although there have been efforts to develop therapies and preventatives based on DBP, its polymorphic nature across several alleles and the presence of multiple strains in endemic regions present unique challenges (Ntumngia et al., 2012). These factors often result in strain-specific protection rather than strain-transcending immunity which leave individuals susceptible to continued infection and disease (Chootong et al., 2010; King et al., 2008; Ntumngia et al., 2012), a problem seen with other polymorphic antigens such as *P. falciparum* AMA-1 (Dutta et al., 2013).

Crystal structure analysis of *P.vivax* DBP (PvDBP) and the ligand domains of its *P. falciparum* homolog PfEBA175 that the central region of PvDBPII is important for dimerization and is the most polymorphic region of the protein, which is consistent with high immune selection pressure. Therefore, the polymorphic nature of the central region of PvDBPII results in natural immunity that is often strain-specific and short-lived, a potential challenge to developing a vaccine since this variation contributes to strain-specificity in naturally-acquired immunity. Further, the epitopes of broadly-neutralizing versus non-protective antibodies are not known, and there is only a limited understanding of the structure of DBP bound to its receptor DARC. These drawbacks have limited the development and efficacy of DBP-based therapies and preventatives.

Provided herein are synthetic *P. vivax* antigens that can stimulate antibody production within a subject. The antibodies produced by the subject in response to the synthetic *P. vivax* antigen can specifically bind and/or otherwise interfere with binding of DBP to DARC and thus can be neutralizing to *P. vivax* invasion and/or infection. Also provided herein are monoclonal antibodies that can specifically bind one or more of the synthetic *P. vivax* antigen. In embodiments, the synthetic antigens can overcome the issues related to strain specific immunity and can provide broad protection against various strains of *P. vivax*.

Synthetic P. *Vivax* Antigens

Provided herein are P. *Vivax* synthetic antigens and nucleic acids encoding the synthetic peptide antigens. In embodiments, the *P. vivax* synthetic antigen can include or be composed entirely of a mutated DBP polypeptide (where the base DPB polypeptide is SEQ ID NO: 1) or fragment of at least 10 amino acids thereof. The mutated DBP polypeptide can include one or more of the following mutations, where the mutations are referenced as to SEQ ID NO.: 1 and wherein the first residue of SEQ ID NO: 1 corresponds to residue 233 of the DBP: V299T, N300A, N301T, T302A, D303T, T304S, N305A, F306A, R308A, F312A, L315A, L317A, K318A, R319A, K320T, L321S, 1322A, 1322T, Y323A, V327S, L333T, N336,T, N336A, N337A, Y338T, R339A, Y340A, Y340T, N341S, K342T, K342A, D343A, F344A, F344T, D347A, 1348A, R349T, Y369T, K371A, E374A, N375T, D384A, E385A. K386T, Q389A, R390T, K392S, W395T, N396S, N396A, E397T, Q401T, Y408A, S409A, V410S, V410A, K411T, K412A, R413A, R413S, L414S, L414A, K415A, G416T, N417T, N417S, F418A, 1419A, W420T, 1421S, 1421A, C422A, L424A, Q433T, Y435A, R436A, W437S, R439A, E440T, W441S, G442A, D444A, Y445T, V446S, S447A, Q454T, T467A, K492A, 1503T, V505A, V511A, and G515S.

In embodiments, the *P. vivax* synthetic antigen can include or be composed entirely of a mutated DBP polypeptide variant (where the base DPB polypeptide variant is SEQ ID NO: 2 or fragment of at least 10 amino acids thereof. The mutated DBP polypeptide varient can include one or more of the following mutations, where the mutations are referenced as to SEQ ID NO.: 2 and wherein the first residue of SEQ ID NO: 2 corresponds to residue 233 of the DBP: V299T, N300A, N301T, T302A, D303T, T304S, N305A, F306A, R308A, F312A, L315A, L317A, K318A, R319A, K320T, L321S, 1322A, 1322T, Y323A, V327S, L333T, N336,T, N336A, N337A, Y338T, R339A, Y340A, Y340T, N341S, K342T, K342A, D343A, F344A, F344T, D347A, 1348A, R349T, Y369T, K371A, E374A, N375T, A384D, A385E, T386K, A389Q, T390R, S392K, W395T, N396S, N396A, E397T, Q401T, Y408A, S409A, V410S, V410A, K411T, K412A, R413A, R413S, L414S, L414A, K415A, G416T, N417T, N417S, F418A, 1419A, W420T, 1421S, 1421A, C422A, L424A, Q433T, Y435A, R436A, W437S, R439A, E440T, W441S, G442A, D444A, Y445T, V446S, S447A, Q454T, T467A, K492A, 1503T, V505A, V511A, and G515S.

In some embodiments, the mutated DBP polypeptide The P. *Vivax* synthetic antigens can be a polypeptide that can include or be composed entirely of a polypeptide having a sequence that is about 90% to 100% identical to any one of SEQ ID NOs: 3, 4, or 5 or a fragment of at least 10 amino acids thereof.

The synthetic *P. vivax* antigen polypeptides provided herein can be encoded by a polynucleotide. The polynucleotide can be expressed and translated in a suitable in vitro or in vivo expression system. Such systems are generally known in the art. In addition to the nucleotides that encode the synthetic *P. vivax* antigen polypeptide, the polynucleotide can include additional nucleotides that can be regulatory and/or encode additional transcribed proteins, such as selectable markers and/or reporter proteins. Example selectable markers and reporter molecules include, but are not limited to, Examples of selectable markers include, but are not limited to, DNA and/or RNA segments that contain restriction enzyme sites; DNA segments that encode products that provide resistance against otherwise toxic compounds including antibiotics, such as, spectinomycin, ampicillin, kanamycin, tetracycline, Basta, neomycin phosphotransferase II (NEO), hygromycin phosphotransferase (HPT)) and the like; DNA and/or RNA segments that encode products that are otherwise lacking in the recipient cell (e.g., tRNA genes, auxotrophic markers); DNA and/or RNA segments that encode products which can be readily identified (e.g., phenotypic markers such as β-galactosidase, GUS; fluorescent proteins such as green fluorescent protein (GFP), cyan (CFP), yellow (YFP), red (RFP), luciferase, and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; epitope tags (e.g. FLAG- and His-tags), and, the inclusion of a DNA sequences required for a specific modification (e.g., methylation) that allows its identification. Other suitable markers will be appreciated by those of skill in the art.

Additional nucleotides can be operatively linked to the synthetic *P. vivax* antigen encoding nucleotides at the 5' and/or 3' end of the synthetic *P. vivax* antigen encoding nucleotides. In embodiments, the synthetic *P. vivax* antigen polynucleotide can include a polyadenylation region at the 3' end of the coding region of the synthetic *P. vivax* antigen polynucleotide. In addition to the synthetic *P. vivax* antigen polynucleotide, nucleotides for linkers and/or polynucleotides that improves or otherwise regulates synthesis, purification, expression, and/or identification of the translated protein can be operatively linked to the synthetic *P. vivax* antigen polynucleotide. In some embodiments, the polynucleotide can include or be composed entirely of a polynucleotide that is 90-100% identical to any one of SEQ ID NOs: 6-11 or a fragment of at least 10 nucleotides thereof.

The polynucleotides provided herein can be incorporated into a vector. In some embodiments, the vector is an expression vector. The expression vector can contain one or more regulatory sequences or one or more other sequences used to facilitate the expression of the polynucleotide. The expression vector can contain one or more regulatory sequences or one or more other sequences used to facilitate the replication of the expression vector. The expression vector can be suitable for expressing the polynucleotide in a bacterial cell. In other embodiments, the expression vector can be suitable for expressing the polynucleotide in a yeast cell. In further embodiments, the expression vector can be suitable for expressing the polynucleotide in a plant cell. In other embodiments, the expression vector can be suitable for expressing the polynucleotide in a mammalian cell. In another embodiment, the vector can be suitable for expressing the polynucleotide in a fungal cell. Suitable expression vectors are generally known in the art. All or part of the vectors can be capable of being transcribed in vitro without a host cell or in a host cell. The vectors can be capable of being replicated by a host cell. All or part of the vector or a RNA molecule produced from the vector template can be capable of being integrated directly or indirectly into a host cell genome. The vectors can be viral vectors, i.e. vectors that are virus based or incorporate viral proteins or nucleic acids corresponding to a viral protein. Suitable viral vectors can include adenoviral, lentiviral, retroviral, and alpha viral vectors.

Monoclonal Antibodies

Also provided herein are monoclonal antibodies that can specifically bind a DBP or fragment thereof. In some embodiments the monoclonal antibody can specifically bind a synthetic *P. vivax* antigen polypeptide or fragment of at least 5 amino acids as provided herein. In some embodiments, a monoclonal antibody can specifically bind a DBP having a sequence 90 to 100% identical to any one or more of SEQ ID NOs: 1-5, 12-16, 53, amino acids 413-417 and 425 of PvDBPII (which are shown as amino acids 171-175 and 183-199 of SEQ ID NO:1), amino acids 218-223 of PvDPBII (amino acid residues 218-223 of SEQ ID NO: 36, FIG. 17A), and/or amino acids 479-480 of PvDPBII (which are shown as amino acids 236 and 237 of SEQ ID NO:1). In some embodiments the minimal epitope can be composed of amino acid residues E413, K414, D416, G417, K425, K428, V429, P430, P431, Q433, N434, K437, S438, D440, and Q441 of PvDPBII (SEQ ID NO: 36). In some embodiments the monoclonal antibody can bind a minimal epitope composed of amino acid residues E413, K414, D416, G417, K425, K428, V429, P430, P431, Q433, N434, K437, S438, D440, and Q441 of PvDPBII. In some embodiments, the epitope can have an epitope identical to EKCDGKINYTDKKVCKVPPCQNACKSYDQ (SEQ ID NO: 60) or any fragment of at least 2 amino acids thereof. In some embodiments the epitope can be identical to EKCDGKINYTDKKVCKVPPCQNACKSYDQ (SEQ ID NO: 61) or any fragment of at least 2 amino acids thereof. In some embodiments the epitope can be identical to KVQTAGIVTPYDIL (SEQ ID NO: 62) or any fragment of at least 2 amino acids thereof. In some embodiments, the monoclonal antibody can specifically bind an epitope identical to EKCDGKINYTDKKVCKVPPCQNACKSYDQ (SEQ ID NO: 60) or any fragment of at least 2 amino acids thereof, an epitope identical to EKCDGKINYTDKKVCKVPPCQNACKSYDQ (SEQ ID NO: 61) or any fragment of at least 2 amino acids thereof, and/or an epitope identical to KVQTAGIVTPYDIL (SEQ ID NO: 62) or any fragment of at least 2 amino acids thereof.

In some embodiments, the monoclonal antibody can include or be composed entirely of a polypeptide identical to any one of SEQ ID NOs: 32-34 or any combination thereof. In some embodiments, the antibody can be a single-variable fragment (scFv) that can include or be composed entirely of a polypeptide identical to any one of SEQ ID NOs: 32-34 or any combination thereof. In some embodiments, the monoclonal antibody can include or be composed entirely of a polypeptide identical to any one of SEQ ID NOs: 63-64 shown in FIG. 33. In some embodiments, the antibody can be a single-variable fragment (scFv) that can include or be composed entirely of a polypeptide identical to any one of SEQ ID NOs: 63-64 or any combination thereof. I Pharmaceutical Formulations and Vaccines The synthetic *P. vivax* antigens and/or antibodies described herein can be provided in a pharmaceutical formulation. As such, also provided herein are pharmaceutical formulations and vaccines that can contain an amount of one or more synthetic *P. vivax* antigens and/or antibodies described herein. The amount of synthetic *P. vivax* antigen(s) can be an amount effective to stimulate an immune response in a subject when administered to a subject and/or prevent and/or treat *P. vivax* invasion of reticulocytes, *P. vivax* infection, and/or malaria. The amount of antibody(ies) can be an amount effective to prevent and/or treat *P. vivax* invasion of reticulocytes, *P. vivax* infection, and/or malaria.

Pharmaceutical formulations can be formulated for delivery via a variety of routes and can contain a pharmaceutically acceptable carrier. Techniques and formulations generally can be found in Remmington's Pharmaceutical Sciences, Meade Publishing Co., Easton, Pa. ($20^{th}$Ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the therapeutic compositions can be formulated in solid form and redissolved or suspended immediately prior to use. Lyophilized forms are also included.

Pharmaceutical compositions of the present invention are characterized as being at least sterile and pyrogen-free. These pharmaceutical formulations include formulations for human and veterinary use.

Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxyl methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

The pharmaceutical formulations can be administered to a subject in need thereof. The subject in need thereof can have a disease, disorder, or a symptom thereof. Example disease or disorder can include, but are not limited to, a cardiovascular disease, a pulmonary disease, a brain disease, a renal disease, a liver disease, a blood disease, a nervous system disease, an intestinal disease, an ocular disease, and cancer. The pharmaceutical formulations can be disposed on or otherwise coupled to or integrated with a medical device, such as, but not limited to, catheters or stents, such that the pharmaceutical formulation is eluted from the medical device over a time period. The pharmaceutical formulation can therefore be delivered to a subject in need thereof during and/or after a procedure such as an angioplasty, vein draft or organ transplant. Other procedures where such a medical device would be useful will be appreciated by those of skill in the art.

A pharmaceutical formulation can be formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. The construct, biologic molecules and pharmaceutical formulations thereof described herein can be disposed on or otherwise integrated with or coupled to a medical device such as, but not limited to, a catheter or stent, such that the construct, biological molecule can be released to the surrounding local area or systemically over a period of time after insertion or implantation into a subject in need thereof. These can also be referred to as drug eluting medical devices.

Pharmaceutical formulations suitable for injectable use can include sterile aqueous solutions (where water soluble) or dispersions and sterile powders for the extemporaneous preparation of sterile injectable solutions or dispersions. For intravenous administration, suitable carriers can include physiological saline, bacteriostatic water, Cremophor EM™ (BASF, Parsippany, N.J.) or phosphate buffered saline (PBS). Injectable pharmaceutical formulations can be sterile and can be fluid to the extent that easy syringability exists. Injectable pharmaceutical formulations can be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as mannitol, sorbitol, sodium chloride in the composition. Prolonged absorption of injectable compositions can be brought about by incorporating an agent which delays absorption, for example, aluminum monostearate and gelatin.

Sterile injectable solutions can be prepared by incorporating any of the synthetic *P. vivax* antigen(s) and/or antibodies as described herein in an amount in an appropriate solvent with one or a combination of ingredients enumerated herein, as required, followed by filtered sterilization. Generally, dispersions can be prepared by incorporating the nucleic acid vectors into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Systemic administration can also be by transmucosal or transdermal means. For transmucosal or transdermal administration, penetrants appropriate to the barrier to be permeated can be used in the formulation. Such penetrants are generally known in the art, and include, for example, for transmucosal administration, detergents, bile salts, and fluidic acid derivatives. Transmucosal administration can be accomplished through the use of nasal sprays or suppositories. For transdermal administration, the synthetic *P. vivax* antigen(s) and/or antibodies described herein can be formulated into ointments, salves, gels, or creams as generally known in the art. In some embodiments, the synthetic *P. vivax* antigen(s) and/or antibodies described can be applied via transdermal delivery systems, which can slowly release the synthetic *P. vivax* antigens and/or antibodies described herein for percutaneous absorption. Permeation enhancers can be used to facilitate transdermal penetration of the active factors in the conditioned media. Transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Administration of the *P. vivax* antigen(s) and/or antibodies described herein is not restricted to a single route, but may encompass administration by multiple routes. For instance, exemplary administrations by multiple routes include, among others, a combination of intradermal and intramuscular administration, or intradermal and subcutaneous administration. Multiple administrations may be sequential or concurrent. Other modes of application by multiple routes will be apparent to the skilled artisan.

The pharmaceutical formulations can be administered to a subject by any suitable method that allows the agent to exert its effect on the subject in vivo. For example, the formulations or other compositions described herein can be administered to the subject by known procedures including, but not limited to, by oral administration, sublingual or buccal administration, parenteral administration, transdermal administration, via inhalation, via nasal delivery, vaginally, rectally, and intramuscularly. The formulations or other compositions described herein can be administered parenterally, by epifascial, intracapsular, intracutaneous, subcutaneous, intradermal, intrathecal, intramuscular, intraperitoneal, intrasternal, intravascular, intravenous, parenchymatous, and/or sublingual delivery. Delivery can be by injection, infusion, catheter delivery, or some other means, such as by tablet or spray.

For oral administration, a formulation as described herein can be presented as capsules, tablets, powders, granules, or as a suspension or solution. The formulation can contain conventional additives, such as lactose, mannitol, cornstarch or potato starch, binders, crystalline cellulose, cellulose derivatives, acacia, cornstarch, gelatins, disintegrators, potato starch, sodium carboxymethylcellulose, dibasic calcium phosphate, anhydrous or sodium starch glycolate, lubricants, and/or or magnesium stearate.

For parenteral administration (i.e., administration by through a route other than the alimentary canal), the formulations described herein can be combined with a sterile aqueous solution that is isotonic with the blood of the subject. Such a formulation can be prepared by dissolving the active ingredient in water containing physiologically-compatible substances, such as sodium chloride, glycine and the like, and having a buffered pH compatible with physiological conditions, so as to produce an aqueous solution, then rendering the solution sterile. The formulation can be presented in unit or multi-dose containers, such as sealed ampoules or vials. The formulation can be delivered by injection, infusion, or other means known in the art.

For transdermal administration, the formulation described herein can be combined with skin penetration enhancers, such as propylene glycol, polyethylene glycol, isopropanol, ethanol, oleic acid, N-methylpyrrolidone and the like, which increase the permeability of the skin to the nucleic acid vectors of the invention and permit the nucleic acid vectors to penetrate through the skin and into the bloodstream. The formulations and/or compositions described herein can be further combined with a polymeric substance, such as ethylcellulose, hydroxypropyl cellulose, ethylene/vinyl acetate, polyvinyl pyrrolidone, and the like, to provide the composition in gel form, which can be dissolved in a solvent, such as methylene chloride, evaporated to the desired viscosity and then applied to backing material to provide a patch.

Dosage Forms

The pharmaceutical formulations or compositions described herein can be provided in unit dose form such as a tablet, capsule or single-dose injection or infusion vial. Where appropriate, the dosage forms described herein can be microencapsulated. The dosage form can also be prepared to prolong or sustain the release of any ingredient. In some embodiments, the complexed active agent can be the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT@ (Roth Pharma, Westerstadt, Germany), zein, shellac, and polysaccharides.

In some embodiments, such as for treatments of plants, the topical formulation of a composition or pharmaceutical formulation described herein can be further formulated as a spray and can include a suitable surfactant, wetting agent, adjuvants/surfactant (stickers, extender, plant penetrant, compatibility agents, buffers, drift control additives, and defoaming agents), or any combination thereof so as to formulated as a spray. The compounds, any optional auxiliary active ingredient, suitable surfactant, wetting agent, adjuvants, or any combination thereof can be formulated as a solution, suspension, or emulsion. The spray dosage from can be administered through a spraying device. In some embodiments, the spraying device can be configured to generate the sprayable formulation as a liquid solution is contacted with the complexed active agent compound or formulation thereof. In other embodiments, the sprayable dosage form is pre-made prior to spraying. As such, the spraying device can act solely as an applicator for these embodiments.

In further embodiments, such as for treatments of plants (e.g. such as a herbicide), the dosage form of composition or pharmaceutical formulation described herein thereof can be further formulated as a dust and can include a suitable dry inert carrier (e.g. talc chalk, clay, nut hull, volcanic ash, or any combination thereof so as to be formulated as a dust. The dust can contain dust particles of varying sizes. In some embodiments, the particle size can be substantially homogenous. In other embodiments, the particle size can be heterogeneous. Dosage forms adapted as a dust can contain one or more adjuvants/surfactants (stickers, extender, plant penetrant, compatibility agents, buffers, drift control additives, and defoaming agents).

In some embodiments, the dosage form can be formulated as a bait. In these embodiments, the complexed active agent compound or other formulation thereof can be further formulated to include a food or other attractive substance that can attract one or more insect or other pest. The bait dosage form can be formulated as a dust, paste, gel, or granule. Dosage forms adapted as baits can contain one or more adjuvants/surfactants (stickers, extender, plant penetrant, compatibility agents, buffers, drift control additives, and defoaming agents).

In additional embodiments, the dosage form can be formulated as granules or pellets that can be applied to the environment. These dosage formulations are similar to dust formulations, but the particles are larger and heavier. The granules can be applied to soil or other environmental area. Dosage forms adapted as granules or pellets can contain one or more adjuvants/surfactants (stickers, extender, plant penetrant, compatibility agents, buffers, drift control additives, and defoaming agents).

The dusts, granules, and pellets described herein can be formulated as wetable dusts, granules, and pellets, soluble dusts granules, and pellets, and/or water-dispersible granules, and/or dry flowables.

The dosage form can be adapted for impregnating (saturating) an object or device, which then can be carried by, worn, or otherwise coupled to an organism in need thereof. In some embodiments, the dosage form can be impregnated onto a collar, bracelet, patch, adhesive tape, livestock ear tags, clothing, blankets, plastics, nets, and paints. The composition or pharmaceutical formulation thereof can be formulated and impregnated in the object or device such that the composition or pharmaceutical formulation evaporates over time, which releases the composition and/or pharmaceutical formulation into the air and/or environment surrounding the organism and/or onto the organism.

The dosage form can be adapted as a fumigant, which is a formulation that forms a gas when utilized or applied. In some embodiments, the composition and/or pharmaceutical formulation thereof can be supplied as a liquid when packaged under pressure and change to a gas when they are released. In other embodiments, the composition and/or pharmaceutical formulation thereof can be supplied as a volatile liquid when enclosed in a container (not under pressure). Others can be formulated as solids that release gases when applied under conditions of high humidity or in the presence of high water vapor. Dosage forms adapted as fumigants can contain one or more adjuvants/surfactants (stickers, extender, plant penetrant, compatibility agents, buffers, drift control additives, and defoaming agents).

Effective Amounts

The pharmaceutical formulations can contain an effective amount of a composition described herein and/or an effective amount of an auxiliary agent. In some embodiments, the effective amount ranges from about 0.001 μg to about 1,000 g or more of the composition described herein. In some embodiments, the effective amount of the composition described herein can range from about 0.001 mg/kg body weight to about 1,000 mg/kg body weight. In yet other embodiments, the effective amount of the composition can range from about 1% w/w to about 99% or more w/w, w/v, or v/v of the total pharmaceutical formulation.

Combination Therapy

The pharmaceutical formulations or other compositions described herein can be administered to a subject either as a single agent, or in combination with one or more other agents. Additional agents include but are not limited to DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics.

Vaccines

The synthetic *P. vivax* antigens can be formulated as a vaccine. The vaccine can contain an effective amount or an effective concentration of one or more of the *P. vivax* antigens provided herein. The amount can be effective to stimulate an immune response, stimulate antibody production, provide protective immunity, immunize, treat, and/or prevent *P. vivax* invasion, infection, and/or malaria in the subject and/or offspring thereof. The effective amount can range from about 0.001 μg to about 1,000 g or more of the composition described herein. In some embodiments, the effective amount of the composition described herein can range from about 0.001 mg/kg body weight to about 1,000 mg/kg body weight. In yet other embodiments, the effective amount of the composition can range from about 1% w/w to about 99% or more w/w, w/v, or v/v of the total vaccine formulation. The vaccines, described herein can be effective to stimulate an immune response, stimulate antibody production, provide protective immunity against one or more *P. vivax* strains, immunize a subject against one or more *P. vivax* strains, treat and/or prevent invasion and/or infection by one or more *P. vivax* strains in the subject and/or offspring thereof. In other words, in embodiments, the vaccines described herein can be capable of providing protection against multiple strains of *P. vivax* as opposed to being strain specific.

The vaccines described herein can include one or more additional agents. The vaccines provided herein can include one or more suitable adjuvants. Suitable adjuvants are generally known in the art and can include, but are not limited to aluminum salts (e.g, aluminum phosphate and aluminum hydroxide), organic adjuvants (e.g. squalene), and oil-based (e.g., MF59). In embodiments, the compositions can contain a suitable pharmaceutically acceptable carrier. Suitable pharmaceutically acceptable carriers include, but are not limited to, water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxyl methylcellulose, and polyvinyl pyrrolidone, which do not deleteriously react with the active composition. Other suitable pharmaceutically acceptable carriers are identified elsewhere herein and will be appreciated by those of ordinary skill in the art.

The vaccines can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition. The vaccines can also include an amount, including an effective amount, of one or more of auxiliary active agents, including but not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics. Suitable compounds for the auxiliary active agents have been previously described herein in relation to the pharmaceutical formulations.

In some embodiments, the vaccines provided herein can be included in a combination vaccine or other combination formulation. In some embodiments, the vaccines provided herein can be included in a combination vaccine or other combination formulation with a *P. falciparum* vaccine or other treatment.

Methods of Treatinq and/or Preventinq *P. vivax* Infection and Mediated Disease

The synthetic *P. vivax* antigens, antibodies, formulations and vaccines thereof provided herein can be administered to a subject by any suitable route. The subject can be a subject in need thereof. The subject in need thereof can be exposed, will be exposed, and/or is at risk of being exposed to a species of the genus *Plasmodium*, including but not limited to, *P. vivax*. Administration of the synthetic *P. vivax* antigen(s), antibody(ies), formulation(s) and/or vaccine(s) thereof provided herein can induce or otherwise stimulate an immune response in the recipient subject and/or an offspring of the recipient subject. Administration of the synthetic *P. vivax* antigen(s), antibody(ies), formulation(s) and/or vaccine(s) thereof provided herein can stimulate antibody production in the recipient subject. In other embodiments, administration of the synthetic *P. vivax* antigen(s), antibody(ies), formulation(s) and/or vaccine(s) thereof provided herein can provide protective immunity against one or more strains of *P. vivax* in a recipient subject and/or an offspring of the recipient subject.

Accordingly, provided herein are methods of inducing or otherwise stimulating an immune response in a subject and/or an offspring of the subject that include the step of administering the synthetic *P. vivax* antigen(s), antibody(ies), formulation(s) and/or vaccine(s) thereof provided herein to a subject one or more times. Also provided herein are methods of stimulating antibody production in a subject and/or offspring of the subject that includes the step of administering the synthetic *P. vivax* antigen(s), antibody(ies), formulation(s) and/or vaccine(s) thereof provided herein to a subject one or more times. Also provided herein are methods of stimulating protective immunity a subject and/or offspring thereof by administering the synthetic *P. vivax* antigen(s), antibody(ies), formulation(s) and/or vaccine(s) thereof provided herein to a subject one or more times. Also provided herein are methods of treating and/or preventing *P. vivax* infection and/or disease by administering the synthetic *P. vivax* antigen(s), antibody(ies), formulation(s) and/or vaccine(s) thereof provided herein to a subject one or more times. In embodiments, the amount of the compound, compositions, formulation and/or vaccine can be an amount effective to stimulate an immune response, stimulate antibody production, provide protective immunity, immunize, treat, and/or prevent infection and/or disease by one or more strains of *P. vivax* in the subject and/or offspring thereof.

The synthetic *P. vivax* antigen(s), antibody(ies), formulation(s) and/or vaccine(s) thereof provided herein can be administered to the subject by any suitable routes. In some embodiments, about 0.01 cc to 10 cc or more of the synthetic *P. vivax* antigen(s), antibody(ies), formulation(s) and/or vaccine(s) thereof provided herein can be administered to a subject. In some embodiments, an amount effective to induce an immune response in the recipient subject and/or offspring thereof. The synthetic *P. vivax* antigen(s), antibody(ies), formulation(s) and/or vaccine(s) thereof provided herein can be administered to the subject one or more times. Where administration occurs more than once the time period between each does can each independently range from days (e.g. 1-7 days), weeks (e.g. 1-52 weeks, or years (e.g. 1-5 years) apart. Administration can occur during any life stage of the subject. Administration can be simultaneously or in series with other vaccines.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Figure 1:
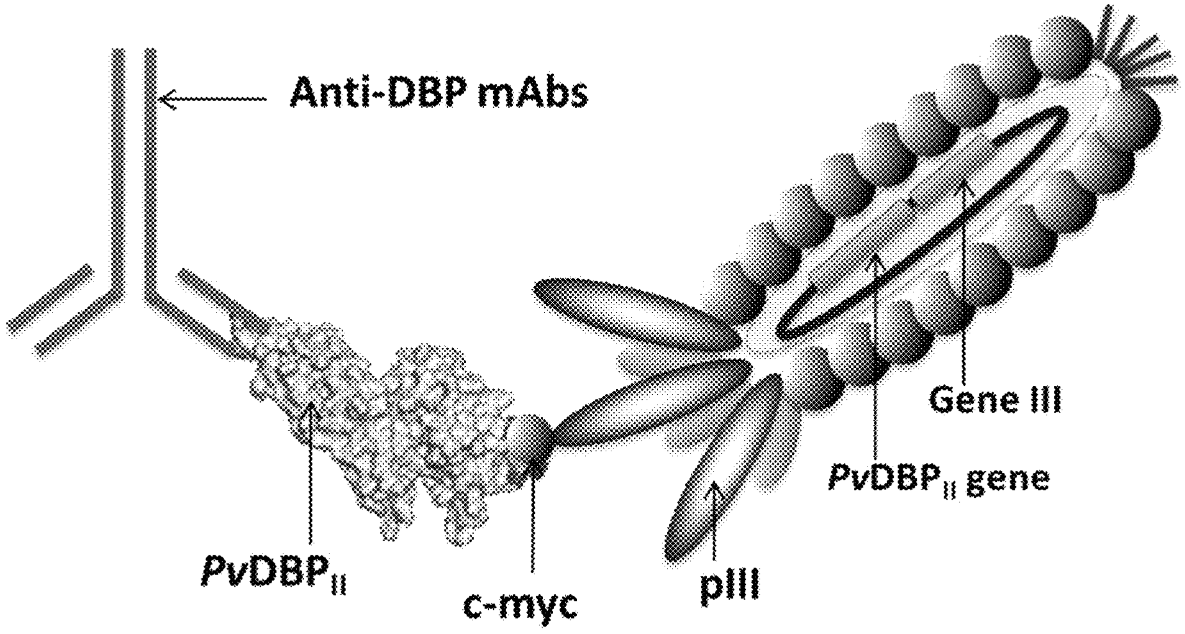
FIG. 1 depicts a general mechanism of certain embodiments of the disclosure.

Minimal reactive epitopes of anti-DBPII mAbs 3C9 and 3D10, which were characterized previously as functionally inhibitory or poorly inhibitory to DBPII-erythrocyte binding, were mapped using phage display expression libraries. The general mechanism can be seen in FIG. 1. Inhibitory mAb 3C9 binds to a conserved conformation-dependent epitope in subdomain 3 while non-inhibitory mAb 3D10 binds to a linear epitope in subdomain 1 of DBPII. Mimotope phage display determined that YK(R/Y/E) as a key motif of the mAb 3D10 epitope. Site directed mutagenesis was used to determine essential residues within each epitope. Immunogenicity studies using synthetic linear peptides of the minimal epitopes determined that the 3C9, but not 3D10, epitope could induce functionally inhibitory anti-DBPII antibodies. Therefore, the highly conserved neutralizing 3C9 epitope offers the potential as a component in a broadly neutralizing, strain-transcending DBP subunit vaccine.

Specifically, the minimal reactive epitopes of these anti-DBPII mAbs were mapped by screening DBPII gene fragment libraries expressed on M13 phage surface for minimal reactive peptide fragments. Additional studies of the epitopes' immunogenicity as KLH conjugates demonstrated the ability of the 3C9 epitope, but not anti-3D10, epitope to elicit functionally inhibitory anti-DBPII serum antibodies that blocked DBPII-erythrocyte binding. The information provided in this Example can contribute to the understanding of a potential target for broadly neutralizing vaccine-elicited protective immunity. In particular, this Example can demonstrate a potential component of a PvDBPII unit vaccine that can be successful in boosting antibody responses targeted against conserved protective epitopes, with functional inhibition against broader allelic variants and diverse *P. vivax* strains.

Materials and Methods

Generation of phage displayed DBPII gene fragment library. The full-length PCR product (20 μg) from DBPII Sal1 haplotype was digested with DNase I at 5 U/ml. The resulting fragments were purified by sodium acetate precipitation and ragged ends blunted with a Vent polymerase (NEB). The pHENH6 vector was digested with Pstl (NEB) and also blunted with Vent polymerase. The resulting products from the randomly fragmented DBPII were cloned into the treated pHENH6 vector and then into TG1 *E. coli* by electroporation. The distribution of the fragments in the library was determined by PCR and sequencing of forty random clones. The distribution of the fragments in the library were determined by PCR and sequencing of forty random clones. The library was then grown in 20 ml of 2×Tryptone-yeast extract media containing 50 μg/ml of ampicillin at 37° C., shaking until OD 600 nm. $1\times10^{11}$PFU of M13K07 helper phage was added and cultured for an extra 1 h at 37° C. without shaking to allow infection. The entire culture was then transferred into 400 ml of super broth, containing 70 μg/ml kanamycin and 50 μg/ml ampicillin, and incubated at 37° C. with shaking overnight. The bacteria was pelleted by centrifugation at 8,000×g for 15 min and the phage precipitated from the supernatant with PEG-NaCl as previously described (Adda C G, et al. 1999. Infect Immun 67:4679-4688 and Coley A M, et al. 2006. Infect Immun 74:2628-2636). The phage was re-suspended in 1 ml of PBS and used subsequently or stored at −80° C.

Panning of phage displayed DBPII gene fragment library. Affinity panning of DBPII Sal1 gene fragment to anti-DBPII mAbs 3D10 and 3C9 was carried out as described previously (Coley et al. 2001. Protein Eng 14:691-698). Briefly, 10 wells of Maxisorp-Nunc ELISA plate were coated over night at 4° C. with 100 μl per well of test mAb at a final concentration of 2.5 μg/ml diluted in PBS. Plates were washed twice with PBS and unbound surfaces blocked with 200 μl of 5% skimmed milk in PBS for 2 h at room temperature. After another round of washing, approximately $1\times10^{11}$ phage/well in 1% skimmed milk in PBS were added to wells and incubated for 1 h at room temperature. Non-adherent phage particles were washed off twice with PBS/0.05% Tween-20. The bound phage was eluted with 100 μl of 0.1M Glycine, pH 2.2 and immediately added to 10 ml of log phase *E. coli* TG1 cells and cultured for 30 min at 37° C. for infection to occur. Ampicillin was added to 50 μg/ml and the culture and incubated for another 30 min at 37° C. before addition of the M13 helper phage and then incubated for another 1 h at 37° C. The culture was then transferred to a 200 ml super broth containing 50 μg/ml of ampicillin and 70 μg/ml of kanamycin and incubated at 37° C. overnight with shaking at 200 rpm. The phage was harvested as described above and another round of panning carried out for a total of up to four panning cycles per antibody. Ten clones from each round of panning were selected, their inserts amplified by PCR and sequenced to determine the identity of the fragments of DBPII that binds to each mAb.

Panning a random peptide library on mAb-3D10. Panning on mAb 3D10 was performed using a random 20mer peptide library (Courtesy of Foley M and Anders R F, La Trobe University, Australia; Adalta Pty Ltd) as described (Coley et al. 2001. Protein Eng 14:691-698 59). Briefly, phage peptide library at 101 phage/well was incubated with mAb 3D10 coated wells for 1 h at room temperature. Eluted phage was allowed to re-infect K91 *E. coli* grown to log phase in 10 ml Tryptone-yeast extract media at 37° C. for 1 h and then grown overnight in 200 ml of super broth with 40 μg/ml of tetracycline. Phage was harvested and further rounds of panning carried out as described above. Clones isolated from round 3 were sequenced to determine the peptide sequences.

ELISA of phage displayed rounds of panning. Enrichment ELISA was performed as previously described (Coley et al. 2001. Protein Eng 14:691-698). Briefly, 100 μl of anti-DBP mAbs antibodies at 2.5 μg/ml in PBS were coated on to wells of 96-well microtiter plates (Maxisorp-Nunc) overnight at 4° C. Anti-PfAMA1 specific, mAb-1F9 or 5G8 (Coley et al. 2001. Protein Eng 14:691-698) was coated on each plate as negative control antibody. The plates were washed twice with PBS 0.05% Tween-20 and blocked for 2 h at room temperature with 200 μl/well of 10% skimmed milk diluted in wash buffer. After three washes, phage diluted in PBS/1% milk to $1\times10^{11}$ pfu/ml was added in triplicates and incubated for 2 hours at room temperature. Plates were washed four times and the wells were incubated with HRP-conjugated anti-M13 mAb (GE Life Sciences) for 1 h at room temperature. The plates were then washed five times and bound phage detected by incubating wells with 100 μl of $H_2O_2$ activated TMB substrate (Sigma). The reaction was stopped with 100 μl 2 N $H_2SO4$ and plates were read at 450 nm absorbance.

Immunoblots. Approximately $1\times10^{12}$ phage particles were boiled in SDS-PAGE sample buffer for 3 min and separated by SDS-PAGE and electrophoretically transferred on to nitrocellulose membrane. The membrane was blocked overnight in 10% skimmed milk diluted in PBS/Tween-20. The membrane was probed with anti-DBPII mAb, washed with PBS/Tween-20 before incubating with an HRP-conjugated anti-mouse secondary antibody. The bound antibody was detected by enhanced chemiluminescence (ECL) substrate (Amersham).

Immunizations. Peptides corresponding to sequences of the epitopes identified from panning on the gene fragment library and mimotopes from panning on the random peptide were synthesized and conjugated to keyhole limpet hemocyanin (KLH) using Maleimide-Activated mcKLH (ThermoScientific 77611) according to the manufacturer's specifications. The following 6 peptides were produced commercially (Pacific Immunology): 3C9 epitope peptide (3C9-e1) from DBPII sub-domain 3; 3D10 epitope peptide (3D10-e1) from DBPII sub-domain 1; 3D10 mimotope 1; (3D10-m1); 3D10 mimotope 2: (3D1-m2); 3D10 mimotope 3: (3D10-m3) and a control peptide.

The conjugated peptides were used to immunize 6-8wks old Balb/c mice (Harlan) to raise immune sera. All animals were handled in compliance with approved IACUC protocol and good animal practice. Briefly, mice in all groups, (n=10) were bled for pre-immune sera and each immunized thrice at three week intervals with 5 μg of peptide conjugated to KLH emulsified in Titermax® Gold adjuvant. Each animal received a 50 μl antigen-adjuvant mix administered subcutaneously at the base of the tail. Mice immunized with KLH and adjuvant alone served as control. All mice were bled for final serum four weeks after the second boost.

Measurement of antibody titers. Total anti-peptide IgG titers in the serum of each group was evaluated by end point titration ELISA against and to recombinant DBPII Sal1 and peptide conjugated to bovine serum albumin (BSA). Imject™ Maleimide-Activated BSA Spin Kit (ThermoScientific 77667) was used as specified by manufacturer to conjugate the peptides. ELISAs were carried out as described previously (Ntumngia et al. 2012. antibodies. Infect Immun. 80:1203-1208.), 0.1 μg of peptide conjugated to BSA or 0.25 μg of recombinant antigen were coated per well of a microtiter plate overnight and blocked with 5% skimmed milk PBS/0.05% Tween 20 detected by 3-fold dilution of mouse sera was used starting at 1:200. Bound antibodies were detected using alkaline phosphatase-conjugated anti-mouse antibody (Kirkegaard & Perry Laboratories). Pre-immune serum, at the lowest dilution, served as background and was subtracted.

Measurement of functional inhibition of DBP-Erythrocyte binding. Pooled immune serum from each group of mice that recognized rDBPII Sal1 by ELISA was tested further for inhibition of DBPII-erythrocyte binding by a modified version of the standard in vitro COS7 cell assay (Chitnis and Miller. 1994. J Exp Med 180:497-506 and Michon et al. 2000. Infect Immun. 68:3164-3171). A panel of naturally occurring DBPII alleles were transiently expressed on the surface of transfected COS7 cells as previously described (Ntumngia et al. 2013. Vaccine 31:4382-4388). Cells were pre-incubated with triple-fold dilution (starting at 1:50) of pooled group sera 42 h post transfection, followed by incubation with human Duffy positive erythrocytes. Inhibition of binding by each serum was calculated as a percentage of Duffy positive erythrocyte binding in immune versus corresponding pre-immune serum control incubated on every plate (Ntumngia et al. 2013. Vaccine 31:4382-4388).

Immunofluorescence assay of COS7-surface expressed DBPII. A few DBPII constructs with single and multiple residue mutations, in epitope residues, were produced (GenScript) on pEGFP vector used for DBPII expression on COS7 cells. COS7 cells transfected with different mutated DBPII transgenes, were incubated on cover slips in 24 well plates for 42 h (Chitnis and Miller. 1994. J Exp Med 180:497-506). The cells were then fixed with PBS/2% formaldehyde for 15 min, washed with PBS and incubated at room temperature with 5 μg/ml of anti-DBPII mAbs 3C9, 3D10 and 2D10 and anti-AMA1 mAb 1F9, as a negative control, for 90 min. After PBS wash, the cells were incubated with rhodamine-conjugated goat anti-mouse secondary antibody (KPL) in PBS/0.1% BSA for 30 min in the dark. The cells were washed with PBS and nuclear stain Hoechst at 1:1000 dilution for 15 min in the dark. After the final wash, the cells on the coverslip was fixed onto a glass slide with flurophoreG and stored at −20° C. until ready to be observed using a fluorescence microscope. Zeiss microscope was used to capture images of 10 cells at 40× magnification for each DBPII-antibody pair at constant exposure time of 88 ms for blue channel, 513 ms for green channel and 2049 ms for red channel. Relative fluorescence unit (RFU) across a cell from end to end was collected. The highest 50 points for the red channel for each cell was used to normalize for the size of cells. The sum of the highest 50 points for 10 cells was used to determine the mean RFU for each DBPII-antibody pair. The mean RFU of DBPII mutants were compared with wild type DBPII Sal1 for the respective antibody.

Results

Figure 2A:
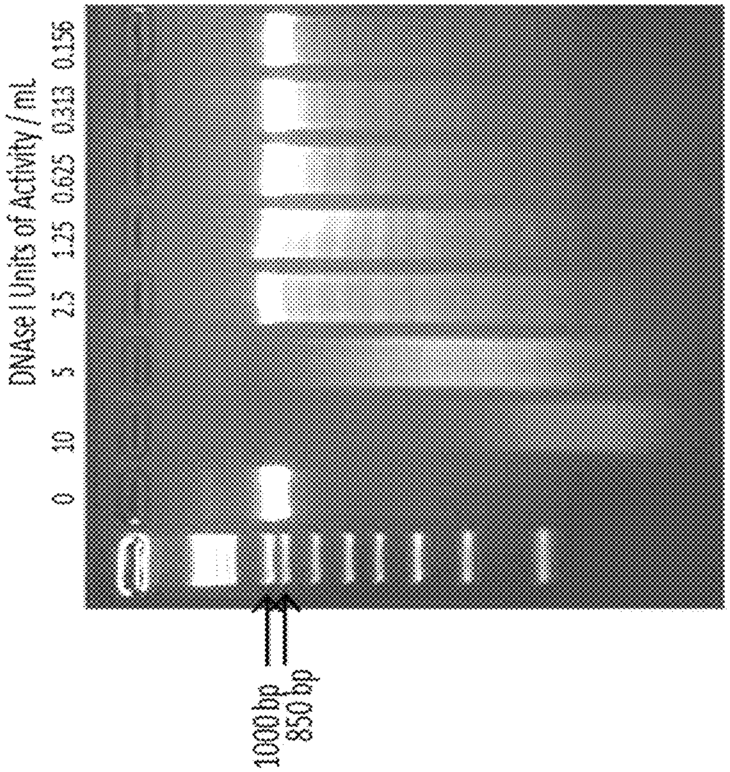
FIGS. 2A-2C show images of DNA gels demonstrating digestion of DBPII Sal1 Digested to fragment the gene.
Figure 2B:
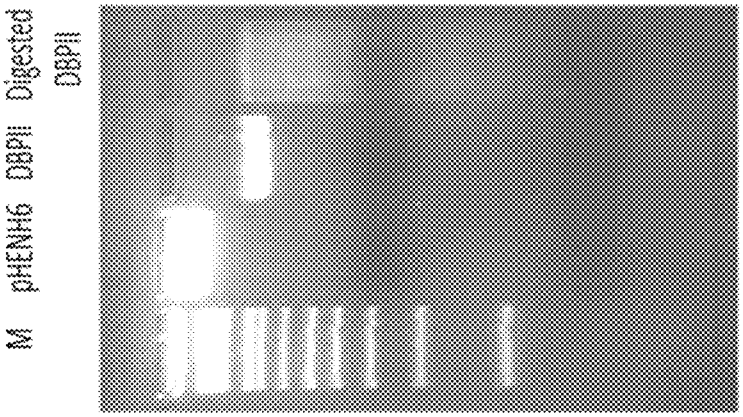
Figure 2C:
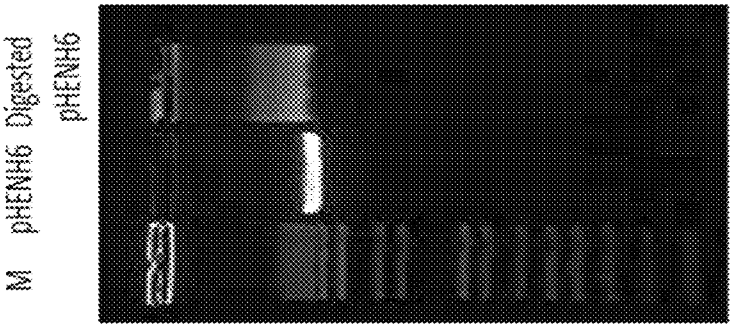

The vector pHENH6 was used to successfully express a large diversity of random length fragments of DBPII on the surface of the engineered phagemid as a chimeric proteins fused with a C-terminal c-myc epitope tag and the pIII minor coat protein (see FIGS. 2A-2C). The variable length DBPII fragments came from a gene fragment library of random length PvDBP coding constructed by DNAseI-digesting DNA encoding DBPII sequences (FIG. 3). Recombinant phagemid library for DBPII Sal1 was estimated to have $7\times10^5$ pfu/μg of plasmid DNA gene fragments. Sequencing of 40 random clones of each library revealed that the fragments in the library spanned the entire coding sequence and no bias towards any particular region was observed (data not shown); however, as expected most of the fragments were ligated out of frame or in the incorrect orientation. Phage stocks generated from the gene fragment libraries were biopanned on mAbs 3D10 and 3C9 to enrich for high affinity binders to each of these antibodies.

Figure 4A:
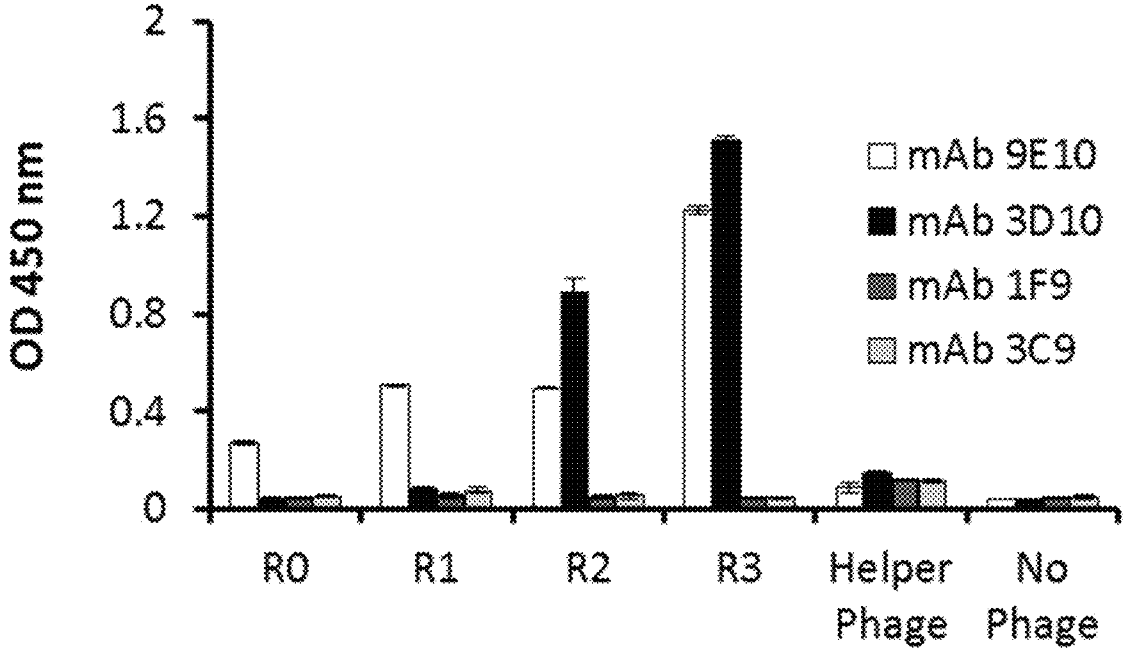
FIGS. 4A-4D demonstrate gene fragments of DBPII Sal1 selected through biopanning. ELISA showing reactivity of phage clones enriched by successive panning on (FIG. 4A) mAb-3D10 and (FIG. 4B) mAb-3C9. A pool of phage from each round of panning was tested for binding to anti-DBPII mAbs 3D10, 3C9 and the anti-c-myc epitope tag antibody mAb-9E10. The PfAMA-1 specific mAb-1F9 served as a negative control antibody. The bars represent mean OD of triplicate wells and Error bars indicate ±SD. Individual clones (n=10) from round 3 (R3) of panning on each of the mAbs were PCR amplified and sequenced. The positions of the various peptides identified are indicated in (FIG. 4C) and (FIG. 4D) for mAbs 3D10 and 3C9 respectively. The degenerate sequence identified from the phage clones by panning on each on the antibodies is shown.
Figure 4B:
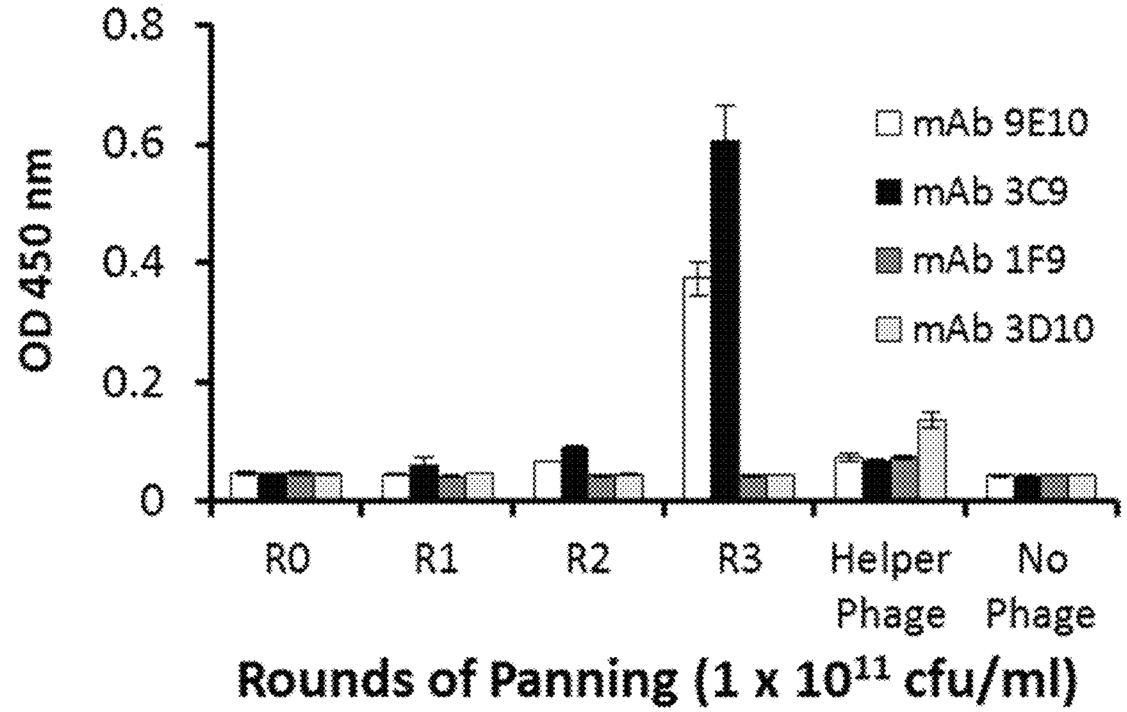

Affinity selection of reactive phage to the target antibody was carried out through the sequential rounds of panning by standard procedures. ELISAs were carried out with positive control mAb 9E10 to standardize library titer in each round of panning, while an anti-PfAMA1 antibody, mAb 1F9, served as a negative control. Panning on mAb 3D10 selected for phage clones that bound well to mAb 3D10, but poorly to mAbs 3C9 and 1F9 for both gene fragment libraries (FIG. 4A). Inversely, panning on mAb 3C9 selected for phage clones from both gene fragment libraries that bound well to mAb 3C9 and poorly to mAbs 3D10 and 1F9 (FIG. 4B). Phage clones isolated from panning on all the antibodies bound well to mAb 9E10, indicating that the procedure had enriched for clones possessing DBPII coding sequence in-frame and in the correct-orientation.

Figure 4C:
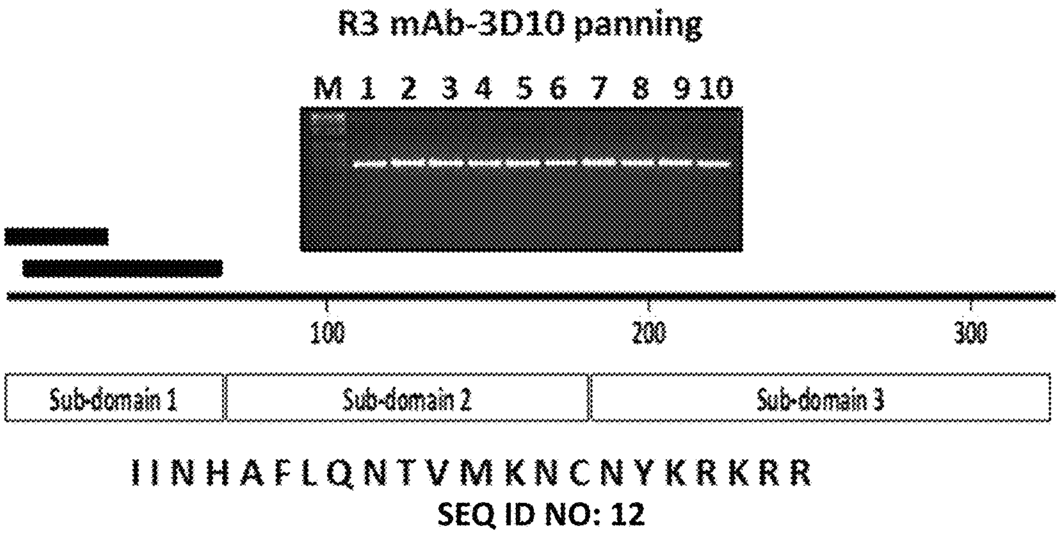
Figure 4D:
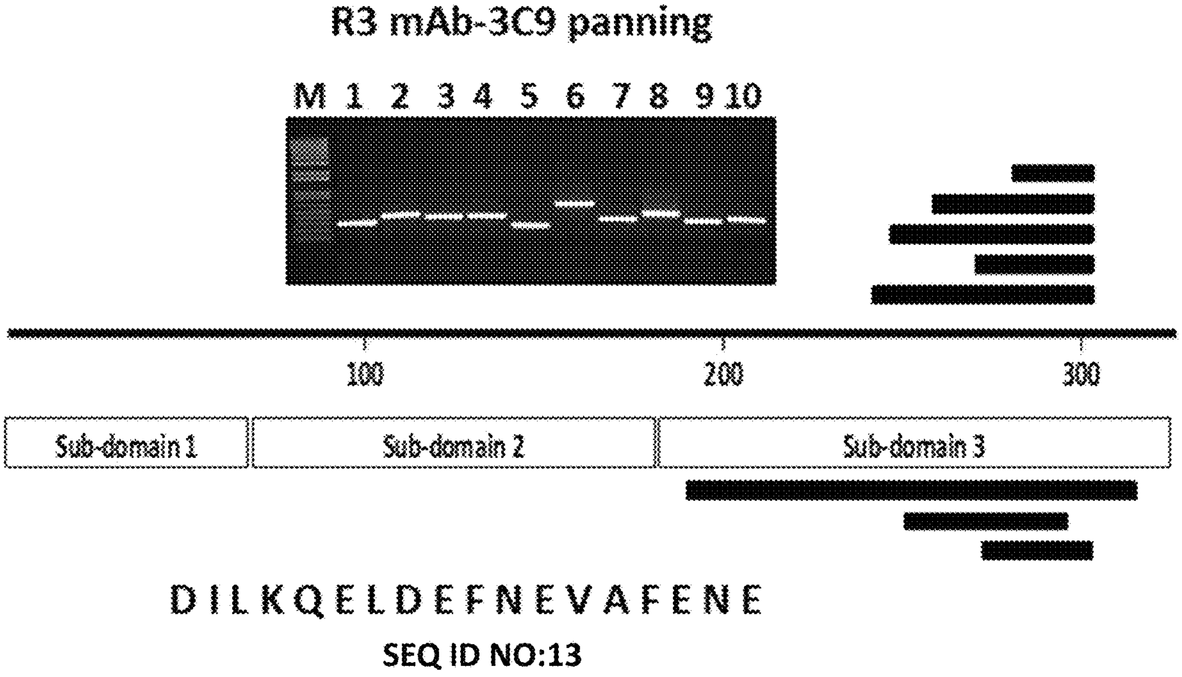

Sequence analysis of 10 clones from each round of panning was used to identify the length and specificity of DBPII CDS inserts. Clones from the last rounds of panning tended to have inserts of similar sizes while those of the early rounds tended to be more variable. Sequencing results further showed that only clones in the last round of panning were in frame and in the right orientation, corroborating ELISA results. Ten clones from the last rounds of panning on mAb 3D10, had overlapping fragments of sub-domain 1 of DBPII in-frame and in the correct orientation (FIG. 4C). Most clones from the last rounds of panning on mAb 3C9 were comprised of overlapping fragments of sub-domain 3 (FIG. 4D).

Figure 5A:
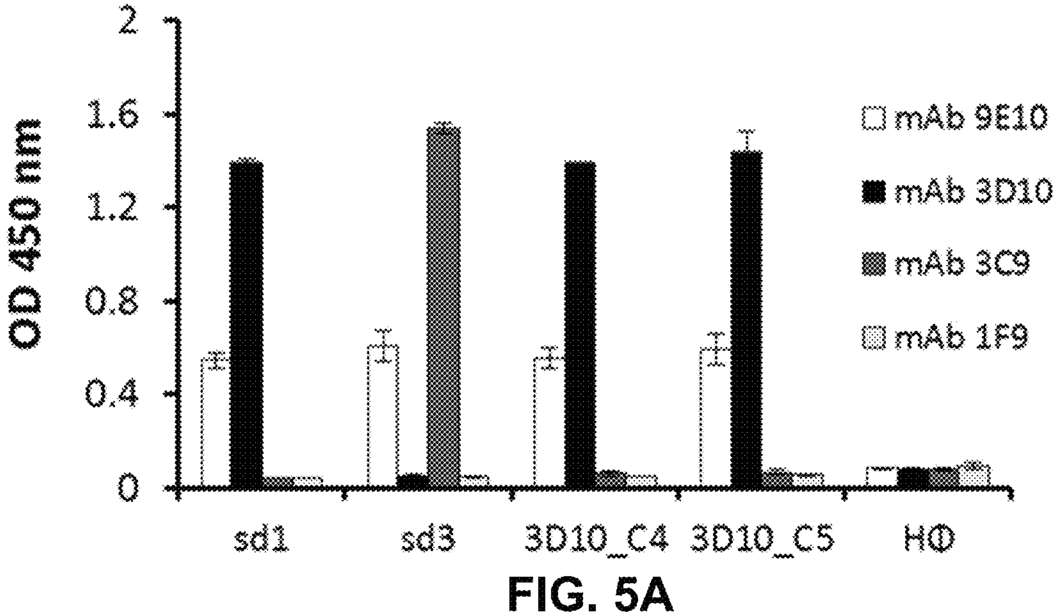
FIGS. 5A-5D demonstrate cross reactivity of isolated phage clones with mAb-3D10 and 3C9. Two phage clones (C4 and C5) and three phage clones (C4, C6, C9) from round three panning of the DBPII gene fragment library on mAbs 3D10 and 3C9 respectively and phage clones expressing sd1 and sd3 fragments of DBPII were tested for cross reactivity with the homologous and heterologous antibodies by ELISA (FIGS. 5A and 5B) and immunoblot analysis (FIGS. 5C and 5D). mAb-3D10 binds specifically to mAB-3D10 isolated phage clones and the sd1 expressing clones, while mAb-3C9 binds only to mAb-3C9 isolated clones and sd3 expressing clones. mAb-1F9 is a non-specific anti-DBPII antibody used as negative control and mAb-9E10 is specific to the c-myc epitope of the phagemid. Each bar represents the mean OD450 of triplicate wells and error bars represent ±SD.
Figure 5B:
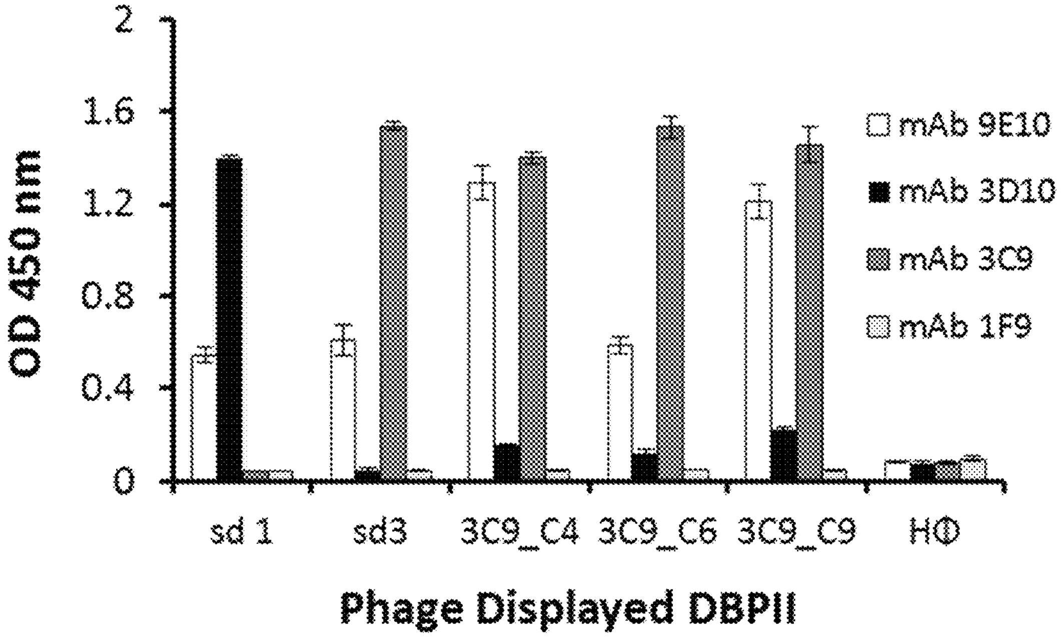
Figure 5C:
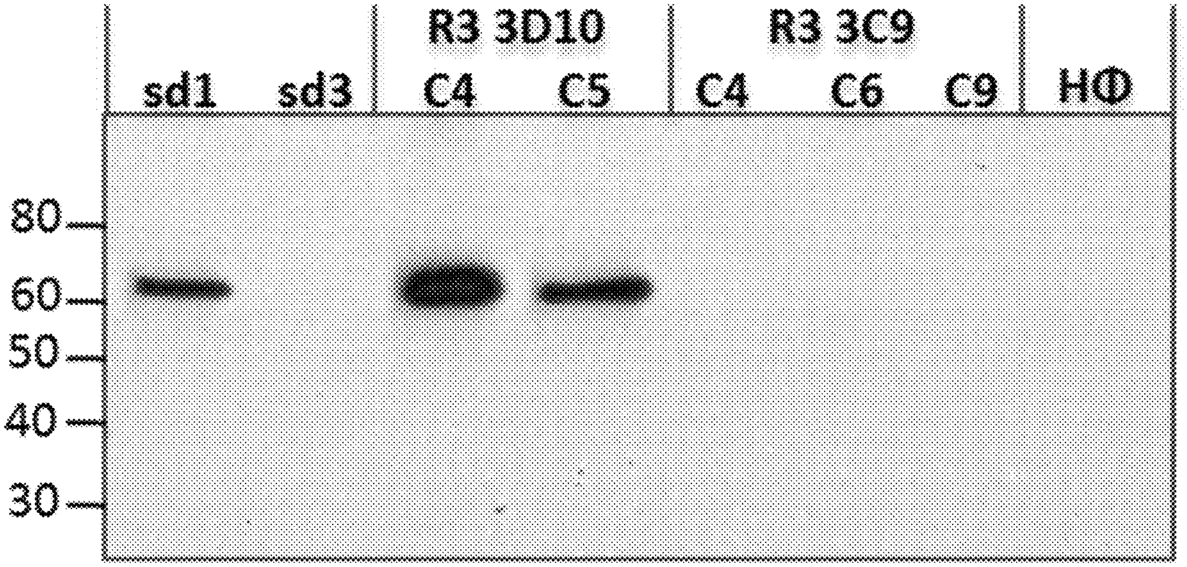
Figure 5D:
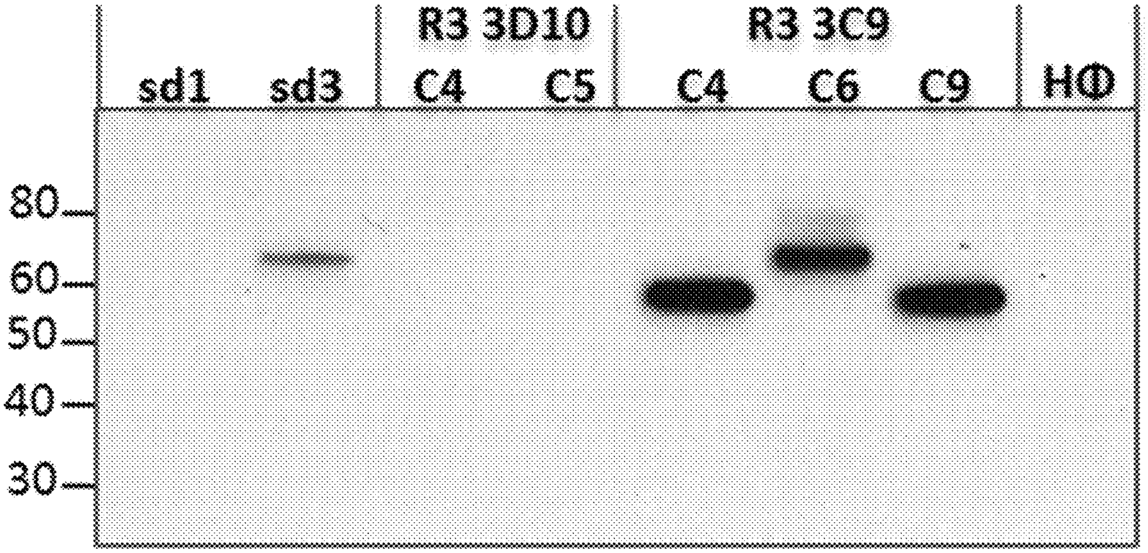
Figure 6:
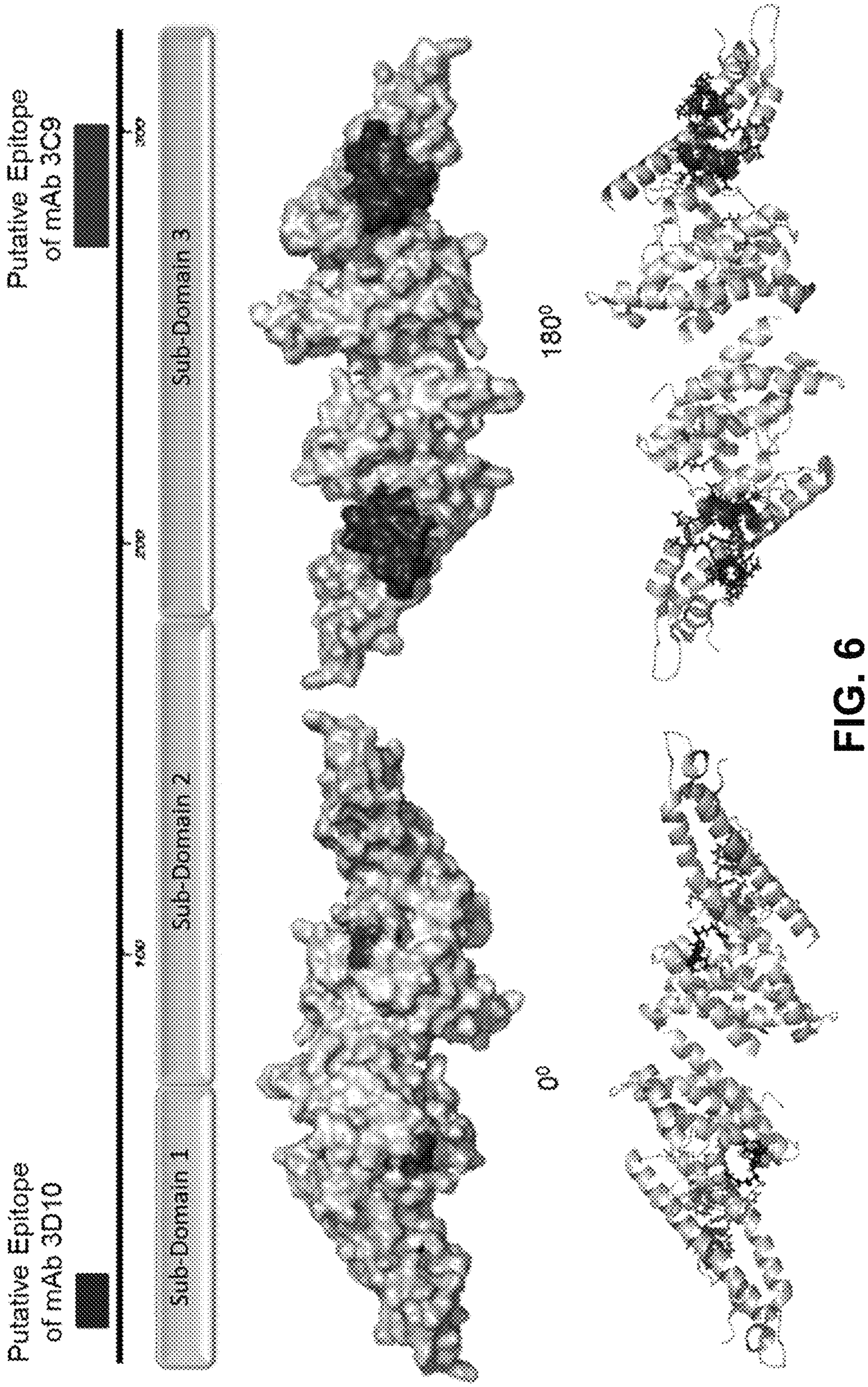
FIG. 6 demonstrates putative epitopes of mAbs 3C9 and 3D10. Crystal structure of DBPII dimer with sub-domains 1 (in green), 2 (in tan) and 3 (in light blue). Putative epitope of inhibitory mAb 3C9 (in red) is on sub-domain 3 while putative epitope of non-inhibitory mAb 3D10 (in navy blue) is on sub-domain 1. The two views represent the front and back of the ligand for the surface model (top) and for secondary structure cartoon (bottom).

Phage were cultured from two clones enriched for during round 3 panning on mAb 3D10 and three clones enriched for during round 3 panning on mAb 3C9. Each phage clone was tested for reactivity to the selecting mAb by ELISA and Western Blot (FIGS. 5A-5D). Results from both assays indicated that mAb 3D10 phage clones bound specifically to mAb 3D10 (FIGS. 5A and 5C). Similarly, mAb 3C9 phage clones were observed to specifically bind to mAb 3C9 (FIGS. 5B and 5D). The observed specificity suggested that the isolated phage clones displayed the minimal fragments of DBPII needed for the mAbs to bind their respective epitopes. Both the 3D10 and 3C9 epitopes mapped to residues determined to be on the surface of the PvDBPII 3D crystal structure (FIG. 6).

Figure 7A:
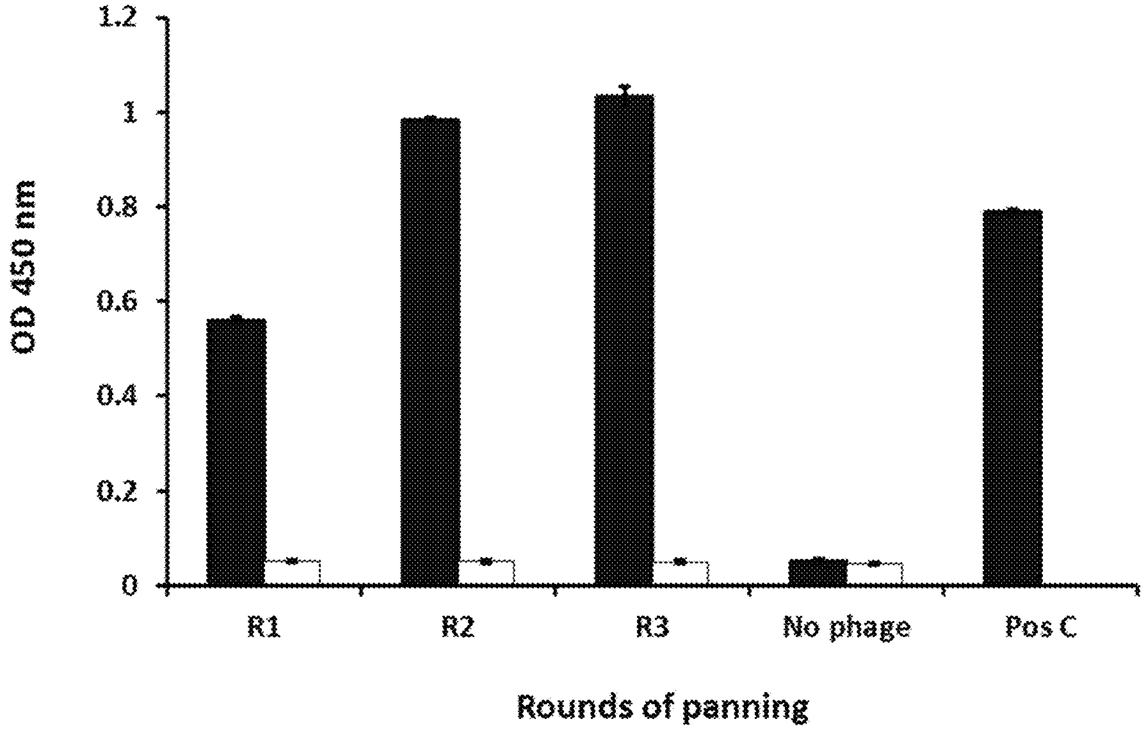

To further characterize the linear epitope for mAb 3D10, a random 20mer peptide library termed Adlib1 (Adalta Pty Ltd.) was also used to pan on the antibody (FIG. 7A). The level of reactivity was assessed by ELISA after 3 rounds of panning to find phage from rounds 1-3 reacted well with mAb 3D10 (black), but relatively poorly to the negative isotype control anti AMA1 mAb 5G8 (white). Ten clones from round 3 were sequenced and 4 sequences were identified with similarity to DBPII, each containing what may be a degenerate sequence motif (FIG. 7B). A recurrent motif within the 3D10 mimotopes is a hydrophilic 3-residue motif YK(R/Y/E). Although the Adlib1 peptide library is unrelated to DBPII, YKR motif matches the 22-amino acid sequence in region of sub-domain 1 selected by mAb 3D10 the PvDBPII gene fragment library (FIG. 4C).

Further characterization to determine the potential immunogenicity of the minimal epitopes was pursued next. The minimal peptides identified from panning with PvDBPII gene fragment libraries and the random peptide library were produced synthetically and conjugated to KLH carrier protein to immunize mice (Table 1). Table 1 shows peptides identified through biopanning used for immunizations. Peptides were conjugated to KLH and used to immunize groups of ten BALB/c mice. Following two boosts sera was collected. Sera was tested for antibodies to corresponding peptides and to rDBPII Sal1 by ELISA.

TABLE 1

| | | ELISA with | |
|---|---|---|---|
| Name | Peptide Sequence | Peptide | rDBPII Sal1 |
| 3C9-e1 | DILKQELDEFNEVAFENE (SEQ ID NO: 13) | + | + |
| 3D10-e2 | IINHAFLQNTVMKNCNYKRKRR (SEQ ID NO: 12) | + | − |
| 3D10-m1 | VGNLDFSRFHKSSLDYKRGQ (SEQ ID NO: 14) | + | − |
| 3D10-m2 | VKFTDRYKYSSMKGYARQGR (SEQ ID NO: 15) | + | − |
| 3D10-m3 | KINMYKEVRTRQLSVRPSPE (SEQ ID NO: 16) | + | − |
| Control | TPDERYRELDSHAQNESC (SEQ ID NO: 53) | + | − |

Figure 8A:
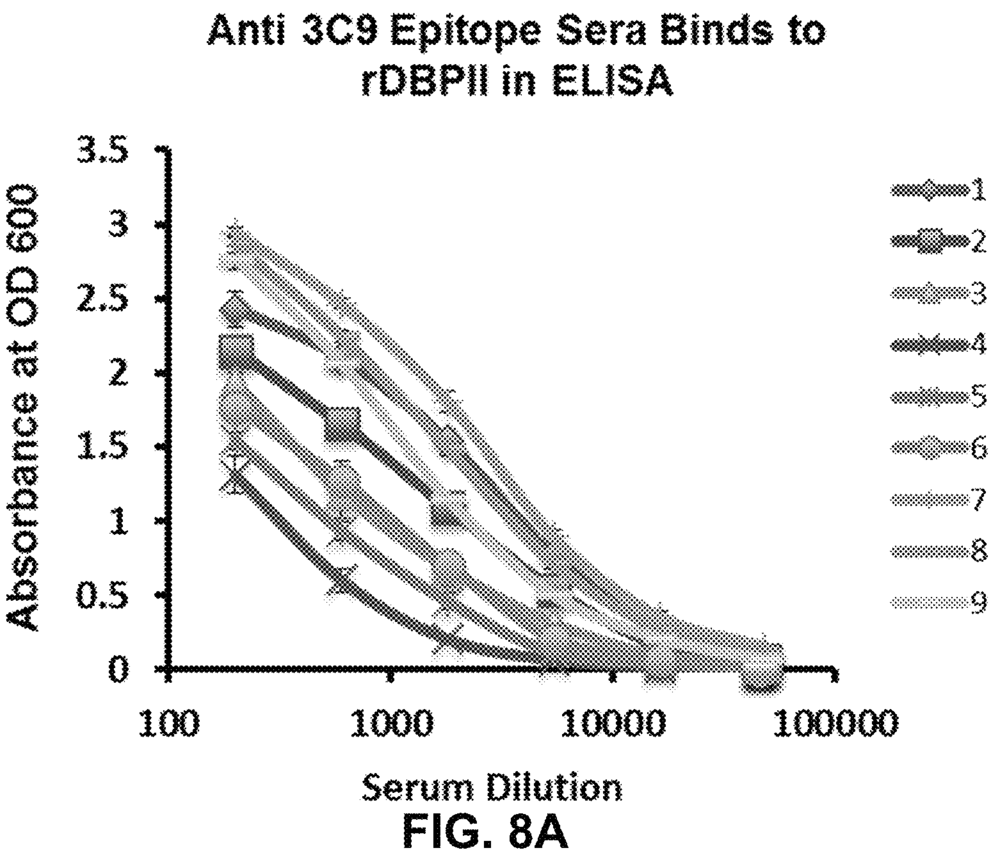
FIGS. 8A-8B demonstrate anti 3C9-e1 sera characterization.

ELISAs were used to determine reactivity of the anti-peptide sera for the minimal peptide epitopes of 3D10 and 3C9. Serum from each mouse was tested for affinity to its homologous peptide. All peptides, with the exception of the 3D10 epitope peptide, were immunogenic. Further, each antiserum was tested for affinity to rDBPII and surprisingly mice immunized with 3C9 epitope peptide produced a measurable antibody response reactive with rDBPII (FIG. 8A).

Figure 8B:
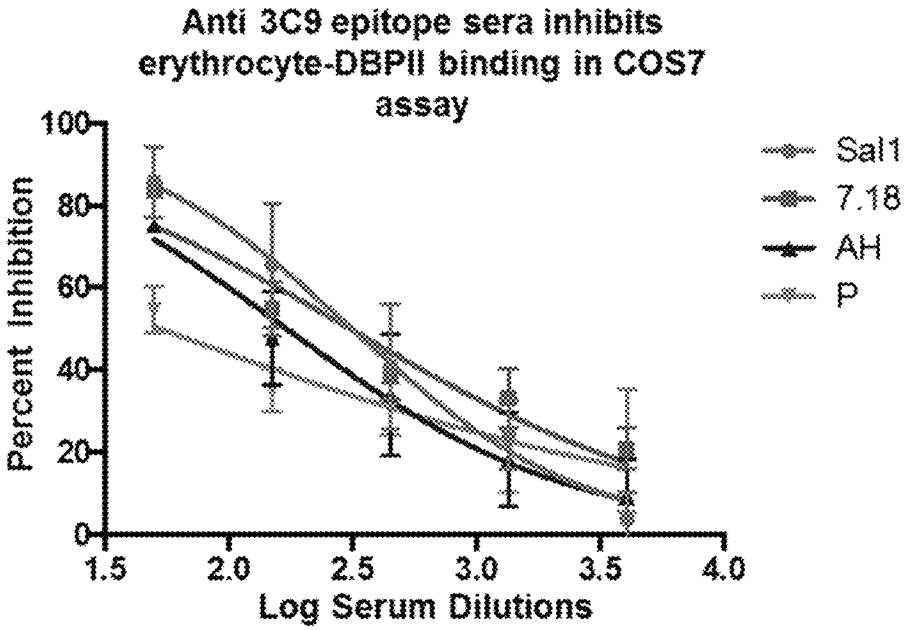

To assess anti-3C9 epitope peptide sera for its potential to broadly inhibit DBPII-erythrocyte binding, a standard in vitro COS7 binding inhibition assay was carried out (FIG. 8B). A concentration-dependent inhibition of binding of DBPII-erythrocytes was observed. Serum dilution that correspond to 50% inhibition ($IC_{50}$) of binding of erythrocytes to the DBPII alleles were 1:313.6 for Sal1, 1:309.1 for 7.18, 1:171.6 for AH and 1:52.73 for P. Binding inhibition curves of each allele was compared to Sal1 using Dunnett's multiple comparison test. Alleles 7.18 and AH showed no significant difference compared to Sal1, suggesting that 3C9-e1 produced and antibody response that recognizes a conserved region of DBPII within these alleles.

Figure 10:
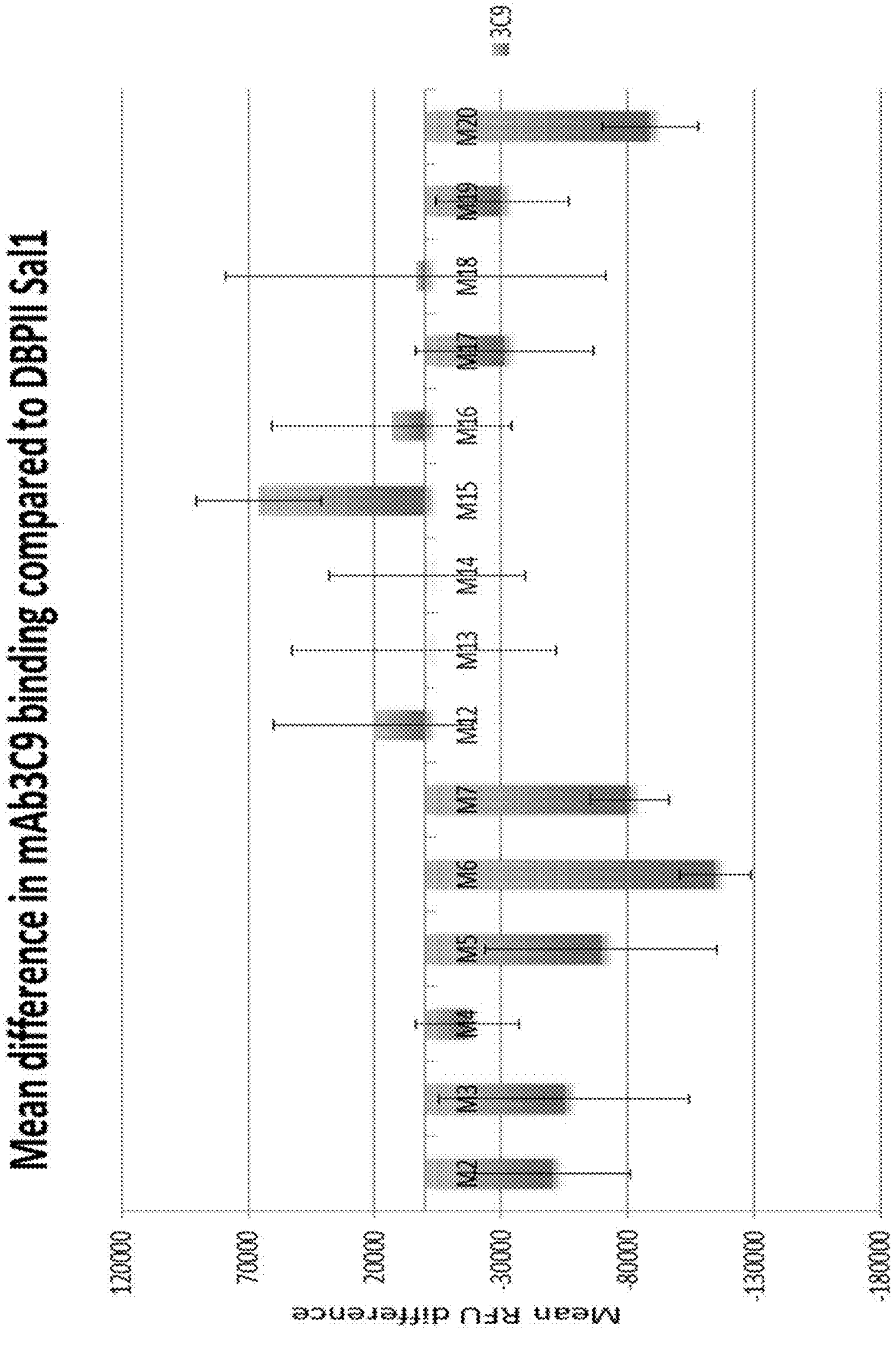
FIG. 10 demonstrates results of an immunofluorescent assay of DBPII mutants expressed on COS7 cells. Fluorescence images of 10 cells for each DBPII-antibody pair was captured. Mean pixel intensity for each DBPII-antibody pair was determined. Each bar represents mean pixel intensity compared to DBPII Sal1 and error bars indicate ±SD.
Figure 11A:
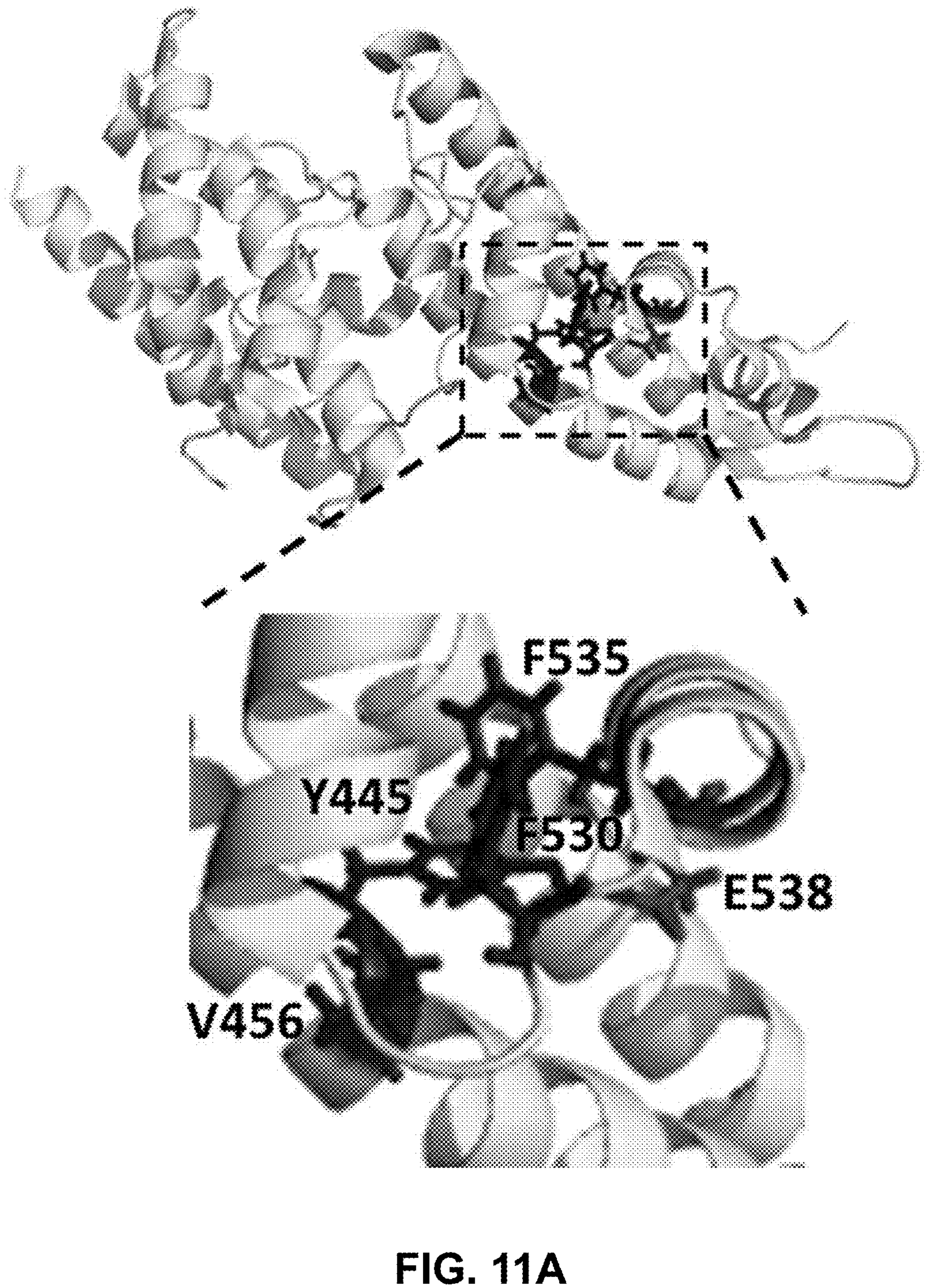
FIGS. 11A-11C demonstrate a crystallographic representation of residues on DBPII important for antibody binding.
Figure 11B:
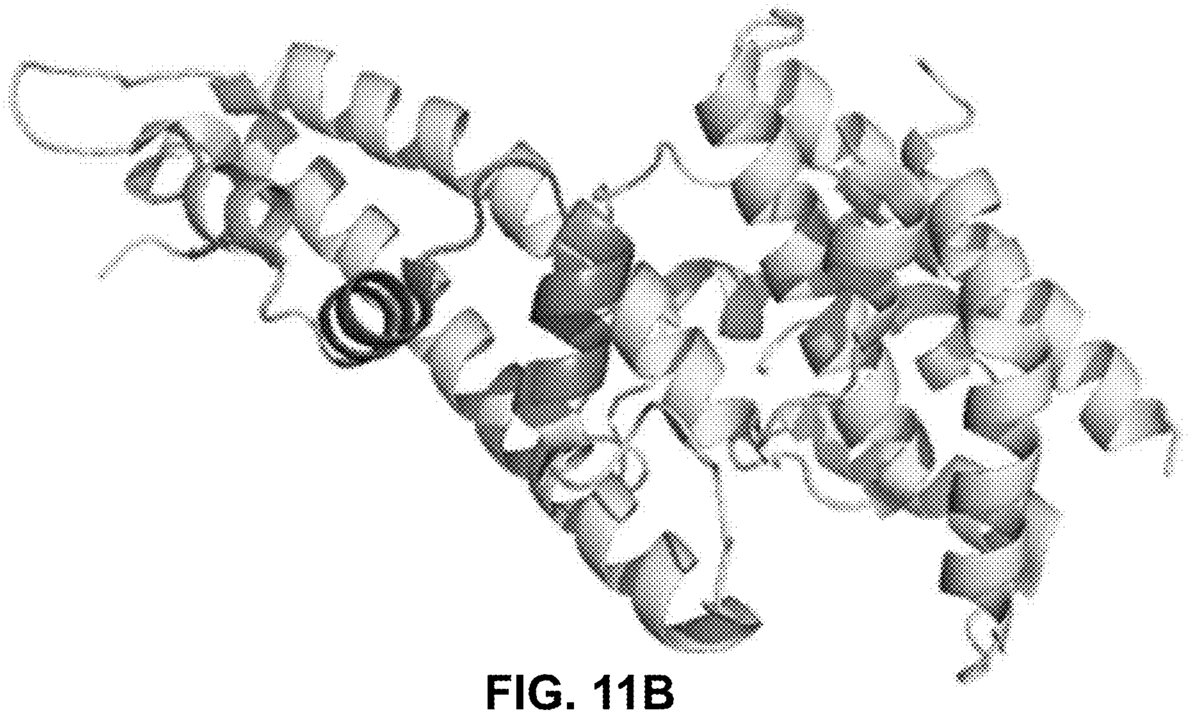
Figure 11C:
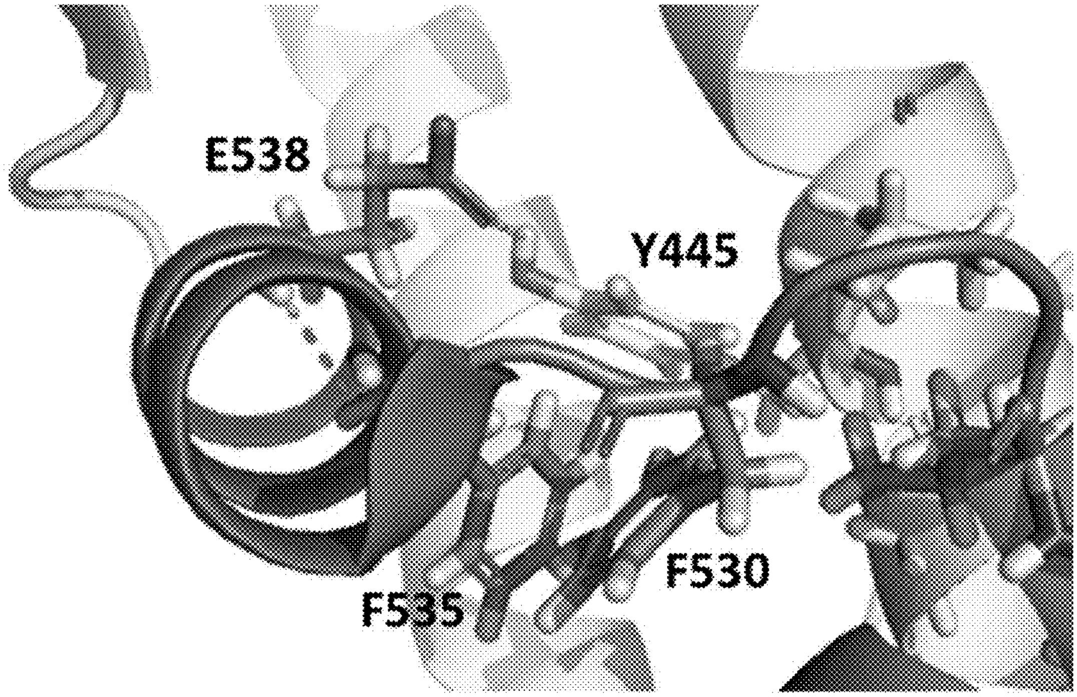

Residues reactive with the mAb and predicted to be surface exposed on the 3D PvDBPII crystal structure (FIG. 9) were further analyzed by site directed mutagenesis (FIG. 10). The purpose of this procedure was to validate specificity of the epitope for 3C9 and determine the relative importance of each residue within the epitope for antibody binding. A surface immunofluorescence assay was used to determine the ability of the antibodies to bind to DBPII mutated at specific residues expressed on the surface of COS7 cells. The relative fluorescence unit (RFU) was used to compare binding of antibody to wild type DBPII Sal1 and mutant.

Mutation of a single residue E538A (M20) within the 3C9 epitope remarkably reduced binding of mAb 3C9 compared to DBPII Sal1 (FIGS. 10 and 11A-11C). Mutant 6, Y445A/V446A/F530A/F535A (M6) also showed reduction in binding to mAb 3C9. Structurally, residues E538 and F535, on the epitope, seem to interact with residues Y445 upstream to the epitope but still in subdomain 3. It is interesting to note that the single mutation of F535 (Mutant 19) had almost no difference in binding to mAb 3C9 compared to DBPII Sal1 and yet this mutation greatly reduced binding to mAb 2D10. A similar effect is observed with the single amino acid substitution E529A (Mutant 14), which greatly reduced binding to mAb 2D10 but no effect on mAb 3C9 binding. Structurally, V446 seems to interact with G442 which when mutated also showed reduction in binding (Mutant 4) to mAb 2D10 and not to mAb 3C9. Multiple mutations to residues Y445A, V446A, F530A and F535A (Mutant 6) reduced binding to both mAb 3C9 and mAb 2D10.

Discussion

PvDBP can faciliate *P. vivax* merozoite invasion of Duffy positive reticulocytes. PvDBP is a member of the Duffy-binding-like erythrocyte binding proteins (DBL-EBPs) family (Adams et al. 1992. Proc Natl Acad Sci USA 89:7085-7089.) that includes *P. falciparum* EBA175, PfEBL1, *P. knowlesi* DBPα,β and γ among others (Adams et al. 2001. Trends Parasitol 17:297-299). Studies of DBP have historically helped to define the understanding of the important biological properties of this important family of malaria parasite ligands. The N-terminal cysteine-rich ligand domain essential of receptor recognition is also under immune selective pressure driving allelic variation of the ligand domain and altering its antigenic character. DBP allelic variation is mainly constrained to polymorphisms in the DBL domain and varies by geographic region (62-64). Some polymorphic residues on DBPII are unique to a certain geographical region while others are common among global *vivax* alleles, like residues K371E, D384G, E385K, K386N, N417K, L4241, W437R and 1503K (62, 63, 65, 66). Generally, variation occurs in non-essential residues flanking residues critical for receptor recognition while variation in some residues is more important than in others. For example, residues 417, 437 and 503 were identified as determinants of antigenic character, since altering these residues conferred a significant change in sensitivity to inhibitory anti-PvDBPII antibodies (VanBuskirk et al. 2004. J Infect Dis 190:1556-1562). Overall evidence indicates that variation plays an important role in strain-specific immunity to PvDBP.

PvDBPII is largely alpha-helical and may be assigned into three sub-domains delineated by six disulphide bonds. While sub-domain1 of PvDBPII is made up of an antiparallel beta-hairpin, sub-domains 2 and 3 are seen as distinct bundles of three alpha-helixes (Batchelor et al. 2011. Nat Struct Mol Biol doi:10.1038/nsmb.2088). NMR studies of PvDBPII in contact with the core region of DARC ectodomain revealed that dimerization of PvDBPII is involved in and driven by receptor engagement as DARC ectodomain form a helix that binds to the dimer interface (Batchelor et al. 2014. PLoS Pathog 10:e1003869). Human anti-PvDBP inhibitory antibodies have been shown to bind to subdomain 2 in a surface region adjacent to the dimer interface (Batchelor et al. 2014. PLoS Pathog 10:e1003869 and Chootong et al., 2010. Infect Immun 78:1089-1095). Given that these dominant Bc epitopes are at the dimer interface and are not determined to be critical for either dimerization of receptor binding, anti-PvDBP immune efficacy appears to be primarily mediated through steric hindrance of dimerization.

Naturally acquired immunity to PvDBPII is present in *P. vivax* endemic areas, anti-DBPII immune response tends to increase with age and exposure (VanBuskirk et al. 2004. J Infect Dis 190:1556-1562; Xainli et al., 2003. Infrect, Immun, 71:2508-2515; Chootong et al. 2010. Infect Immun 78:1089-1095; and Cole-Tobian J L, et al. 2002. J Infect Dis 186:531-539). Studies have shown that about 8-10% of *P. vivax*-exposed individuals produce high titer strain-transcending or broadly neutralizing antibodies (King et al. 2008. Proc Natl Acad Sci USA 105:8363-8368), associated with 50% reduction in risk of infection with *P. vivax* (King et al. 2008. Proc Natl Acad Sci USA 105:8363-8368 and Chootong P, et al. 2010. Infect Immun 78:1089-1095). Concurrently, the antibody responses to PvDBP seen in people living in *P. vivax* endemic areas and the elevated levels of amino acid sequence polymorphisms are consistent with the hypothesis that the molecule is under immune selective pressure, especially as the PvDBPII polymorphisms are concentrated in the ligand domain region II, which has a nucleotide substitution rate four times higher than the rest of the molecule (Ampudia E, et al. 1996. Mol Biochem Parasitol 78:269-272; Tsuboi et al. 1994. Infect Immun 62:5581-5586; Cole-Tobian et al. 2002. J Infect Dis 186:531-539; Michon et al. 1998. Am J Trop Med Hyg 59:597-599; Fraser T, et al. 1997. Infect Immun 65:2772-2777). In previous studies, epitopes reactive with polyclonal human immune antibodies were identified using an array of overlapping linear peptides attached to plastic pins. This methodology proved to be surprisingly robust in identifying conformational epitopes, especially the dominant Bc epitope. This epitope termed "DEK" for its first three amino acids was confirmed subsequently to be a major target of naturally occurring human immune antibodies and a major determinant for controlling strain specific immunity elicited by vaccination (Ntumngia et al. 2013. I Vaccine 31:4382-4388 and Ntumngia and Adams. 2012. Clin Vaccine Immunol 19:30-36). This Example demonstrates the identification of specific epitope targets of mAbs induced by vaccination in mice, using phage display technology.

Phage display technology can be used for elucidating the molecular nature of protein-protein interactions (Smith GP. 1985. Science 228:1315-1317; Wilson D R, Finlay B B. 1998. Can. J. Microbiol. 44:313-329; and Coley et al. 2001. Protein Eng 14:691-698), and the methodology for DBPII was established. Recombinant filamentous phage was engineered to display DBPII (Sal1 and 7.18 alleles) on its surface as part of the pIII capsid protein. Selective panning of recombinant phage libraries on antibodies was used to isolate target epitopes or peptide mimics. Positive epitope-containing clones reactive with the anti-DBPII inhibitory antibodies were enriched by successive panning assays. The sequence identity of the selected peptides was determined by DNA sequencing. The identified recombinant fragments and peptides represent epitope-specific reagents that were used to evaluate reactivity of epitope-specific antibodies. A surprising outcome in this Example is the discovery that Bc epitope targets of highly inhibitory anti-DBP are located in subdomain III away from the dimer interface and residues determined to be important for erythrocyte binding. Only minimal epitope target of an inhibitory antibody could be defined whereas the minimal target of most inhibitory mAbs was the entire subdomain III (FIGS. 8A-8B, 9, and 10). In contrast the minimal epitope of the non-inhibitory mAb 3D10 was located in a surface region of subdomain I closer to the dimer interface.

Site directed mutagenesis studies revealed that binding inhibitory mAbs 3C9 and 2D10 are both sensitive to disruption of Y445, V446, F530 and F535 pocket present on the surface of sub-domain 3. Although F530 and F535 make up part of the 3C9 epitope identified using phage displaying DBPII gene fragment library, single amino acid mutation of these residues did not disrupt binding of 3C9. Without being bound by theory, this suggests that there is some synergistic interaction of these aromatic residues that make up the 3C9 and 2D10 binding pocket on DBPII. E538 seems to have polar interactions with F535 in the epitope and Y445 in the neighboring helix, which seems to be more important for binding of mAb 3C9 than mAb 2D10. However, V446 seems to interact with G442, which is more important for binding of mAb 2D10 than mAb 3C9.

The 3C9 minimal peptide epitope was further characterized by vaccination studies to determine its potential as a subunit synthetic vaccine. The immunogenicity of the 'protective' 3C9 epitope was compared to the minimal peptide epitope of 3D10. Although 3D10 represented the highest titer mAb within the anti-DBP panel created, and was reacted equally to all DBP alleles tested by ELISA, it has virtually no ability to block DBPII to erythrocytes (Ntumngia et al. 2012. Infection and immunity 80:1203-1208).

Various studies have examined the functional efficacy of vaccine-induced anti-DBP antibodies to block DBP erythrocyte binding or inhibition of merozoite invasion of erythrocyte (Ntumngia et al. 2013. Vaccine 31:4382-4388; Grimberg et al. 2007. PLoS Med 4:e337; Devi et al. 2007. Vaccine 25:5166-5174; and Arevalo-Herrera M, et al. 2005. Am J Trop Med Hyg 73:25-31). As a general rule properly refolded recombinant rDBPII that is capable of erythrocyte binding activity is required for induction of inhibitory anti-DBPII antibodies. Indeed the epitope targets of the protective mAb 3C9 (conformational) and non-protective mAb 3D10 (partially linear) are consistent with this observation. In the current approach, the DBP peptide immunogens, including the synthetic linear peptides of the 3C9 or 3D10 epitopes were conjugated to carrier KLH, were used to immunize mice. The 3D10 immunogens included mimotope peptides of epitope targets isolated from a random peptide library. Surprisingly, it was observed in this Example that a 3C9 epitope peptide successfully induced an antibody response reactive to the immunizing peptide, the refolded peptide as well as inhibitory to DBPII erythrocyte binding.

This result suggests that the 3C9 linear peptide has some inherent structural tendency to assume its 3D conformation displayed on the surface of native DBP and is the target of inhibitory antibody. Peptides like 3C9 epitope peptide, capable of eliciting protective antibodies, can be used for the design of a sub-unit vaccine against asexual blood stage *vivax* malaria.

Example 2

Demonstrated in this Example is a crystal structure of DBP-II bound to a scFv derived from mAb 2D10 that identifies a specific inhibitory epitope within SD3. The structure was confirmed by small angle x-ray scattering (SAXS) and validated the epitope through immunofluorescence and assess direct protein-protein interaction using ELISA. It was also demonstrated extensively that a second antibody, mAb 2H2, possesses a virtually identical paratope and binds to a similar region of DBP-II as mAb 2D10. Finally, through an extensive surface mutant panel, the epitope of two additional inhibitory antibodies, mAb 3D10 and mAb 2C6, was identified, and their epitopes were located to sub-domain 1 (SD1) and sub-domain 3 (SD3), respectively. Sequence analysis of these partial antibody epitopes reveal that they are conserved amongst different *P. vivax* strains, signifying that these sites are important targets of strain-transcending global protection and that these are the first bnAbs identified targeting a *Plasmodium* protein. The results also establish the existence of protective motifs outside of dimerization or receptor binding surfaces on DBP-II. Together, the mapping data expands the currently known inhibitory epitope repertoire and introduce a globally conserved protective target that elicits bnAbs for DBP-II vaccine design.

Using crystallography, small angle X-ray scattering, mutational mapping, and binding assays, epitopes for four monoclonal antibodies (mAbs) that engage DBP were defined. mAbs 2D10 and 2H2 share an epitope encompassed by residues 413-417 and 425-441. mAb 2C6 engages a different face of subdomain 3 in DBP that include residues 479-480, while mAb 3D10 engages an epitope in subdomain 1 that encompasses residues 218-223. All the epitopes are invariant among DBP alleles and lack known polymorphisms. 2D10 potently neutralizes *P. vivax* parasite growth in vivo indicating the 2D10/2H2 epitope is broadly neutralizing. This leads to the design of potent DBP-based vaccines for *P. vivax* malaria.

Materials and Methods

Protein expression and purification. Sal-1 DBP-II, BirA-tagged Sal-1 DBP-II, and DBP-II mutants were expressed in *E. coli* as inclusion bodies as previously described Batchelor, et al. 2014. PLoS Pathog 10, e1003869 and Batchelor et al. 2011. Nat Struct Mol Biol 18, 908-914). Inclusion bodies were solublized in 6 M guanidinium hydrochloride and refolded through oxidative refolding via rapid dilution into 400 mM L-arginine, 50 mM Tris pH 8.0, 10 mM EDTA, 0.1 mM PMSF, 2 mM reduced glutathione, and 0.2 mM oxidized glutathione. Refolded proteins were captured on SP Sepharose Fast Flow resin (GE Healthcare). Eluted protein was additionally purified by sequential size exclusion chromatography (GF200). Sal-1 DBP-II used for crystallization was additionally purified by ion exchange chromatography (HiTrapS) and a final size exclusion chromatography (GF75) into 10 mM HEPES pH 7.4, 100 mM NaCl.

Fab generation and purification. Fab fragments for 2D10, 2H2, and 2C6 were generated from the respective IgG's using immobilized papain resin and protein A resin (Thermo Scientific) as per manufacturer's protocols and as previously described (Chen et al. 2013. PLoS Pathog 9, e1003390). The eluted Fab fragments were further purified by size exclusion chromatography in 10 mM HEPES pH 7.4, 100 mM NaCl.

Antibody sequencing. RNA was extracted from hybridoma cells using QiaShredder (Qiagen) and RNeasy Mini Kit (Qiagen). 5' RACE Kit (Invitrogen) was used to obtain cDNA for the heavy and light chain variable regions. RACE primers for the heavy chain were: GSP1 for IgG, isotype was 5' TGCATTTGAACTCCTTGCC 3' (SEQ ID NO: 54) and GSP2 for $IgG_1$ isotype was 5' CTTTGGGGG-GAAGATGAAG 3' (SEQ ID NO: 55). RACE primers for the light chain were: GSP1 for $C_K$ was 5' CACTCAT-TCCTGTTGAAGC 3' (SEQ ID NO:56) and GSP2 for $C_K$ was 5' CTTGTGAGTGGCCTCACAGG 3' (SEQ ID NO:57). cDNA was TOPO cloned (Invitrogen) and sequenced.

Synthesis and expression of mAb 2D10 scFv. The variable region of the light chain was linked to the variable region of the heavy chain using a (GGGGS )s (SEQ ID NO:58) linker and cloned into the pHLSec mammalian expression vector using restriction sites Agel/Kpnl (Aricescu et al. 2006. Acta Crystallogr D Biol Crystallogr 62, 1243-1250). scFv was obtained by transient transfection in HEK293F cells. Media was harvested five days post-transfection, diluted 1:3 into 20 mM Tris pH 8.0, 200 mM NaCl, 5 mM imidazole and captured on Ni-NTA resin, washed with 20 mM Tris pH 8.0, 200 mM NaCl, 10 mM imidazole, and eluted with 20 mM Tris pH 8.0, 200 mM NaCl, 300 mM imidazole. Protein elution was additionally purified on size exclusion chromatography (GF75) into 10 mM HEPES pH 7.4, 100 mM NaCl.

Protein crystallization and data collection. DBP-II/$2D10_{scFv}$ complexes were created by mixing DBP-II and scFv in a 0.9:1 molar ratio and incubated at 4° Celsius for 30 minutes. Complex was purified by size exclusion chromatography (GF75) with 10 mM HEPES pH 7.4, 100 mM NaCl. DBP-II/$2D10_{scFv}$ crystals were grown by hanging-drop vapor diffusion by mixing 1 μL of protein solution at 18 mg/mL with either 3 μL or 4 μL of reservoir containing 1% w/v tryptone, 50 mM HEPES sodium salt pH 7.0, 12% w/v PEG 3,350. Plate clusters grew within a week. Individual plates were obtained from shattering clusters and flash frozen with 30% PEG 400 as cryoprotectant in liquid nitrogen. Data was collected to a resolution of 3.5 Å at beamline 4.2.2 of the Advanced Light Source, Lawrence Berkeley National Laboratory and processed with XDS (Kabsch, W. 2010. Xds. Acta Crystallogr D Biol Crystallogr 66, 125-132).

Structure solution and analysis. The DBP-II/$2D10_{scFv}$ structure was solved by molecular replacement in PHASER (McCoy, et al. 2007. Phaser crystallographic software. J. Appl. Crystallogr 40, 658-674) using the DBP domain from 4NUV and a modeled scFv domain from PIGS (Prediction of Immunoglobulin Structure) (Marcatili, et al. 2008. Bioinformatics 24, 1953-1954) as starting models. Initial rigid body refinement in PHENIX (Adams et al., 2002. Acta Crystallogr D Biol Crystallogr. 58:1948-54) resulted in R-work/R-free of 41.24%/42.48%. Due to the quality of the crystal and resolution of data, careful refinement using DEN refinement in CNS (Schroder et al., 2010) was performed. Subsequent repeated rounds of refinement in PHENIX with tight geometric constraints and manual rebuilding in COOT (Emsley, P., and Cowtan, K. 2004. Acta Crystallogr D Biol Crystallogr 60, 2126-2132) led to a final refined model with final R-factor/R-free of 28.59%/33.32% with good geometry as reported by MOLPROBITY (Davis et al., 2007). The MOLPROBITY score of 1.73 places this structure in the top $100^{th}$ percentile of structure 3.25 Å-4.25 Å. 97.84% of residues lie in favored, 2.16% of residues lie in additionally allowed, and 0% lie in disallowed regions of the Ramachandran plot.

Immunofluorescence assay. The two mAb 2D10 epitope mutants were created by mutating the sequence at the center of the antibody footprint. Amino acids N479 and K482 were mutated to either alanine or arginine. Adherent HEK293T cells were grown in 6-well tissue culture plates and transfected with DNA containing gene sequences of either wild-type PfEBA-175, Sal-1 DBP-II, alanine mutant, or arginine mutant in the pRE4 vector (Cohen, et al. 1988. J Virol 62, 1932-1940). The cells were probed with 10 μg/mL of mAb 2D10, mAb 2H2, or mAb 2C6, washed, probed with 1 μg/mL of either Alexafluor-546 labeled α-mouse IgG1 (Invtrogen) or 1 μg/mL of Alexafluor-568 labeled α-mouse IgG, washed, and imaged with a fluorescent microscope. Fluorescent quantification was done automatically using ImageJ.

Small-angle X-ray scattering. Data for DBP-II/Fab complexes of mAb 2D10, 2H2, and 2C6 was collected at the SIBYLS beamline 12.3.1 at the ALS using standard procedures (Hura, et al. 2009. Nat Methods 6, 606-612.), and analyzed using the ATSAS package version 2.5.2-1 (Petoukhov, et a. 2012. J. Appl Crystallogr 45: 342-350). Data quality and radiation damage was assessed by analyzing datasets using PRIMUS. The experimental profile was compared to the DBP-II/$2D10_{scFv}$ structure with a Fab model using CRYSOL. Ab initio model generation was performed in DAMMIF and the filtered average envelope of ten models was obtained by DAMAVER. SUPCOMB20 was used to align structures and SAXS reconstructions. The molecular weight estimate was obtained using SAXS-MOW.

ELISA binding assays with anti-DBP antibodies. The ELISAs were performed as previously described (Salinas, et al. (2014). Critical Glycosylated Residues in Exon Three of Erythrocyte Glycophorin A Engage *Plasmodium falciparum* EBA-175 and Define Receptor Specificity. M. Bio 5 and Salinas, N. D., and Tolia, N. H. 2014. Protein Expr Purif 95, 188-194). Briefly, BSA, Sal1 DBP-II, and DBP-II mutants were coated on the plate overnight at 4°. The plates were washed with PBS/Tween-20 and then blocked with 2% BSA in PBS/Tween-20 for one hour at room temperature. The plates were washed with PBS/Tween-20 and then incubated with anti-DBP antibodies (2D10, 2H2, 3D10, 2C6) individually for one hour at room temperature. The plates were again washed with PBS/Tween-20 and then incubated with an anti-mouse secondary antibody conjugated to Alexafluro-488 for 30 minutes at room temperature. After a final wash step, the fluorescence was measured using a POLARstar Omega (BMG Labtech) plate reader.

Biotinylation of BirA tagged Sal-1 DBP-II. BirA tagged Sal-1 DBP-II was buffered exchanged into biotinylation buffer (100 mM Tris pH 7.5, 200 mM NaCl, 5 mm $MgCl_2$). 50 μL of BiomixA (Avidity), 50 μL of BiomixB (Avidity), and 100 μL of d-biotin (Avidity) was added to the protein along with BirA ligase and incubated overnight at 4° Celsius. Reaction mix was buffer exchanged into PBS prior to use.

Competition ELISA with anti-DBP antibodies. 10 μg of mAb 2D10 was coated per well on the plate overnight at 4° Celsius. The plates were washed with PBS/Tween-20 and then blocked with 2% BSA in PBS/Tween-20 for one hour at room temperature. The plates were washed with PBS/Tween-20 and then incubated with 100 μL mixtures of 2.5 μg of biotinylated Sal-1 DBP-II and either 1 μg, 10 μg, or 100 μg of competitor for 1 hour at room temperature. The plates were again washed with PBS/Tween-20 and incubated with 100 μL of 1:5000 dilution of Streptavidin-HRP (Thermo Scientific) for 1 hour at room temperature. After a final wash step, 100 μL of TMB (Sigma) was added and the reaction was quenched with 100 μL of 2 M $H_2SO_4$. Absorbance at 450 nm was measured using a POLARstar Omega (BMG Labtech) plate reader.

Invasion inhibition assays with anti-DBP antibodies. Anti-DBPII mAbs were tested for ability to inhibit *P. vivax* invasion of human erythrocytes as described (Russel B et al. 2011). Purified Ig of each mAb was adjusted to 200 ng/ml, which is the IC50 determined by in vitro binding inhibition COS cell assays (Ntumngia, et al. 2012 J. H. 2012. Infect Immun. 80:1203-1208). Briefly, enriched reticulocytes from cord blood and mature *P. vivax* schizonts purified from patients infected with *P. vivax* were incubated in the presence or absence of 200 ng/ml of anti-DBPII monoclonal antibody for 24 hrs. Invasion inhibition was expressed as the percentage of erythrocytes with rings (i.e., newly invaded cells) per 4000 erythrocytes in presence of test antibody relative to erythrocytes with rings in the absence of antibodies.

Results

Figure 12A:
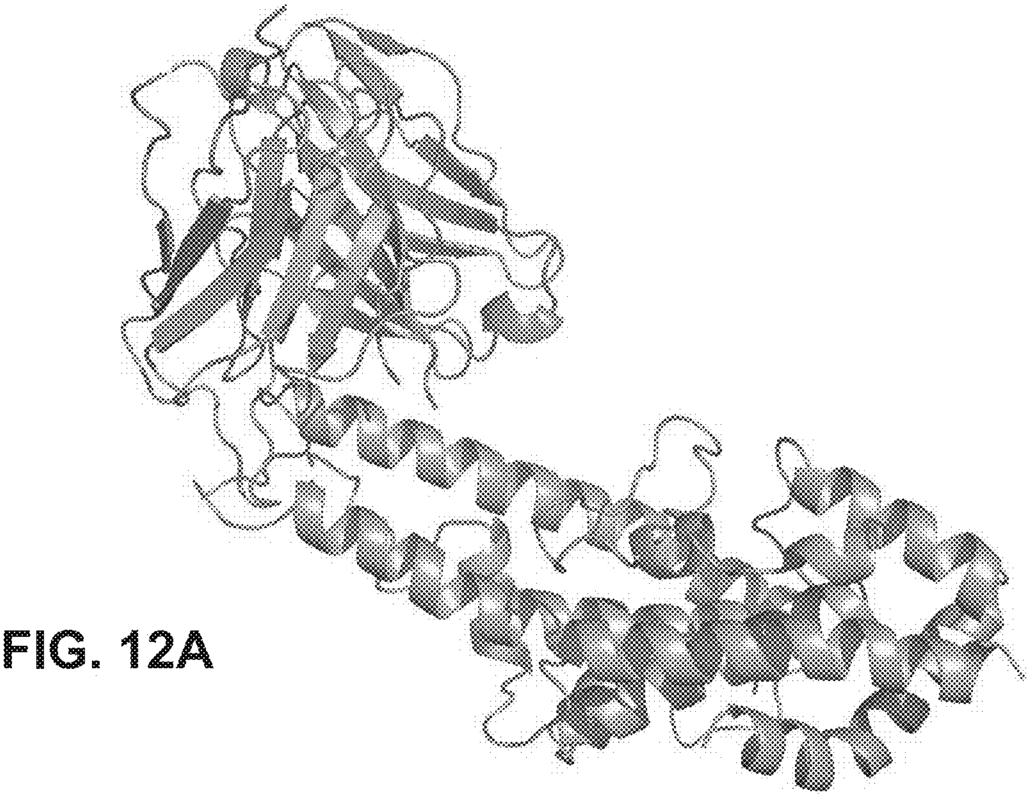
FIGS. 12A-12C demonstrate the crystal structure of the DBP-II/2D10$_{scFv}$ complex.
Figure 12B:
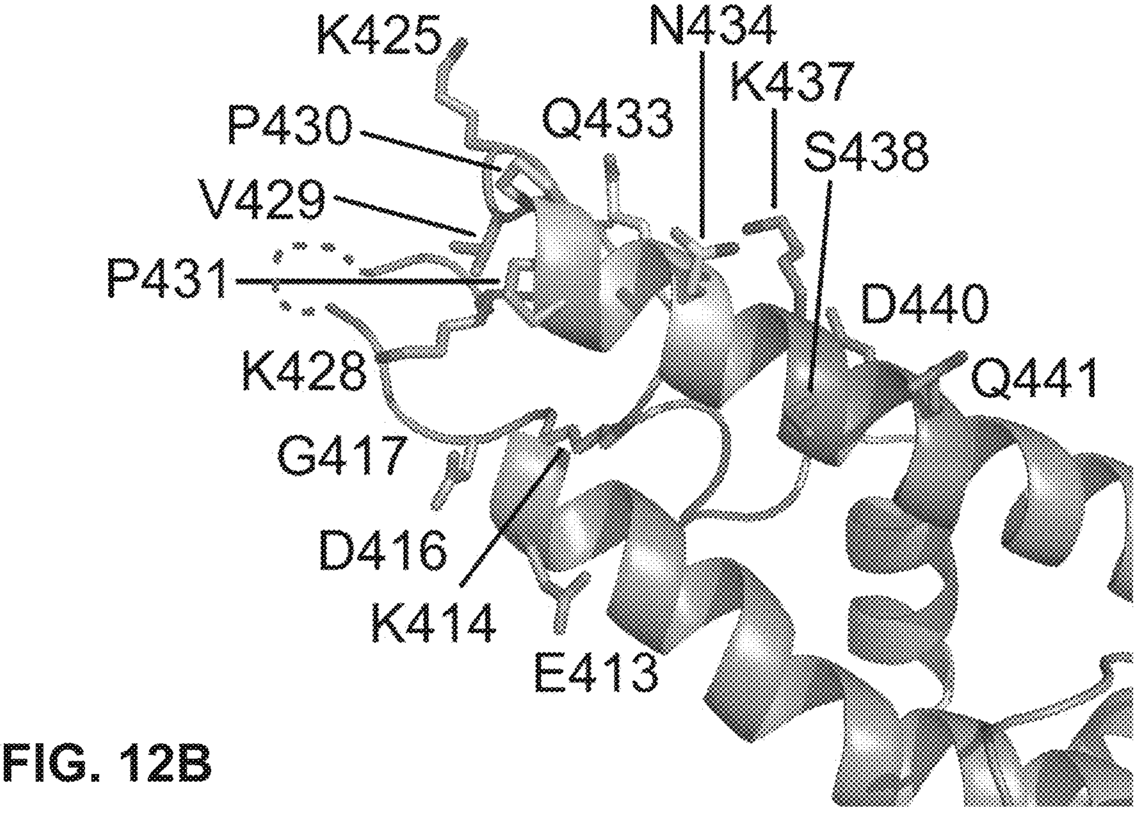
Figure 12C:
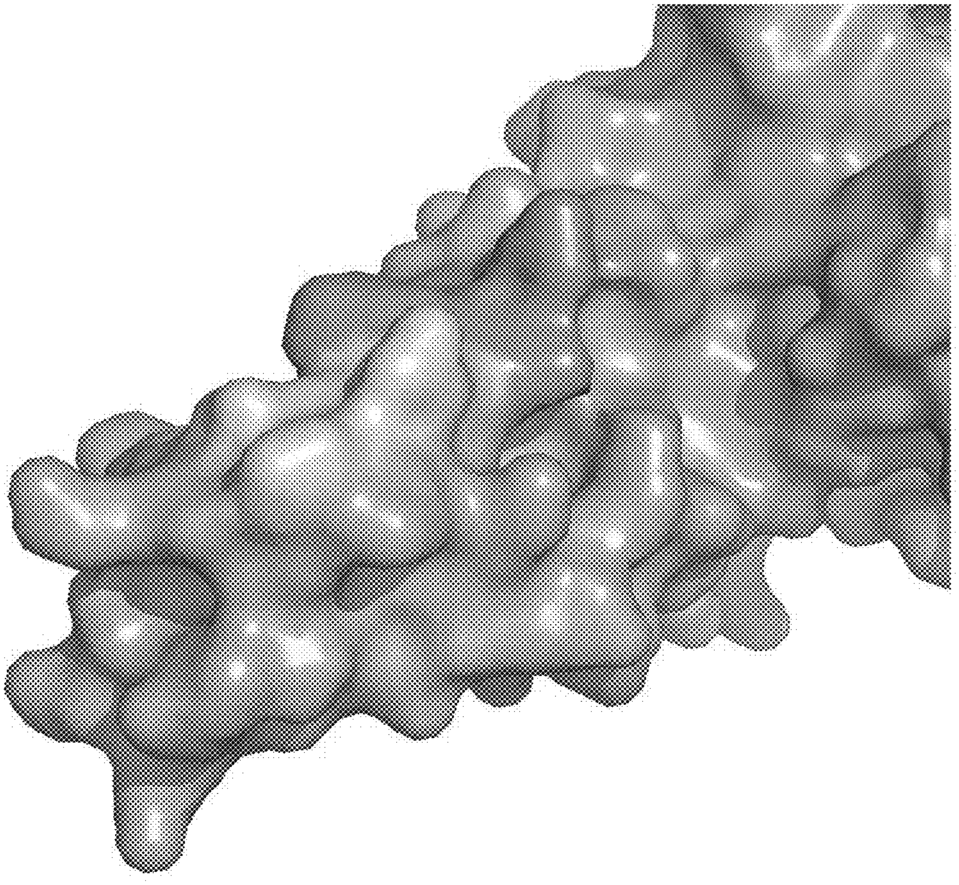

Structure of the DBP-II/2D10-scFv complex. The crystal structure of an engineered scFv construct of mAb 2D10 was solved in complex with DBP-II to a resolution of 4.0 Å (FIGS. 12A-12C, Table 2). Table 2 shows the data collection and refinement statistics for the DBP-II 2D10 scFv complex. Data were collected from a single crystal.* Highest resolution shell is shown in parenthesis.

TABLE 2

| | DBP-II/$2D10_{scFv}$ |
|---|---|
| Data collection | |
| Space group | $P2_1$ |
| Cell dimensions | |
| a, b, c (Å) | 84.74, 63.90, 108.86 |
| α, β, γ (°) | 90, 100.25, 90 |
| Resolution (Å) * | 20-4.0 (4.24-4.0) |
| $R_{sym}$ * | 0.117 (0.239) |
| //σ/ * | 6.71 (3.64) |
| Completeness (%) * | 92.9 (92.9) |
| Redundancy * | 2.73 (2.68) |
| Refinement | |
| Resolution (Å) | 20-4.0 |
| No. reflections | 9236 |
| $R_{work}/R_{free}$ | 28.59/33.32 |
| No. atoms | |
| Protein | 7721 |
| Ligand/ion | 0 |
| Water | 0 |
| B-factors | |
| Protein | 87.51 |
| Ligand/ion | 0 |
| Water | 0 |
| R.m.s. deviations | |
| Bond lengths (Å) | 0.004 |
| Bond angles (®) | 0.948 |

Figure 13:
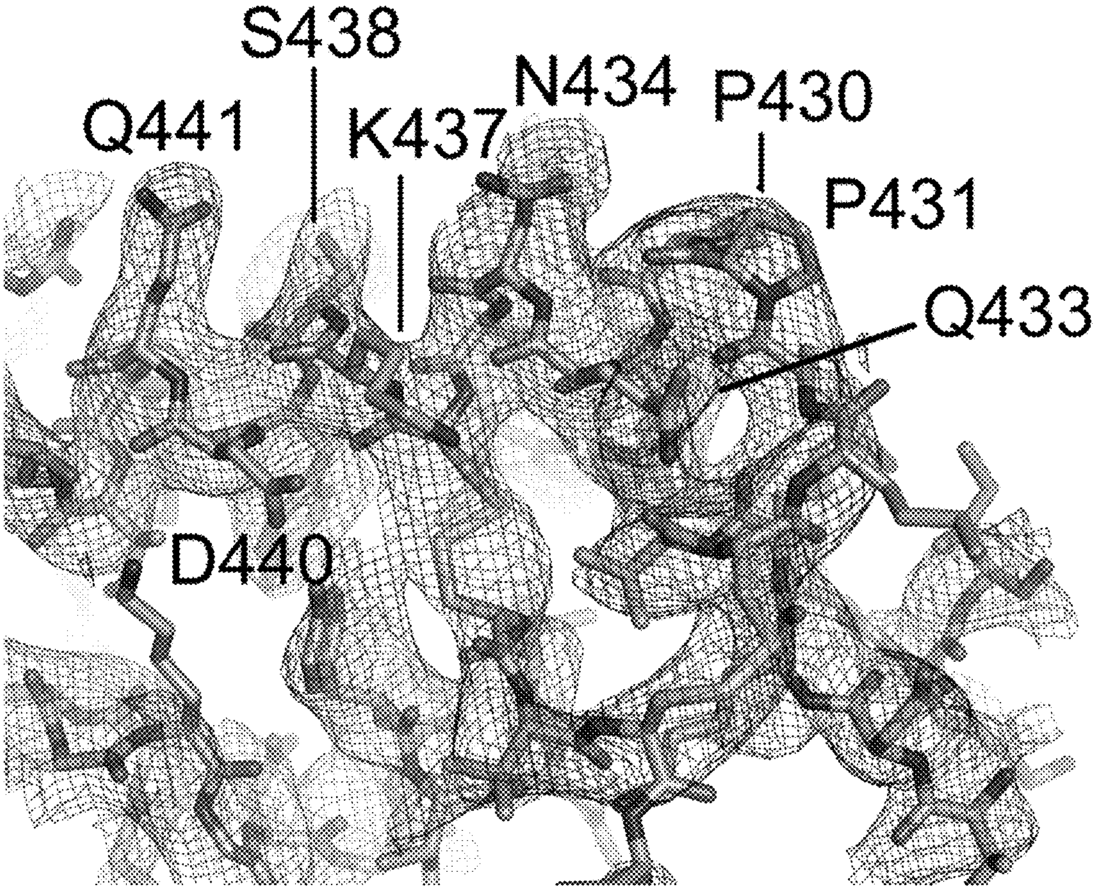
FIG. 13 demonstrates 2Fo-Fc electron density contoured at 1σ around the epitope clearly identifying contact sites in DBP. The antibody is removed for clarity and only DBP and associated electron density is shown. In this orientation, clear electron density for residues 433 to 441 that comprise part of the epitope for 2D10 are observed.

At this resolution the residues in DBP-II contacted by the antibody can be clearly identified as the backbone density is clear and several side chains located in the epitope are ordered (FIG. 13). 2D10 binds to a conformational epitope primarily composed of amino acids 413-417 and 425-441 that make up the end of a three helix bundle within subdomain 3 (SD3) of Sal-1 DBP-II (FIGS. 12A-12C, Table 3). Table 3 demonstrates contact residues between DBP and mAb 2D10.

TABLE 3

| Residues in DBP | Interface with 2D10 chains | Residues in 2D10 Light | Residues in 2D10 Heavy |
|---|---|---|---|
| E413 | Light | Y31 | S31 |
| K414 | Light | Q32 | W33 |
| D416 | Light | D33 | R50 |
| G417 | Light | K35 | Y52 |
| K425 | Light | Y37 | D55 |
| K428 | Light | L55 | D57 |
| V429 | Light | L96 | H59 |
| P430 | Light, Heavy | V97 | E99 |
| P431 | Light | E98 | E100 |
| Q433 | Light, Heavy | Y99 | T101 |
| N434 | Light, Heavy | L101 | A102 |
| K437 | Heavy | | G105 |
| S438 | Heavy | | |
| D440 | Heavy | | |
| Q441 | Heavy | | |

All three complementary determining regions (CDRs) in both the heavy and light chain make contacts; the heavy and light chains contribute buried surface areas of 649 $Å^2$ and 855 $Å^2$, respectively, for a total of 1504 $A^2$. The complex has a slightly greater-than-average shape complementarity at 0.70, with the average range being 0.64-0.68, and perfect complementarity at 1.00 (Lawrence, M. C., and Colman, P. M. 1993. J Mol Biol 234, 946-950). Binding of mAb 2D10 does not significantly change the overall structure of Sal-I DBP-II with an rmsd of 0.692 Å. Thus, the inhibitory effects of mAb 20D10 is not due to disruption of the DEL fold, but rather its physical location on DPB-II and disruption of native protein function.

Figure 14A:
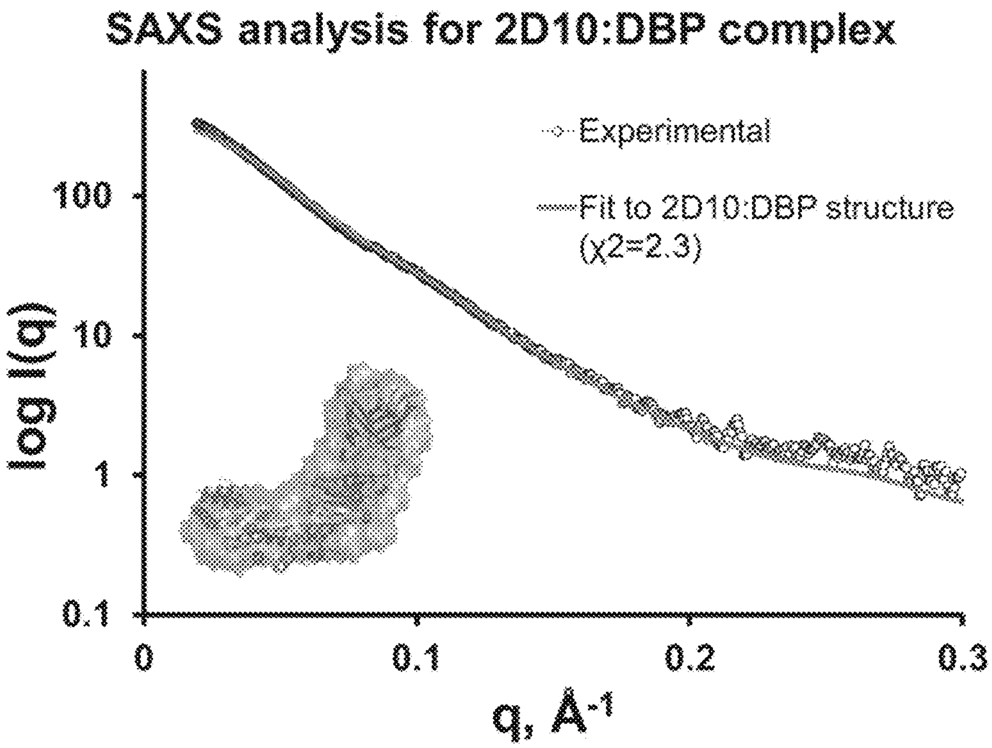

Small angle x-ray scattering of the DBP-II/2D$10_{Fab}$ complex. To support the crystal structure, SAXS analysis was performed on the DBP-II/2D$10_{Fab}$ complex (FIG. 14A). SAXS returns a molecular envelope of species in solution, circumventing crystal packing artifacts, and is an independent method to determine the structure of the complex. As the SAXS data was collected on a Fab complex, the DBP-II/2D$10_{Fab}$ structure was modeled by aligning a 2D$10_F$ab model on the 2D$10_{scFv}$ structure. The predicted scatter from the DBP-II/2D$10_{Fab}$ structure fit the SAXS profile with a $X^2$ value of 2.30. $X^2$ values of less than 3 are indicative of a correct fit (Petoukhov, M. V., and Svergun, 0.I. 2005. Biophys J 89, 1237-1250). SAXS can also determine the molecular weight of samples (Fischer et al. 2010. J App Crystallography 43, 101-109). SAXS MOW returned an estimated molecular weight for the DBP-II/2D$10_{Fab}$ of 94.9 kDa. This value is consistent with the theoretical mass (87 kDa) of a complex of a monomer of DBP (~37 kDa) and a Fab monomer (~50 kDa). Thus, the SAXS analysis strongly validates the 2D10 epitope.

Figure 14B:
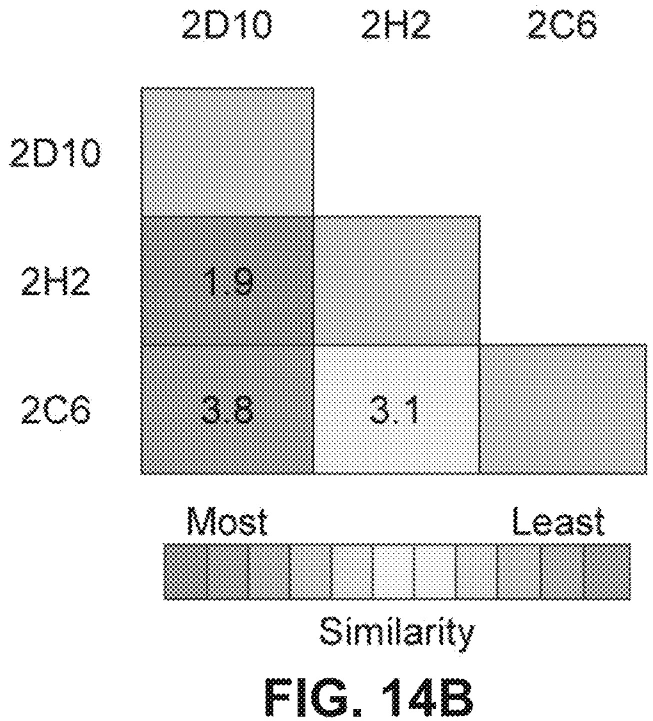

Pair-wise SAXS Profile comparison of 2D10, 2H2, and 2C6. SAXS data for DBP-II/2$H2_{Fab}$ for DBP-II/2$C6_{Fab}$ were obtained and a pair-wise comparison to the DBP-II/2D$10_{Fab}$ data was performed to identify if these complexes were structurally similar using the volatility of ratio ($V_R$) metric (Hura et. al. 2013. Nat Methods 10, 453-454). Structurally similar complexes will have low $V_R$ while structurally distinct complexes have high $V_R$. The low $V_R$ of 1.9 between DBP-II/2D$10_{Fab}$ and DBP-II/2$H2_{Fab}$ complexes (FIG. 14B) demonstrated these two complexes are similar. The high $V_R$ between DBP-II/2$C6_{Fab}$ and either DBP-II/2D$10_{Fab}$ (3.8) or DBP-II/2$H2_F$ab (3.1) indicate DBP-II/2$C6_{Fab}$ has a distinct architecture from the other two complexes.

mAb 2H2 and mAb 2D10 share high sequence identity in the CDRs of both Heavy and Light Chains. Sequence analysis of mAb 2D10 and mAb 2H2 revealed high sequence identity throughout the entire variable regions of the light and heavy chains, as well as, within individual complementarity determining regions (CDR) (FIG. 14C). The overall sequence identity of the entire variable heavy and variable light is 89% and 96%, respectively. Within the heavy chain variable region, CDR1, CDR2, and CDR3 share sequence identity at 86%, 100%, and 11%, respectively. Within the light chain variable region, all three CDR regions are highly identical: 100% for both CDR1 and CDR2, and 67% for CDR3. These alignments suggest mAb 2D10 and mAb 2H2 share antigenic determinants on DBP-II. Furthermore, it's likely that mAb 2D10 and 2H2 share a common B-cell ancestor during lineage development.

In contrast, a different conformationally dependent mAb 2C6 shared little or no sequence identity to 2D10 or 2H2 in CDR1 of the heavy chain (29%) and CDR3 (0%). CDR2 of the heavy chain had slightly higher sequence identity of 75%. In the light chain, there was no similarity for either CDR2 and CDR3 between 2C6 and 2D10 or 2H2. CDR1 did have 71% sequence identity to 2D10 and 2H2. These divergent CDRs further supports that 2D10 and 2H2 share epitopes while 2C6 engages a unique epitope on DBP.

Figure 14D:
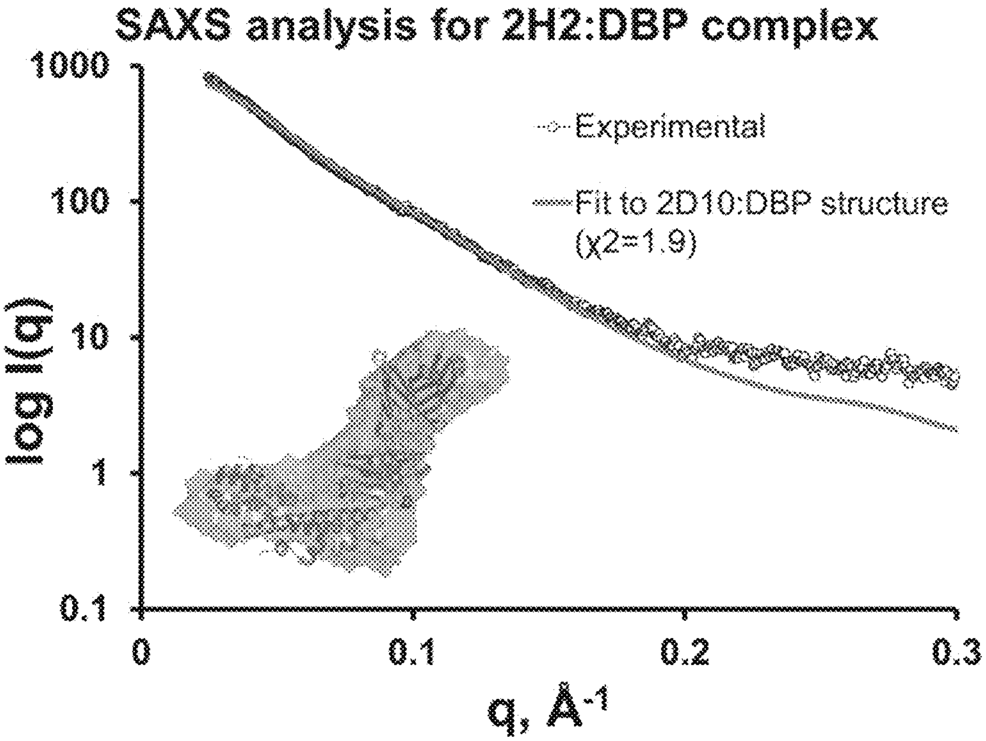

Small angle x-ray scattering of the DBP-II/2$H2_{Fab}$ complex supports shared binding site with 2D10. The SAXS profiles of Fab complexes were compared with the DBP-II/2D$10_{Fab}$ model (FIG. 14D). The predicted scatter from the DBP-II/2D$10_{Fab}$ model fit the DBP-II/2$H2_{Fab}$ SAXS profile with a $X^2$ of 1.9. $X^2$ values less than 3 are indicative of a correct fit (Petoukhov, M. V., and Svergun, D. I. 2005. Biophys J 89, 1237-1250). SAXS MOW analysis returned an estimated molecular weight for the DBP-II/2$H2_{Fab}$ complex of 82.6 kDa consistent with the theoretical mass of 87 kDa of a 1:1 complex. This analysis demonstrates that 2D10 and 2H2 engage DBP in a similar manner and share the same epitope as the DBP-II/2D10 structure can explain the DBP-II/2H2 SAXS data.

Figure 14E:
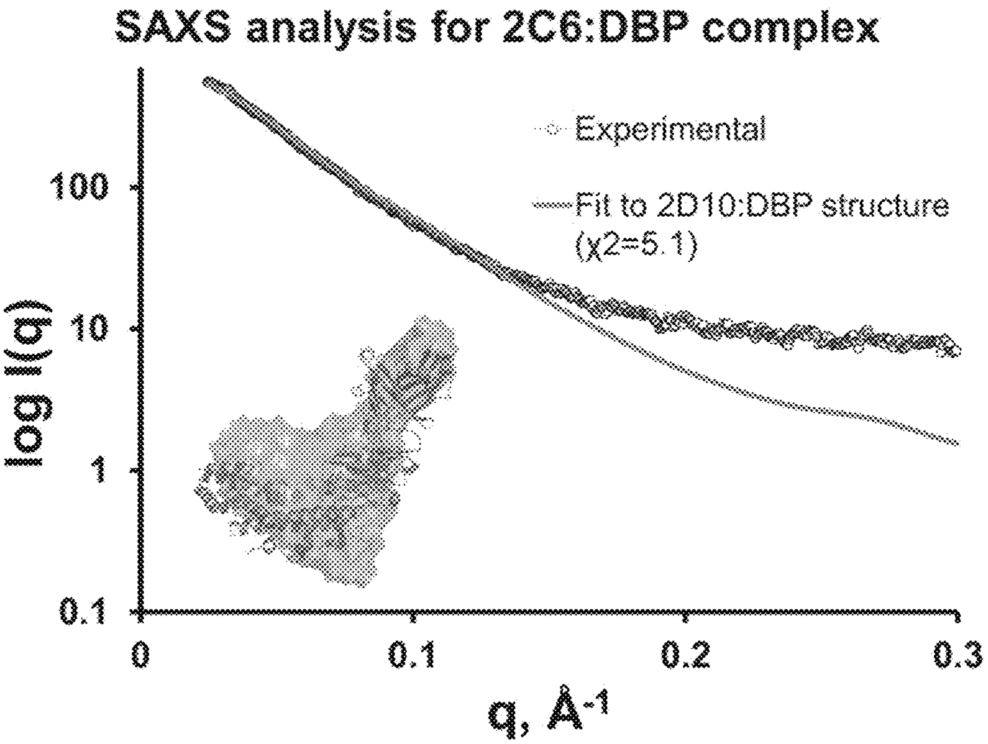

In contrast, the predicted scatter from the DBP-II/2D$10_{Fab}$ model did not fit the DBP-II/2$C6_{Fab}$ SAXS profile returning a $X^2$ of 5.1 (FIG. 14E), much higher than the significance cut-off value of 3 (Petoukhov, M. V., and Svergun, D. I. 2005. Biophys J 89, 1237-1250). The molecular weight of the complex was also determined by SAXS MOW analysis to ensure the difference in profiles was not due to aggregation or oligomerization. SAXS MOW returned a molecular weight of 77 kDa for the DBP-II/2$C6_{Fab}$ complex, consistent with theoretical mass of 87 kDa for non-aggregated sample.

Figure 15A:
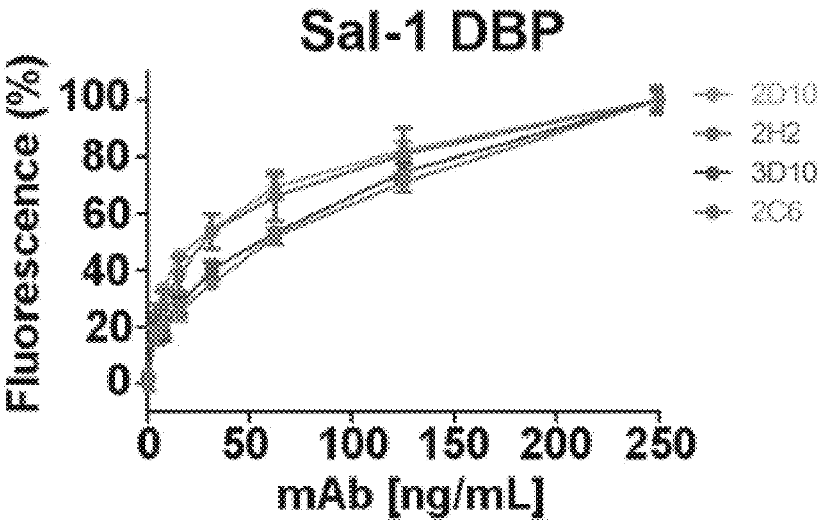
FIGS. 15A-15G show graphs demonstrating the determination of antibody epitopes by direct and competition ELISA. mAb's 2D10, 2H2, 3D10, and 2C6 were tested for binding against a panel of Sal-1 DBP mutants as described in the methods.
Figure 15B:
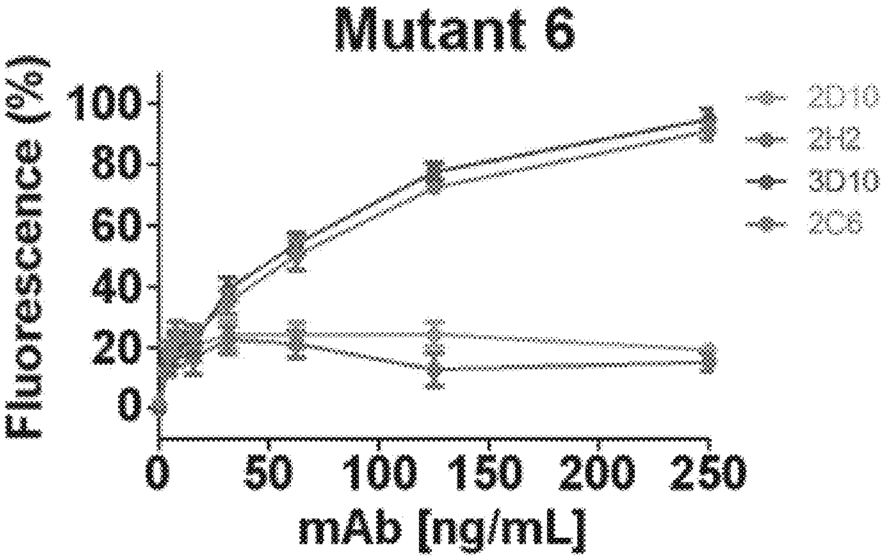
Figure 15C:
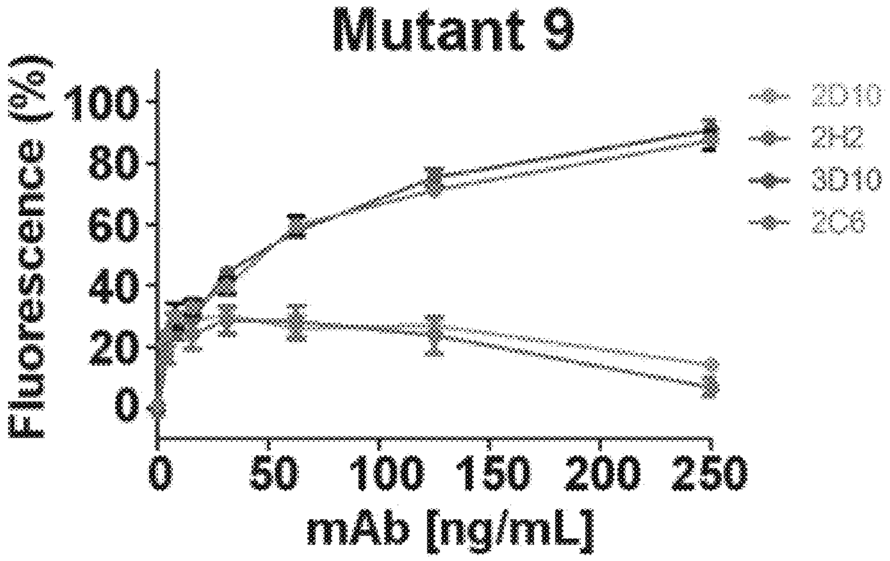

Mutation of the 2D10 epitope affects binding to both 2D10 and 2H2. The structural analyses revealed that mAb 2D10 and 2H2 recognize a distinct epitope on DBP-II which was assessed further through mutational studies using ELISA assays. Two residues at the center of the antibody footprint, N434 and K437, were both mutated to either alanine or arginine (mutant 6 and 9 respectively). Sal-1 DBP-II and both mutants were expressed and purified, and these proteins were adsorbed onto ELISA plates along with a BSA negative control. Both mAbs 2D10 and 2H2 recognized Sal-I DBP-II (FIG. 15A), but did not bind either of the mutants (FIGS. 15B-15D) verifying that the epitope identified through the crystal structure is engaged by mAbs 2D10 and 2H2 (FIGS. 15A-15C). As a control for proper protein folding in the ELISA assays, the proteins were probed with a conformationally dependent anti-DBP-II antibodies 2C6 and 3D10 that do not recognize the same epitope. 2C6 and 3D10 bind WT DBP-II, and both alanine and arginine mutants equally well, demonstrating that all proteins used were folded correctly (FIGS. 15A-15C).

Figure 16A:
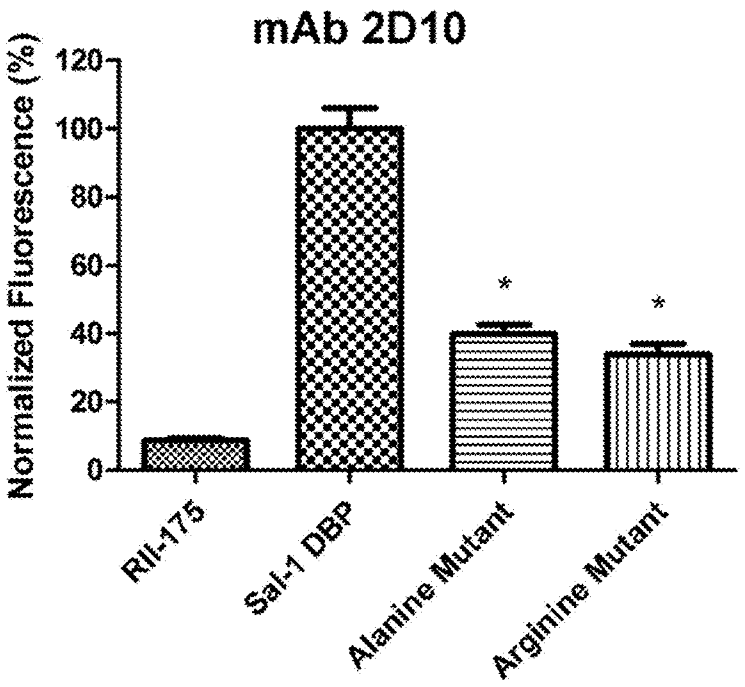
FIGS. 16A-16C show graphs demonstrating immunofluorescence staining of monoclonal antibodies. Immunofluorescence staining of *P. falciparum* RII-175, *P. vivax* Sal-1 DBP-II, and both alanine and arginine mutants (mutant 6 and 9 respectively) expressed on the surface of 293T cells with mAb's (FIG. 16A) 2D10, (FIG. 16B) 2C6, and (FIG. 16C) 2H2.
Figure 16B:
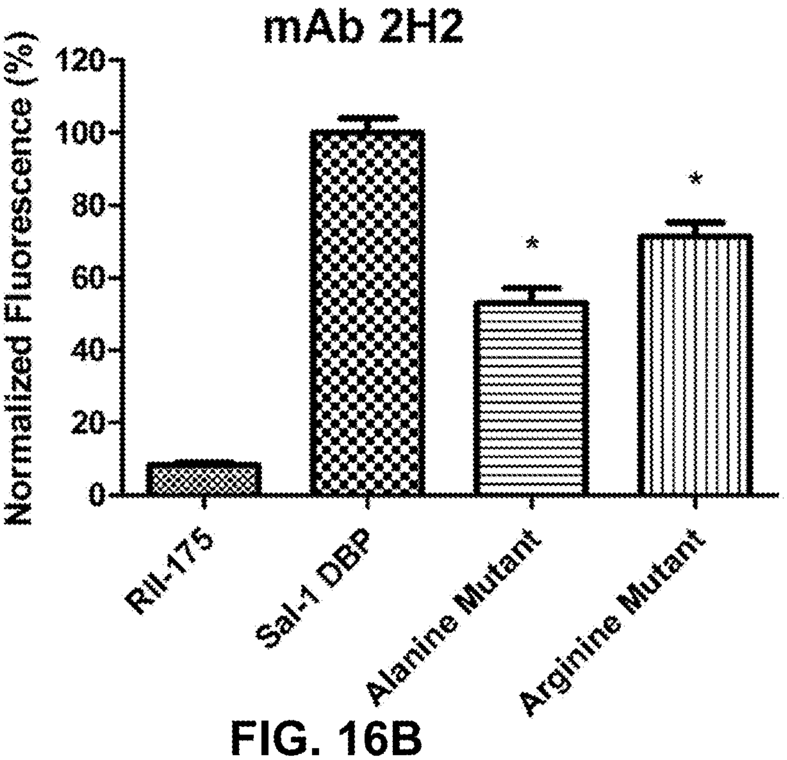
Figure 16C:
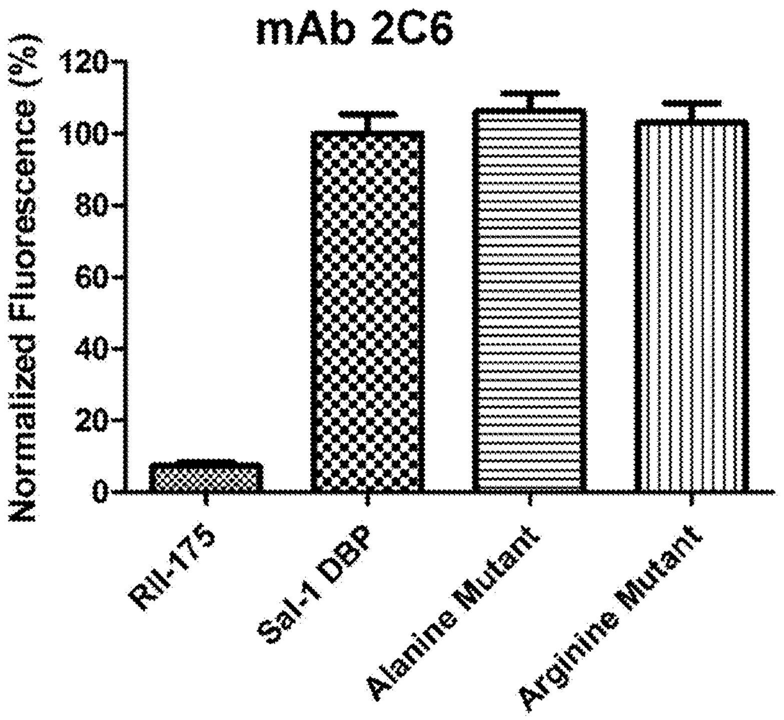

Immunofluorescence binding assays were also conducted to verify the epitope. Sal1 DBP-II, both mutants, and *P. falciparum* PfEBA-175 Region II (RII-175), as the DBL negative control, were expressed on the surface of HEK-293T mammalian cells (Batchelor et al. 2011. Nat Struct Mol Biol 18:908-914; Lin, et al. 2012. J Biol Chem 287: 36830-36836; Malpede et al. 2013. J Biol Chem 288:12406-12415; Sim et al. (1994). Science 264:1941-1944; and Tolia, et al. 2005. Cell 122:183-193). Recognition of surface expressed ligands by 2D10 and 2H2 was assessed by fluorescence microscopy. Again, 2D10 and 2H2 recognized Sal-1 DBP-II, but not either of the epitope mutants nor the RII-175 negative control (FIGS. 16A-16B). mAb 2C6 was utilized as a control for proper folding and expression on the surface of HEK-293T cells and subsequently was able to bind Sal-1 DBP-II and both mutants (FIG. 16C). Together these results demonstrate that mAb 2H2 and 2D10 share both paratope and epitope.

Mutational screens identify mAb 3D10 and mAb 2C6 binding residues. Difficulties in crystallizing DBP-II/Fab and DBP-II/scFv complexes of other anti-DBP-II antibodies led to alternative methods to map epitopes. an extensive panel of DBP-II variants was created in which putative epitopes predicted by DiscoTope (Haste Andersen et. al. 2006. Prediction of residues in discontinuous B-cell epitopes using protein 3D structures. Protein Sci 15:2558-2567) and surface residues identified through Swiss PDB Viewer were mutated. Each variant was expressed, purified, adsorbed on ELISA plates, and probed with mAbs 2C6 and 3D10, using mAbs 2D10 and 2H2 as controls (FIGS. 15D-15F, FIGS. 17A-17B, and FIGS. 18A-18L).

Mutant 1 contains changes at residues 218 and 221-223 in the N-terminus of sub-domain 1 (SD1) of DBP-II. This mutant shows ablated binding to mAb 3D10, but not to mAbs 2D10, 2H2, or 2C6 (FIG. 15D). mAb 3D10 is a weakly inhibitory antibody with a COS7 assay $IC_{50}$ of 25 μg/mL, several orders of magnitude weaker inhibition than that of mAbs 2D10 and 2H2 (Ntumngia et al. 2012. Clin Vaccine Immunol 19: 30-36). The decreased potency could be attributed to the fact that this motif is not implicated in primary DARC receptor binding or DBP-II dimerization, nor suggested as a location for secondary DARC binding (Batchelor et al. 2014. PLoS Pathog 10:e1003869 and Siddiqui et al. 2012. Infect Immun 80: 2920-2928).

Figure 15D:
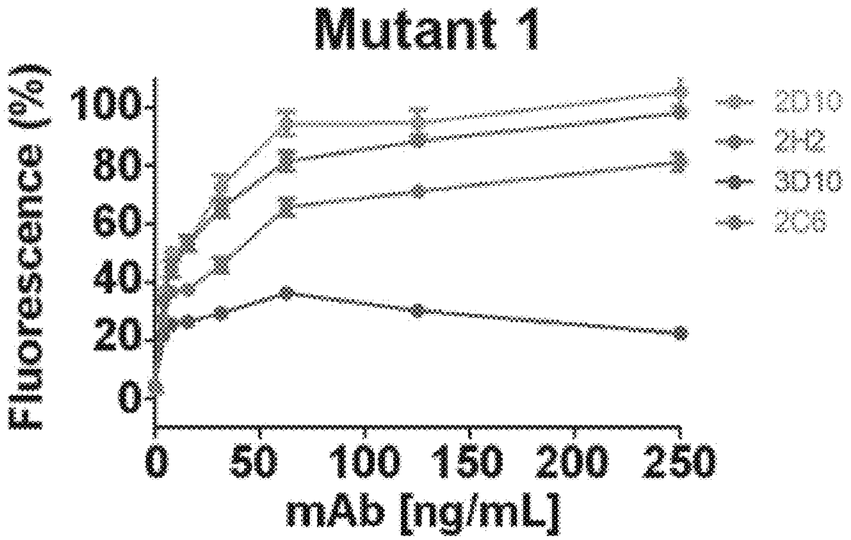
Figure 15E:
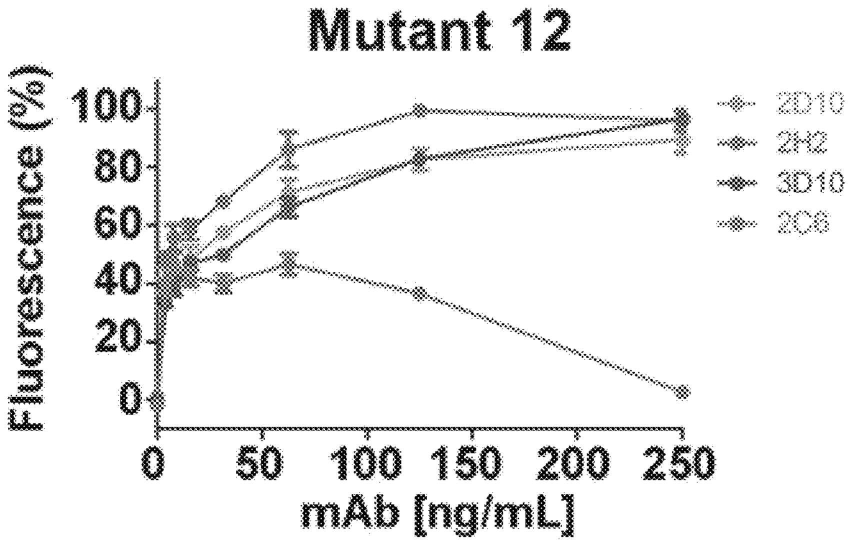

Mutant 12 contains changes at residues 479 and 480 in the C-terminus of sub-domain 3 (SD3) of DBP-II and shows ablated binding to mAb 2C6, but not to mAbs 2D10, 2H2, or 3D10 (FIG. 15E). The mutated site is on a different face of the SD3 helical bundle as compared to mAbs 2D10 and 2H2, and is located on the end closer to SD2. The identification of a second, distinct, inhibitory site within SD3 of DBP-II introduces the notion that multiple regions of DBP-II outside of the dimerization and receptor-binding motifs in SD1 and SD2 are also important in protein function.

Figure 15F:
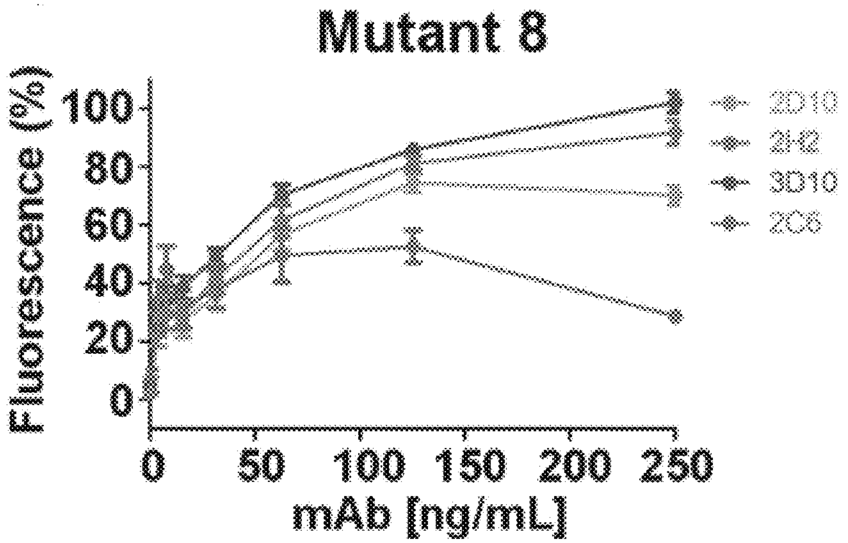
Figure 17A:
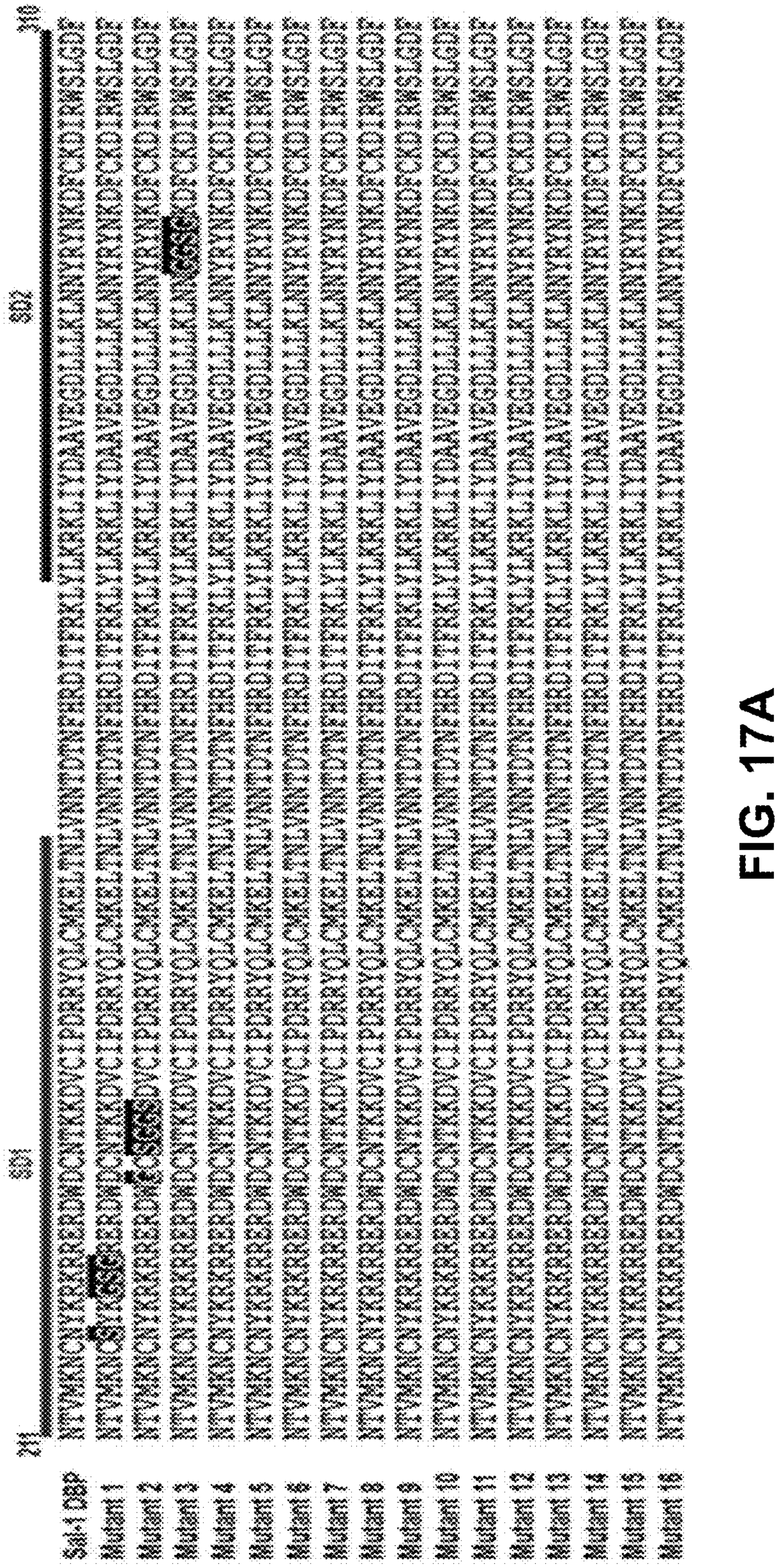
Figure 18A:
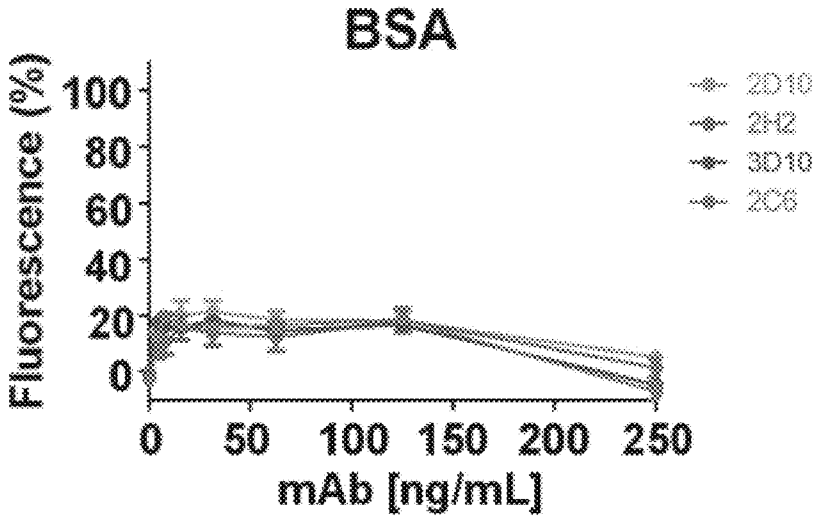
FIGS. 18A-18L show graphs demonstrating binding of monoclonal antibodies to a panel of Sal-1 DBP mutants. mAb's 2D10, 2H2, 3D10, and 2C6 were tested for binding against a panel of Sal-1 DBP mutants and BSA as described in the methods.
Figure 18B:
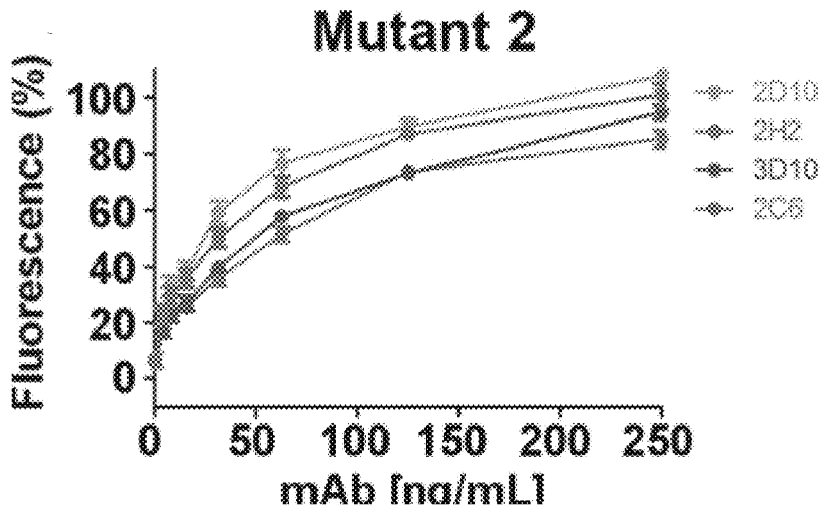
Figure 18C:
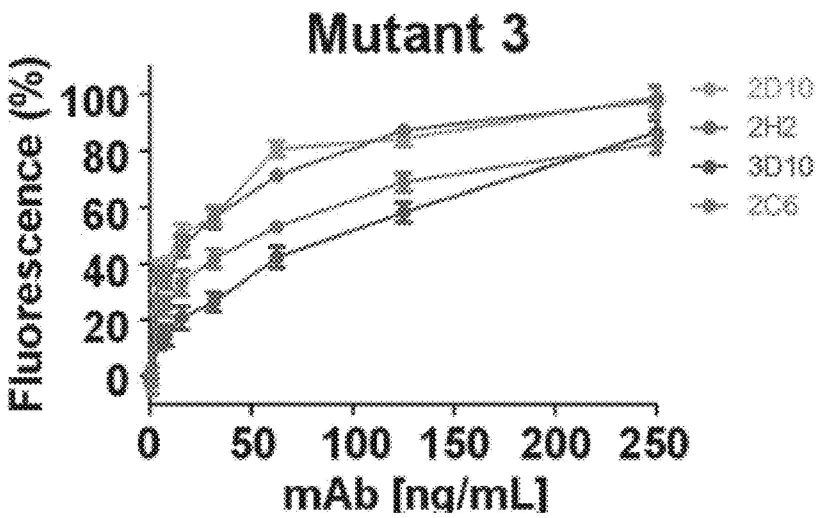
Figure 18D:
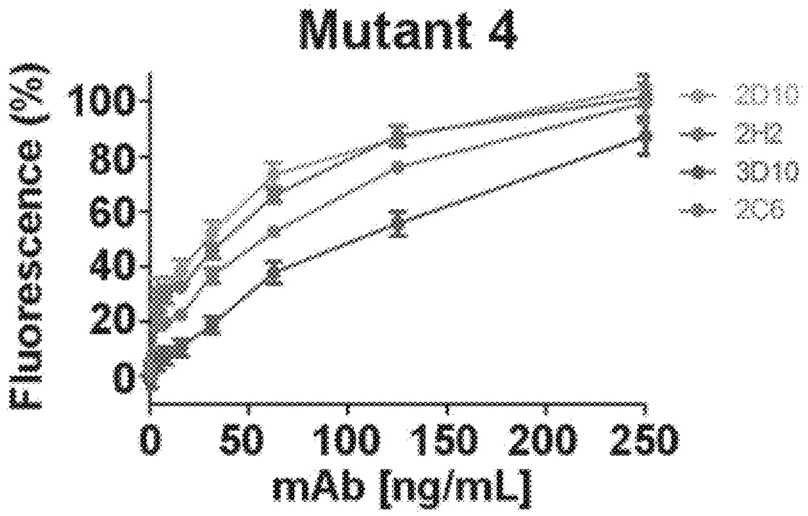
Figure 18E:
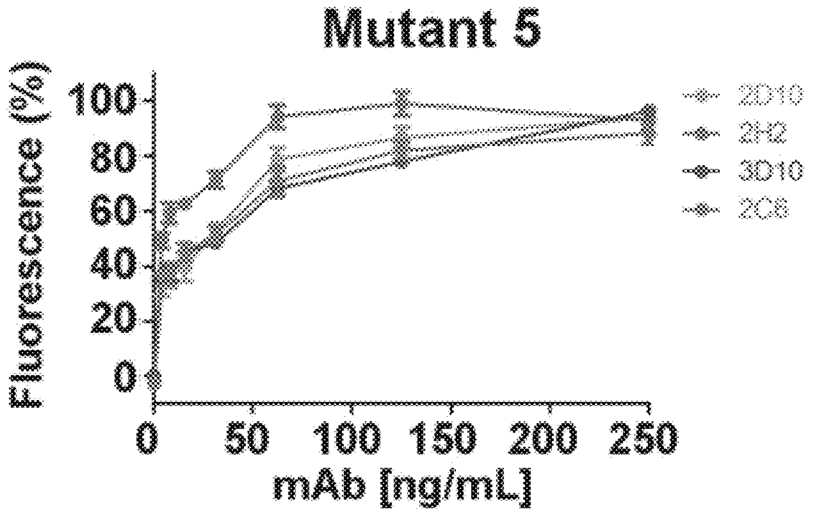
Figure 18F:
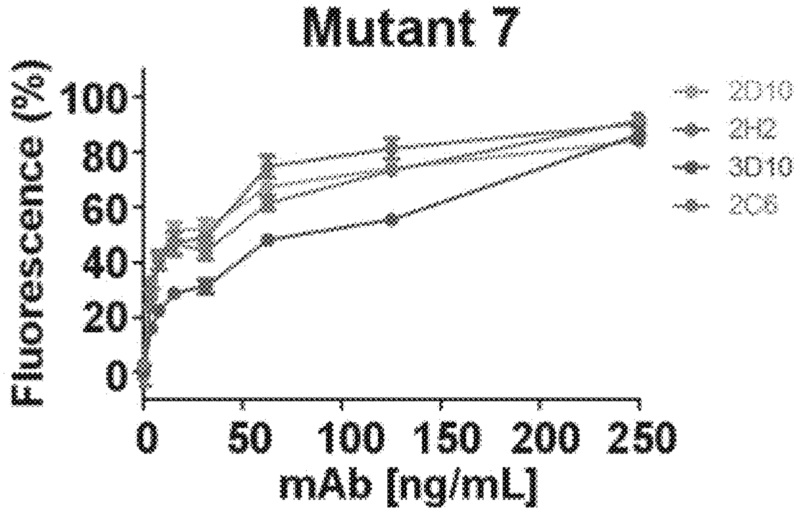
Figure 18G:
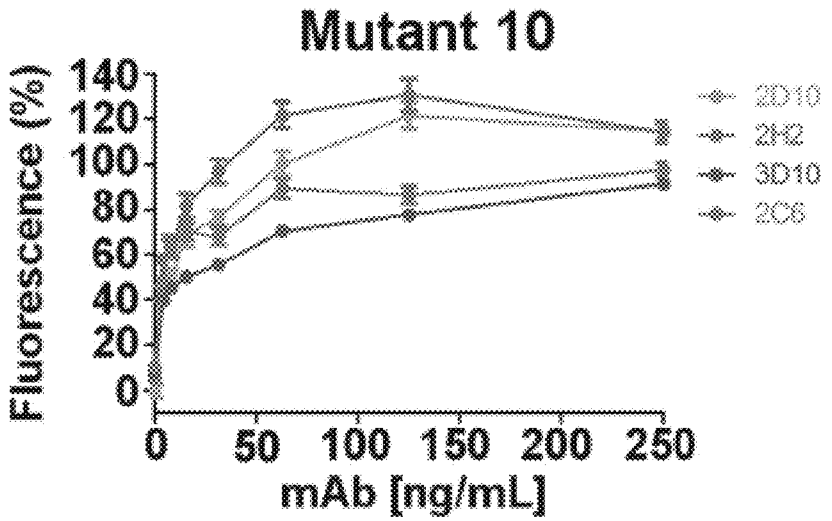
Figure 18H:
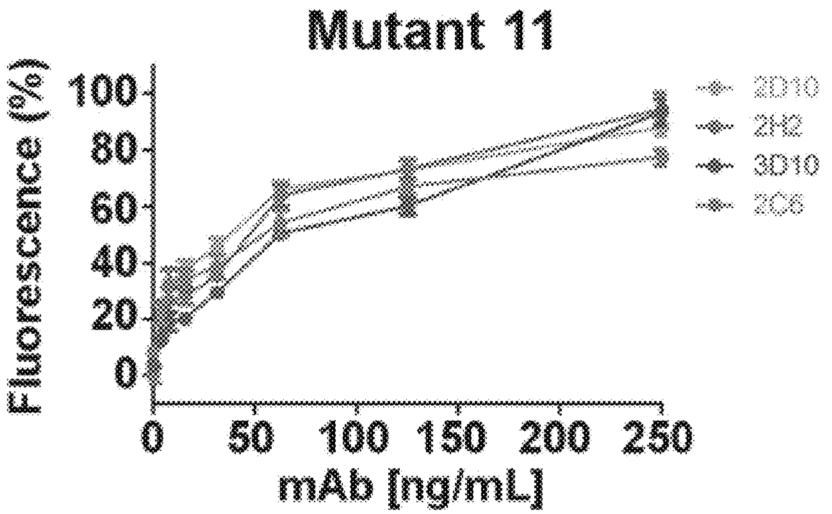
Figure 18I:
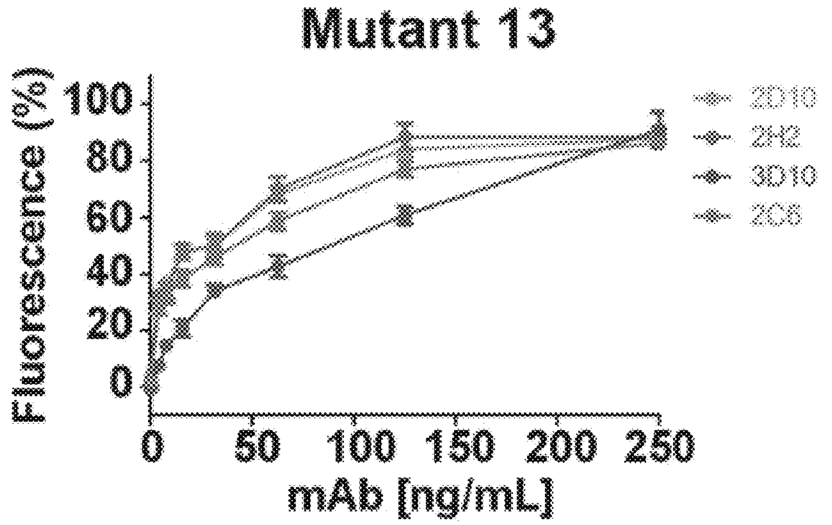
Figure 18J:
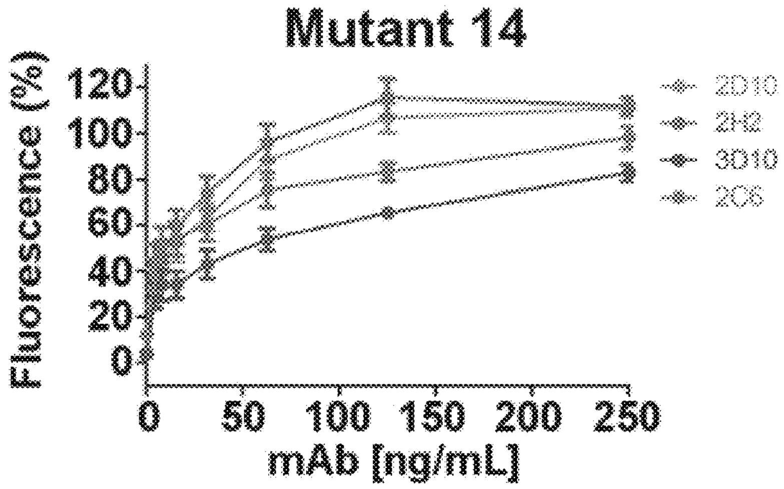
Figure 18K:
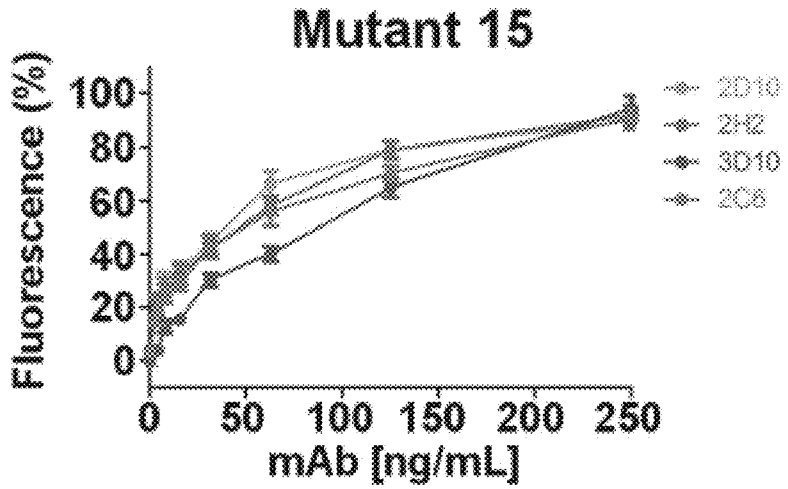
Figure 18L:
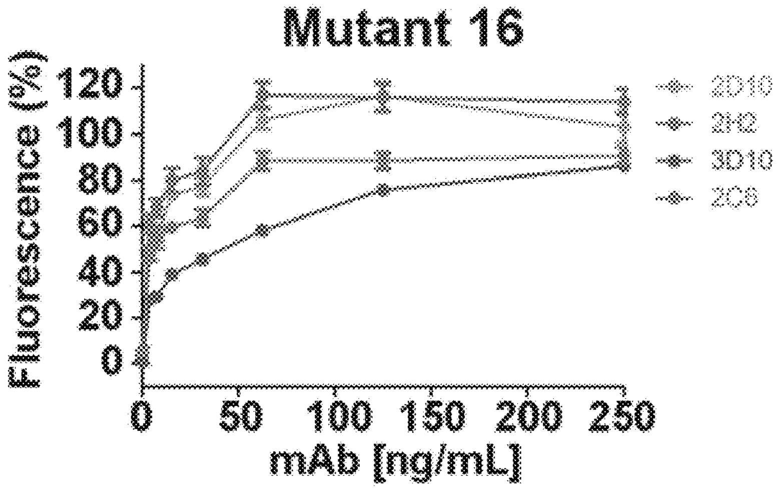

One of the mutants, Mutant 8, demonstrated preferential ablation of mAb 2H2 binding over mAb 2D10 (FIG. 15F). Mutant 8 contains mutated residues upstream of amino acids N434 and K437 changed in mutants 6 and 9 (FIGS. 17A-17B). This demonstrates that mAbs 2D10 and 2H2 do not have identical epitopes, but instead share overlapping binding regions on DBP-II. This is supported by highly similar, but not identical, amino acid sequences within their CDR regions (FIG. 15D).

Figure 15G:
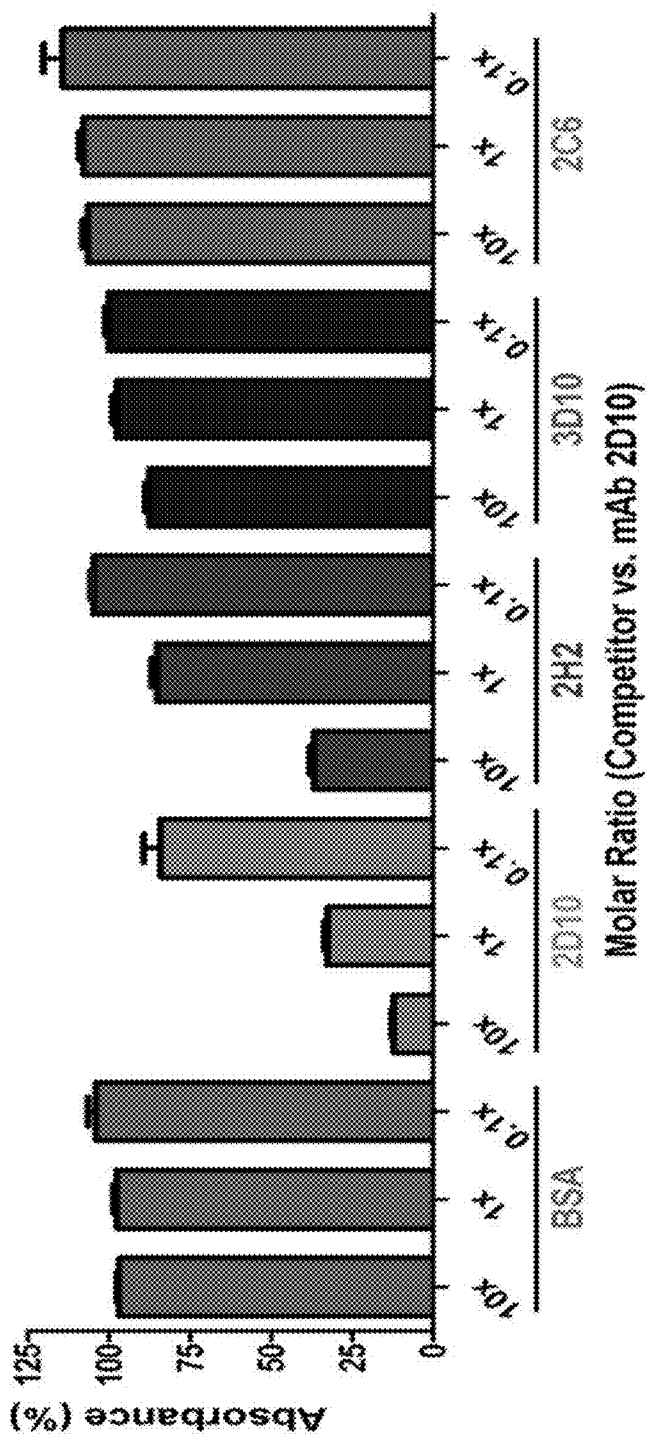

Antibody competition ELISA validates mapped epitopes. Competition ELISAs with mAbs 2D10, 2H2, 3D10, and 2C6 were performed to assess the ability of these antibodies to compete with 2D10. Each of the four mAbs was tested for competition with immobilized mAb 2D10 in binding DBP-II (FIG. 15G). mAb 2D10 served as a positive control and was able to compete with itself in a dose-dependent manner. mAb 2H2 was also able to compete with mAb 2D10 in a dose-dependent manner for binding to DBP-II. The contrasting efficacy of the competition profile for mAb 2H2 compared with mAb 2D10 is likely due to their similar, but not identical, antibody footprints and possible differences in apparent affinity (FIGS. 15B-15C, 15F and FIGS. 19A-19B). This is supported by differences in amino acid sequences between the CDRs, particularly CDR3 of the heavy chain (FIG. 14D). Neither mAb 3D10 nor mAb 2C6 competed with mAb 2D10, as their binding sites are located elsewhere (FIGS. 15D-15E and FIGS. 19A-19B). Together, the results strongly support that mAb 2D10 and mAb 2H2 bind to similar epitope surfaces on DBP-II, share paratopes within their CDRs, and in turn, likely possess similar inhibitory mechanisms of activity.

Figure 20:
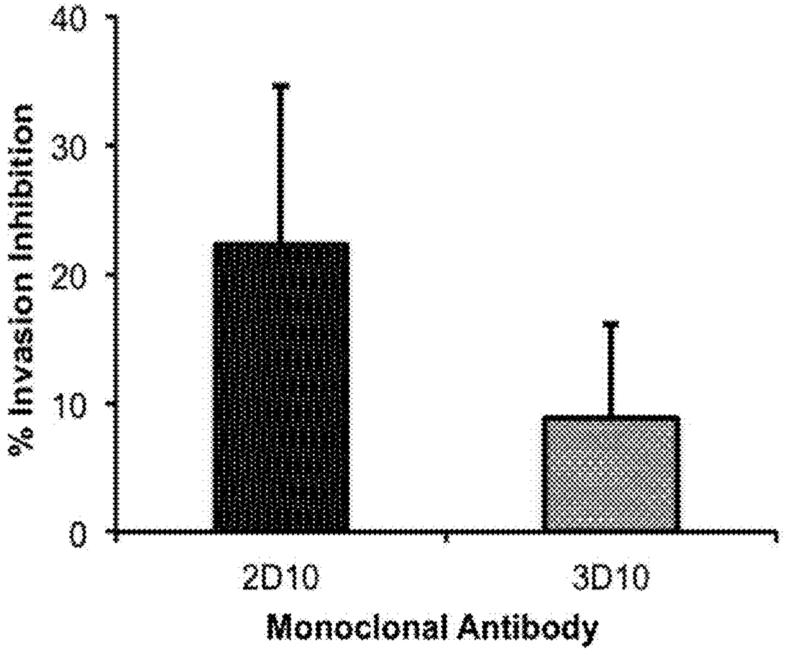
FIG. 20 shows a graph demonstrating mAbs 2D10 compared to 3D10, assayed for invasion inhibition efficiencies against clinical isolates of *P. vivax*. Isolates of *P. vivax* obtained directly from patients were co-incubated with mAbs 2D10 and 3D10 and mixed with susceptible human reticulocytes. Percent inhibitions were normalized to invasion efficiencies obtained in the absence of antibodies. Assays were conducted in triplicate on 10 isolates in two independent experiments involving reticulocyte concentrates from cord blood samples of different ABO types. Each bar represents the mean inhibition (%±SD) of each mAb on *P. vivax* invasion.
Figure 21A:
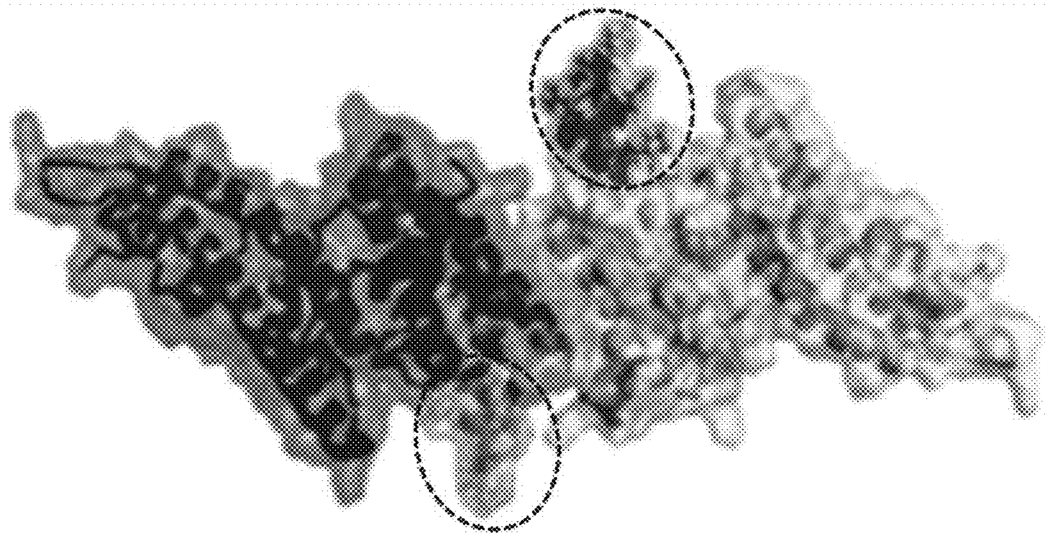
FIGS. 21A-21D demonstrate the crystal structure of DBPII dimer. Monomers are shown in light gray and dark gray. Positions of mutated residues to create the various DEKnull antigens are indicated in encircled regions.
Figure 21B:
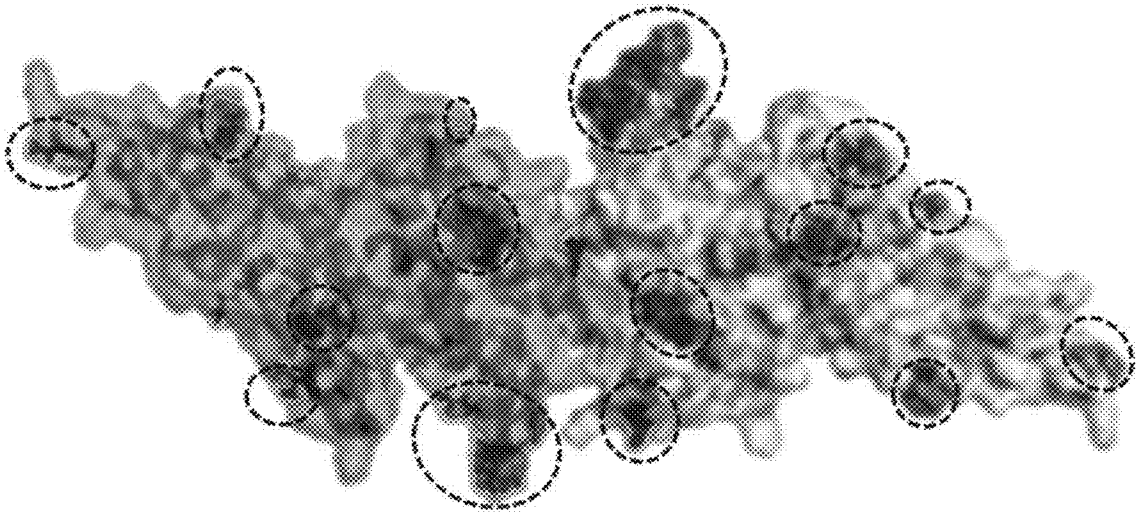
Figure 21C:
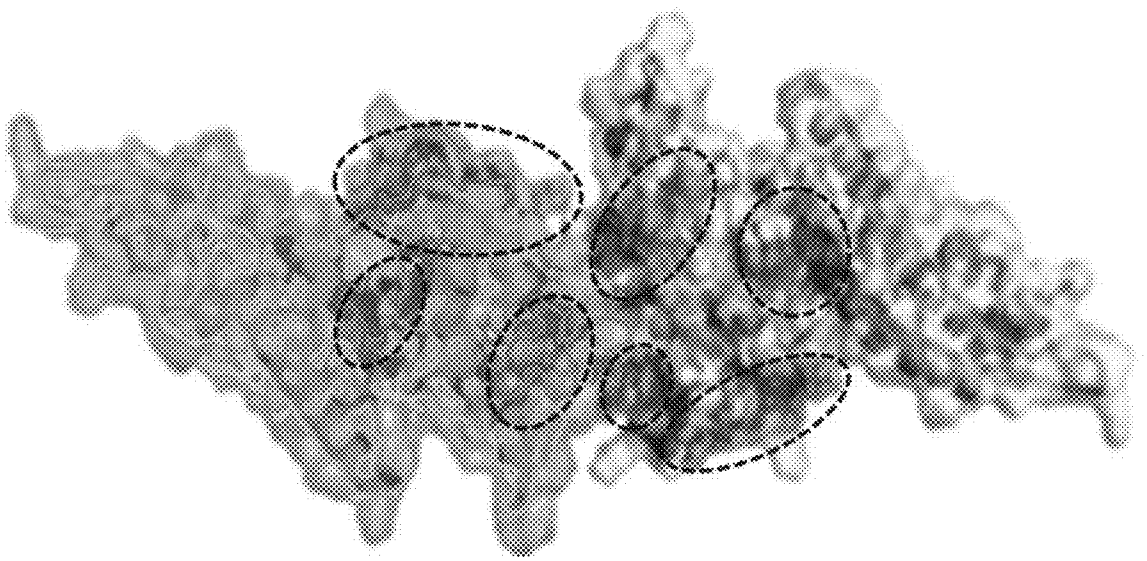
Figure 21D:
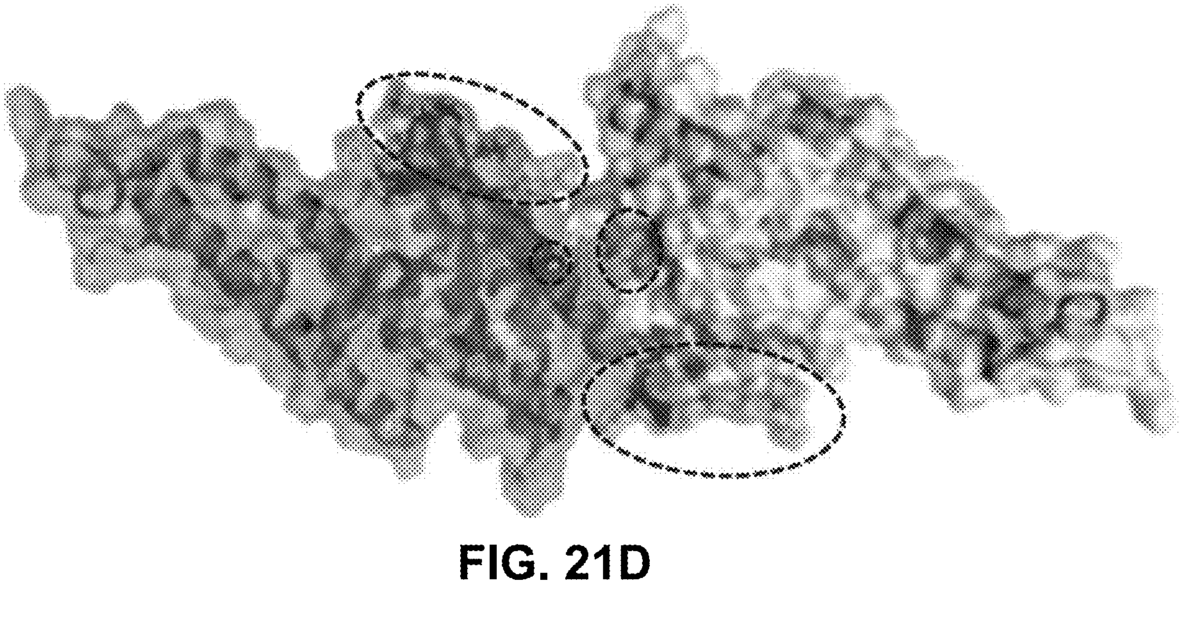
Figure 23A:
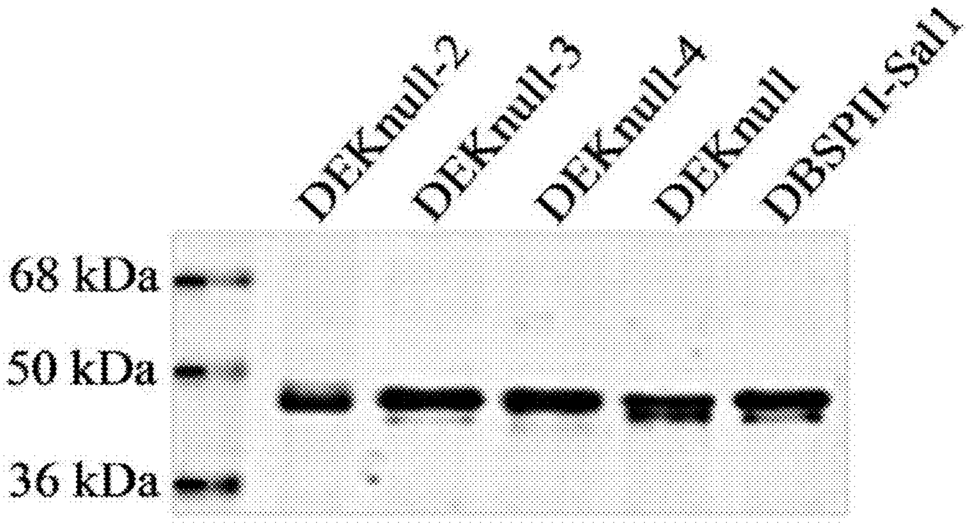
FIGS. 23A-23D show images of blots demonstrating results of purification of recombinant antigens.
Figure 23B:
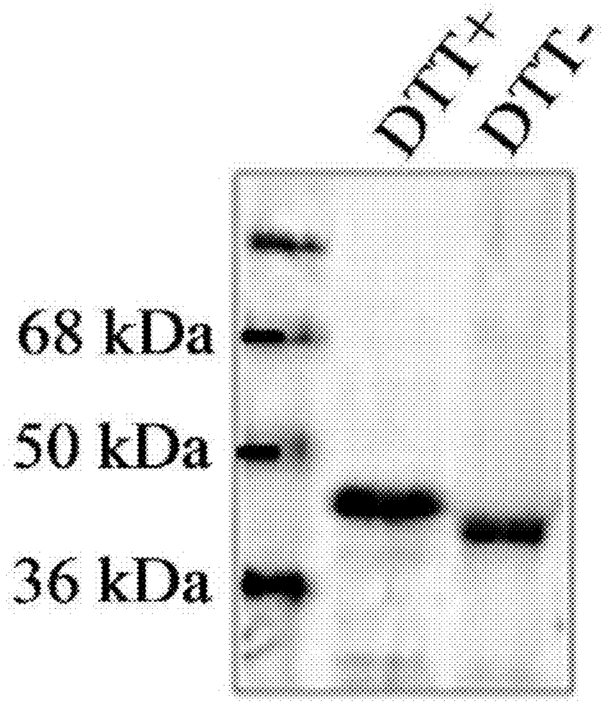
Figure 23C:
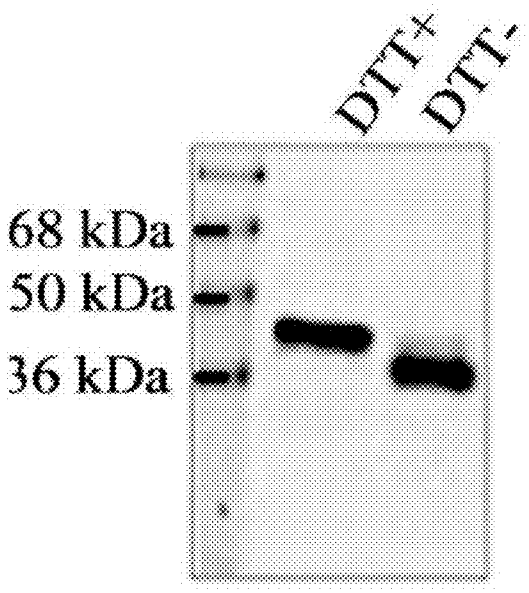
Figure 23D:
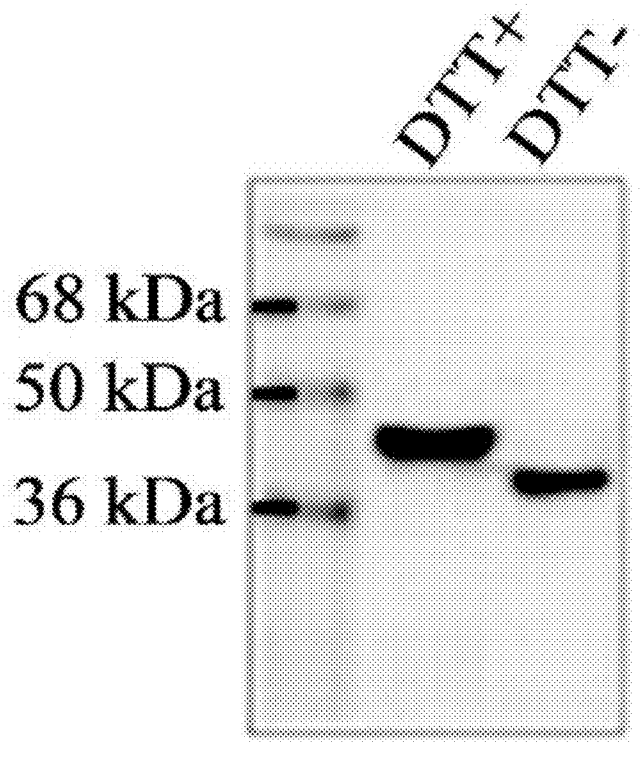

Antibody inhibition of reticulocyte invasion by *P. vivax* human isolates. Inhibitory anti-DBP-II functional activity of mAb 2D10 compared to mAb 3D10 was confirmed with ex vivo invasion assays performed with *P. vivax* patient isolates. Anti-DBPII mAbs were tested for ability to inhibit *P. vivax* invasion of human erythrocytes as described (Russel B et al. 2011). The evaluation used the concentration of 200 ng/ml that had been determined to inhibit 50% inhibition of binding in static DBP-RBC binding using the standard COS7 assay. The mAB 2D10 provided a significant level of inhibition relative to mAb 3D10 against a diverse collection of *P. vivax* clinical isolates confirming the strain transcending nature of its inhibitory effect (FIG. 20).

Discussion

The central role of DBP-II in eliciting the majority of clinical, symptomatic *P. vivax* infection demonstrates its importance as a vaccine target against *P. vivax* malaria (Miller et al. 1976. N Engl J Med 295:302-304). Anti-DBP-II antibodies have long been established to possess potent protective potential in inhibiting all aspects of DBP-DARC receptor binding and parasite invasion (Batchelor et al. 2014. PLoS Pathog 10:e1003869; Batchelor et al. 2011. Nat Struct Mol Biol 18:908-914; Chootonget al. 2010. Infect Immun 78:1089-1095; Grimberg et al. 2007. PLoS Med 4, e337; and Ntumngia et al. 2012. Infect Immun 80:1203-1208). The presence of polymorphisms within DBP-II, however, pose unique vaccine design challenges that must be addressed in order to maximize the effectiveness of DBP-II based vaccines. Two current parallel approaches towards resolving this issue involve either multi-allele vaccines or artificially engineered synthetic immunogens (Chen et al. 2015. PLoS Negl Trop Dis 9: e0003644; Ntumngia, F. B., and Adams, J. H. 2012. Clin Vaccine Immunol 19:30-36; Ntumngia et al. 2014. Clin Vaccine Immunol 21:1215-1223; and Ntumngia et al. 2013. Vaccine 31:4382-4388). A DBP-II based *P. vivax* vaccine can be an amalgam of both strategies to have a single antigen that possesses protective epitopes, lacks non-protective motifs, and has comparable protectivity as multi-allelic formulations. This Example demonstrates identification and characterization of conserved, inhibitory epitopes. The epitopes can be used in vaccine designs and can allow for artificial engineering of the sequence to enhance immunogenicity and antibody affinity to improve vaccine efficacy (Dormitzer et al. 2012. Nat Rev Microbiol 10:807-813 and Welsh, R. M., and Fujinami, R. S. 2007. Nat Rev Microbiol 5:555-563).

Presented in this Example the first x-ray crystal structure of DBP-II bound to an inhibitory antibody, mAb 2D10. The epitope lies within residues 413-417 and 425-441 at the tail end of the helical bundle that comprises sub-domain 3 (SD3) (FIGS. 12A-12C). Through extensive analysis involving SAXS, ELISA and immunofluorescence staining, it was demonstrated that a second inhibitory antibody, mAb 2H2, shares paratope and epitope properties with mAb 2D10. Furthermore, through a DBP-II mutant panel, the partial epitopes of a weakly inhibitory antibody mAb 3D10 was mapped to the N-terminal end of sub-domain 1 (SD1), and highly inhibitory antibody mAb 2C6 was mapped to a distinct helical face on sub-domain 3 (SD3) (FIGS. 15A-15F).

Genetic analysis of DBP-II reveals high $d_N/d_S$ ratios, a pattern seen when selection pressure drives allelic diversity as a mechanism for immune invasion (Baum, J., et al. 2003. Genetics. 163:1327-1336; Cole-Tobian, J., and King, C. L. 2003. Mol Biochem Parasitol 127:121-132; and Ntumngia, F. B., and Adams, J. H. 2012. Clin Vaccine Immunol 19:30-36). This results in diverse, highly polymorphic populations within endemic regions that commonly manifest as mixed infections with multiple strains. These polymorphisms have high potential to result in strain-specific immune responses that render individuals susceptible to future infections by other strains (Welsh and Fujinami, 2007).

The polymorphic nature of DBP-II is reminiscent of highly variable surface proteins of viral pathogens. Broadly neutralizing antibodies (bnAbs) that engage the conserved receptor-binding site of HIV have been identified and some bnAbs have the ability to neutralize up to 90% of known HIV strains (Zhou et al. 2015. Cell 161:1280-1292). Similarly, bnAbs that recognized the conserved stem region of hemagglutinin are broadly protective against influenza (Ekiert, D. C., and Wilson, I. A. 2012. Curr Opin Virol 2:134-141). Using similar paradigms, the broadly conserved epitopes identified in this study provide a clear framework to counteract DBP-II polymorphisms and allelic variation to generate strain-transcending protection for *P. vivax* malaria.

Figure 19A:
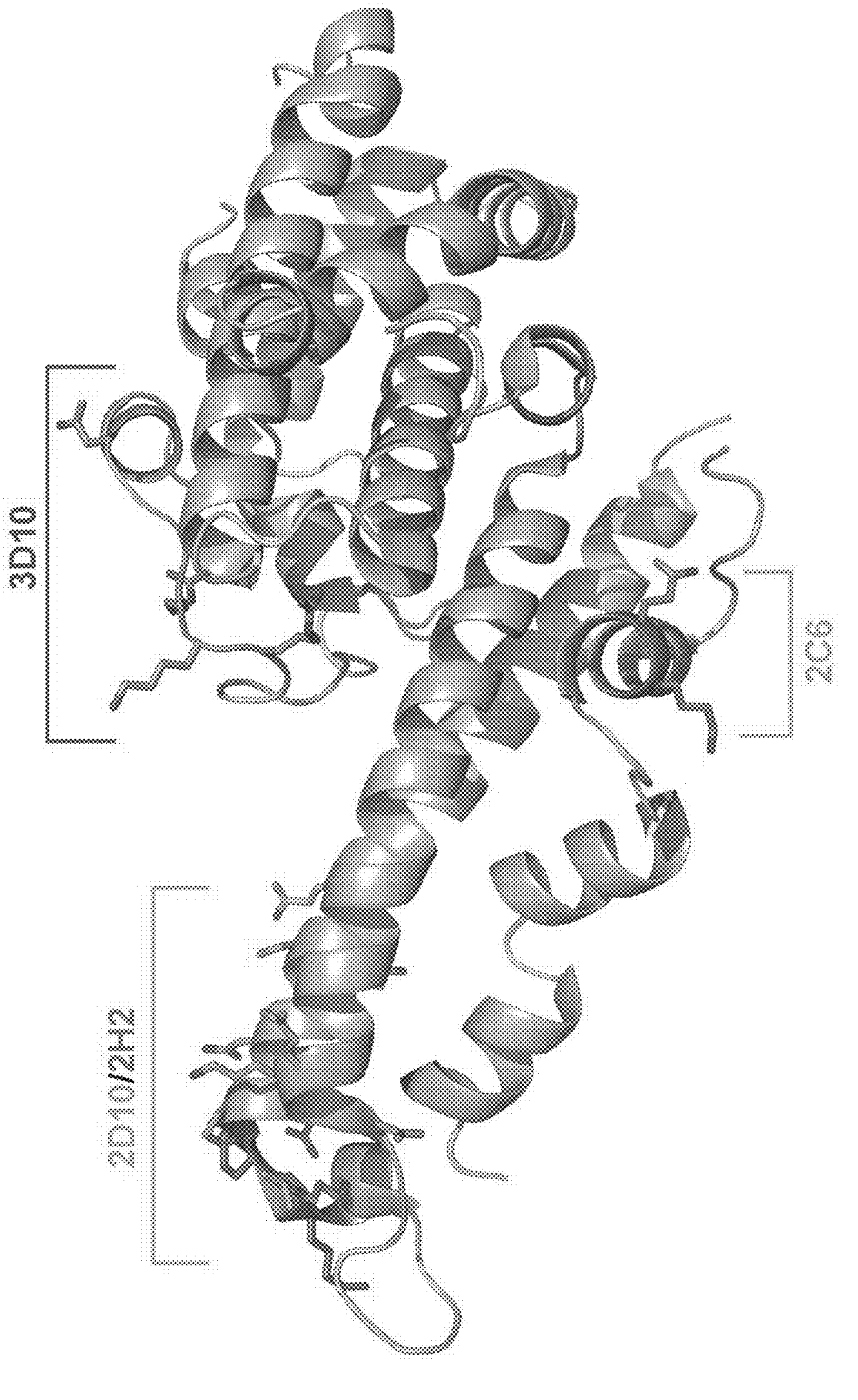

Alignment of DBP-II residues contacted by mAb 2D10 as determined from the crystal structure alongside naturally occurring identified polymorphisms on the Sal-I DBP-II sequence reveal mutual exclusion of amino acids (FIG. 19B). This demonstrates that mAb 2D10 recognizes a broadly conserved epitope and likely functions as a bnAb that will be effective against multiple pathogen strains—and the first of its kind identified in *Plasmodium* parasites. An additional implication is that the location on SD3 of Sal-I DBP-II that mAb 2D10 binds to is a conserved, functionally relevant site common in all *P. vivax* isolates. Although it was shown that mAb 2H2 shares similar epitopes and paratopes as mAb 2D10 (FIGS. 15A-15F and FIGS. 19A-19B), subtle differences in binding were identified by the mutant panel. In addition, partial epitopes of mAb 3D10 and mAb 2C6 were identified through mutational analysis. Comparison of these epitopes with variance in DBP suggests that mAb 2H2, mAb 3D10 and mAb 2C6 recognized conserved epitopes in SD3 and SD1 and may function as bnAbs, although additional functional analyses are required. The identification of these protective motifs is invaluable and will aid tremendously in the design of DBP-II based vaccines that will impart global strain-transcending protection (Chen et al. 2015. PLoS Negl Trop Dis 9:e0003644; Ntumngia, F. B., and Adams, J. H. 2012. Clin Vaccine Immunol 19:30-36; Ntumngia et al. 2014. Clin Vaccine Immunol 21:1215-1223).

Previous domain-mapping studies of mAb 2D10 and mAb 2H2 targeted these antibodies to sub-domain 3 (SD3) of DBP-II and showed that they were able to prevent the binding of SD3 alone to red blood cells (Siddiqui et al. 2012. Infect Immun 80:2920-2928). This result implicates a secondary receptor-binding event between that of DARC and DBP-II outside of previously identified primary DARC binding sites in sub-domains 2 (Batchelor et al. 2014. PLoS Pathog 10: e1003869 and Batchelor et al. 2011. Nat Struct Mol Biol 18, 908-914), and that these antibodies were able to prevent this interaction. The exact identification of the mAb 2D10/2H2 epitope posits the tail end of SD3 as the secondary receptor binding site with any number of the three extracellular loops linking the seven transmembrane regions of DARC. This model corresponds with what is known about the activity of DARC and other members of the G-protein coupled receptor (GPCR) family. The N-terminus of GPCRs are important for ligand binding, but the extracellular loops play key roles in determining ligand specificity, and efficient receptor activation and signaling (Tournamille et al. 1997. J Biol Chem 272:16274-16280). In the case of DBP-II/DARC, it is proposed that residues 1-63 of the N-terminal DARC ectodomain is responsible for the bulk of interactions with DBP-II, but the other extracellular domains of DARC cooperate in a coordinated manner to provide necessary ligand specificity to enhance the receptor-binding interaction.

In conclusion, presented herein was crystallographic, biophysical and biochemical mapping data on four anti-DBP-II monoclonal antibodies: three strongly inhibitory and one weakly inhibitory. The epitopes of these antibodies are conserved amongst all isolated *P. vivax* strains and thus generate bnAbs necessary for global protection. These findings characterize motifs that can be included in all future DBP-II vaccine designs. The results presented here shed light into the enigmatic nature of the exact mechanistic and structural process of how DBP engages DARC on reticulocytes during the invasion process. The identification of additional DBP-DARC interaction sites can be used to further characterize the DBP-DARC interaction. The results from both endeavors can bolster the ability to create broadly protective vaccines against *P. vivax* malaria.

Example 3

Immunogen design and recombinant antigen production. The production of recombinant DBPII-Sal1, DEKnull, and other antigens from naturally occurring variant DBPII alleles was previously reported (Ntumngia and Adams, 2012. Clin. Vacc. Immunol. 19:30-36 and Ntumngia, et al., 2013. Vaccine 31:4382-4388). The Sal1 sequence was used as a template to create three novel DBPII antigens by mutating (i) all the polymorphic residues (17 VanBuskirk, et al., 2004. PNAS 101:15754-15759) (ii) all binding residues (VanBuskirk, et al., 2004. PNAS 101:15754-15759) and (iii) all residues important for dimerization (Batchelor, et al., 2011. Nat Struct Mol Biol.), into small, non-polar or non-charged residues such as alanine, threonine or serine to produce the antigens DEKnull-2, DEKnull-3 and DEKnull-4 respectively (FIGS. 21A-21D and 22). The genes coding for the three novel antigens were codon-optimized for *E. coli* expression and the DNA commercially synthesized and cloned into pET21a+ expression vector (Novagen), with a C-terminal 6×His tag to facilitate purification by affinity chromatography. Protein expression was carried out in *E. coli* BL21(DE3) LysE cells (Invitrogen). After pilot expression, positive clones expressing the different antigens were selected for large-scale protein expression. Cultured cells at OD650=1.0 were induced with 1 mM IPTG final concentration for 3 hr at 30° C. Cells were harvested by centrifugation and expressed proteins were purified from inclusion bodies by affinity chromatography using Ni+ Sepharose 6 fast flow (GE Lifesciences) and finally refolded by rapid dilution as previously reported (Ntumngia and Adams, 2012. Clin. Vacc. Immunol.: 19:30-36; Ntumngia, et al., 2013. Vaccine 31:4382-4388; and Singh, et al., 2001. J Biol Chem 276:17111-17116).

Functional analysis of refolded antigens. A standard erythrocyte-binding assay was used to test for functional ligand activity by a standard in vitro erythrocyte-binding assay (Ntumngia, et al., 2013. Vaccine 31:4382-4388 and Singh, et al., 2001. J Biol Chem 276:17111-17116). Briefly, recombinant antigens were incubated with Duffy positive and Duffy negative erythrocytes in RPMI/1% BSA and separated on silicon oil (Dow Corning). Bound antigens were eluted from the erythrocyte surface by re-suspending the cells in 300 mM NaCl. Eluted proteins were separated by SDS-PAGE, transferred on to nitrocellulose membrane and probed with an anti-DBPII antibody, mAb-3D10 (Ntumngia, et al., 2012. Infection and immunity 80:1203-1208).

Immunizations. Polyclonal antibodies were raised in 6-8 weeks old BALB/c mice (Harlan). All animals were handled in compliance with good animal practice and approved IACUC protocol. Groups of mice (n=15) were bled for pre-immune sera and each immunized twice at three-week intervals either with 25 μg of recombinant Sal1 (SEQ ID NO.: 1), DEKnull (SEQ ID NO.: 2), DEKnull-2 (SEQ ID NO.: 3), DEKnull-3 (SEQ ID NO.: 4) or DEKnull-4 (SEQ ID NO.:5) emulsified in Titermax gold adjuvant. Each animal received a 50 μl antigen-adjuvant mix administered subcutaneously at the base of the tail. Mice immunized with adjuvant alone served as control. All mice were exsanguinated and final serum collected three weeks after the second immunization.

Measurement of antibody titers. Total anti-DBPII IgG titers in the serum of each mouse was evaluated by end-point titration ELISA against naturally occurring variant DBPII alleles Sal1, 7.18, P and 27.16 (Ntumngia, et al., 2012. Infection and Immunity 80:1203-1208.) and the corresponding homologous antigens. A standard anti-DBPII monoclonal antibody, mAb-3D10 (Ntumngia, et al., 2012. Infection and Immunity 80:1203-1208.)) was used on each plate to standardize variations in OD values from plate-to-plate. Briefly, 0.2 μg of recombinant antigen were coated per well of a microtiter plate, blocked with 5% skimmed milk and each well incubated in 3-fold dilution of mouse sera as previously reported (Ntumngia, et al., 2013. Vaccine 31:4382-4388). Bound antibodies were then detected with an alkaline phosphatase-conjugated anti-mouse antibody (KPL). All OD values were normalized at a point on the standard curve where OD630≈1.0 and antibody values were expressed as ELISA units (EU), determined as a ratio of the OD630 generated by the test antibody and OD630 of the standard (Ntumngia, et al., 2013. Vaccine 31:4382-4388). Preimmune sera and sera from mouse immunized with adjuvant alone served as negative controls.

Measurement of functional inhibition of DBP-Erythrocyte binding. Immune serum from each group of mice was tested for inhibition of DBPII-erythrocyte binding by the standard COS7 cell assay (Chitnis and Miller, 1994. J. Exp Med 180:497-506). A panel of naturally occurring DBPII alleles (Ntumngia, et al., 2013. Vaccine 31:4382-4388) were transiently expressed on the surface of transfected COS7 cells as previously described (Chitnis and Miller, 1994. J. Exp Med 180:497-506). After 42 hr post transfection, the cells were pre-incubated with triple-fold dilution of pooled sera from each immunization group prior to incubating with human Duffy positive erythrocytes. Percent inhibition of binding by each serum was evaluated relative to controls incubated with pre-immune serum as earlier described.

Immunofluorescence assay. Transfected COS 7 cells were incubated on cover slips in a 24 well plate for 42 hr (Chitnis and Miller, 1994. J. Exp Med 180:497-506). The cells were then fixed with PBS/2% formaldehyde for 15 min, washed 3× with PBS and incubated at room temperature with 5 μg/ml of anti-DBPII monoclonal antibody, mAb-3C9 for 90 min. After three washes with PBS, the cells were incubated with rhodamine-conjugated goat anti-mouse secondary antibody in PBS/0.1% BSA for 30 min in dark moist chamber. Cell DNA was counter stained with DAPI. After three washes, the cells were observed using a fluorescence microscope.

Statistical analysis. A 4-parameter logistic regression was used to provide dose-response curves and the end-point titer for each antibody. Based on the dose-response curves, an ELISA unit of 1.0 (on the log-phase of the curve) was chosen for all further comparisons of the antibody titer. Since the data were not normally distributed, a Kruskal Wallis was used to determine if there is an overall significant differences between the antibodies, followed by a Bonferroni multiple comparison (SAS). A non-linear regression was used to provide the dose-response curves for the anti-DBPII inhibitory concentrations (GraphPad). IC50s were calculated based on the percent inhibition and were compared for overall significant differences using the Kruskal-Wallis. As a follow-up, a Dunnett's adjusted multiple comparison was used, with Sal1 as the control for the multiple comparison (SAS).

Results

Antigen production. The variant rDEKnull antigens were expressed in *Escherichia coli*, purified from inclusion bodies and refolded by rapid dilution. Mobility shift of refolded and denatured antigens on SDS-PAGE is a simple indication that disulfide bonds exist in the refolded antigens (FIGS. 23A-23D). The natural conformation of the refolded recombinant antigens was confirmed with conformation dependent anti-DBPII monoclonal antibodies mAb-3C9 and 2D10 (Ntumngia, et al., 2012. Infection and immunity 80:1203-1208). With the exception of rDEKnull-3, all the antigens show strong reactivity with the refolded antigens (FIG. 24A). The lack of reactivity of refolded rDEKnull-3 to mAb-3C9 and 2D10 was confirmed by Western blot analysis (FIG. 24B). The functional and biological activity of the refolded antigens was confirmed by a standard in vitro erythrocyte binding assay, which shows binding of recombinant DEKnull-2 and native Sal1 to Duffy positive but not Duffy negative erythrocytes and no binding observed for recombinant DEKnull-3 and DEKnull-4 (FIG. 25A). This functional activity was confirmed by COS7 cell surface-expressed recombinant DEKnull-2 and Sal1 but not DEKnull-3 and DEKnull-4 to Duffy positive erythrocytes in an in vitro COS7 cell binding assay (FIG. 26A-26J). An immunofluorescence assay confirms cell-surface expression of the different antigens on the COS7 cell (FIG. 27A-270).

Immune response to recombinant antigens. The immunogenicity of the recombinant antigens was evaluated in mice. Groups of mice were injected with either recombinant Sal1 or the variant DEKnull antigens. Immune response of each mouse serum was determined by end-point antibody titer ELISA against the Sal antigen and three other naturally occurring variant DBPII alleles. Antibody titers were expressed in ELISA units (EU) (Ntumngia, et al., 2013. Vaccine 31:4382-4388). With the exception of recombinant DEKnull-3, immune sera from each immunization group produced highly reactive antibodies to the parent Sal1 antigen, which was used as template (FIG. 28A) and the other naturally occurring recombinant DBPII alleles (FIGS. 29A-29E). An ELISA unit of 1.0 was used as base to compare the relative antibody responses to the variant DBPII alleles. Interestingly, there was no significant difference in antibody response between anti-Sal1 and anti-DEKnull-2 sera against the parent recombinant Sal1 antigen. The anti-DEKnull-2 serum however, produced a relatively higher antibody titers and better immune response against all the variant DBPII alleles (FIG. 28B), while anti-DEKnull-4 responses were significantly lower than that of anti-Sal1, anti-DEKnull and anti-DEKnull-2. Since the DEKnull-3 antigen was poorly immunogenic, it was excluded from all analysis.

Inhibition of DBPII-erythrocyte binding. To determine the quality of the antibodies in the immune sera generated by immunization with the different antigens, pooled immune sera from each group was tested for anti-DBPII activity by evaluating its ability to inhibit DBPII-erythrocyte binding of the native Sal1 and three other native DBPII allelic variants in an in vitro COS7 cell assay. Each serum titrated by end-point dilution was pre-incubated with either COS7 cell surface-expressed DBPII-Sal1, 7.18, P or AH (Ntumngia, et al., 2013. Vaccine 31:4382-4388) before adding human erythrocytes. With the exception of immune sera against recombinant DEKnull-3, all the immune sera contained potent anti-DBPII inhibitory activity against Sal1, which was used as template (FIG. 30A) and three other naturally occurring DBPII alleles 7.18, P or AH (FIGS. 31A-E). The serum dilution to give 50% inhibition of DBPII-erythrocyte binding (IC50) was used as a quantitative measure to compare the inhibitory activities of the different immune sera. Interestingly, the immune serum against recombinant DEKnull-2 produced a relatively higher and more consistent inhibitory response against the different alleles than Sal1, the original DEKnull and the DEKnull-4 antigens (FIG. 30B). A Dunnett's adjusted multiple comparison was used to grouped the sera, using Sal1 as the control, into three statistical groups, (Sal1 and DEKnull; DEKnull-2 and DEKnull-4), with a potential for the DEKnull-2 vaccine overall to induce a significantly stronger anti-DBPII inhibitory antibodies to all the variant DBPII alleles than both the native Sal1 and original DEKnull and DEKnull-4 ($p<0.005$) (FIG. 32).

Discussion

*Plasmodium vivax* merozoite invasion of reticulocytes is a rapid process believed to involve interactions between the Duffy binding protein and the Duffy antigen receptor of chemokines (DARC) (Miller, et al., 1976. The New England journal of medicine 295:302-304). This interaction is crucial for invasion and continued bloodstage infection, thus representing an attractive target for vaccine development. However, potential confounding challenges that may compromise its use as vaccine have been revealed in studies of naturally occurring serologic responses to DBP after infection. Naturally acquired antibodies to DBPII are prevalent in residents of areas where *vivax* malaria is endemic and these antibodies can inhibit DBPII binding and merozoite invasion of human reticulocytes. Unfortunately, anti-DBP antibodies tend to be poorly inhibitory, strain-specific, and short-lived (Chootong, et al., 2010. Infect Immun 78:1089-1095 and Ceravolo, et al., 2009. Naturally acquired inhibitory antibodies to *Plasmodium vivax* Duffy binding protein are short-lived and allele-specific following a single malaria infection. Clin. Exp. Immunol. 156:502-510). Remarkably, strain-specific serologic activity can be altered by even single amino acid substitutions found in allelic variants of DBPII (VanBuskirk, et al., 2004. J. Infect. Dis. 190:1556-1562). This phenomenon is seen not only with DBP, but also with other single *Plasmodium* allele vaccine candidates (VanBuskirk, et al., 2004. J. Infect. Dis. 190:1556-1562; King, et al., 2008. PNAS 105:8363-8368; Hodder et al., 2001. Infect. Immun. 69:3286-3294; and Genton et al., 2002. J. Infect. Dis. 185:820-827). While naturally strain-transcending, broadly neutralizing antibodies are less prevalent, there is a significant correlation of their antibody reactivity to certain epitopes and inhibition of DBPII-receptor function (Chootong, et al., 2010. Infect Immun 78:1089-1095). Epitopes at or near the dimer interface of DBPII appear to represent the primary targets of naturally occurring protective anti-DBPII antibodies that can inhibit merozoite invasion of host erythrocytes (Batchelor, et al., 2011. Nat Struct Mol Biol.). However, these epitopes also contain most of the variable residues resulting from DBP allelic diversity (Chootong, et al., 2010. Infect Immun 78:1089-1095). These data are consistent with the hypothesis that DBP variation is an immune evasion mechanism responsible for strain-specific immunity and stable broadly neutralizing immunity is achieved when antibodies target functionally-conserved epitopes thereby blocking DBP dimerization and inhibiting invasion (Batchelor, et al., 2011. Nat Struct Mol Biol. and Ntumngia and Adams, 2012. Clin. Vacc. Immunol. 19:30-36).

To overcome the natural tendency for eliciting a strain-specific response in a DBPII vaccine, synthetic DBPII alleles were evaluated for their ability to broaden efficacy of strain-transcending inhibition of DBPII-erythrocyte binding against diverse DBPII alleles. In a previous study, an initial synthetic DBPII immunogen termed DEKnull, lacking a variant immunodominant epitope in DBPII maintained structural similarity with the parental DBPII and induced antibodies to conserved epitopes on native DBPII (Ntumngia and Adams, 2012. Clin. Vacc. Immunol. 19:30-36 and Chen, et al., 2015. PLoS neglected tropical diseases 9:e0003644). Although the anti-DBPII inhibitory response induced by DEKnull was lower than that of the naturally occurring allele used as template, the anti-DEKnull antibodies partially overcame strain-specific immunity commonly observed with variant DBPII alleles (Ntumngia and Adams, 2012. Clin. Vacc. Immunol. 19:30-36 and Ntumngia, et al., 2013. Vaccine 31:4382-4388). To enhance the immunogenicity of DEknull and its protective efficacy against diverse DBPII strains, three novel DBPII immunogens were evaluated that altered: the polymorphic residues, which are not important for receptor recognition (DEKnull-2), the functional residues important for binding (DEKnull-3) (VanBuskirk, et al., 2004. 101:15754-15759), and the residues important for dimerization (DEKnull-4) (Batchelor, et al., 2011.

Nat Struct Mol Biol.). As expected, refolded rDEKnull-2, despite lacking all the polymorphic residues, maintained its DBP functional activity by binding to DARC on human erythrocytes in the standard erythrocyte-binding assay. Similarly, COS7 cell surface-expressed rDEKnull-2 also bound to DARC positive human erythrocytes while DEKnull-3 and 4 did not (FIGS. 25-270). Mutating the functional residues and residues important for dimerization respectively compromised the biological activity of the DEKnull-3 and DEKnull-4 antigens. This data for DEKnull-2 confirms the hypothesis that the polymorphic residues in DBPII are generally not important for receptor recognition (VanBuskirk, et al., 2004. 101:15754-15759). Conformation dependent anti-DBPII inhibitory mAbs 3C9 and 2D10 (Ntumngia, et al., 2012. Infection and Immunity 80:1203-1208.)) recognized recombinant DEKnull, DEKnull-2, DEKnull-4 and native Sal1 but not DEKnull-3 in both ELISA and Western blot analysis (FIGS. 24A-24B). To role out the possibility of lack of conformation in the refolded DEKnull-3 antigen as a reason for the lack of reactivity with mAbs-3C9 and 2D10, the different antigens were expressed on the surface of transfected COS7 cells and probed with mAb-3C9 in an immunofluorescence assay (IFA). The COS7 cell assay has an advantage in that cell surface-expressed antigens mimics the native protein on the surface of the parasite and avoids the difficult process of purification and refolding of the recombinant antigens. The GFP expression is used as a transfection marker to confirm expression of the different antigens on the cell surface. As expected, all the COS7 cell surface-expressed antigens, with the exception of DEKnull-3, bound to mAb-3C9 (FIGS. 27A-270), thus confirming that the lack of reactivity of refolded DEKnull-3 to mAb 3C9 and 2D10 and its lack of binding to DARC were not due to lack of conformation but a simple indication that the mutations in DEKnull-3 destroyed the functional epitopes of this antibodies and the residues important for receptor recognition.

With the exception of DEKnull-3, immunizations with the different DEKnull immunogens induced high titer immune sera against the different DBPII allelic variants. The DEKnull-2 immunogen induced a relatively higher and similar anti-DBPII reactivity profiles to all the variant DBPII alleles compared to the Sal1 and the original DEKnull immunogen. The potential biological and functional anti-DBPII activity of the anti-DEKnull-2 antibodies with respect to blocking DBPII-DARC interaction was also stronger and broader across the different DBPII alleles than antibodies against Sal1 and DEKnull. Multiple comparison analysis shows overall anti-DEKnull-2 inhibitory responses to variant DBPII alleles to be significantly higher than that of native Sal1 and the anti-DEKnull antibodies (FIG. 32). These data suggest that the DEKnull-2 vaccine, which lacks the polymorphic residues in DBPII was able to induce an immune response towards the more functionally conserved epitopes on DBPII that are targets of neutralizing anti-DBP antibodies.

In summary, synthetic DBPII immunogens were engineered by altering the polymorphic residues, the binding residues or the residues important for dimerization. Each strategy altered the nature of functional anti-DBPII antibodies elicited and importantly the design that altered the polymorphic residues (DEKnull-2) induced more broadly neutralizing antibodies against a range of diverse allelic DBPII variants, suggesting that it is a better vaccine candidate than the parent Sal1 or the original DEKnull antigens. Polymorphisms in DBPII play a role in induction of strain-specific immunity, a phenomenon, which is responsible for failure of two blood stage *P. falciparum* vaccine candidates to protect against clinical disease (Genton, et al., 2000. Vaccine 18:2504-2511 and Thera, et al., 2011. The New England Journal of medicine 365:1004-1013). The data suggest that epitope specificity is important in vaccine design and that antigen engineering to direct immune response to conserved functional regions, such as the DARC binding residues and/or DBP dimer interface, is a viable and practical approach. These results demonstrate an approach that can be used generally to improve efficacy of other malaria vaccine candidates.

Example 4

```
(DBPH Sail)
                                                            SEQ ID NO: 1
TISSAIINHAFLQNTVMKNCNYKRKRRERDWDCNTKKDVCIPDRRYQLCMKELTNLVNNTDTNFHRDITF

RKLYLKRKLIYDAAVEGDLLLKLNNYRYNKDFCKDIRWSLGDFGDIIMGTDMEGIGYSKVVENNLRSIFG

TDEKAQQRRKQWWNESKAQIWTAMMYSVKKRLKGNFIWICKLNVAVNIEPQIYRWIREWGRDYVSELPTE

VQKLKEKCDGKINYTDKKVCKVPPCQNACKSYDQWITRKKNQWDVLSNKFISVKNAEKVQTAGIVTPYDI

LKQELDEFNEVAFENEINKRDGAYIELCVCSVEEAKKNTQEVVTNVDN

(DEKnull)
                                                            SEQ ID NO: 2
TISSAIINHAFLQNTVMKNCNYKRKRRERDWDCNTKKDVCIPDRRYQLCMKELTNLVNNTDTNFHRDITF

RKLYLKRKLIYDAAVEGDLLLKLNNYRYNKDFCKDIRWSLGDFGDIIMGTDMEGIGYSKVVENNLRSIFG

TAATAQATRSQWTSESKAQIWTAMMYSVKKRLKGNFIWICKLNVAVNIEPQIYRWIREWGRDYVSELPTE

VQKLKEKCDGKINYTDKKVCKVPPCQNACKSYDQWITRKKNQWDVLSNKFISVKNAEKVQTAGIVTPYDI

LKQELDEFNEVAFENEINKRDGAYIELCVCSVEEAKKNTQEVVTNVDN

(DEKnull-2)
                                                            SEQ ID NO: 3
TISSAIINHAFLQNTVMKNCNYKRKRRERDWDCNTKKDVCIPDRRYQLCMKELTNLVNNTDTNFHADITF

RKLYLKAKLIYDAAVEGDLLTKLNNYRYNKDFCKDIRWSLGDFGDIIMGTDMEGIGTSAVVENNLRSIFG
```

-continued

TAATAQARRSQWTSESKAQIWTAMMYSVKKRLKGTFIWICKANVAVNIEPQIYRSIREWGRDYVAELPTE

VTKLKEKCDGKINYADKKVCKVPPCQNACKSYDQWITRKANQWDVLSNKFTSAKNAEKAQTASIVTPYDI

LKQELDEFNEVAFENEINKRDGAYIELCVCSVEEAKKNTQEVVTNVDN (DEKnull-3)

SEQ ID NO: 4

TISSAIINHAFLQNTVMKNCNYKRKRRERDWDCNTKKDVCIPDRRYQLCMKELTNLTATATSAAHRDITF

RKLYAARTSAYDAAVEGDLLLKLTNYRASTDACKAATWSLGDFGDIIMGTDMEGIGYSKVVATNLRSIFG

TDEKAQQRRKQWTATSKAQIWTAMMAASTAASKGNAIWSCKLNVAVNIEPTIAAWIATSARATSSELPTE

VQKLKEKCDGKINYTDKKVCKVPPCQNACKSYDQWITRKKNQWDVLSNKFISVKNAEKVQTAGIVTPYDI

LKQELDEFNEVAFENEINKRDGAYIELCVCSVEEAKKNTQEVVTNVDN (DEKnull-4)

SEQ ID NO: 5

TISSAIINHAFLQNTVMKNCNYKRKRRERDWDCNTKKDVCIPDRRYQLCMKALTNLVNNTDTNFHRDITA

RKAYLAAKLTADAASEGDLLLKLAATATSAATCKDIRWSLGDFGDIIMGTDMEGIGYSKVVENNLRSIFG

TDEKAQQRRKQWWNESKATIWTAMMASATASAATSAATAAKLNVAVNIEPQIYRWIREWGRDYVSELPTE

VQKLKEKCDGKINYTDKKVCKVPPCQNACKSYDQWITRKKNQWDVLSNKFISVKNAEKVQTAGIVTPYDI

LKQELDEFNEVAFENEINKRDGAYIELCVCSVEEAKKNTQEVVTNVDN

DEKnull-2

SEQ ID NO: 6

ACCATTAGCAGCGCGATTATTAACCATGCGTTTCTGCAGAACACCGTGATGAAAAACTGCAACTATAAAC

GCAAACGCCGCGAACGCGATTGGGATTGCAACACCAAAAAAGATGTGTGCATTCCGGATCGCCGCTATCA

GCTGTGCATGAAAGAACTGACCAACCTGGTGAACAACACCGATACCAACTTTCATGCGGATATTACCTTT

CGCAAACTGTATCTGAAAGCGAAACTGATTTATGATGCGGCGGTGGAAGGCGATCTGCTGACCAAACTGA

ACAACTATCGCTATAACAAAGATTTTTGCAAAGATATTCGCTGGAGCCTGGGCGATTTTGGCGATATTAT

TATGGGCACCGATATGGAAGGCATTGGCACCAGCGCGGTGGTGGAAAACAACCTGCGCAGCATTTTTGGC

ACCGCGGCGACCGCGCAGGCGCGCCGCAGCCAGTGGACCAGCGAAAGCAAAGCGCAGATTTGGACCGCGA

TGATGTATAGCGTGAAAAAACGCCTGAAAGGCACCTTTATTTGGATTTGCAAAGCGAACGTGGCGGTGAA

CATTGAACCGCAGATTTATCGCAGCATTCGCGAATGGGGCCGCGATTATGTGGCGGAACTGCCGACCGAA

GTGACCAAACTGAAAGAAAAATGCGATGGCAAAATTAACTATGCGGATAAAAAAGTGTGCAAAGTGCCGC

CGTGCCAGAACGCGTGCAAAAGCTATGATCAGTGGATTACCCGCAAAGCGAACCAGTGGGATGTGCTGAG

CAACAAATTTACCAGCGCGAAAAACGCGGAAAAAGCGCAGACCGCGAGCATTGTGACCCCGTATGATATT

CTGAAACAGGAACTGGATGAATTTAACGAAGTGGCGTTTGAAAACGAAATTAACAAACGCGATGGCGCGT

ATATTGAACTGTGCGTGTGCAGCGTGGAAGAAGCGAAAAAAAACACCCAGGAAGTGGTGACCAACGTGGA

TAAC

DEKnull-2 consensus codons

SEQ ID NO: 7

ACNATHWSNWSNGCNATHATHAAYCAYGCNTTYYTNCARAAYACNGTNATGAARAAYTGYAAYTAYAARM

GNAARMGNMGNGARMGNGAYTGGGAYTGYAAYACNAARAARGAYGTNTGYATHCCNGAYMGNMGNTAYCA

RYTNTGYATGAARGARYTNACNAAYYTNGTNAAYAAYACNGAYACNAAYTTYCAYGCNGAYATHACNTTY

MGNAARYTNTAYYTNAARGCNAARYTNATHTAYGAYGCNGCNGTNGARGGNGAYYTNYTNACNAARYTNA

AYAAYTAYMGNTAYAAYAARGAYTTYTGYAARGAYATHMGNTGGWSNYTNGGNGAYTTYGGNGAYATHAT

HATGGGNACNGAYATGGARGGNATHGGNACNWSNGCNGTNGTNGARAAYAAYYTNMGNWSNATHTTYGGN

ACNGCNGCNACNGCNCARGCNMGNMGNWSNCARTGGACNWSNGARWSNAARGCNCARATHTGGACNGCNA

TGATGTAYWSNGTNAARAARMGNYTNAARGGNACNTTYATHTGGATHTGYAARGCNAAYGTNGCNGTNAA

-continued

YATHGARCCNCARATHTAYMGNWSNATHMGNGARTGGGGNMGNGAYTAYGTNGCNGARYTNCCNACNGAR

GTNACNAARYTNAARGARAARTGYGAYGGNAARATHAAYTAYGCNGAYAARAARGTNTGYAARGTNCCNC

CNTGYCARAAYGCNTGYAARWSNTAYGAYCARTGGATHACNMGNAARGCNAAYCARTGGGAYGTNYTNWS

NAAYAARTTYACNWSNGCNAARAAYGCNGARAARGCNCARACNGCNWSNATHGTNACNCCNTAYGAYATH

YTNAARCARGARYTNGAYGARTTYAAYGARGTNGCNTTYGARAAYGARATHAAYAARMGNGAYGGNGCNT

AYATHGARYTNTGYGTNTGYWSNGTNGARGARGCNAARAARAAYACNCARGARGTNGTNACNAAYGTNGA

YAAY

DEKnull-3

SEQ ID NO: 8

ACCATTAGCAGCGCGATTATTAACCATGCGTTTCTGCAGAACACCGTGATGAAAAACTGCAACTATAAAC

GCAAACGCCGCGAACGCGATTGGGATTGCAACACCAAAAAAGATGTGTGCATTCCGGATCGCCGCTATCA

GCTGTGCATGAAAGAACTGACCAACCTGACCGCGACCGCGACCAGCGCGGCGCATCGCGATATTACCTTT

CGCAAACTGTATGCGGCGCGCACCAGCGCGTATGATGCGGCGGTGGAAGGCGATCTGCTGCTGAAACTGA

CCAACTATCGCGCGAGCACCGATGCGTGCAAAGCGGCGACCTGGAGCCTGGGCGATTTTGGCGATATTAT

TATGGGCACCGATATGGAAGGCATTGGCTATAGCAAAGTGGTGGCGACCAACCTGCGCAGCATTTTTGGC

ACCGATGAAAAAGCGCAGCAGCGCCGCAAACAGTGGACCGCGACCAGCAAAGCGCAGATTTGGACCGCGA

TGATGGCGGCGAGCACCGCGGCGAGCAAAGGCAACGCGATTTGGAGCTGCAAACTGAACGTGGCGGTGAA

CATTGAACCGACCATTGCGGCGTGGATTGCGACCAGCGCGCGCGCGACCAGCAGCGAACTGCCGACCGAA

GTGCAGAAACTGAAAGAAAAATGCGATGGCAAAATTAACTATACCGATAAAAAAGTGTGCAAAGTGCCGC

CGTGCCAGAACGCGTGCAAAAGCTATGATCAGTGGATTACCCGCAAAAAAAACCAGTGGGATGTGCTGAG

CAACAAATTTATTAGCGTGAAAAACGCGGAAAAAGTGCAGACCGCGGGCATTGTGACCCCGTATGATATT

CTGAAACAGGAACTGGATGAATTTAACGAAGTGGCGTTTGAAAACGAAATTAACAAACGCGATGGCGCGT

ATATTGAACTGTGCGTGTGCAGCGTGGAAGAAGCGAAAAAAAACACCCAGGAAGTGGTGACCAACGTGGA

TAAC

DEKnull-3 consensus codons

SEQ ID NO: 9

ACNATHWSNWSNGCNATHATHAAYCAYGCNTTYYTNCARAAYACNGTNATGAARAAYTGYAAYTAYAARM

GNAARMGNMGNGARMGNGAYTGGGAYTGYAAYACNAARAARGAYGTNTGYATHCCNGAYMGNMGNTAYCA

RYTNTGYATGAARGARYTNACNAAYYTNACNGCNACNGCNACNWSNGCNGCNCAYMGNGAYATHACNTTY

MGNAARYTNTAYGCNGCNMGNACNWSNGCNTAYGAYGCNGCNGTNGARGGNGAYYTNYTNYTNAARYTNA

CNAAYTAYMGNGCNWSNACNGAYGCNTGYAARGCNGCNACNTGGWSNYTNGGNGAYTTYGGNGAYATHAT

HATGGGNACNGAYATGGARGGNATHGGNTAYWSNAARGTNGTNGCNACNAAYYTNMGNWSNATHTTYGGN

ACNGAYGARAARGCNCARCARMGNMGNAARCARTGGACNGCNACNWSNAARGCNCARATHTGGACNGCNA

TGATGGCNGCNWSNACNGCNGCNWSNAARGGNAAYGCNATHTGGWSNTGYAARYTNAAYGTNGCNGTNAA

YATHGARCCNACNATHGCNGCNTGGATHGCNACNWSNGCNMGNGCNACNWSNWSNGARYTNCCNACNGAR

GTNCARAARYTNAARGARAARTGYGAYGGNAARATHAAYTAYACNGAYAARAARGTNTGYAARGTNCCNC

CNTGYCARAAYGCNTGYAARWSNTAYGAYCARTGGATHACNMGNAARAARAAYCARTGGGAYGTNYTNWS

NAAYAARTTYATHWSNGTNAARAAYGCNGARAARGTNCARACNGCNGGNATHGTNACNCCNTAYGAYATH

YTNAARCARGARYTNGAYGARTTYAAYGARGTNGCNTTYGARAAYGARATHAAYAARMGNGAYGGNGCNT

AYATHGARYTNTGYGTNTGYWSNGTNGARGARGCNAARAARAAYACNCARGARGTNGTNACNAAYGTNGA

YAAY

-continued

DEKnull-4

SEQ ID NO: 10

ACCATTAGCAGCGCGATTATTAACCATGCGTTTCTGCAGAACACCGTGATGAAAAACTGCAACTATAAAC

GCAAACGCCGCGAACGCGATTGGGATTGCAACACCAAAAAAGATGTGTGCATTCCGGATCGCCGCTATCA

GCTGTGCATGAAAGCGCTGACCAACCTGGTGAACAACACCGATACCAACTTTCATCGCGATATTACCGCG

CGCAAAGCGTATCTGGCGGCGAAACTGACCGCGGATGCGGCGAGCGAAGGCGATCTGCTGCTGAAACTGG

CGGCGACCGCGACCAGCGCGGCGACCTGCAAAGATATTCGCTGGAGCCTGGGCGATTTTGGCGATATTAT

TATGGGCACCGATATGGAAGGCATTGGCTATAGCAAAGTGGTGGAAAACAACCTGCGCAGCATTTTTGGC

ACCGATGAAAAAGCGCAGCAGCGCCGCAAACAGTGGTGGAACGAAAGCAAAGCGACCATTTGGACCGCGA

TGATGGCGAGCGCGACCGCGAGCGCGGCGACCAGCGCGGCGACCGCGGCGAAACTGAACGTGGCGGTGAA

CATTGAACCGCAGATTTATCGCTGGATTCGCGAATGGGGCCGCGATTATGTGAGCGAACTGCCGACCGAA

GTGCAGAAACTGAAAGAAAAATGCGATGGCAAAATTAACTATACCGATAAAAAAGTGTGCAAAGTGCCGC

CGTGCCAGAACGCGTGCAAAAGCTATGATCAGTGGATTACCCGCAAAAAAAACCAGTGGGATGTGCTGAG

CAACAAATTTATTAGCGTGAAAAACGCGGAAAAAGTGCAGACCGCGGGCATTGTGACCCCGTATGATATT

CTGAAACAGGAACTGGATGAATTTAACGAAGTGGCGTTTGAAAACGAAATTAACAAACGCGATGGCGCGT

ATATTGAACTGTGCGTGTGCAGCGTGGAAGAAGCGAAAAAAAACACCCAGGAAGTGGTGACCAACGTGGA

TAAC

DEKnull-4 consensus codons

SEQ ID NO: 11

ACNATHWSNWSNGCNATHATHAAYCAYGCNTTYYTNCARAAYACNGTNATGAARAAYTGYAAYTAYAARM

GNAARMGNMGNGARMGNGAYTGGGAYTGYAAYACNAARAARGAYGTNTGYATHCCNGAYMGNMGNTAYCA

RYTNTGYATGAARGCNYTNACNAAYYTNGTNAAYAAYACNGAYACNAAYTTYCAYMGNGAYATHACNGCN

MGNAARGCNTAYYTNGCNGCNAARYTNACNGCNGAYGCNGCNWSNGARGGNGAYYTNYTNYTNAARYTNG

CNGCNACNGCNACNWSNGCNGCNACNTGYAARGAYATHMGNTGGWSNYTNGGNGAYTTYGGNGAYATHAT

HATGGGNACNGAYATGGARGGNATHGGNTAYWSNAARGTNGTNGARAAYAAYYTNMGNWSNATHTTYGGN

ACNGAYGAPAARGCNCARCARMGNMGNAARCARTGGTGGAAYGARWSNAARGCNACNATHTGGACNGCNA

TGATGGCNWSNGCNACNGCNWSNGCNGCNACNWSNGCNGCNACNGCNGCNAARYTNAAYGTNGCNGTNAA

YATHGARCCNCARATHTAYMGNTGGATHMGNGARTGGGGNMGNGAYTAYGTNWSNGARYTNCCNACNGAR

GTNCAPAARYTNAARGARAARTGYGAYGGNAARATHAAYTAYACNGAYAARAARGTNTGYAARGTNCCNC

CNTGYCARAAYGCNTGYAARWSNTAYGAYCARTGGATHACNMGNAARAARAAYCARTGGGAYGTNYTNWS

NAAYAARTTYATHWSNGTNAARAAYGCNGARAARGTNCARACNGCNGGNATHGTNACNCCNTAYGAYATH

YTNAARCARGAPYTNGAYGARTTYAAYGARGTNGCNTTYGARAAYGARATHAAYAARMGNGAYGGNGCNT

AYATHGARYTNTGYGTNTGYWSNGTNGARGARGCNAARAARAAYACNCARGARGTNGTNACNAAYGTNGA

YAAY

DEK null based on P22290.2 and FIG. 22

TISSAIINHAFLQNTVMKNCNYKRKRRERDWDCNTKKDVCIPDRRYQLCMKELTNLVNNTDTNFHRDITF

RKLYLKRKLIYDAAVEGDLLLKLNNYRYNKDFCKDIRWSLGDFGDIIMGTDMEGIGYSKVVENNLRSIFG

TAATAQATRKQWWNESKAQIWTAMMYSVKKRLKGNFIWICKLNVAVNIEPQIYRWIREWGRDYVSELPTE

VQKLKEKCDGKINYTDKKVCKVPPCQNACKSYDQWITRKKNQWDVLSNKFISVKNAEKVQTAGIVTPYDI

LKQELDEFNEVAFENEINKRDGAYIELCVCSVEEAKKNTQEVVTNVDN

We claim:

1. A method comprising:

administering an amount of a composition comprising a synthetic *P. vivax* polypeptide to a subject in need thereof one or more times, wherein the synthetic *P. vivax* polypeptide is SEQ ID NO: 3.

2. The method of claim 1, wherein the composition further comprises an adjuvant.

3. The method of claim 1, wherein the subject in need thereof is infected with or at risk of being infected with a species of *Plasmodium*.

* * * * *

UNITED STATES PATENT AND TRADEMARK OFFICE

CERTIFICATE OF CORRECTION

PATENT NO. : 11,787,845 B1
APPLICATION NO. : 17/103275
DATED : October 17, 2023
INVENTOR(S) : John H. Adams et al.

It is certified that error appears in the above-identified patent and that said Letters Patent is hereby corrected as shown below:

In the Specification

Column 18, Line 32, "1322A, 1322T" should be --I322A, I322T--.

Column 18, Line 65, "1348A" should be --I348A--.

Column 18, Line 40, "1419A" should be --I419A--.

Column 18, Line 40, "1421S, 1421A" should be --I421S, I421A--.

Column 18, Line 43, "1503T" should be --I503T--.

Column 18, Line 54, "1322A, 1322T" should be --I322A, I322T--.

Column 18, Line 57, "1348A" should be --I348A--.

Column 18, Line 61, "1419A" should be --I419A--.

Column 18, Line 62, "1421S, 1421A" should be --I421S, I421A--.

Column 18, Line 64, "1503T" should be --I503T--.

Column 24, Line 63, "EUDRAGIT@" should be --EUDRAGIT®--.

Column 26, Line 16, "µg" should be --pg--.

Column 26, Line 45, "µg" should be --pg--.

Column 30, Line 11, "101" should be --$10^{11}$--.

Signed and Sealed this
Twenty-sixth Day of December, 2023

Katherine Kelly Vidal

Katherine Kelly Vidal
*Director of the United States Patent and Trademark Office*

Column 34, Line 61, “1503K” should be --I503K--.

Column 49, Line 9, “Sal” should be --Sal1--.

Column 49, Line 25, “anti-Sall” should be --anti-Sal1--.

Column 51, Line 32, “27A-270” should be --27A-27O--.